US007094598B2

(12) United States Patent
Nabel et al.

(10) Patent No.: US 7,094,598 B2
(45) Date of Patent: Aug. 22, 2006

(54) DEVELOPMENT OF A PREVENTIVE VACCINE FOR FILOVIRUS INFECTION IN PRIMATES

(75) Inventors: Gary J. Nabel, Washington, DC (US); Zhi-yong Yang, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/997,120

(22) Filed: Nov. 24, 2004

(65) Prior Publication Data

US 2006/0148087 A1    Jul. 6, 2006

Related U.S. Application Data

(62) Division of application No. 10/491,121, filed as application No. PCT/US02/30251 on Sep. 24, 2002.

(60) Provisional application No. 60/326,476, filed on Oct. 1, 2001.

(51) Int. Cl.
| C12N 15/00 | (2006.01) |
| C12P 21/06 | (2006.01) |
| C12N 5/00 | (2006.01) |
| C12N 15/63 | (2006.01) |

(52) U.S. Cl. .................. 435/320.1; 435/69.1; 435/325; 435/455

(58) Field of Classification Search ............... 435/69.1, 435/320.1, 325, 455
See application file for complete search history.

(56) References Cited

U.S. PATENT DOCUMENTS 6,171,596 B1    1/2001   Earl et al.
6,200,959 B1    3/2001   Haynes et al.

FOREIGN PATENT DOCUMENTS

WO    WO 99/32147    7/1999
WO    WO 01/16183    3/2001

OTHER PUBLICATIONS

Lee at al, Eur J Biochem. 271(6):1094-105, 2004.*
Pereira et al Nucleic Acids Res.28(3):663-668. 2000.*
Aoki, K. et al. 1999 "Efficient generation of recombinant adenoviral vectors by Cre-lox recombination in vitro," Mol. Med. 5:224-231.
Baize, S. et al. 1999 "Defective humoral responses and extensive intravascular apoptosis are associated with fatal outcome in Ebola virus-infected patients," Nature Med. 5:423-426.
Bray, M. et al. 1998 "A mouse model for evaluation of prophylaxis and therapy of Ebola hemorrhagic fever," J. Infect. Dis. 178:651-661.
Connolly, B.M. et al. 1998 "Pathogenesis of experimental Ebola virus infection in guinea pigs," J. Infect. Dis. 179:S203-S217.

Davis, A.R. et al. 1985 "Expression of hepatitis B surface antigen with a recombinant adenovirus," PNAS USA 82:7560-7564.
Feldmann, H. et al. 1994 "Characterization of filoviruses based on differences in structure and antigenicity of the virion glycoprotein," Virology 199:469-473.
Fisher-Hoch, S.P. et al. 1985 "Pathophysiology of shock and hemorrhage in a fulminating viral infection (Ebola)," J. Infect. Dis. 152:887-894.
Geisbert, T.W. et al. 2002 "Evaluation in nonhuman primates of vaccines against Ebola virus." Emerg. Infect. Dis. 8(5):503-507.
Hanke, T. et al. 1998 "Enhancement of MHC class I-restricted peptide-specific T cell induction by a DNA prime/MVA boost vaccination regime," Vaccine 16:439-445.
Kiley, M.P. et al. 1980 "Ebola virus: identification of virion structural proteins," J. Gen. Virol. 49:333-341.
Krieg, A.M. et al. 1995 "CpG motifs in bacterial DNA trigger direct B-cell activation," Nature 374:546-549.
Ksiazek, T.G. et al. 1992 "Enzyme immunosorbent assay for Ebola virus antigens in tissues of infected primates," J. Clin. Microbiol. 30:947-950.
Letvin, N.L. et al. 1997 " Potent, protective anti-HIV immune responses generated by bimodal HIV envelope DNA plus protein vaccination,"PNAS USA 94:9378-9383.
Maryuama, T. et al. 1999 "Ebola virus can be effectively neutralized by antibody produced in natural human infection," J. Virol. 73:6024-6030.
Natuk, R.J. et al. 1992 "Adenovirus-human immunodeficiency virus (HIV) envelope recombinant vaccines elicit high-titered HIV-neutralizing antibodies in the dog model," PNAS USA 89:7777-7781.
Ohno, T. et al. 1994 "Gene therapy for vascular smooth muscle cell proliferation after arterial injury," Science 265:781-784.
Pushko, P. et al. 2001 "Individual and bivalent vaccines based on alphavirus replicons protect guinea pigs against infection with Lassa and Ebola viruses," J. Virol. 75(23):11677-11685.
Robinson, H.L. et al. 1999 "Neutralizing antibody-independent containment of immunodeficiency virus challenges by DNA priming and recombinant pox virus booster immunizations," Nature Med. 5:526-534.
Sanchez, A. et al. 1996 "The virion glycoproteins of Ebola viruses are encoded in two reading frames and are expressed through transcriptional editing," PNAS USA 93:3602-3607.
Sanchez, A. et al. 1998 "Biochemical analysis of the secreted and virion glycoproteins of Ebola virus," J. Virol. 72:6442-6447.
Sato, Y. et al. 1996 "Immunostimulatory DNA sequences necessary for effective intradermal gene immunization," Science 273:352-354.
Schneider, J. et al. 1998 "Enhanced immunogenicity for CD8+T cell induction and complete protective efficacy of malaria DNA vaccination by boosting with modified vaccinia virus Ankara," Nature Med. 4:397-402.

(Continued)

Primary Examiner—Sumesh Kaushal
(74) Attorney, Agent, or Firm—Knobbe, Martens, Olson & Bear, LLP

(57) ABSTRACT

The present invention relates generally to viral vaccines and, more particularly, to filovirus vaccines and methods of eliciting an immune response against a filovirus or disease caused by infection with filovirus.

7 Claims, 51 Drawing Sheets

OTHER PUBLICATIONS

Sedegah, M. et al. 1994 "Protection against malaria by immunization with plasmid DNA encoding circumsporozoite protein," *PNAS USA* 91:9866-9870.

Sedegah, M. et al. 1998 "Boosting with recombinant vaccinia increases immunogenicity and protective efficacy of malaria DNA vaccine," *PNAS USA* 95:7648-7653.

Sullivan, N.J. et al. 2000 "Development of a preventive vaccine for Ebola virus infection in primates," *Nature* 408:605-609.

Sullivan, N.J. et al. 2000 "Ebola virus pathogenesis and vaccine development," Symposium on Marburg and Ebola Viruses, Marburg, Germany, Oct. 1-4, 2000, Abstract 23, p. 35.

Sullivan, N.J. et al. 2003 "Accelerated vaccination for Ebola virus haemorrhagic fever in non-human primates," *Nature* 424:681-684.

Tang, D.C. et al. 1992 "Genetic immunization is a simple method for eliciting an immune response," *Nature* 356:152-154.

Ulmer, J.B. et al. 1993 "Heterologous protection against influenza by injection of DNA encoding a viral protein," *Science* 259:1745-1749.

Vanderzanden, L. et al. 1998 "DNA vaccines expressing either the GP or NP genes of Ebola virus protect mice from lethal challenge," *Virology* 246:134-144.

Wang, B. et al. 1993 "Gene inoculation generates immune responses against human immunodeficiency virus type 1," *PNAS USA* 90:4156-4160.

Wilson, J. et al. 2000 "Epitopes involved in antibody-mediated protection from Ebola virus," *Science* 287:1664-1666.

Xiang, Z.Q. et al. 1996 "A replication-defective human adenovirus recombinant serves as a highly efficacious vaccine carrier," *Virology* 219:220-227.

Xiang, Z.Q. et al. 1999 "Induction of genital immunity by DNA priming and intranasal booster immunization with a replication-defective adenoviral recombinant," *J. Immunol.* 162:6716-6723.

Xu, L. et al. 1998 "Immunization for Ebola virus infection," *Nature Med.* 4:37-42.

Yang, Z. et al. 1998 "Distinct cellular interactions of secreted and transmembrane Ebola virus glycoproteins," *Science* 279:1034-1037.

Yang, Z. et al. 2000 "Identification of the Ebola virus glycoprotein as the main viral determinant of vascular cell cytotoxicity and injury," *Nature Med.* 6:886-889.

Yang, Z.Y. et al. 2003 "Overcoming immunity to a viral vaccine by DNA priming before vector boosting," *J. Virol.* 77(1):799-803.

Barouch, D.H. et al., 2005, "A Human T-Cell Leukemia Virus Type 1 Regulatory Element Enhances the Immunogenicity of Human Immunodeficiency Virus Type 1 DNA Vaccines in Mice and Non-human Primates," J. Virol. 79:8828-8834.

* cited by examiner pVR1012x/s Ebola GP(Z)

*Dra* III (6986)
*Xho* I (6850)
*Xma* I (6576)
Kan r
*Pvu* I (6454)
*Hin* d III (6330)

*Nde* I (185)
*Nde* I (571)
CMV enhancer
*Nco* I (697)
*Sac* II (992)
CMV IE 5' UTR
*Sph* I (1092)
CMV IE Intron
*Hpa* I (1755)
*Nco* I (1848)
*Sal* I (1875)
*Pml* I (1882)
*Eco* RV (1894)
*Not* I (1899)
*Xba* I (1906)
*Sal* I (2081)

VRC6001
7188 bp

*Sfi* I (4747)
TbGH
*Sph* I (4377)
*Eco* RV (2597)
Ebola GP (Z)

FIG. 2 pVR1012-GP(Z) delta MUC delta FUR

Plasmid map of pVRC 6003 (6561 bp) showing the following features and restriction sites:
- Nde I (185)
- Nde I (571)
- CMV enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire delta MUC, delta FUR
- EarI/3436bp
- Pst I (3130)
- Bcl I (3215)
- Kpn I (3565)
- Sph I (3784)
- Kpn I (3812)
- bovine growth hormone poly A
- Hin d III (5703)
- Pvu I (5827)
- kanamycin resistance
- Xho I (6223)
- Dra III (6359)

FIG. 4 pVR1012-GP(Z) delta GP2

- Dra III (6522)
- Nde I (185)
- Xho I (6386)
- Msc I (248)
- kanamycin resistance
- Nde I (571)
- Pvu I (5990)
- CMV enhancer
- Hind III (5866)
- Sac II (992)
- CMV IE 5' UTR
- Sph I (1092)
- CMV IE Intron
- Pvu II (1701)
- Hpa I (1755)
- Pst I (1865)
- Sal I (1875)
- Pml I (1882)
- Bcl I (1886)
- Eco RV (1894)
- Not I (1899)
- Xba I (1906)
- Bst XI (4062)
- Sal I (2081)
- bovine growth hormone poly A
- Eco RV (2597)
- Kpn I (3975)
- Pvu II (2704)
- Sph I (3947)
- Ebola GP Zaire
- Kpn I (3728)
- Pst I (3022)
- Bsp MI (3460)
- delta GP2(BclI/BspEI)

pVRC 6004
6724 bp

FIG. 5 pVR1012-GP(Z) delta GP2 delta C-term A pVRC 6005
6887 bp

- Dra III (6685)
- Xho I (6549)
- kanamycin resistance
- Pvu I (6153)
- Hind III (6029)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Bcl I (1886)
- Eco RV (1894)
- Not I (1899)
- Xba I (1906)
- Sal I (2081)
- Eco RV (2597)
- Ebola GP Zaire(MscII/BspMI)
- Pst I (3022)
- Bsp I (3088)
- Bcl I (3414)
- MscI/BspMI
- Bsp MI (3623)
- Kpn I (3891)
- Sph I (4110)
- Kpn I (4138)
- bovine growth hormone poly A
- Bst XI (4225)

FIG. 6 pVR1012-GP(Z) delta GP2 delta FUS pVRC 6007
7106 bp

- Dra III (6904)
- Xho I (6768)
- kanamycin resistance
- Pvu I (6372)
- Hind III (6248)
- Nde I (185)
- Msc I (248)
- Nde I (571)
- CMV enhancer
- Sac II (992)
- CMV IE 5' UTR
- Sph I (1092)
- CMV IE Intron
- Hpa I (1755)
- Sal I (1875)
- Pml I (1882)
- Eco RV (1894)
- Not I (1899)
- Xba I (1906)
- Sal I (2081)
- Eco RV (2597)
- Ebola GP Zaire(3508/3555)
- 3508/3555
- Msc I (3575)
- Bst XI (3732)
- Bsp MI (3842)
- Kpn I (4110)
- Sph I (4329)
- Kpn I (4357)
- bovine growth hormone poly A
- Bst XI (4444)

FIG. 8 pVR1012-GP(Z) delta TM

- Dra III (6712)
- Xho I (6576)
- kanamycin resistance
- Pvu I (6180)
- Hind III (6056)
- Nde I (185)
- Msc I (248)
- Nde I (571)
- CMV enhancer
- Sac II (992)
- CMV IE 5' UTR
- Sph I (1092)
- CMV IE Intron
- Hpa I (1755)
- Sal I (1875)
- Pml I (1882)
- Eco RV (1894)
- Not I (1899)
- Xba I (1906)
- Sal I (2081)
- Eco RV (2597)
- Ebola Glycoprotein Zaire Subtype (U31033)
- Msc I (3623)
- Bst XI (3780)
- Bgl II (3930)
- Sph I (4137)
- Kpn I (4165)
- bovine growth hormone poly A
- Bst XI (4252)

pVRC 6008
6914 bp

FIG. 9 pVR1012-GP(Z) delta SGP pVRC 6052
6467 bp

- Dra III (6265)
- Xho I (6129)
- kanamycin resistance
- Pvu I (5733)
- Hind III (5609)
- Nde I (185)
- Msc I (248)
- Nde I (571)
- CMV enhancer
- Sac II (992)
- CMV IE 5' UTR
- Sph I (1092)
- CMV IE Intron
- Pvu II (1701)
- Hpa I (1755)
- Sal I (1875)
- Pml I (1882)
- Eco RV (1894)
- Not I (1899)
- Xba I (1906)
- Bst XI (3805)
- bovine growth hormone poly A
- Kpn I (3718)
- Sph I (3690)
- Kpn I (3471)
- Ebola GP (delta SGP)
- Pvu II (2932)
- Msc I (2936)
- Bst XI (3093)
- Bsp MI (3203)

Plasmid map: VRC6101, 6913 bp

Labeled features and sites:
- pVR1012x/s Ebola GP(R)(dTM)
- CMV enhancer
- Sac II (992)
- CMV IE 5' UTR
- Sph I (1092)
- CMV IE Intron
- Pvu II (1701)
- Hpa I (1755)
- Sal I (1875)
- Pml I (1882)
- Bcl I (1886)
- Eco RV (1927)
- Xmn I (1955)
- Bcl I (2061)
- Xmn I (2693)
- Ebola GP (Reston)(dTM)
- Sal I (3002)
- Pvu I (3420)
- Bgl II (3455)
- Pvu II (3474)
- Kpn I (3715)
- Xba I (3874)
- Bgl II (3895)
- Sph I (4102)
- Kpn I (4130)
- bovine growth hormone poly A
- Sfi I (4472)
- Hin d III (6055)
- Pvu I (6179)
- Kan
- Cla I (6484)
- Xho I (6575)
- Dra III (6711)

pAdApt Ebola GP(R) (dTM)

- Pvu I (7502)
- Amp
- Ad5(bp1-454)
- Nde I (843)
- CMV enhancer
- Pml I (1279)
- Bcl I (1283)
- Eco RV (1291)
- Bcl I (1425)
- Nde I (2001)
- VRC6110 8131 bp
- Pml I (6026)
- Xho I (5823)
- Nar I (5554)
- Kas I (5553)
- Ebola GP(Reston)(dTM)
- Pvu I (2784)
- Kpn I (3079)
- Xba I (3238)
- Ad5(bp3511-6093)
- Bovine Growth Hormone Poly A
- Kpn I (3494)
- LoxP

FIG. 12 pVR1012-GP(S)

pVRC 6200
7082 bp

- Dra III (6880)
- Nde I (185)
- Cla I (6653)
- Msc I (248)
- Nde I (571)
- kanamycin resistance
- CMV enhancer
- Pvu I (6348)
- Hind III (6224)
- Sac II (992)
- CMV IE 5' UTR
- Bsp EI (1436)
- CMV IE Intron
- Hpa I (1755)
- Sal I (1875)
- Pml I (1882)
- Bcl I (1886)
- Not I (1899)
- Not I (1928)
- Xmn I (4650)
- bovine growth hormone poly A
- Kpn I (4333)
- Xba I (4077)
- Ebola Glycoprotein Sudan subtype (#U28134)
- Hpa I (3491)

FIG. 13 pVR1012x/s Ebola GP(S)

- Dra III (6885)
- Xho I (6749)
- Cla I (6658)
- Xma I (6475)
- Kan r
- Pvu I (6353)
- Hin d III (6229)
- Nde I (185)
- Nde I (571)
- CMV enhancer
- Sac II (992)
- CMV IE 5' UTR
- Sph I (1092)
- CMV IE Intron
- Hpa I (1755)
- Sal I (1875)
- Pml I (1882)
- Bcl I (1886)
- Not I (1899)
- Xho I (2161)
- Xma I (2394)

VRC6201
7087 bp

- Sfi I (4646)
- TbGH
- Sph I (4276)
- Xba I (4048)
- Hpa I (3462)
- Ebola GP(S)

FIG. 14 pVR1012-GP(S) delta TM pVRC 6202
6940 bp

- Dra III (6738)
- Cla I (6511)
- kanamycin resistance
- Pvu I (6206)
- Hind III (6082)
- Nde I (185)
- Msc I (248)
- Nde I (571)
- CMV enhancer
- Sac II (992)
- CMV IE 5' UTR
- Bsp EI (1436)
- CMV IE Intron
- Hpa I (1755)
- Sal I (1875)
- Not I (1903)
- Eco RV (1922)
- Eco RV (2191)
- Ebola Glycoprotein Sudan Subtype (#U28134)
- Hpa I (3466)
- Kpn I (4191)
- bovine growth hormone poly A
- Xmn I (4508)

FIG. 15 pVR1012-GP(IC)

*Dra* III (6800)
*Xho* I (6664)
*Cla* I (6573)
kanamycin resistance
*Pvu* I (6268)
*Hin*d III (6144)

*Nde* I (185)
*Msc* I (248)
*Nde* I (571)
CMV enhancer
*Sac* II (992)
CMV IE 5' UTR
*Sph* I (1092)
*Bsp* EI (1436)
CMV IE Intron
*Hpa* I (1755)
*Pst* I (1865)
*Sal* I (1875)
*Pml* I (1882)
*Eco* RV (1894)
*Not* I (1899)
*Xba* I (1906)
*Xho* I (2665)
Ebola Glycoprotein Ivory Coast subtype (#U28006)
*Bst* XI (2982)
*Bsp* MI (3485)
*Msc* I (3619)
*Xba* I (3997)
*Bgl* II (4018)
*Sph* I (4225)
*Kpn* I (4253)
bovine growth hormone poly A
*Bst* XI (4340)
*Xmn* I (4570)

pVRC 6300
7002 bp

FIG. 16 pVR1012x/s Ebola GP(IC)

Dra III (6834)
Xho I (6698)
Cla I (6607)
Xma I (6424)
Kan r
Pvu I (6302)
Hin d III (6178)
Nde I (185)
Nde I (571)
CMV enhancer
Sac II (992)
CMV IE 5' UTR
Sph I (1092)
CMV IE Intron
Hpa I (1755)
Pst I (1865)
Sal I (1875)
Pml I (1882)
Eco RV (1894)
Not I (1899)
Xba I (1906)
Eco RI (1910)
Xho I (2665)
Ebola GP(IC)
Sfi I (4595)
TbGH
Sph I (4225)
Bgl II (4018)
Xba I (3997)
Eco RI (3993)

VRC6301
7036 bp

FIG. 17 pVR1012x/s Ebola GP(IC)(dTM)

Plasmid map of VRC6303 (6889 bp) showing the following features and restriction sites:

- Nde I (185)
- Nde I (571)
- CMV Enhancer
- Sac II (992)
- CMV IE 5' UTR
- Sph I (1092)
- CMV IE Intron
- Hpa I (1755)
- Pst I (1865)
- Sal I (1875)
- Pml I (1882)
- Bam HI (2536)
- Xho I (2645)
- Ebola GP(Ivory Coast)(dTM)
- Bam HI (3397)
- Bgl II (3871)
- Sph I (4078)
- Kpn I (4106)
- Bovine Growth Hormone Poly A
- Sfi I (4448)
- Hin d III (6031)
- Pvu I (6155)
- Kan
- Cla I (6460)
- Xho I (6551)
- Dra III (6687)

FIG. 19 pVR1012x/s-sGP(IC)

Plasmid map of pVRC 6351 (7023 bp) showing the following features and restriction sites:
- Dra III (6821)
- Xho I (6685)
- Cla I (6594)
- kanamycin resistance
- Pvu I (6289)
- Hind III (6165)
- Nde I (185)
- Msc I (248)
- Nde I (571)
- CMV enhancer
- Sac II (992)
- CMV IE 5' UTR
- Sph I (1092)
- Bsp EI (1436)
- CMV IE Intron
- Hpa I (1755)
- Pst I (1865)
- Sal I (1875)
- Pml I (1882)
- Eco RV (1894)
- Not I (1899)
- Xba I (1906)
- Xho I (2665)
- Ebola Secreted Glycoprotein Ivory Coast (#U28006)
- Bst XI (2982)
- Bsp MI (3485)
- Msc I (3619)
- Xba I (3997)
- Bgl II (4018)
- Sph I (4225)
- Kpn I (4253)
- bovine growth hormone poly A
- Bst XI (4340)
- Sfi I (4582)

FIG. 21

FIG. 23 pAdApt Ebola GP(S)

- Xmn I (7938)
- Pvu I (7709)
- Amp
- Ad5(1-454)
- Nde I (843)
- CMV Enhancer
- Sal I (1272)
- Pml I (1279)
- Bcl I (1283)
- Not I (1296)
- Xho I (1558)
- Sal I (6336)
- Pml I (6233)
- Xho I (6030)
- Nar I (5761)
- Kas I (5760)
- Ad5(3511-6093)
- VRC6601
- 8338 bp
- Ebola GP(Sudan)
- Hpa I (2859)
- Xba I (3445)
- TbGH
- Kpn I (3701)
- LoxP

FIG. 26

FIG. 27 pAdApt Ebola GP(Z)

- Pvu I (7810)
- Amp
- Ad5(1-454)
- Nde I (843)
- CMV enhancer
- Pml I (1279)
- Eco RV (1291)
- Not I (1296)
- Xba I (1303)
- Cla I (1321)
- Cla I (1372)
- Eco RV (1994)
- Pml I (6334)
- Xho I (6131)
- Nar I (5862)
- Kas I (5861)
- Ad5(3511-6093)
- Ebola GP(Zaire)
- Kpn I (3555)
- TbGH
- Kpn I (3802)
- Bgl II (3848)
- LoxP VRC6603
8439 bp

*Dra* III (6245)
*Xho* I (6109)
*Cla* I (6018)
Kan
*Pvu* I (5713)
*Hin* d III (5589)

pVR1012x/s Lassa GP
*Nde* I (185)
*Nde* I (571)
CMV Enhancer
*Sac* II (992)
CMV IE 5' UTR
*Sph* I (1092)
CMV IE/Intron
*Pvu* II (1701)
*Hpa* I (1755)
*Pst* I (1865)
*Sal* I (1875)
*Pml* I (1882)
*Eco* RV (1894)
*Not* I (1899)
*Xba* I (1906)
*Eco* RI (1950)

VRC6800
6447 bp

*Sfi* I (4006)
Bovine Growth Poly A
*Sph* I (3649)
*Bgl* II (3442)
*Bam* H I (3436)
*Hin* d III (3273)
*Dra* III (2785)
*Pvu* II (2848)
Lassa GP(Strain LP)

pVR1012x/s Lassa GP(dTM)

- Dra III (6056)
- Xho I (5920)
- Cla I (5829)
- Kan
- Pvu I (5524)
- Hin d III (5400)
- Nde I (185)
- Nde I (571)
- CMV Enhancer
- Sac II (992)
- CMV IE 5' UTR
- Sph I (1092)
- CMV IE/Intron
- Pvu II (1701)
- Hpa I (1755)
- Pst I (1865)
- Sal I (1875)
- Pml I (1882)
- Eco RV (1894)
- Not I (1899)
- Xba I (1906)
- Eco RI (1950)
- Lassa GP(dTM)(Strain LP)
- Dra III (2785)
- Pvu II (2848)
- Bam H I (3247)
- Bgl II (3253)
- Sph I (3460)
- Bovine Growth Poly A
- Sfi I (3817)

VRC6801
6258 bp

FIG. 34

FIG. 38 pVR1012x/s Lassa(codon optimized)

Dra III (6034)
Xho I (5898)
Cla I (5807)
Xma I (5624)
kanamycin resistance
Pvu I (5502)
Hin dIII (5378)

Nde I (185)
Nde I (571)
CMV enhancer
Sac II (992)
CMV IE 5' UTR
Sph I (1092)
CMV IE Intron VRC6802
6236 bp Hpa I (1755)
Sal I (1875)
Pml I (1882)
Eco RV (1894)
Not I (1899)
Xba I (1906)
Eco RV (1914)
Sfi I (2054)
Lassa (codon optimized)

Sfi I (3795)
bovine growth hormone poly A
Sph I (3425)
Bgl II (3218)
Bam HI (3212)
Pml I (3208)

FIG. 41 pVR1012x/s Marburg (codon optimized)

Dra III (6700)
Xho I (6564)
Cla I (6473)
Xma I (6290)
kanamycin resistance
Pvu I (6168)
Hin d III (6044)

Nde I (185)
Nde I (571)
CMV enhancer
Nco I (697)
Sac II (992)
CMV IE 5' UTR
CMV IE Intron
Pvu II (1701)
Hpa I (1755)
Nco I (1848)
Sal I (1875)
Pml I (1882)
Eco RV (1894)
Not I (1899)
Xba I (1906)
Eco RV (1914)
Hpa I (2433)
Marburg (codon optimized)

VRC6703
6902 bp

Sfi I (4461)
bovine growth hormone poly A
Bgl II (3884)
Bam HI (3878)
Pml I (3874)
Dra III (3207)

Domain: GP — GP/sGP Identity, Mucin-like, Furin Cleavage Site, Fusion, Trimerization, TM A
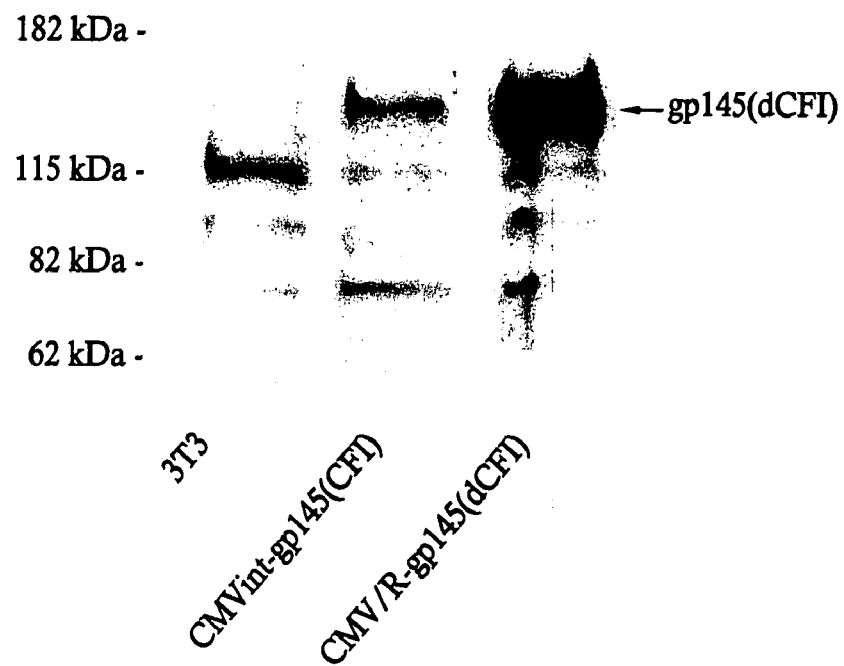
B
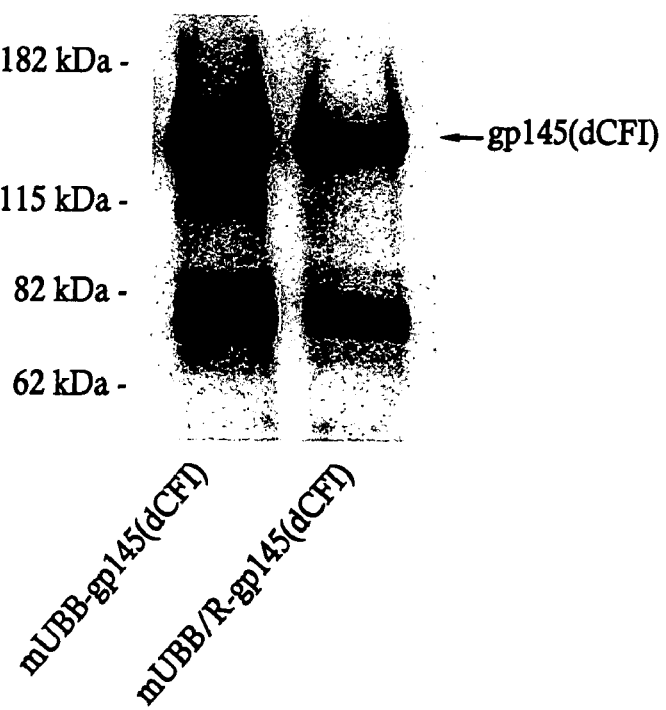
FIG. 50

DEVELOPMENT OF A PREVENTIVE VACCINE FOR FILOVIRUS INFECTION IN PRIMATES

RELATED APPLICATIONS

This application is a divisional and claims the benefit of priority of U.S. patent application Ser. No. 10/491,121 filed Aug. 23, 2004, which represents the U.S. National Phase of International Application No. PCT/US02/30251 filed Sep. 24, 2002, designating the United States of America and published in English on Apr. 10, 2003, as WO 03/028632, which claims the benefit of priority of U.S. Provisional Application No. 60/326,476 filed Oct. 1, 2001, all of which are hereby expressly incorporated by reference in their entireties.

FIELD OF THE INVENTION

The present invention relates generally to viral vaccines and, more particularly, to filovirus vaccines and methods of eliciting an immune response against a filovirus or a disease caused by infection with filovirus.

BACKGROUND OF THE INVENTION

The Ebola viruses, and the genetically-related Marburg virus, are filoviruses associated with outbreaks of highly lethal hemorrhagic fever in humans and primates in North America, Europe, and Africa (Peters, C. J. et al. in: *Fields Virology*, eds. Fields, B. N. et al. 1161–1176, Philadelphia, Lippincott-Raven, 1996; Peters, C. J. et al. 1994 *Semin Virol* 5:147–154). Ebola viruses are negative-stranded RNA viruses comprised of four subtypes, including those described in the Zaire, Sudan, Reston, and Ivory Coast episodes (Sanchez, A. et al. 1996 *PNAS USA* 93:3602–3607). Although several subtypes have been defined, the genetic organization of these viruses is similar, each containing seven linearly arrayed genes. Among the viral proteins, the envelope glycoprotein exists in two alternative forms, a 50–70 kilodalton (kDa) secreted protein of unknown function encoded by the viral genome and a 130 kDa transmembrane glycoprotein generated by RNA editing that mediates viral entry (Peters, C. J. et al. in: *Fields Virology*, eds. Fields, B. N. et al. 1161–1176, Philadelphia, Lippincott-Raven, 1996; Sanchez, A. et al. 1996 *PNAS USA* 93:3602–3607). Other structural gene products include the nucleoprotein (NP), matrix proteins VP24 and VP40, presumed nonstructural proteins VP30 and VP35, and the viral polymerase (reviewed in Peters, C. J. et al. in: *Fields Virology*, eds. Fields, B. N. et al. 1161–1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 *PNAS USA* 93:3602–3607), suggesting that immunization may be useful in protecting against this disease. Previous attempts to elicit protective immune responses against Ebola virus using traditional active and passive immunization approaches have, however, not succeeded in primates (Peters, C. J. et al. in: *Fields Virology*, eds. Fields, B. N. et al. 1161–1176, Philadelphia, Lippincott-Raven, 1996; Clegg, J. C. S. et al. 1997 *New Generation Vaccines*, eds.: Levine, M. M. et al. 749–765, New York, N.Y. Marcel Dekker, Inc.; Jahrling, P. B. et al. 1996 *Arch Virol Suppl* 11:135–140). It would thus be desirable to provide a vaccine to elicit an immune response against a filovirus or disease caused by infection with filovirus. It would further be desirable to provide methods of making and using said vaccine.

SUMMARY OF THE INVENTION

Outbreaks of hemorrhagic fever caused by the Ebola virus are associated with high mortality rates that are a distinguishing feature of this human pathogen. The highest lethality is associated with the Zaire subtype, one of four strains identified to date (Feldmann, H. et al. 1994 *Virology* 199: 469–473; Sanchez, A. et al. 1996 *PNAS USA* 93:3602–3607). Its rapid progression allows little opportunity to develop natural immunity, and there is currently no effective anti-viral therapy. Therefore, vaccination offers a promising intervention to prevent infection and limit spread. Here we describe a highly effective vaccine strategy for Ebola virus infection in primates. A combination of DNA immunization and boosting with adenoviral vectors that encode viral proteins generated cellular and humoral immunity in cynomolgus macaques. Challenge with a lethal dose of the highly pathogenic, wild-type, 1976 Mayinga strain of Ebola Zaire virus resulted in uniform infection in controls, who progressed to a moribund state and death in less than one week. In contrast, all vaccinated animals were asymptomatic for more than six months, with no detectable virus after the initial challenge. These findings demonstrate that it is possible to develop a preventive vaccine against Ebola virus infection in primates.

BRIEF DESCRIPTION OF THE DRAWINGS

FIG. 2 shows VRC6001 (pVR1012 x/s-GP(Z)) construct map (see, Ebola/Marburg/Lassa Plasmids, and Recombinant Adenoviruses in Table 2).

FIG. 4 shows VRC6003 (pVR1012-GP(Z) delta MUC delta FUR) construct map (see, Ebola/Marburg/Lassa Plasmids, and Recombinant Adenoviruses in Table 2).

FIG. 5 shows VRC6004 (pVR1012-GP(Z) delta GP2) construct map (see, Ebola/Marburg/Lassa Plasmids, and Recombinant Adenoviruses in Table 2).

FIG. 6 shows VRC6005 (pVR1012-GP(Z) delta GP2 delta C-term A) construct map (see, Ebola/Marburg/Lassa Plasmids, and Recombinant Adenoviruses in Table 2).

FIG. 8 shows VRC6007 (pVR1012-GP(Z) delta GP2 delta FUS) construct map (see, Ebola/Marburg/Lassa Plasmids, and Recombinant Adenoviruses in Table 2).

FIG. 9 shows VRC6008 (pVR1012-GP(Z) delta TM) construct map (see, Ebola/Marburg/Lassa Plasmids, and Recombinant Adenoviruses in Table 2).

FIG. 10 shows VRC 6052 (pVR1012-GP(Z) delta SGP) construct map (see, Ebola/Marburg/Lassa Plasmids, and Recombinant Adenoviruses in Table 2).

FIG. 11 shows VRC 6101 (pVR1012 x/s Ebola GP(R) (dTM)) construct map (see, Ebola/Marburg/Lassa Plasmids, and Recombinant Adenoviruses in Table 2).

FIG. 12 shows VRC 6110 (pAdApt Ebola GP(R) (dTM)) construct map (see, Ebola/Marburg/Lassa Plasmids, and Recombinant Adenoviruses in Table 2).

FIG. 13 shows VRC6200 (pVR1012-GP(S)) construct map (see, Ebola/Marburg/Lassa Plasmids, and Recombinant Adenoviruses in Table 2).

FIG. 14 shows VRC 6201 (pVR1012 x/s Ebola GP(S)) construct map (see, Ebola/Marburg/Lassa Plasmids, and Recombinant Adenoviruses in Table 2).

FIG. 15 shows VRC6202 (pVR1012-GP(S) delta TM) construct map (see, Ebola/Marburg/Lassa Plasmids, and Recombinant Adenoviruses in Table 2).

FIG. 16 shows VRC6300 (pVR1012-GP(IC)) construct map (see, Ebola/Marburg/Lassa Plasmids, and Recombinant Adenoviruses in Table 2).

FIG. 17 shows VRC6301 (pVR1012 x/s-GP(IC)) construct map (see, Ebola/Marburg/Lassa Plasmids, and Recombinant Adenoviruses in Table 2).

FIG. 19 shows VRC 6303 (pVR1012 x/s Ebola GP (IC) (dTM)) construct map (see, Ebola/Marburg/Lassa Plasmids, and Recombinant Adenoviruses in Table 2).

FIG. 21 shows VRC6351 (pVR1012 x/s-SGP(IC)) construct map (see, Ebola/Marburg/Lassa Plasmids, and Recombinant Adenoviruses in Table 2).

Figure 23:
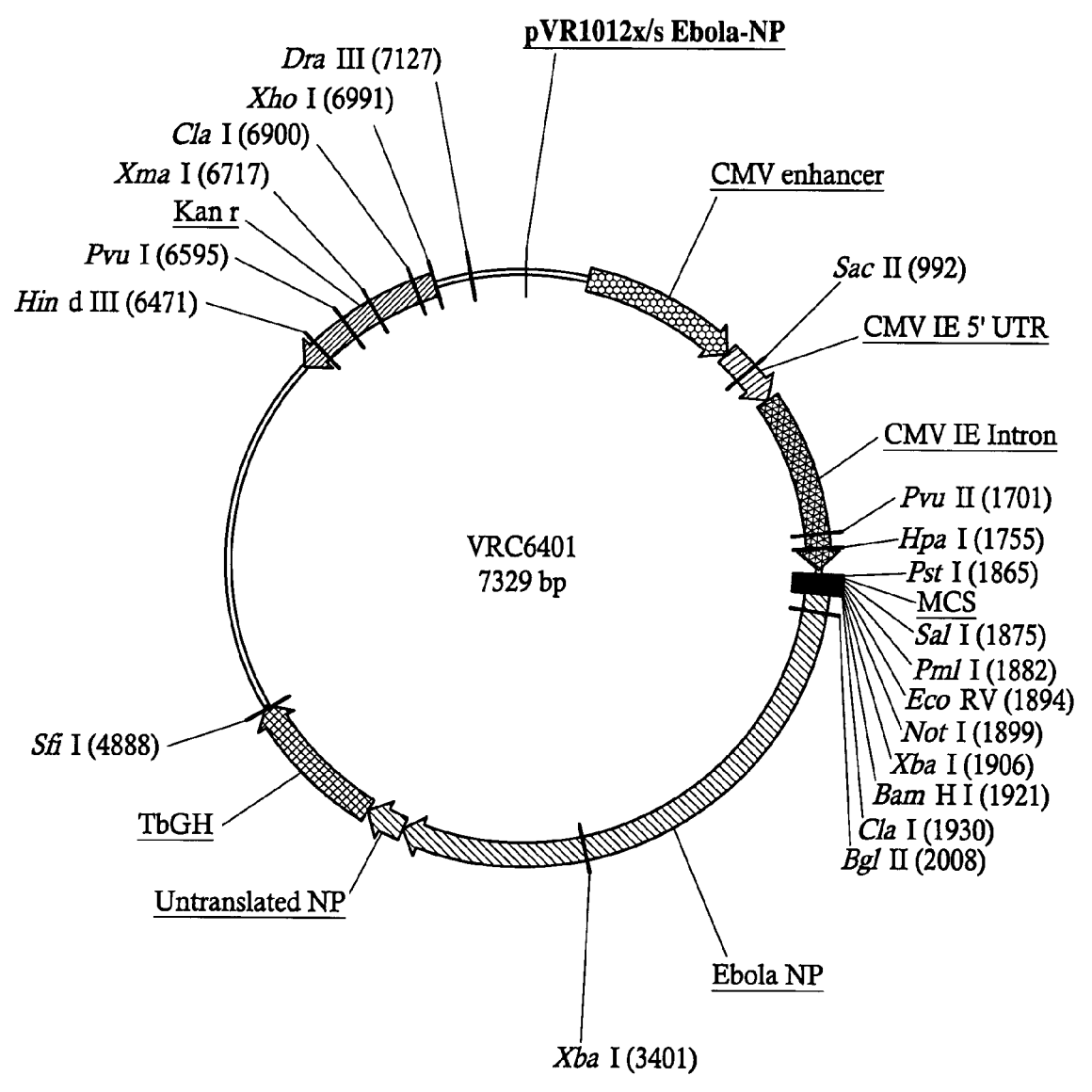

FIG. 23 shows VRC6401 (pVR1012 x/s-NP) construct map (see, Ebola/Marburg/Lassa Plasmids, and Recombinant Adenoviruses in Table 2).

FIG. 26 shows VRC6601 (pAdApt Ebola GP(S)) construct map (see, Ebola/Marburg/Lassa Plasmids, and Recombinant Adenoviruses in Table 2).

Figure 27:
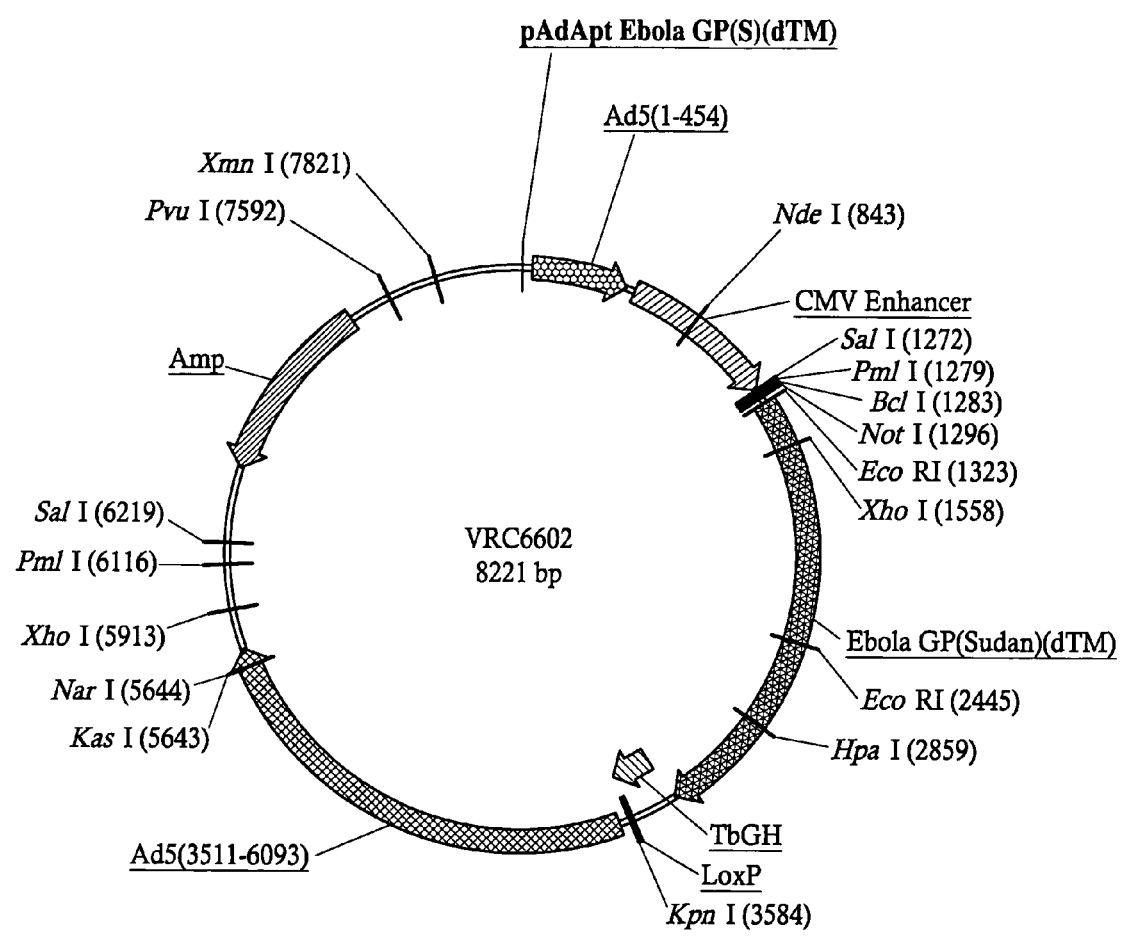

FIG. 27 shows VRC 6602 (pAdApt Ebola GP(S)(dTM)) construct map (see, Ebola/Marburg/Lassa Plasmids, and Recombinant Adenoviruses in Table 2).

FIG. 28 shows VRC6603 (pAdApt Ebola GP(Z)) construct map (see, Ebola/Marburg/Lassa Plasmids, and Recombinant Adenoviruses in Table 2).

FIG. 33 shows VRC6800 (pVR1012 x/s Lassa GP) construct map (see, Ebola/Marburg/Lassa Plasmids, and Recombinant Adenoviruses in Table 2).

FIG. 34 shows VRC6801 (pVR1012 x/s Lassa GP (dTM) construct map (see, Ebola/Marburg/Lassa Plasmids, and Recombinant Adenoviruses in Table 2).

FIG. 38 shows pVR1012 Ebola GP (Z, P87666) delta TM/h (codon optimized) construct map (see, Ebola/Marburg/Lassa Plasmids, and Recombinant Adenoviruses in Table 2).

FIG. 41 shows VRC6802, pVR1012 x/s Lassa delta TM/h (codon optimized) construct map (see, Ebola/Marburg/Lassa Plasmids, and Recombinant Adenoviruses in Table 2).

FIG. 42 shows VRC6703, pVR1012 x/s Marburg delta TM/h (codon optimized) construct map (see, Ebola/Marburg/Lassa Plasmids, and Recombinant Adenoviruses in Table 2).

Figure 43:
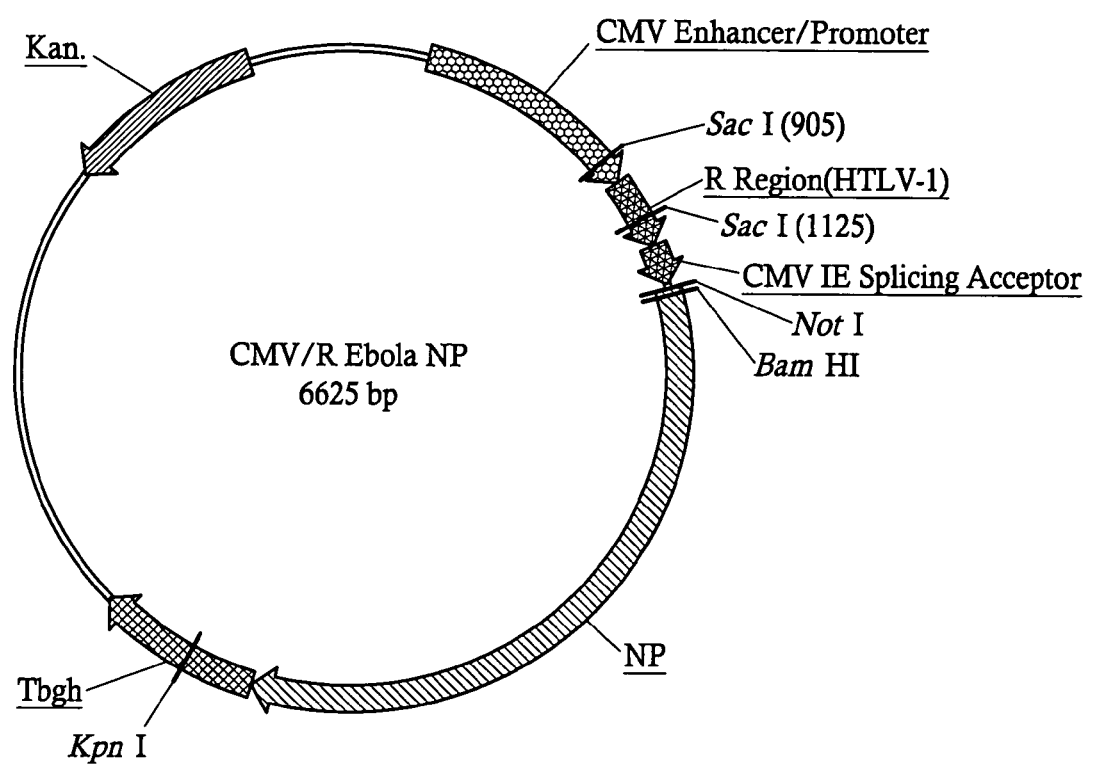

FIG. 43 shows CMV/R Ebola NP construct map (see, Ebola/Marburg/Lassa Plasmids, and Recombinant Adenoviruses in Table 2).

FIG. 44 is a diagrammatic representation of secreted glycoprotein (SGP) and glycoprotein (GP) molecules of Ebola virus (Zaire species isolated in 1976) showing important structural features. The white N-terminal regions of SGP and GP correspond to identical (shared) sequences, while the black C termini identify sequences unique to GP or SGP molecules. The common signalase cleavage sites for both SGP and GP and the furin cleavage site for GP0 (uncleaved form of GP) (↓) were determined by N-terminal sequencing. Also shown are cysteine residues (S), predicted N-linked glycosylation sites (Y-shaped projections), a predicted fusion peptide, a heptad repeat sequence, and a transmembrane anchor sequence. In Ebola viruses, the positions of these structures are conserved and their sequences are very similar or, in the case of N-linked glycosylation sites, are at least concentrated in the central region of GP. Signalase cleavage site is SEQ ID NO: 48, Furin cleavage site is SEQ ID NO: 49, and Fusion peptide is SEQ ID NO: 50.

FIG. 46 shows induction of the cytopathic effects by Ebola virus glycoproteins and mapping of the molecular determinants of cytopathicity.

FIG. 50(A–B) shows enhanced expression of modified CMV expression vector, CMV/R.

TABLE 1

Figure 1:
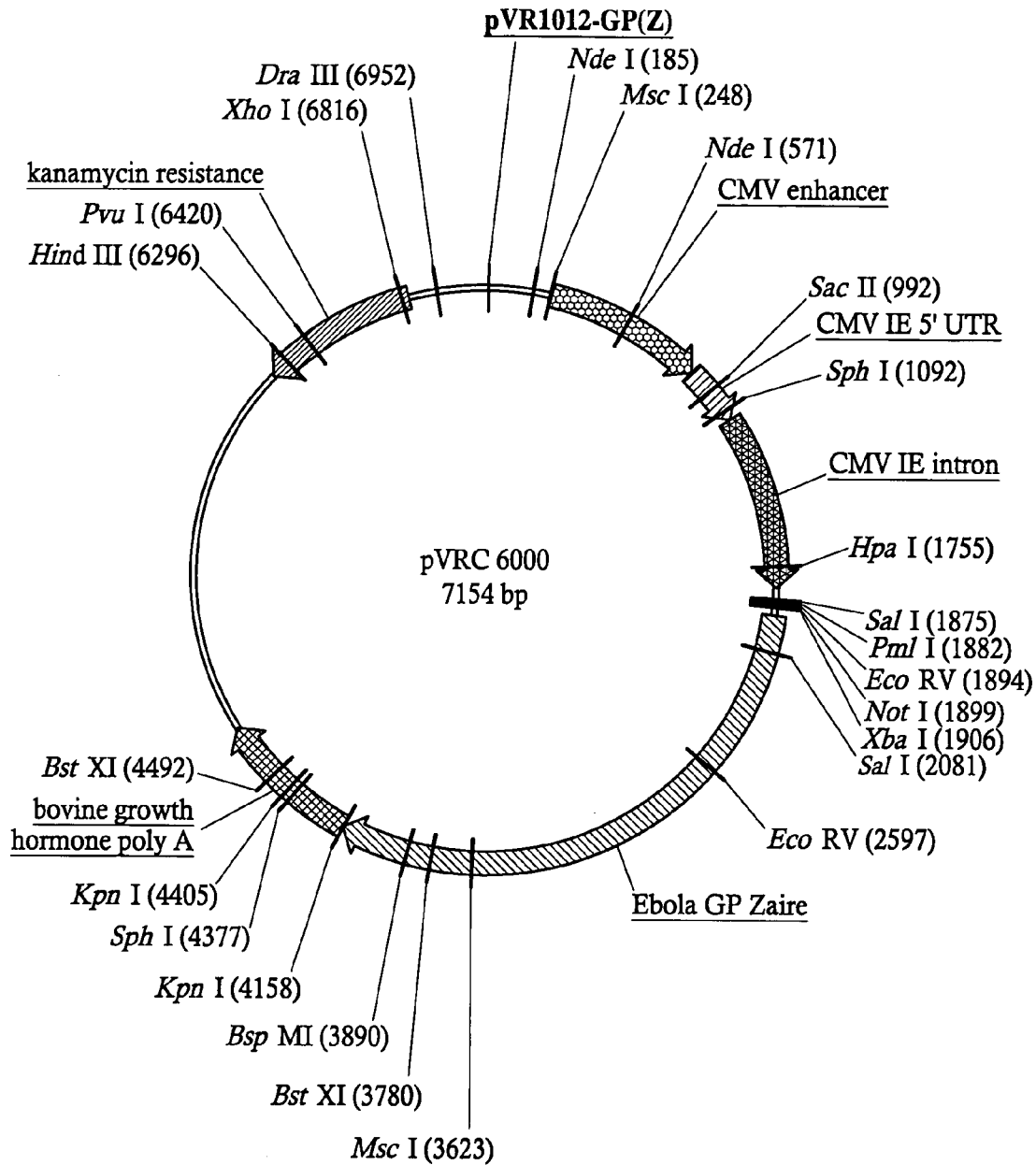
FIG. 1 shows VRC6000 (pVR1012-GP(Z)) construct map (see, Ebola/Marburg/Lassa Plasmids, and Recombinant Adenoviruses in Table 2).
Figure 3:
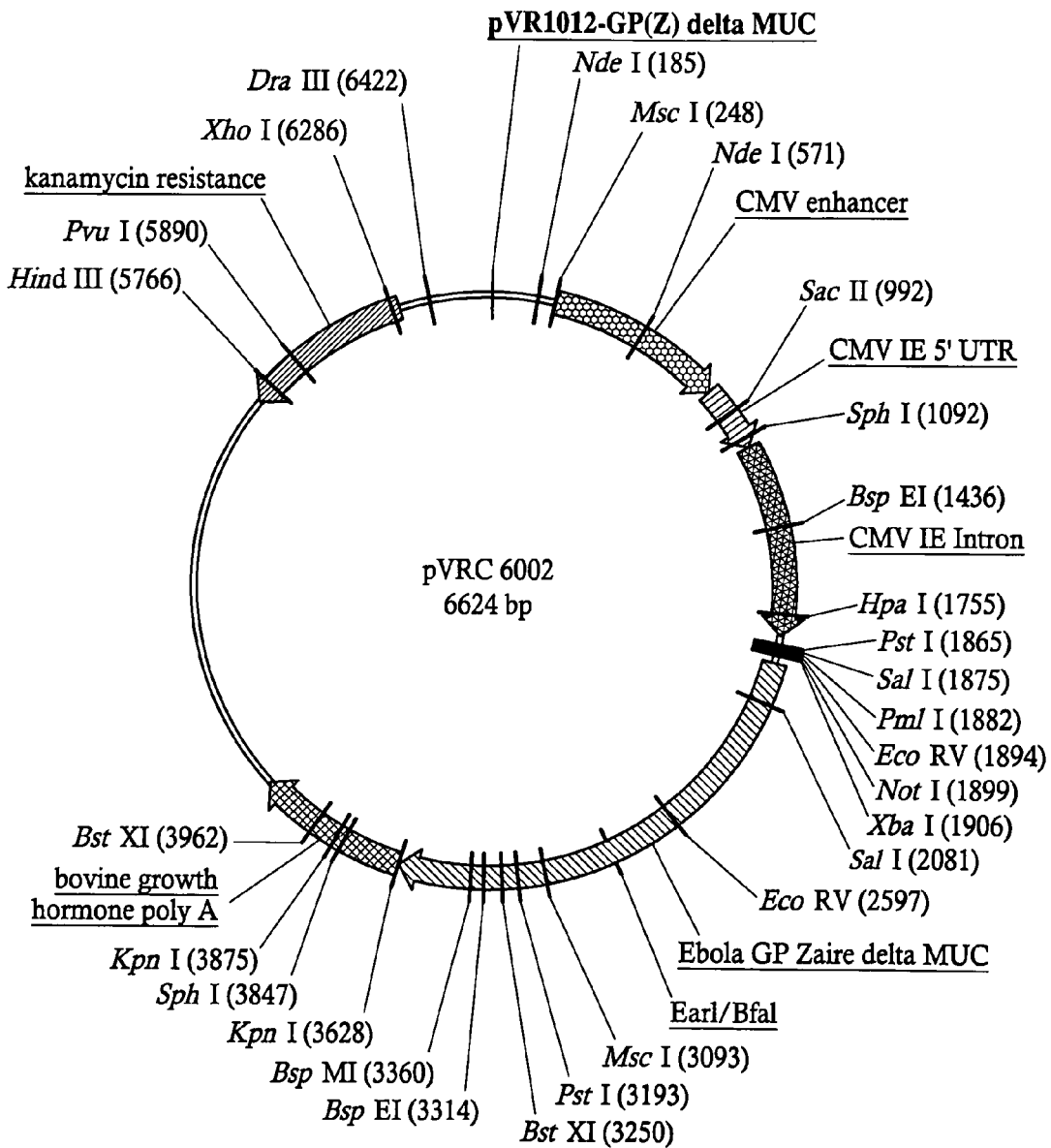
FIG. 3 shows VRC6002 (pVR1012-GP(Z) delta MUC) construct map (see, Ebola/Marburg/Lassa Plasmids, and Recombinant Adenoviruses in Table 2).
Figure 7:
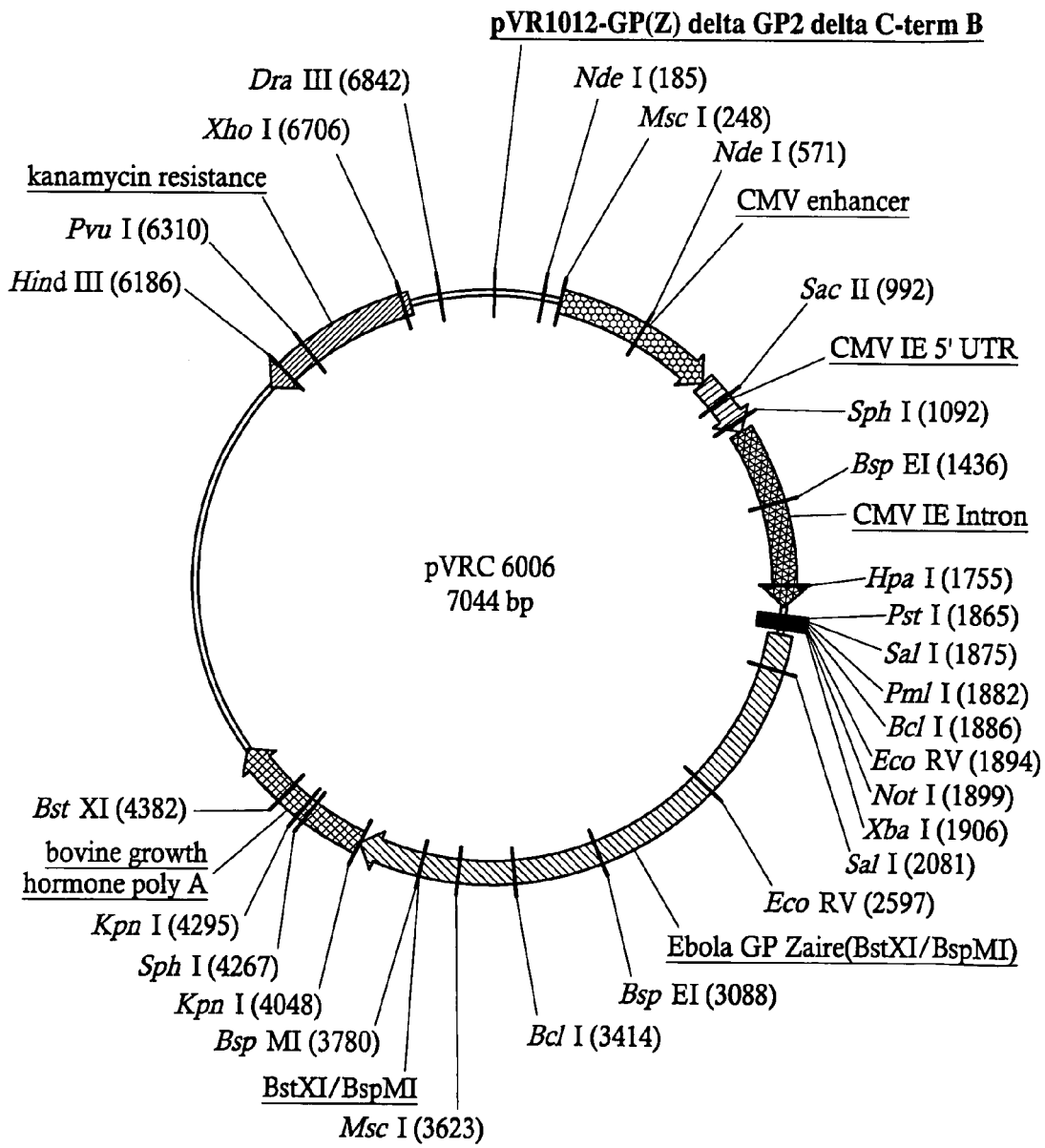
FIG. 7 shows VRC6006 (pVR1012-GP(Z) delta GP2 delta C-term B) construct map (see, Ebola/Marburg/Lassa Plasmids, and Recombinant Adenoviruses in Table 2).
Figure 18:
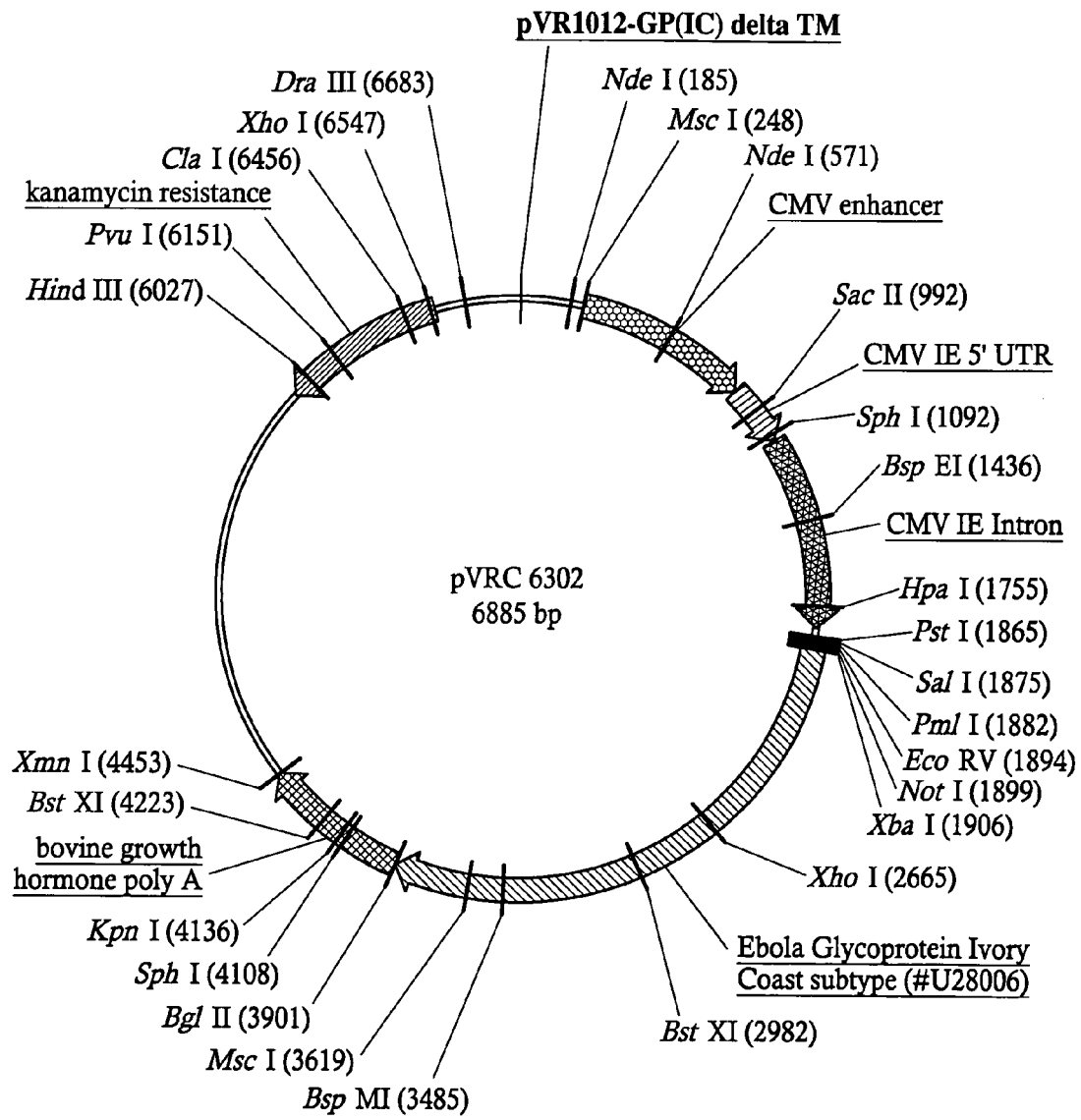
FIG. 18 shows VRC6302 (pVR1012-GP(IC) delta TM) construct map (see, Ebola/Marburg/Lassa Plasmids, and Recombinant Adenoviruses in Table 2).
Figure 20:
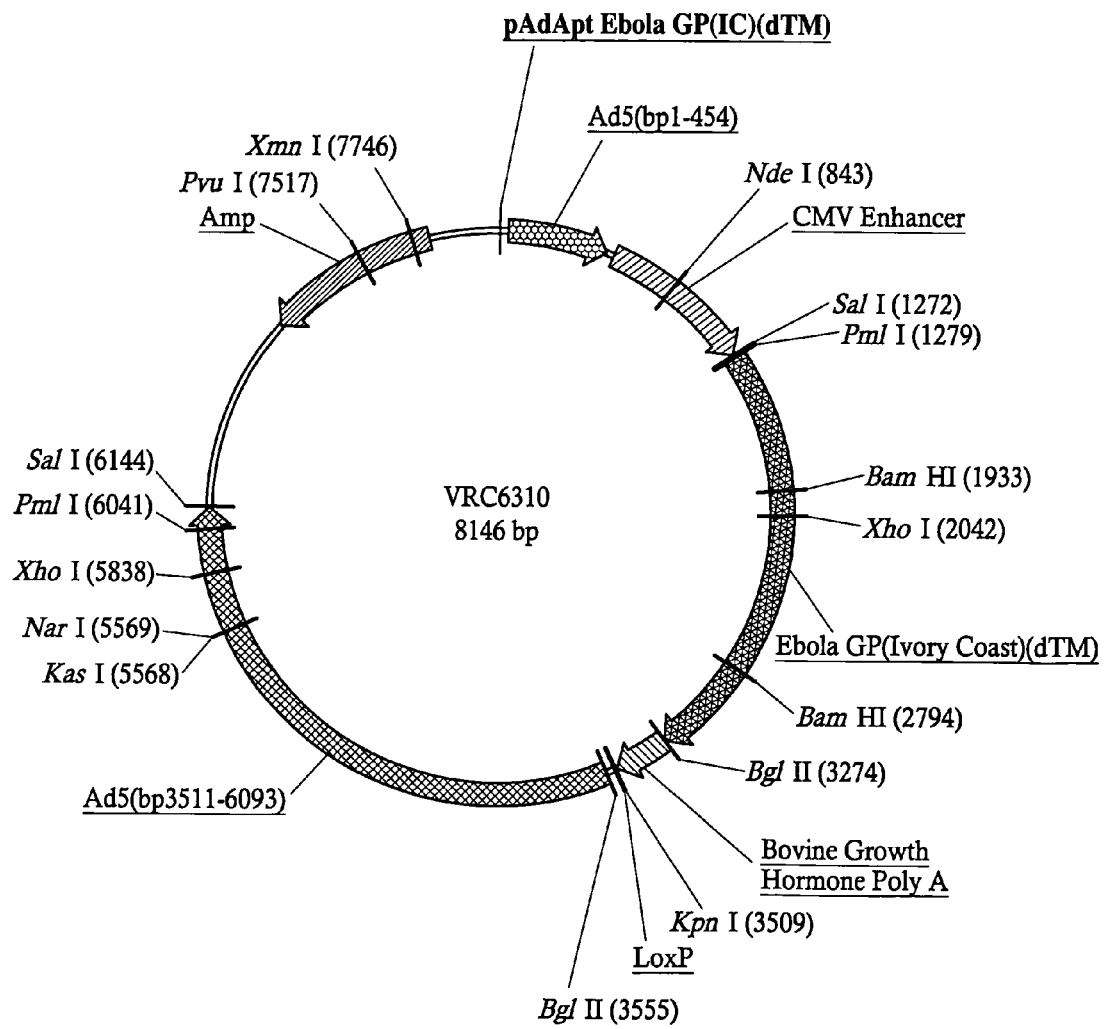
FIG. 20 shows VRC 6310 (pAdApt Ebola GP (IC) (dTM)) construct map (see, Ebola/Marburg/Lassa Plasmids, and Recombinant Adenoviruses in Table 2).
Figure 22:
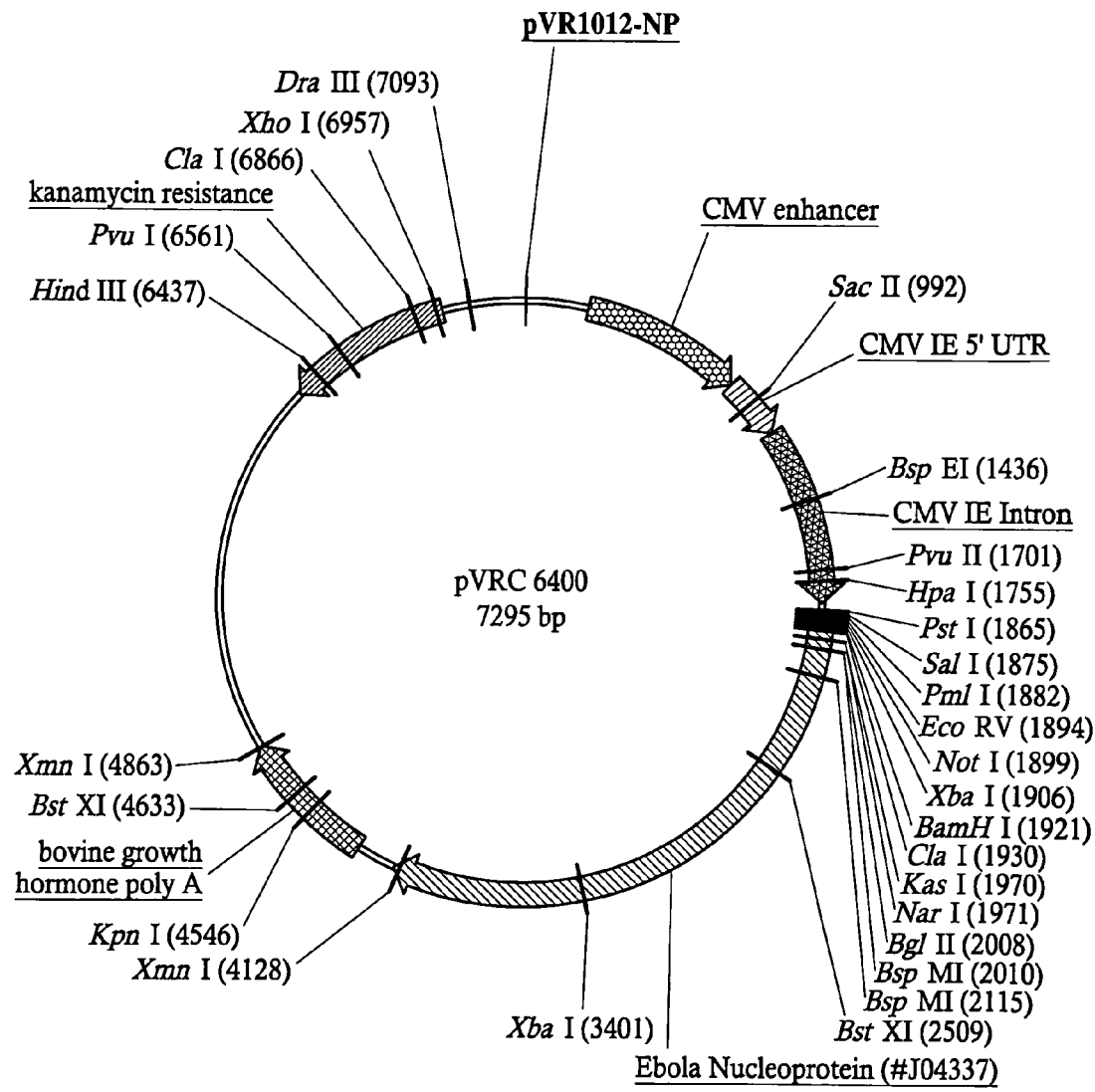
FIG. 22 shows VRC6400 (pVR1012-NP) construct map (see, Ebola/Marburg/Lassa Plasmids, and Recombinant Adenoviruses in Table 2).
Figure 24:
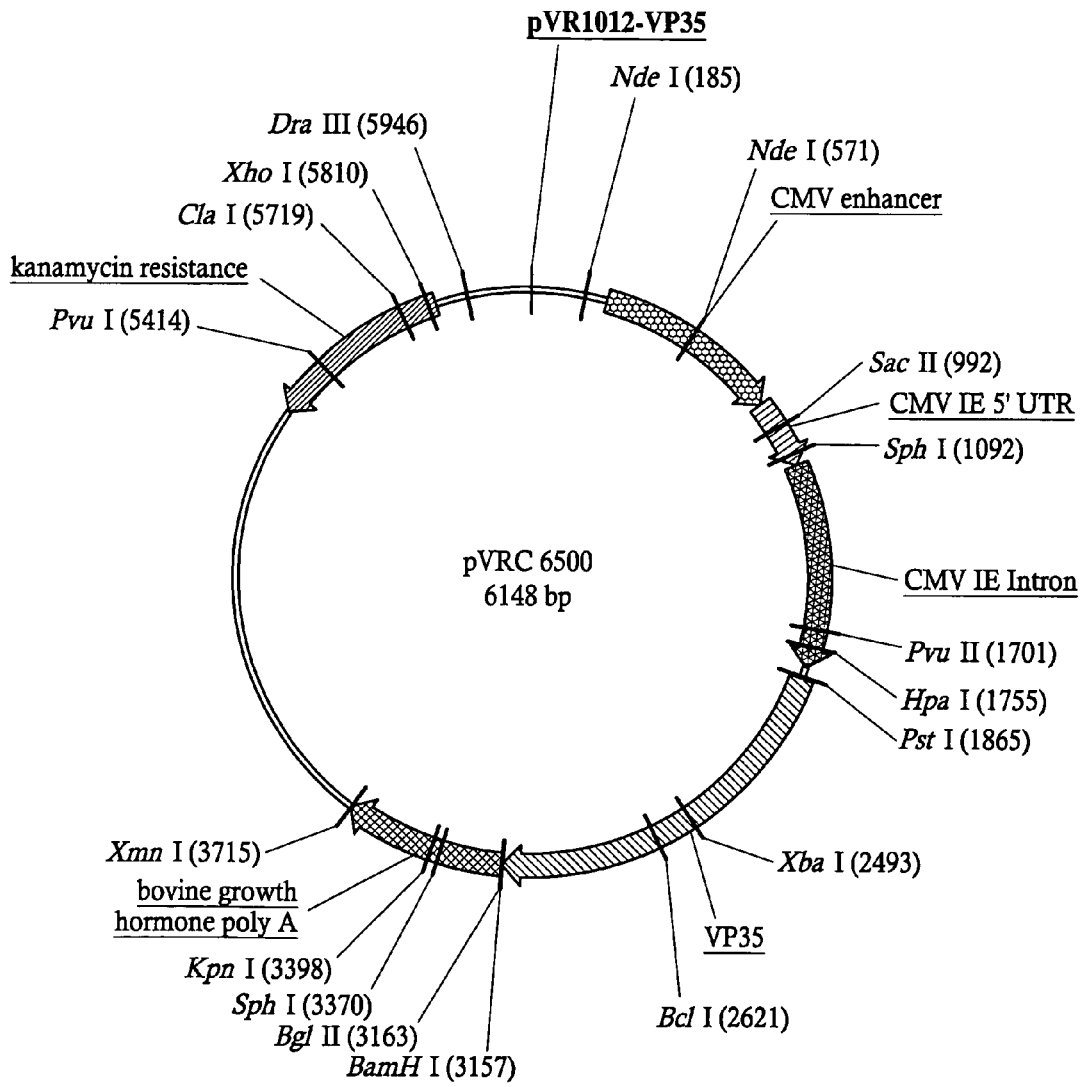
FIG. 24 shows VRC6500 (pVR1012-VP35) construct map (see, Ebola/Marburg/Lassa Plasmids, and Recombinant Adenoviruses in Table 2).
Figure 25:
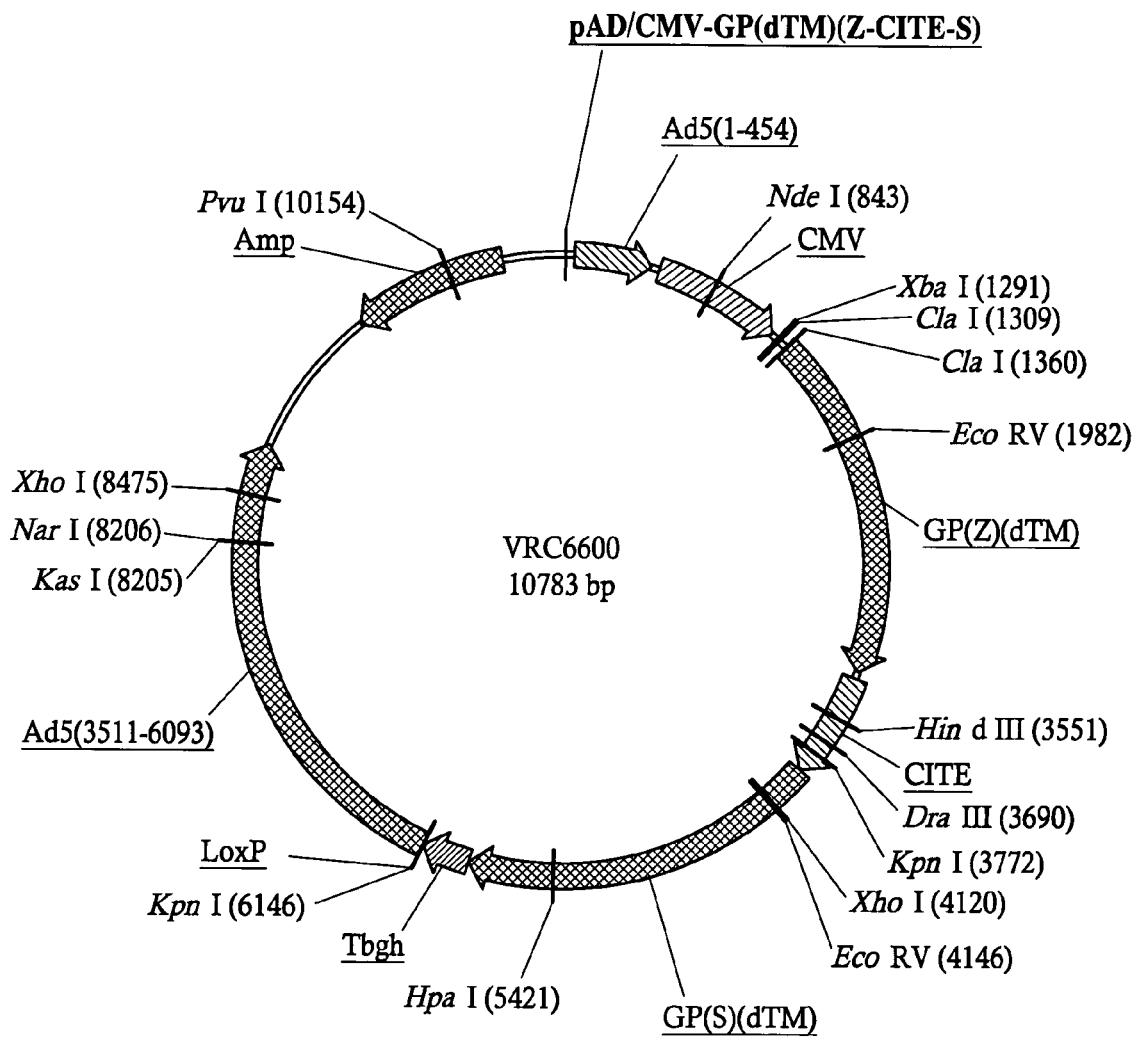
FIG. 25 shows VRC6600 (pAD/CMV-GP(dTM)(Z-CITE-S) construct map (see, Ebola/Marburg/Lassa Plasmids, and Recombinant Adenoviruses in Table 2).
Figure 29:
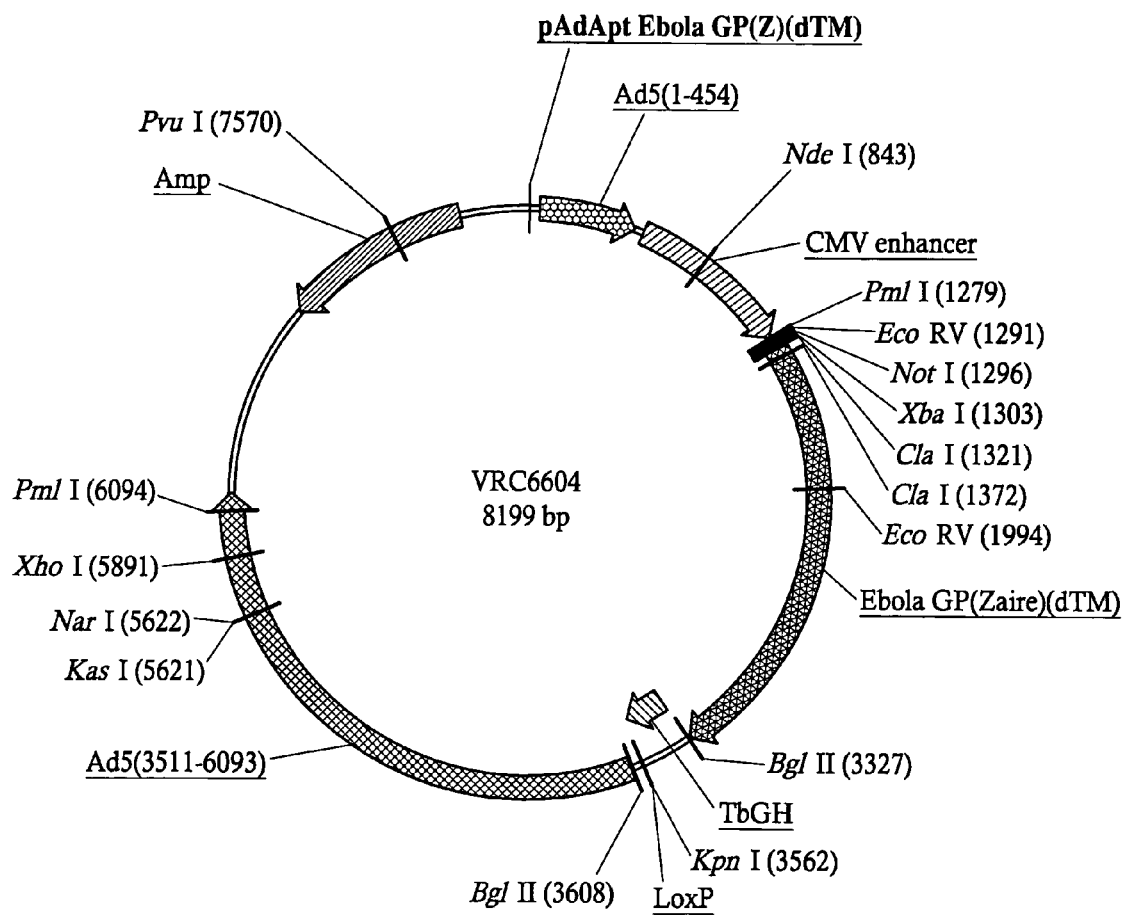
FIG. 29 shows VRC 6604 (pAdApt Ebola GP(Z)(dTM)) construct map (see, Ebola/Marburg/Lassa Plasmids, and Recombinant Adenoviruses in Table 2).
Figure 30:
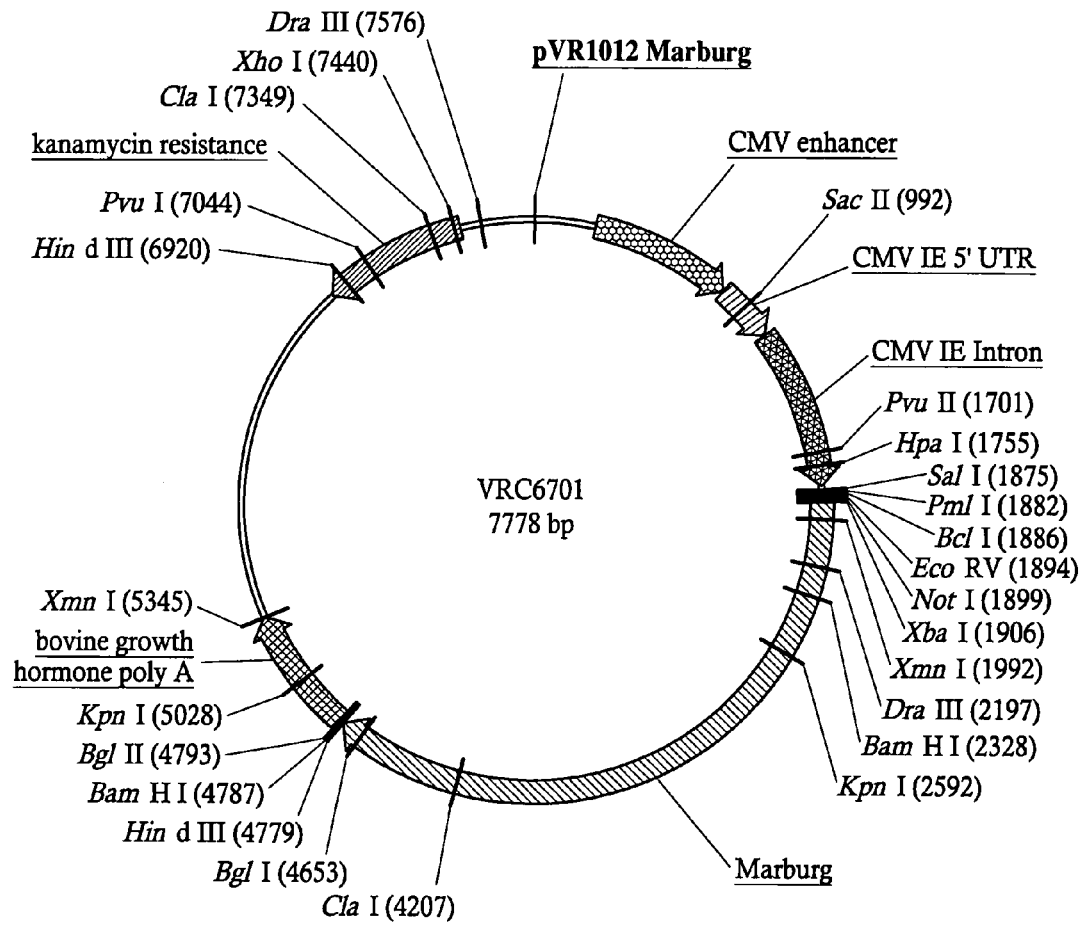
FIG. 30 shows VRC6701 (pVR1012-Marburg) construct map (see, Ebola/Marburg/Lassa Plasmids, and Recombinant Adenoviruses in Table 2).
Figure 31:
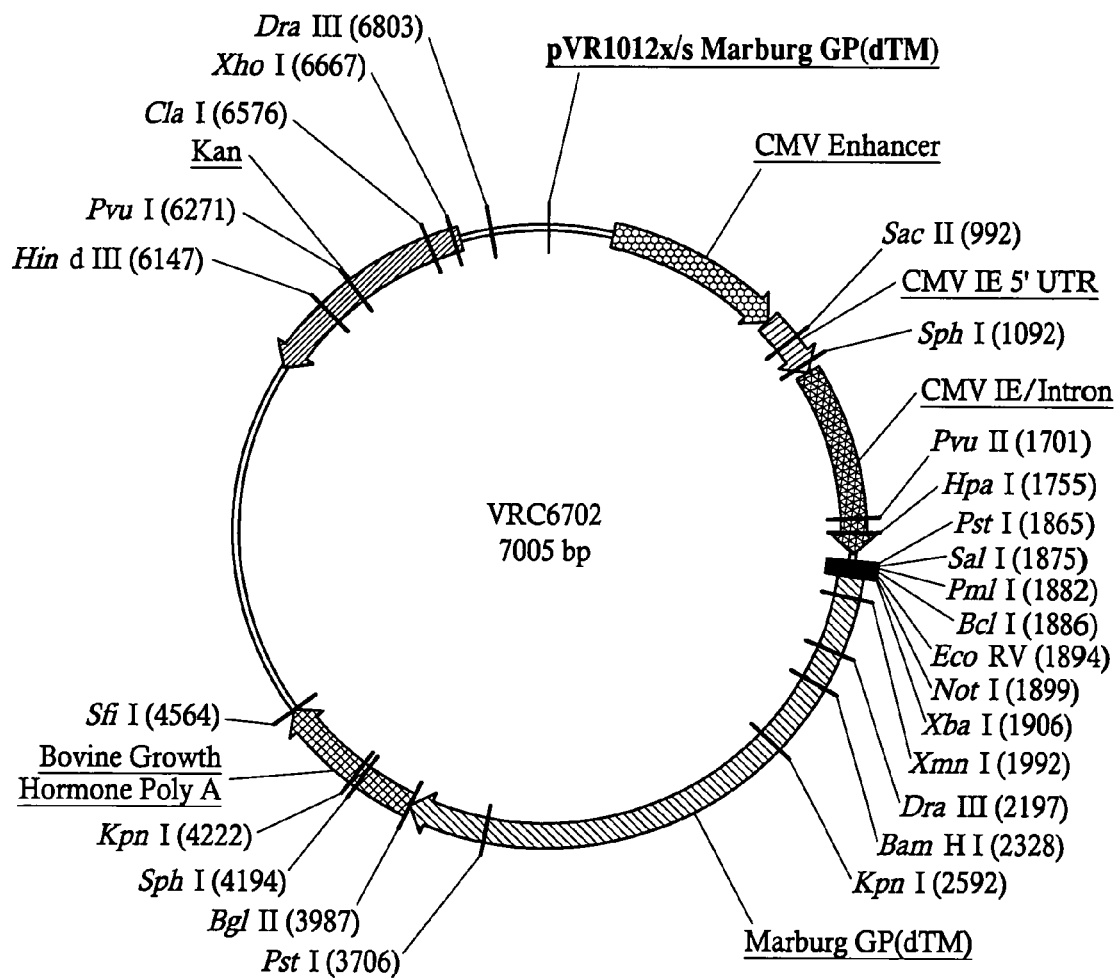
FIG. 31 shows VRC 6702 (pVR1012 x/s Marburg GP (dTM)) construct map (see, Ebola/Marburg/Lassa Plasmids, and Recombinant Adenoviruses in Table 2).
Figure 32:
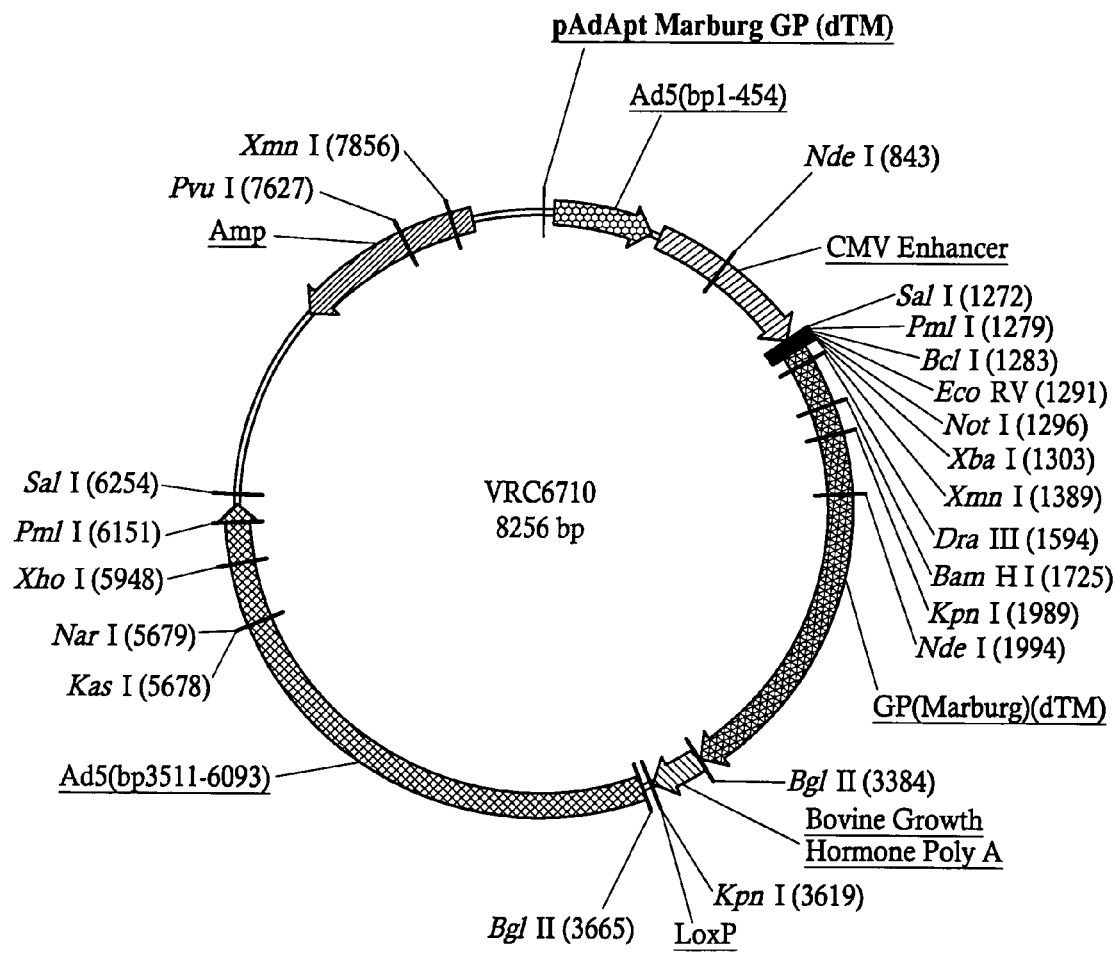
FIG. 32 shows VRC 6710 (pAdApt Marburg GP (dTM)) construct map (see, Ebola/Marburg/Lassa Plasmids, and Recombinant Adenoviruses in Table 2).
Figure 35:
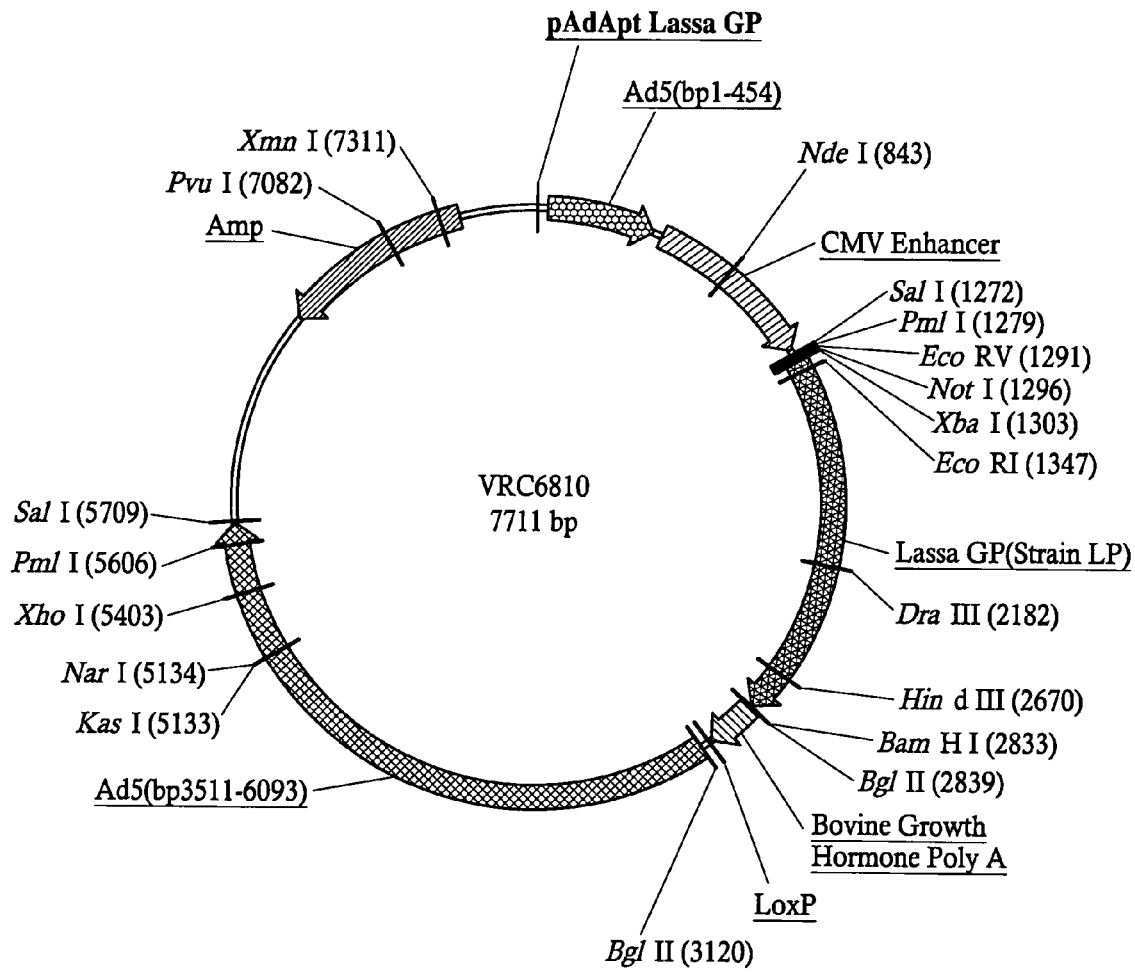
FIG. 35 shows VRC6810 (pAdApt Lassa GP) construct map (see, Ebola/Marburg/Lassa Plasmids, and Recombinant Adenoviruses in Table 2).
Figure 36:
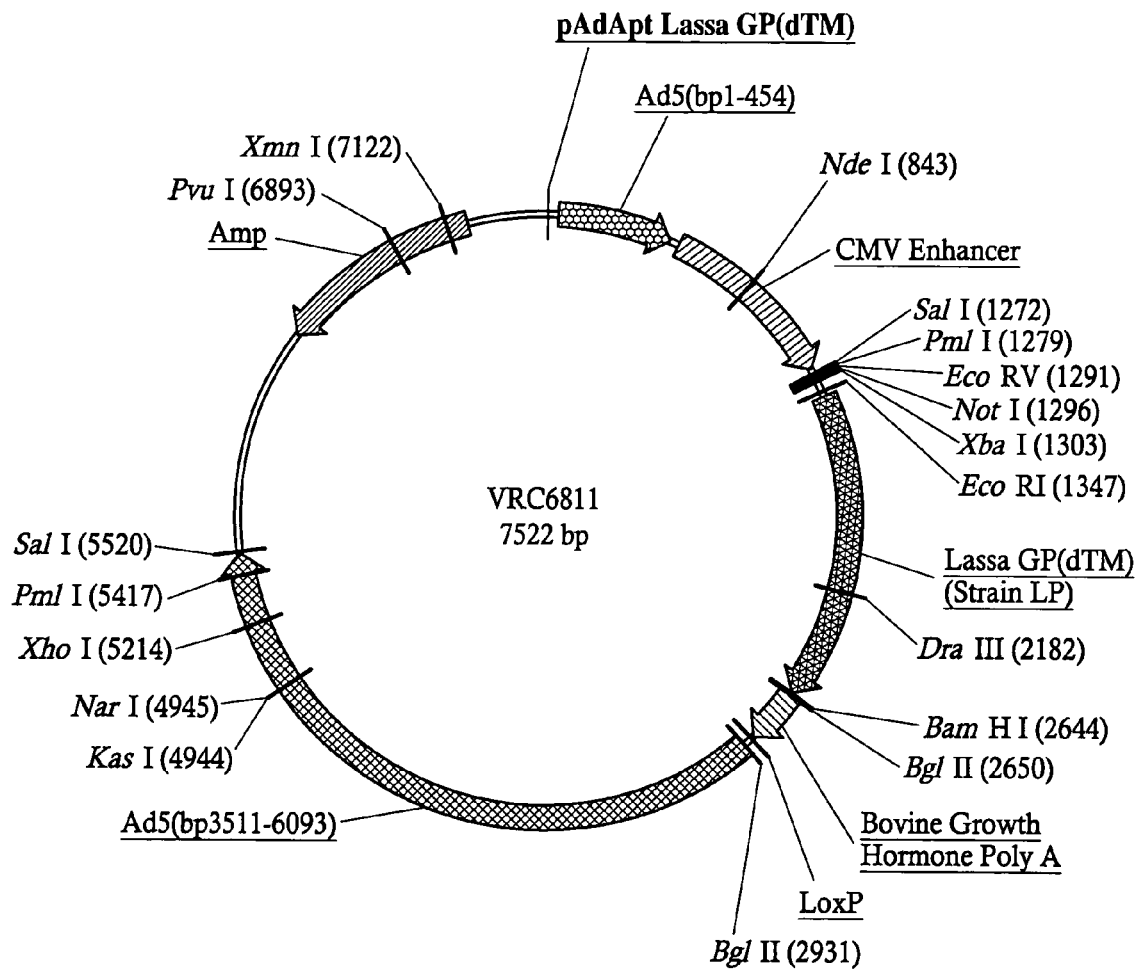
FIG. 36 shows VRC6811 (pAdApt Lassa GP (dTM)) construct map (see, Ebola/Marburg/Lassa Plasmids, and Recombinant Adenoviruses in Table 2).
Figure 37:
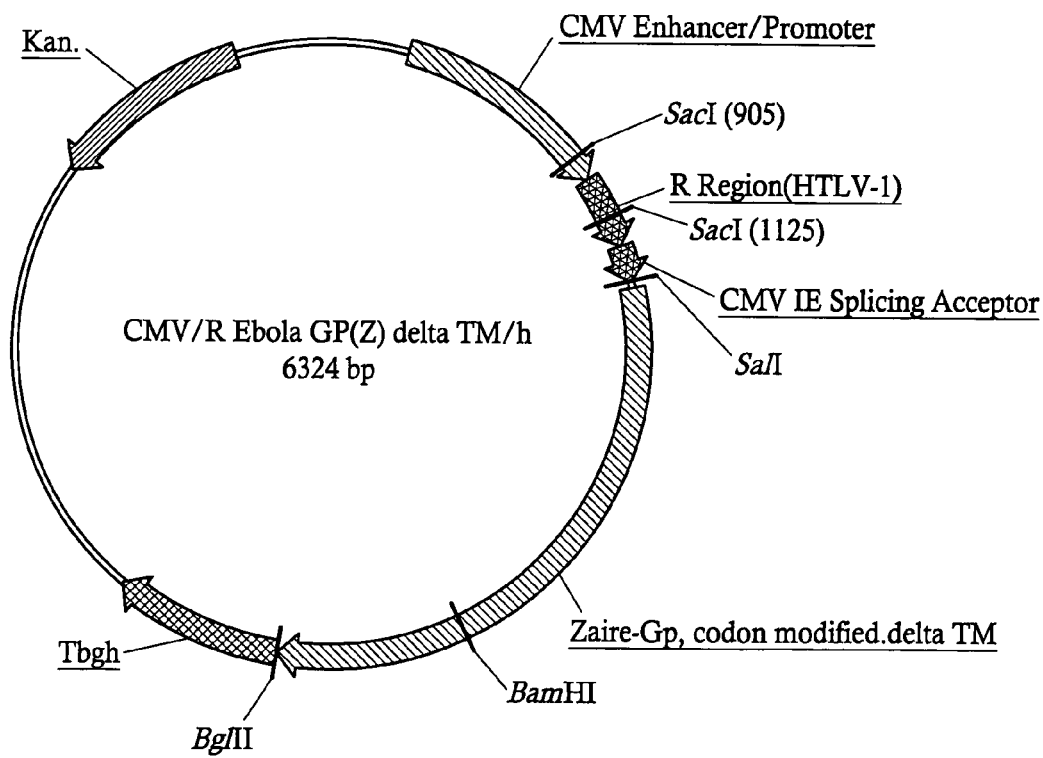
FIG. 37 shows CMV/R Ebola GP (Z) deltaTM/h (codon optimized) construct map (see, Ebola/Marburg/Lassa Plasmids, and Recombinant Adenoviruses in Table 2).
Figure 39:
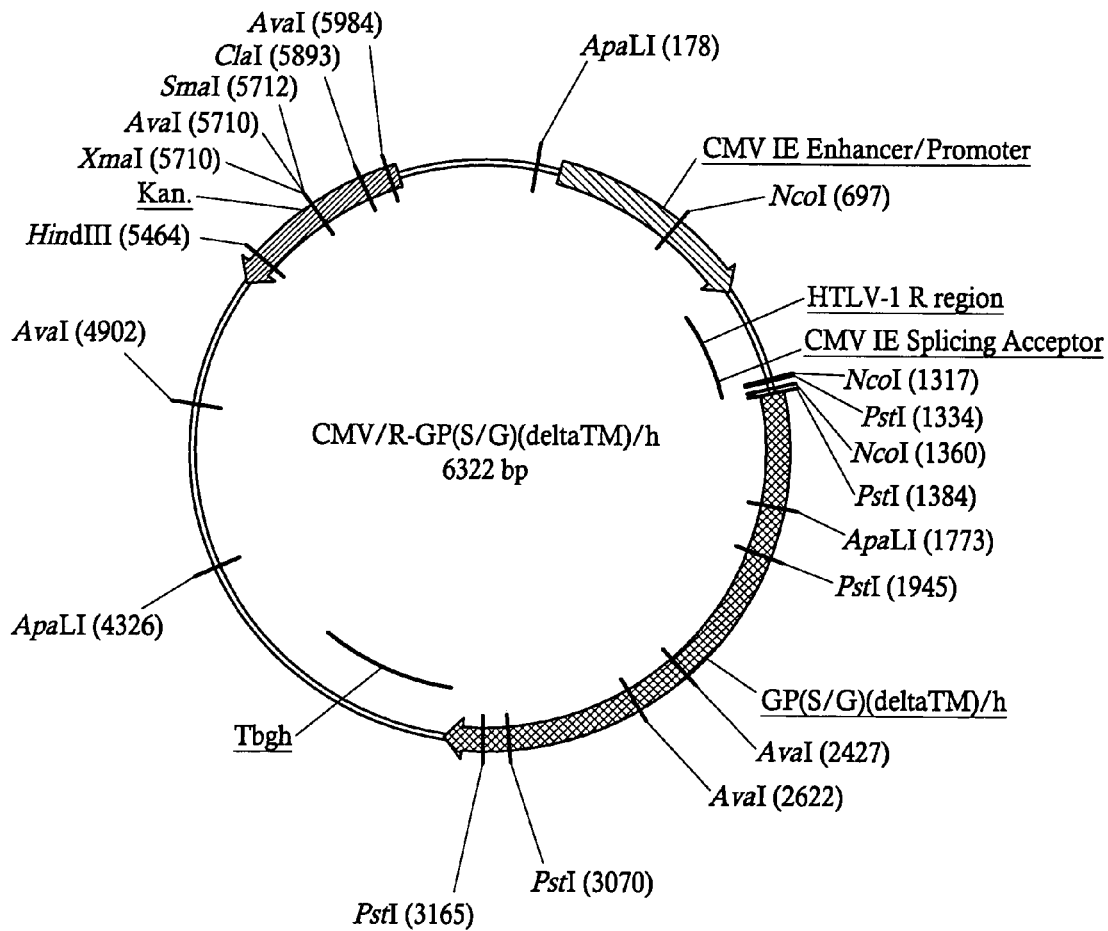
FIG. 39 shows CMV/R Ebola GP (S/Gulu) delta TM/h (codon optimized) construct map (see, Ebola/Marburg/Lassa Plasmids, and Recombinant Adenoviruses in Table 2).
Figure 40:
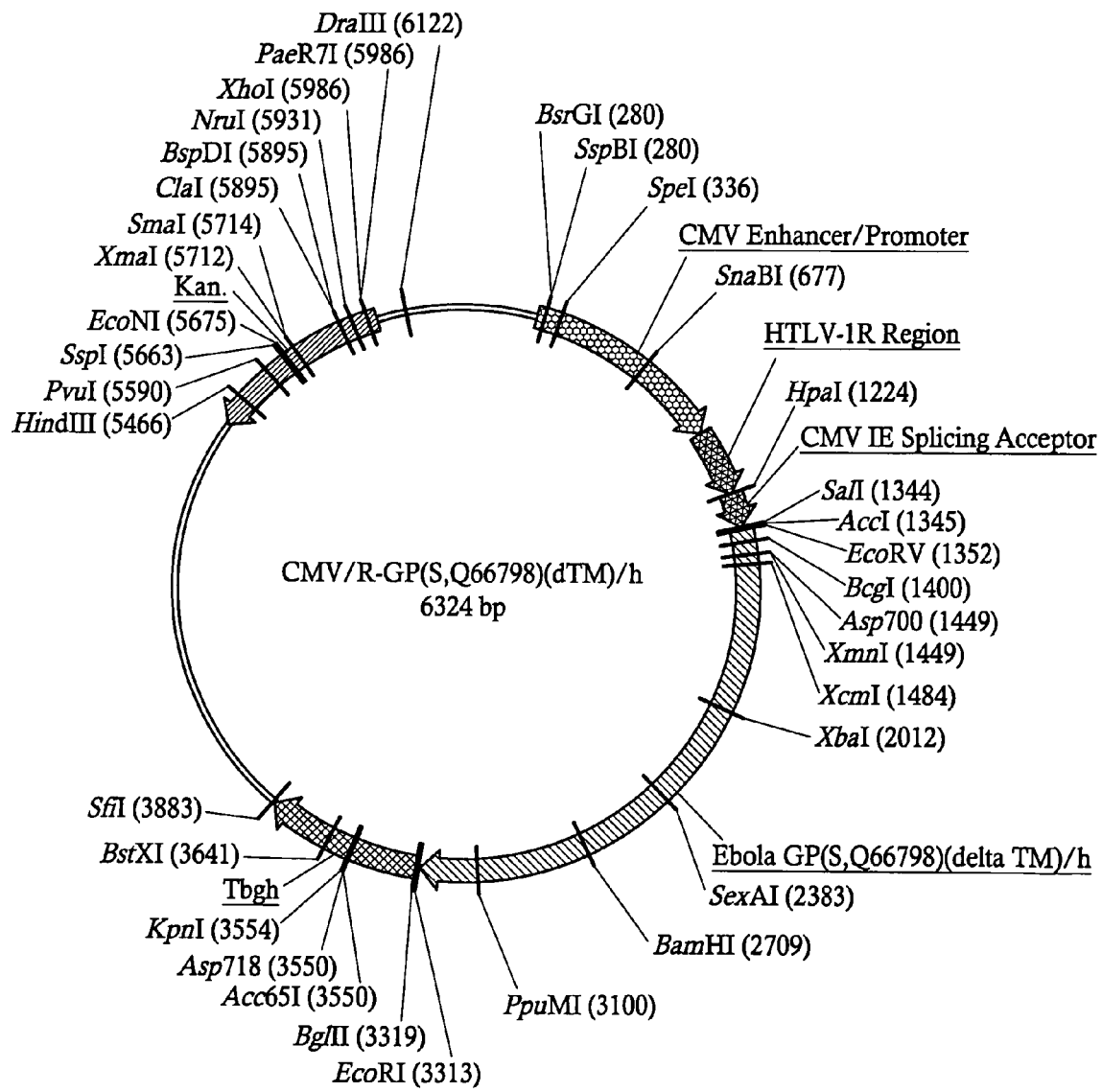
FIG. 40 shows CMV/R Ebola GP (S,Q66798) delta TM/h (codon optimized) construct map (see, Ebola/Marburg/Lassa Plasmids, and Recombinant Adenoviruses in Table 2).

Ebola/Marburg/Lassa GenBank Accession Numbers.

| Gene | GenBank Accession number |
|---|---|
| Ebola Zaire GP | U23187, P87666 |
| Ebola Zaire NP | J04337 |
| Ebola Sudan GP | U28134, Q66798 |
| Ebola Sudan NP | AF173836 |
| Ebola Ivory Coast GP | U28006 |
| Ebola Ivory Coast NP | JO4336 |
| Ebola Reston GP | U23152 |
| Ebola Reston NP | |
| Marburg GP | Z12132 |
| Marburg NP | X68495 |
| Lassa GP | AF181853 |
| Lassa NP | AF246121 |

TABLE 2

Ebola/Marburg/Lassa Plasmids, and Recombinant Adenoviruses

| Construct | Construct Name/Description | Construct Map Name | SEQ ID NO | FIG. |
|---|---|---|---|---|
| VRC6000 | VRC6000 (pVR1012-GP(Z)) | pVR1012-GP(Z) | 1 | 1 |
| VRC6001 | VRC6001 (pVR1012x/s-GP(Z)) | pVR1012x/s Ebola GP(Z) | 2 | 2 |
| VRC6002 | VRC6002 (pVR1012-GP(Z) delta MUC) | pVR1012-GP(Z) delta MUC | 3 | 3 |
| VRC6003 | VRC6003 (pVR1012-GP(Z) delta MUC delta FUR) | pVR1012-GP(Z) delta MUC delta FUR | 4 | 4 |
| VRC6004 | VRC6004 (pVR1012-GP(Z) delta GP2) | pVR1012-GP(Z) delta GP2 | 5 | 5 |
| VRC6005 | VRC6005 (pVR1012-GP(Z) delta GP2 delta C-term A) | pVR1012-GP(Z) delta GP2 delta C-term A | 6 | 6 |
| VRC6006 | VRC6006 (pVR1012-GP(Z) delta GP2 delta C-term B) | pVR1012-GP(Z) delta GP2 delta C-term B | 7 | 7 |
| VRC6007 | VRC6007 (pVR1012-GP(Z) delta GP2 delta FUS) | pVR1012-GP(Z) delta GP2 delta FUS | 8 | 8 |
| VRC6008 | VRC6008 (pVR1012-GP(Z) delta TM) | pVR1012-GP(Z) delta TM | 9 | 9 |
| VRC6052 | VRC6052 (pVR1012-GP(Z) delta SGP) | pVR1012-GP(Z) delta SGP | 10 | 10 |
| VRC6101 | VRC6101 (pVR1012x/s Ebola GP(R) (dTM)) | pVR1012x/s Ebola GP(R)(dTM) | 11 | 11 |
| VRC6110 | VRC6110 (pAdApt Ebola GP(R) (dTM)) | pAdApt Ebola GP(R) (dTM) | 12 | 12 |
| VRC6200 | VRC6200 (pVR1012-GP(S)) | pVR1012-GP(S) | 13 | 13 |
| VRC6201 | VRC6201 (pVR1012x/s Ebola GP(S)) | pVR1012x/s Ebola GP(S) | 14 | 14 |
| VRC6202 | VRC6202 (pVR1012-GP(S) delta TM) | pVR1012-GP(S) delta TM | 15 | 15 |
| VRC6300 | VRC6300 (pVR1012-GP(IC)) | pVR1012-GP(IC) | 16 | 16 |
| VRC6301 | VRC6301 (pVR1012x/s-GP(IC)) | pVR1012x/s Ebola GP(IC) | 17 | 17 |
| VRC6302 | VRC6302 (pVR1012-GP(IC) delta TM) | pVR1012-GP(IC) delta TM | 18 | 18 |
| VRC6303 | VRC6303 (pVR1012x/s Ebola GP (IC) (dTM)) | pVR1012x/s Ebola GP(IC)(dTM) | 19 | 19 |
| VRC6310 | VRC6310 (pAdApt Ebola GP (IC) (dTM)) | pAdApt Ebola GP(IC))(dTM) | 20 | 20 |
| VRC6351 | VRC6351 (pVR1012x/s-sGP(IC)) | pVR1012x/s—sGP(IC) | 21 | 21 |
| VRC6400 | VRC6400 (pVR1012-NP) | pVR1012-NP | 22 | 22 |
| VRC6401 | VRC6401 (pVR1012x/s-NP) | pVR1012x/s Ebola-NP | 23 | 23 |
| VRC6500 | VRC6500 (pVR1012-VP35) | pVR1012-VP35 | 24 | 24 |
| VRC6600 | VRC6600 (pAD/CMV-GP(dTM)(Z-CITE-S) | pAD/CMV-GP(dTM)(Z-CITE-S) | 25 | 25 |
| VRC6601 | VRC6601 (pAdApt Ebola GP(S)) | pAdApt Ebola GP(S) | 26 | 26 |
| VRC6602 | VRC6602 (pAdApt Ebola GP(S) (dTM)) | pAdApt Ebola GP(S)(dTM) | 27 | 27 |
| VRC6603 | VRC6603 (pAdApt Ebola GP(Z)) | pAdApt Ebola GP(Z) | 28 | 28 |
| VRC6604 | VRC6604 (pAdApt Ebola GP(Z)(dTM)) | pAdApt Ebola GP(Z)(dTM) | 29 | 29 |
| VRC6701 | VRC6701 (pVR1012-Marburg) | pVR1012 Marburg | 30 | 30 |
| VRC6702 | VRC6702 (pVR1012x/s Marburg GP (dTM)) | pVR1012x/s Marburg GP(dTM) | 31 | 31 |
| VRC6710 | VRC6710 (pAdApt Marburg GP (dTM)) | pAdApt Marburg GP (dTM) | 32 | 32 |
| VRC6800 | VRC6800 (pVR1012x/s Lassa GP) | pVR1012x/s Lassa GP | 33 | 33 |

TABLE 2-continued

Ebola/Marburg/Lassa Plasmids, and Recombinant Adenoviruses

| Construct | Construct Name/Description | Construct Map Name | SEQ ID NO | FIG. |
|---|---|---|---|---|
| VRC6801 | VRC6801 (pVR1012x/s Lassa GP (dTM) | pVR1012x/s Lassa GP (dTM) | 34 | 34 |
| VRC6810 | VRC6810 (pAdApt Lassa GP) | pAdApt Lassa GP | 35 | 35 |
| VRC6811 | VRC6811 (pAdApt Lassa GP (dTM)) | pAdApt Lassa GP (dTM) | 36 | 36 |
| | CMV/R Ebola GP (Z) delta TM/h (codon optimized) | CMV/R Ebola GP(Z) delta TM/h | 37 | 37 |
| | pVR1012 EbolaGP(Z, P87666) delta TM/h (codon optimized) | pVR1012x/s Ebola GP(Z) delta TM/h (P87666) | 38 | 38 |
| | CMV/R Ebola GP (S/Gulu) delta TM/h (codon optimized) | CMV/R-GP(S/G)(deltaTM)/h | 39 | 39 |
| | CMV/R Ebola GP (S, Q66798) delta TM/h (codon optimized) | CMV/R-GP(S, Q66798)(dTM)/h | 40 | 40 |
| VRC6802 | VRC6802, pVR1012x/s Lassa delta TM/h (codon optimized) | pVR1012x/s Lassa (codon optimized) | 41 | 41 |
| VRC6703 | VRC6703, pVR1012x/s Marburg delta TM/h (codon optimized) | pVR1012x/s Maxburg (codon optimized) | 42 | 42 |
| | CMV/R Ebola NP | CMV/R Ebola NP | 43 | 43 |

DETAILED DESCRIPTION OF THE INVENTION

Filovirus vaccines are provided comprising a nucleic acid molecule encoding a filoviral structural protein operatively-linked to a control sequence in a pharmaceutically acceptable excipient. In one embodiment, the nucleic acid molecule encodes the transmembrane form of the viral glycoprotein (GP). In another embodiment, the nucleic acid molecule encodes the secreted form of the viral glycoprotein (SGP). In yet another embodiment, the nucleic acid molecule encodes the viral nucleoprotein (NP).

The present invention further includes vaccines comprising nucleic acid molecules encoding filoviral structural proteins other than GP, SGP, and NP, e.g., other structural gene products which elicit an immune response against a filovirus or disease caused by infection with filovirus. The nucleic acid molecules of the vaccines of the present invention encode structural gene products of any Ebola viral strain including the Zaire, Sudan, Ivory Coast and Reston strains. Nucleic acid molecules encoding structural gene products of the genetically-related Marburg virus strains may also be employed. Moreover, the nucleic acid molecules of the present invention may be modified, e.g., the nucleic acid molecules set forth herein may be mutated, as long as the modified expressed protein elicits an immune response against a pathogen or disease. For example, the nucleic acid molecule may be mutated so that the expressed protein is less toxic to cells. The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

The present invention also provides methods for immunizing a subject against disease caused by infection with filovirus comprising administering to the subject an immunoeffective amount of a filovirus vaccine. Methods of making and using filovirus vaccines are also provided by the present invention including the preparation of pharmaceutical compositions.

Biochemical Analysis of Secreted and Virion Glycoproteins of Ebola Virus.

Ebola (EBO) viruses are members of the Filovirdae and cause a severe, often fatal form of hemorrhagic fever disease in human and/or non-human primates. The glycoprotein (GP) gene of filoviruses is the fourth gene (of seven) from the 3' end of the negative-strand RNA genome. All EBO viruses characterized thus far have the same unconventional type of GP gene organization that results in the expression of a secreted, nonstructural glycoprotein (SGP) in preference to the structural GP. The SGP is encoded in a single frame (0 frame), while the GP is encoded in two frames (0 and −1 frames). Expression of the GP occurs when the two frames are connected through a transcriptional editing event that results in the insertion of a single extra adenosine (added to a run of seven adenosines).

Figure 44:
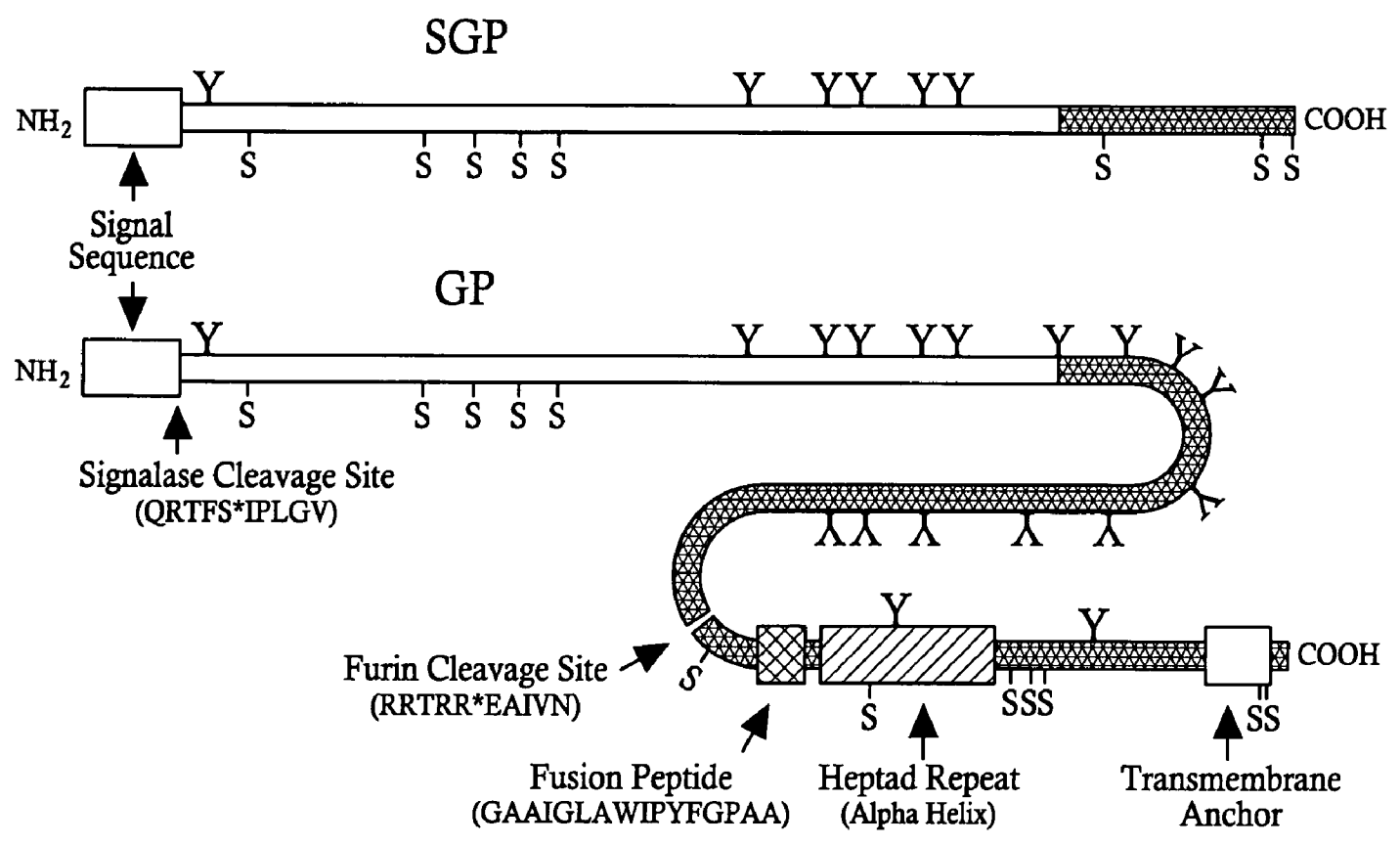

Referring to FIG. 44, for Zaire species of EBO virus, the N-terminal 295 residues (including signal sequence) of the SGP (364 total residues) and GP (676 total residues) are identical, but the length and composition of their C-terminal sequences are unique. The GP, a type 1 transmembrane protein, is found on the surface of the infectious virion and functions in attachment structure in the binding and entry of the virus into susceptible cells. Comparisons of GP predicted amino acid sequences for all species of EBO virus show a general conservation in the N-terminal and C-terminal regions (each approximately one-third of the total sequence) and are separated by a highly variable middle section. This protein is highly glycosylated, containing large amounts of N- and O-linked glycans, and for Marburg (MBG) virus (another type of filovirus) has been shown to form trimers. Just N terminal to the transmembrane anchor sequence of the GP (residues 650 to 672) is a motif (residues 585 to 609) that is highly conserved in filoviruses. This sequence also has a high degree of homology with a motif in the glycoproteins of oncogenic retroviruses that has been shown to be immunosuppressive in vitro. Partially overlapping this motif is a heptad repeat sequence (53 residues; positions 541 to 593) that is thought to function in the formation of intermolecular coiled coils in the assembly of trimers, similar to structures predicted for the surface glycoproteins of other viruses. Immediately N terminal to this sequence is a predicted fusion peptide followed closely by a putative multi-basic cleavage site for a subtilisin/kexin-like convertase, firin. Cleavage by furin has been indirectly demonstrated by use of specific inhibitors and is predicted to occur at the last arginine in the sequence RRTRR↓ (position 501 from the beginning of the open reading frame [ORF]). Although the role of the SGP is less defined, recent studies have shown that SGP can bind to neutrophils, while GP binds to endothelial cells. The different binding patterns of SGP and GP suggest that despite having identical N-terminal amino acid sequences (~280 residues), these glycoproteins are structurally very distinct from one another.

Figure 45:
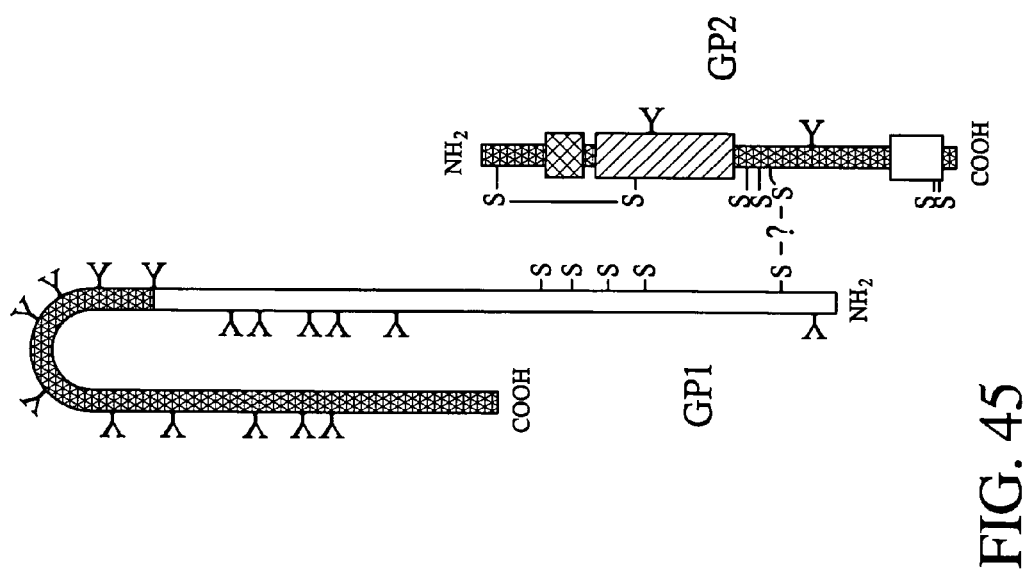
FIG. 45 is a diagrammatic representation of the structural GP. Shown is the predicted orientation of the GP1–GP2 heterodimer linked by undetermined disulfide bonding (indicated by the question mark). Intramolecular disulfide bonds that are shown come from prior predictions based on similarities to retrovirus glycoprotein structures. See FIG. 44 for other features of the amino acid sequence.

Referring to FIG. 45, the glycoproteins expressed by a Zaire species of Ebola virus were analyzed for cleavage, oligomerization, and other structural properties to better define their functions. The 50- to 70-kDa secreted and 150-kDa virion/structural glycoproteins (SGP and GP, respectively), which share the 295 N-terminal residues, are cleaved near the N terminus by signalase. A second cleavage event, occurring in GP at a multibasic site (RRTRR↓) (SEQ ID NO: 51) that is likely mediated by furin, results in two glycoproteins (GP1 and GP2) linked by disulfide bonding. This furin cleavage site is present in the same position in the GPs of all Ebola viruses (R[R/K]X[R/K]R↓), and one is predicted for Marburg viruses (R[R/K]KR↓), although in a different location. Based on the results of cross-linking studies, investigators were able to determine that Ebola virion peplomers are composed of trimers of GP1–GP2 heterodimers and that aspects of their structure are similar to those of retroviruses (including lentiviruses like HIV-1 and HIV-2), paramyxoviruses, and influenza viruses. Investigators also determined that SGP is secreted from infected cells almost exclusively in the form of a homodimer that is joined by disulfide bonding.

Referring to FIG. 46, investigators defined the main viral determinant of Ebola virus pathogenicity; synthesis of the virion glycoprotein (GP) of Ebola virus Zaire induced cytotoxic effects in human endothelial cells in vitro and in vivo. This effect mapped to a serine-threonine-rich, mucin-like domain of this type I transmembrane glycoprotein, one of seven gene products of the virus. Gene transfer of GP into explanted human or porcine blood vessels caused massive endothelial cell loss within 48 hours that led to a substantial increase in vascular permeability. Deletion of the mucin-like region of GP abolished these effects without affecting protein expression or function. GP derived from the Reston strain of virus, which causes disease in non-human primates but not in man, did not disrupt the vasculature of human blood vessels. In contrast, the Zaire GP induced endothelial cell disruption and cytotoxicity in both non-human primate and human blood vessels, and the mucin domain was required for this effect. These findings indicate that GP, through its mucin domain, is the viral determinant of Ebola pathogenicity and likely contributes to hemorrhage during infection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a wild-type filovirus structural gene product; and DNA molecules which comprise a sequence substantially different from those described above but which, due to the degeneracy of the genetic code, still encode an ORF of a wild-type filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus structural gene product is intended fragments at least about 15 nt., and more preferably at least about 20 nt., still more preferably at least about 30 nt., and even more preferably, at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus structural gene product. By a fragment at least 20 nt. in length, for example, is intended fragments which include 20 or more contiguous bases from the nucleotide sequence of the ORF of a wild-type filovirus structural gene product.

Preferred nucleic acid fragments of the present invention include nucleic acid molecules encoding epitope-bearing portions of the filovirus structural protein. In particular, such nucleic acid fragments of the present invention include nucleic acid molecules encoding epitope-bearing domains of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), and more preferably at least about 20 nt., still more preferably at least about 30 nt., and even more preferably about 30–70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus structural gene product. Variants may occur naturally, such as a natural allelic variant. By an "allelic variant" is intended one of several alternate forms of a gene occupying a given locus on a genome of an organism. (*Genes II*, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the filovirus structural gene product or portions thereof. Also especially preferred in this regard are conservative substitutions.

Further embodiments of the invention include nucleic acid molecules comprising a polynucleotide having a nucleotide sequence at least 95% identical, and more preferably at least 96%, 97%, 98% or 99% identical to a nucleotide sequence encoding a polypeptide having the amino acid sequence of a wild-type filovirus structural gene product or fragment thereof or a nucleotide sequence complementary thereto.

By a polynucleotide having a nucleotide sequence at least, for example, 95% "identical" to a reference nucleotide sequence encoding a filovirus structural gene product is intended that the nucleotide sequence of the polynucleotide is identical to the reference sequence except that the polynucleotide sequence, may include up to five point mutations per each 100 nucleotides of the reference nucleotide sequence encoding the Ebola virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981 *Advances in Applied Mathematics* 2:482–489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequences shown herein in the Sequence Listing which encode a polypeptide having Ebola, Marburg, or Lassa virus polypeptide activity. By "a polypeptide having Ebola, Marburg, or Lassa virus polypeptide activity" is intended polypeptides exhibiting Ebola, Marburg, or Lassa virus polypeptide activity in a particular biological assay. For example, GP, SGP or NP protein activity can be measured for changes in immunological character by an appropriate immunological assay.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide "having Ebola, Marburg, or Lassa virus polypeptide activity". In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Ebola, Marburg, or Lassa virus polypeptide activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306–1310, wherein the authors indicate that proteins are surprisingly tolerant of amino acid substitutions.

Polypeptides and Fragments

The invention further provides a filovirus polypeptide having the amino acid sequence encoded by an open reading frame (ORF) of a wild-type filovirus structural gene, or a peptide or polypeptide comprising a portion thereof (e.g., SGP).

It will be recognized in the art that some amino acid sequences of the filovirus polypeptides can be varied without significant effect of the structure or function of the protein. If such differences in sequence are contemplated, it should be remembered that there will be critical areas on the protein which determine activity.

Thus, the invention further includes variations of the filovirus polypeptide which show substantial filovirus polypeptide activity or which include regions of filovirus protein such as the protein portions discussed below. Such mutants include deletions, insertions, inversions, repeats, and type substitutions. As indicated, guidance concerning which amino acid changes are likely to be phenotypically silent can be found in Bowie, J. U. et al. 1990 *Science* 247:1306–1310.

Thus, the fragment, derivative or analog of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein (see Table A).

TABLE A

| Conservative Amino Acid Substitutions | |
|---|---|
| Aromatic | Phenylalanine |
| | Tryptophan |
| | Tyrosine |
| Ionizable: Acidic | Aspartic Acid |
| | Glutamic Acid |
| Ionizable: Basic | Arginine |
| | Histidine |
| | Lysine |
| Nonionizable Polar | Asparagine |
| | Glutamine |
| | Selenocystine |
| | Serine |
| | Threonine |
| Nonpolar (Hydrophobic) | Alanine |
| | Glycine |
| | Isoleucine |
| | Leucine |
| | Proline |
| | Valine |
| Sulfur Containing | Cysteine |
| | Methionine |

Of course, the number of amino acid substitutions a skilled artisan would make depends on many factors, including those described above. Generally speaking, the number of amino acid substitutions for any given filovirus polypeptide will not be more than 50, 40, 30, 20, 10, 5 or 3.

Amino acids in the filovirus polypeptides of the present invention that are essential for function can be identified by methods known in the art, such as site-directed mutagenesis or alanine-scanning mutagenesis (Cunningham &. Wells 1989 *Science* 244:1081–1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus polypeptide can be substantially purified by the one-step method described in Smith and Johnson 1988 *Gene* 67:31–40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, and more preferably at least 96%, 97%, 98%, or 99% identical to those described above.

By a polypeptide having an amino acid sequence at least, for example, 95% "identical" to a reference amino acid sequence of an filovirus polypeptide is intended that the amino acid sequence of the polypeptide is identical to the reference sequence except that the polypeptide sequence may include up to five amino acid alterations per each 100 amino acids of the reference amino acid of the filovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another aspect, the invention provides portions of the polypeptides described herein with at least 30 amino acids and more preferably at least 50 amino acids. Preferred portions of the present invention include polypeptides comprising an epitope-bearing portion of a filovirus structural protein. In particular, preferred portions of the present invention include polypeptides comprising an epitope-bearing domain of a filovirus structural protein, where the domain is the GP/SGP identity domain, the mucin-like domain, the furin cleavage site, the fusion peptide domain, the heptad repeat domain, the transmembrane anchor domain, and the intracellular domain, and any combination thereof, for example, a filovirus glycoprotein having a truncation at the carboxy terminus to delete the transmembrane anchor and intracellular domain, a filovirus glycoprotein having a truncation at the carboxy terminus to delete the heptad repeat domain and transmembrane anchor and intracellular domain, a filovirus glycoprotein having a truncation at the carboxy terminus to delete the fusion peptide domain, heptad repeat domain, and transmembrane anchor and intracellular domain, a filovirus glycoprotein having a truncation at the carboxy terminus to delete the furin cleavage site, fusion peptide domain, heptad repeat domain, and transmembrane anchor and intracellular domain, and a filovirus glycoprotein having a truncation at the carboxy terminus to delete the mucin-like domain, furin cleavage site, fusion peptide domain, heptad repeat domain, and transmembrane anchor and intracellular domain. Another example is a filovirus glycoprotein having an amino, internal, or carboxy deletion to delete the mucin-like domain, the furin cleavage site, the fusion peptide domain, the heptad repeat domain, the transmembrane anchor domain, or the intracellular domain.

The polypeptides of the invention may be produced by any conventional means (Houghten, R. A. 1985 *PNAS USA* 82:5131–5135). The "Simultaneous Multiple Peptide Synthesis (SMPS)" process is described in U.S. Pat. No. 4,631, 211 to Houghten et al. (1986).

The present invention also relates to vectors which include the nucleic acid molecules of the present invention, host cells which are genetically engineered with the recombinant vectors, and the production of filovirus polypeptides or fragments thereof by recombinant techniques.

The present invention relates to "prime and boost" immunization regimes in which the immune response induced by administration of a priming composition is boosted by administration of a boosting composition. The present invention is based on the inventors' experimental demonstration that effective boosting can be achieved using replication-defective adenovirus vectors, following priming with any of a variety of different types of priming compositions. The present invention employs replication-deficient adenovirus which, as the experiments described below show, has been found to be an effective means for providing a boost to an immune response primed to antigen using any of a variety of different priming compositions.

Replication-deficient adenovirus derived from human serotype 5 has been developed as a live viral vector by Graham and colleagues (Graham & Prevec 1995 *Mol Biotechnol* 3:207–20; Bett et al. 1994 *PNAS USA* 91:8802–6). Adenoviruses are non-enveloped viruses containing a linear double-stranded DNA genome of around 3600 bp. Recombinant viruses can be constructed by in vitro recombination between an adenovirus genome plasmid and a shuttle vector containing the gene of interest together with a strong eukaryotic promoter, in a permissive cell line which allows viral replication. High viral titres can be obtained from the permissive cell line, but the resulting viruses, although capable of infecting a wide range of cell types, do not replicate in any cells other than the permissive line, and are therefore a safe antigen delivery system. Recombinant adenoviruses have been shown to elicit protective immune responses against a number of antigens including tick-borne encephalitis virus NS1 protein (Jacobs et al. 1992 *J Virol* 66:2086–95) and measles virus nucleoprotein (Fooks et al. 1995 *Virology* 210:456–65).

Remarkably, the experimental work described below demonstrates that use of embodiments of the present invention allows for recombinant replication-defective adenovirus expressing an antigen to boost an immune response primed by a DNA vaccine. The replication-defective adenovirus was found to induce an immune response after intramuscular immunization. In prime/boost vaccination regimes the replication-defective adenovirus is also envisioned as being able to prime a response that can be boosted by a different recombinant virus or recombinantly produced antigen.

Non-human primates immunized with plasmid DNA and boosted with replication-defective adenovirus were protected against challenge. Both recombinant replication-deficient adenovirus and plasmid DNA are vaccines that are safe for use in humans. Advantageously, the inventors found that a vaccination regime used intramuscular immunization for both prime and boost can be employed, constituting a general immunization regime suitable for inducing an immune response, e.g., in humans.

The present invention in various aspects and embodiments employs a replication-deficient adenovirus vector encoding an antigen for boosting an immune response to the antigen primed by previous administration of the antigen or nucleic acid encoding the antigen.

A general aspect of the present invention provides for the use of a replication-deficient adenoviral vector for boosting an immune response to an antigen.

One aspect of the present invention provides a method of boosting an immune response to an antigen in an individual, the method including provision in the individual of a replication-deficient adenoviral vector including nucleic acid encoding the antigen operably linked to regulatory sequences for production of antigen in the individual by expression from the nucleic acid, whereby an immune response to the antigen previously primed in the individual is boosted.

An immune response to an antigen may be primed by genetic immunization, by infection with an infectious agent, or by recombinantly produced antigen.

A further aspect of the invention provides a method of inducing an immune response to an antigen in an individual, the method comprising administering to the individual a priming composition comprising the antigen or nucleic acid encoding the antigen and then administering a boosting composition which comprises a replication-deficient adenoviral vector including nucleic acid encoding the antigen operably linked to regulatory sequences for production of antigen in the individual by expression from the nucleic acid.

A further aspect provides for use of a replication-deficient adenoviral vector, as disclosed, in the manufacture of a medicament for administration to a mammal to boost an immune response to an antigen. Such a medicament is generally for administration following prior administration of a priming composition comprising the antigen.

The priming composition may comprise any viral vector, including adenoviral, or other than adenoviral, such as a vaccinia virus vector such as a replication-deficient strain such as modified virus Ankara (MVA) (Mayr et al. 1978 *Zentralbl Bakteriol* 167:375–90; Sutter and Moss 1992 *PNAS USA* 89:10847–51; Sutter et al. 1994 *Vaccine* 12:1032–40) or NYVAC (Tartaglia et al. 1992 *Virology* 118:217–32), an avipox vector such as fowlpox or canarypox, e.g., the strain known as ALVAC (Kanapox, Paoletti et al. 1994 *Dev Biol Stand* 1994 82:65–9), or a herpes virus vector.

The priming composition may comprise DNA encoding the antigen, such DNA preferably being in the form of a circular plasmid that is not capable of replicating in mammalian cells. Any selectable marker should not be resistant to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present invention, administration of a priming composition is followed by boosting with first and second boosting compositions, the first and second boosting compositions being the same or different from one another, e.g., as exemplified below. Still further boosting compositions may be employed without departing from the present invention. In one embodiment, a triple immunization regime employs DNA, then adenovirus (Ad) as a first boosting composition, and then MVA as a second boosting composition, optionally followed by a further (third) boosting composition or subsequent boosting administration of one or other or both of the same or different vectors. Another option is DNA then MVA then Ad, optionally followed by subsequent boosting administration of one or other or both of the same or different vectors.

The antigen to be included in respective priming and boosting compositions (however many boosting compositions are employed) need not be identical, but should share epitopes. The antigen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

Within the replication-deficient adenoviral vector, regulatory sequences for expression of the encoded antigen will include a promoter. By "promoter" is meant a sequence of nucleotides from which transportation may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter. Other regulatory sequences including terminator fragments, polyadenylation sequences, enhancer sequences, marker genes, internal ribosome entry site (IRES) and other sequences may be included as appropriate, in accordance with the knowledge and practice of the ordinary person skilled in the art: see, for example, *Molecular Cloning: a Laboratory Manual*, $2^{nd}$ edition, Sambrook et al. 1989 Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., John Wiley & Sons, 1994.

Suitable promoters for use in aspects and embodiments of the present invention include the cytomegalovirus immediate early (CMV IE) promoter, with or without intron A, and any other promoter that is active in mammalian cells.

Either or both of the priming and boosting compositions may include an adjuvant or cytokine, such as alpha-interferon, gamma-interferon, platelet-derived growth factor (PDGF), granulocyte macrophage-colony stimulating factor (GM-CSF) granulocyte-colony stimulating factor (gCSF), tumor necrosis factor (TNF), epidermal growth factor (EGF), IL-1, IL-2, IL-4, IL-6, IL-8, IL-10 and IL-12, or encoding nucleic acid therefor.

Administration of the boosting composition is generally weeks or months after administration of the priming composition, preferably about 2–3 weeks or 4 weeks, or 8 weeks, or 16 weeks, or 20 weeks, or 24 weeks, or 28 weeks, or 32 weeks.

Preferably, administration of priming composition, boosting composition, or both priming and boosting compositions, is intramuscular immunization.

Intramuscular administration of adenovirus vaccines or plasmid DNA may be achieved by using a needle to inject a suspension of the virus or plasmid DNA. An alternative is the use of a needless injection device to administer a virus or plasmid DNA suspension (using, e.g., Biojector™) or a freeze-dried powder containing the vaccine (e.g., in accordance with techniques and products of Powderject), providing for manufacturing individually prepared doses that do not need cold storage. This would be a great advantage for a vaccine that is needed in rural areas of Africa.

Adenovirus is a virus with an excellent safety record in human immunizations. The generation of recombinant viruses can be accomplished simply, and they can be manufactured reproducibly in large quantities. Intramuscular administration of recombinant replication-deficient adenovirus is therefore highly suitable for prophylactic or therapeutic vaccination of humans against diseases which can be controlled by an immune response.

The individual may have a disease or disorder such that delivery of the antigen and generation of an immune response to the antigen is of benefit or has a therapeutically beneficial effect.

Most likely, administration will have prophylactic aim to generate an immune response against a pathogen or disease before infection or development of symptoms.

Diseases and disorders that may be treated or prevented in accordance with the present invention include those in which an immune response may play a protective or therapeutic role.

Components to be administered in accordance with the present invention may be formulated in pharmaceutical compositions. These compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., intravenous, cutaneous or subcutaneous, intramucosal (e.g., gut), intranasal, intramuscular, or intraperitoneal routes.

As noted, administration is preferably intradermal, subcutaneous or intramuscular.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A slow-release formulation may be employed.

Following production of replication-deficient adenoviral particles and optional formulation of such particles into compositions, the particles may be administered to an individual, particularly human or other primate.

Administration may be to another mammal, e.g., rodent such as mouse, rat or hamster, guinea pig, rabbit, sheep, goat, pig, horse, cow, donkey, dog or cat.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences*, 16th edition, Osol, A. ed., 1980.

In one preferred regimen, DNA is administered (preferably intramuscularly) at a dose of 10 micrograms to 50 milligrams/injection, followed by adenovirus (preferably intramuscularly) at a dose of $5 \times 10^7 - 1 \times 10^{12}$ particles/injection.

The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

A composition may be administered alone or in combination with other treatments, either simultaneously or sequentially dependent upon the condition to be treated.

Delivery to a non-human mammal need not be for a therapeutic purpose, but may be for use in an experimental context, for instance in investigation of mechanisms of immune responses to an antigen of interest, e.g., protection against disease.

Further aspects and embodiments of the present invention will be apparent to those of ordinary skill in the art, in view of the above disclosure and following experimental exemplification, included by way of illustration and not limitation, and with reference to the attached figures.

Development of a Preventive Vaccine for Ebola Virus Infection in Primates

Genetic immunization has been shown to influence both humoral and cellular immune activation pathways and to protect against infection by human pathogens (Tang, D. C. et al. 1992 *Nature* 356:152–154; Ulmer, J. B. et al. 1993 *Science* 259:1745–1749; Wang, B. et al. 1993 *PNAS USA* 90:4156–4160; Sedegah, M. et al. 1994 *PNAS USA* 91:9866–9870). The effectiveness of plasmid vaccines is thought to result from host cell protein synthesis and endogenous presentation of the immunogen, and possibly to immunostimulatory effects of plasmid DNA itself (Krieg, A. M. et al. 1995 *Nature* 374:546–549; Sato, Y. et al. 1996 *Science* 273:352–354). DNA vaccines have been shown to elicit specific immune responses to Ebola virus antigens and to protect guinea pigs (Xu, L. et al. 1998 *Nat Med* 4:7–42) and mice (Vanderzanden, L. et al. 1998 *Virology* 246:134–144) against challenge with Ebola virus adapted to produce lethal infection in rodents (Connolly, B. M. et al. 1999 *J Infect Dis* 179:S203–S217; Bray, M. et al. 1998 *J Infect Dis* 178:651–661). Although both cell-mediated and humoral immune responses were elicited, antibody titer correlated with the degree of protection in animals immunized with plasmids encoding proteins from the Zaire subtype of Ebola virus.

A broadly effective vaccine would need to provide immunity to the multiple Ebola subtypes isolated in human infections (Zaire, Sudan and Ivory Coast), but a multivalent vaccine might dilute the specific immune response demonstrated for the single subtype vaccine. To address this concern, we analyzed the efficacy of the original Ebola Zaire DNA vaccine in comparison to its use in combination with DNA from Ebola subtypes Sudan and Ivory Coast. As in a previous study (Xu, L. et al. 1998 *Nat Med* 4:7–42), immunization with a single plasmid encoding Zaire subtype virion glycoprotein, GP(Z), generated a substantial virus-specific antibody response and conferred protective immunity in guinea pigs (Table I). Inclusion of a plasmid expressing Ebola nucleoprotein, NP, did not affect the antibody titer to Ebola GP(Z) or diminish its protective efficacy. Further broadening of the vaccine components to include NP and three subtypes of Ebola glycoprotein, Zaire, Ivory Coast and Sudan, GP(Z,IC,S)+NP, yielded a pre-challenge immune response comparable to the single-plasmid vaccine. Moreover, complete protection from infection with Ebola Zaire was achieved in guinea pigs that received the multivalent vaccine (Table I, subjects 13–16). Anamnestic antibody was not induced by the virus challenge, indicating that the vaccine itself provided an immune response sufficient to efficiently clear the virus. These findings show that multivalent plasmid immunization did not substantially diminish glycoprotein (GP)-specific antibody production and its protective efficacy in a rodent model.

TABLE I

Multivalent genetic immunization in guinea pigs

| ID | Immunization | ELISA IgG | Survival |
| --- | --- | --- | --- |
| 1 | Plasmid | 0 | No |
| 2 | Plasmid | 0 | No |
| 3 | Plasmid | 0 | No |
| 4 | Plasmid | 0 | No |
| 5 | GP(Z) | 6400 | Yes |
| 6 | GP(Z) | 6400 | Yes |
| 7 | GP(Z) | 6400 | Yes |
| 8 | GP(Z) | 3200 | Yes |
| 9 | GP(Z) + NP | 6400 | Yes |
| 10 | GP(Z) + NP | 6400 | Yes |
| 11 | GP(Z) + NP | 6400 | Yes |
| 12 | GP(Z) + NP | 6400 | Yes |
| 13 | GP(Z, IC, S) + NP | 6400 | Yes |
| 14 | GP(Z, IC, S) + NP | 1600 | Yes |
| 15 | GP(Z, IC, S) + NP | 6400 | Yes |
| 16 | GP(Z, IC, S) + NP | 6400 | Yes |

Figure 47:
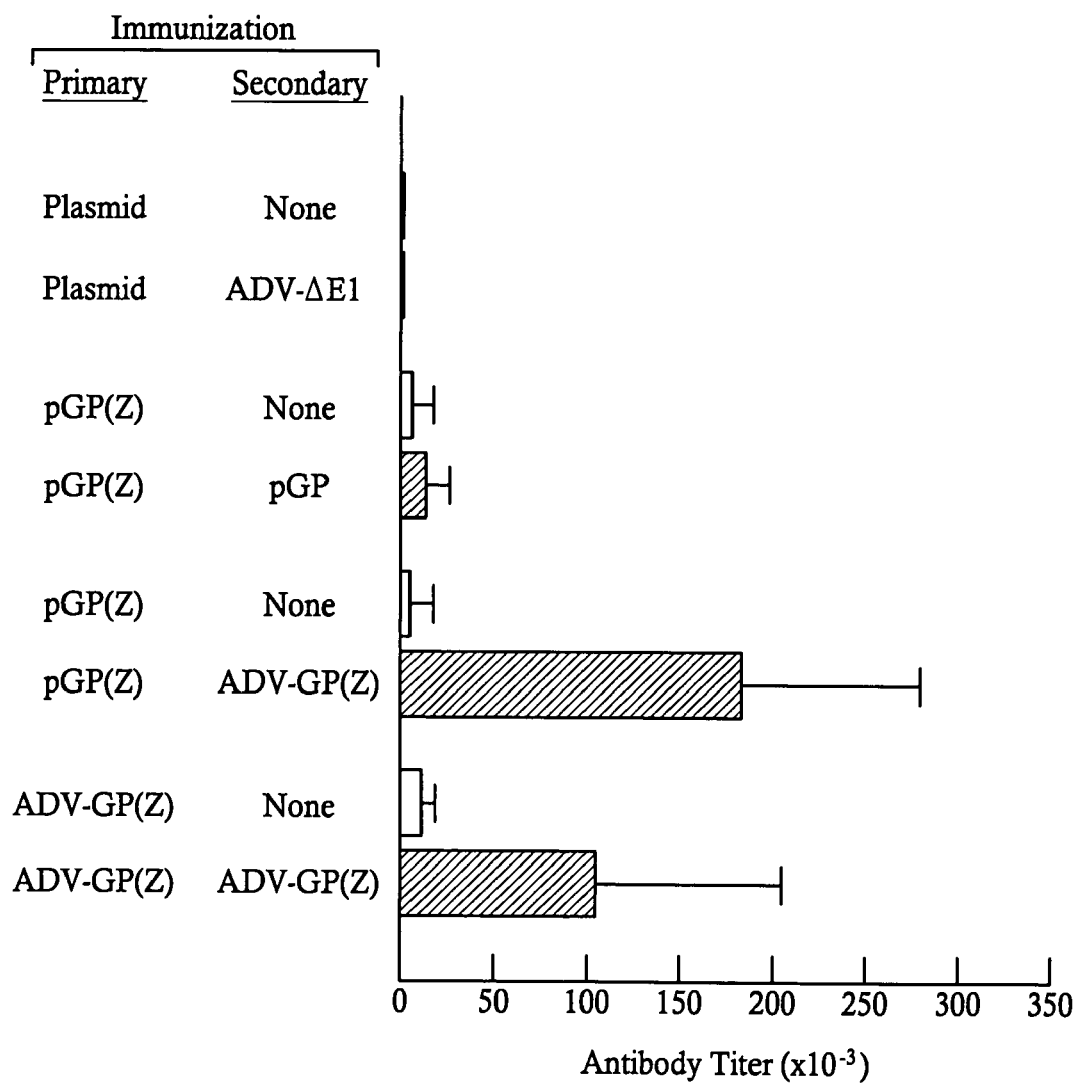
FIG. 47 shows Ebola-specific antibody responses generated by different DNA/adenovirus prime-boost combinations. Data are the means of the reciprocal endpoint dilution for each group of mice and error bars represent the standard deviation.

Because protection in the rodent model of Ebola virus infection correlated with antibody titers, and efficient humoral responses may influence clinical outcome in human disease (Baize, S. et al. 1999 *Nat Med* 5:423426; Maruyama, T. et al. 1999 *J Virol* 73:6024–6030), we considered it important to elicit a strong humoral response for vaccines tested in primates, although cell-mediated immunity is coordinately induced and likely contributes to protection (Xu, L. et al. 1998 *Nat Med* 4:37–42). Recently, regimens of DNA priming followed by administration of viral vectors have demonstrated enhanced immune responses compared to vaccines using DNA alone (Sedegah, M. et al. 1998 *PNAS USA* 95:7648–7653; Hanke, T. et al. 1998 *Vaccine* 16:439–445; Robinson, H. L. et al. 1999 *Nat Med* 5:526–534; Schneider, J. et al. 1998 *Nat Med* 4:397–402). Recombinant, replication-deficient adenoviruses can be grown to high titer, infect antigen-presenting cells, and induce potent immune responses (Davis, A. R. et al. 1985 *PNAS USA* 82:7560–7564; Natuk, R. J. et al. 1992 *PNAS USA* 89:7777–7781; Xiang, Z. Q. et al. 1996 *Virology* 219:220–227). Adenoviruses have shown a boosting effect in mice (Xiang, Z. Q. et al. 1999 *J Immunol* 162:6716–6723), but the combination of DNA and adenovirus has not been tested for efficacy in an infectious challenge model, and the success of this approach in primates is yet unknown. We therefore developed a recombinant adenoviral vector that directs high level GP expression ADV-GP(Z) and used this vector to test whether a modified prime-boost strategy would augment the antibody response to Ebola virus obtained with naked DNA alone. Mice were injected with DNA and adenovirus vectors either singly or in combinations, and cell-mediated and humoral immune responses were assessed. A 10- to 100-fold increase in antibody titer was found in mice injected with DNA followed by an adenovirus boost, compared to DNA immunization alone (FIG. 47). An increase in cytotoxic T cell responses was also observed with this combination. Immunization with ADV-GP(Z) alone yielded antibody titers that were not significantly different from those obtained with the DNA prime, adenovirus boost immunization. These data suggest that immunogenicity of the Ebola GP DNA vaccine in mice is improved by boosting with recombinant adenovirus and that this strategy might represent a useful approach to enhance immune responses in non-human primates.

Figure 48:
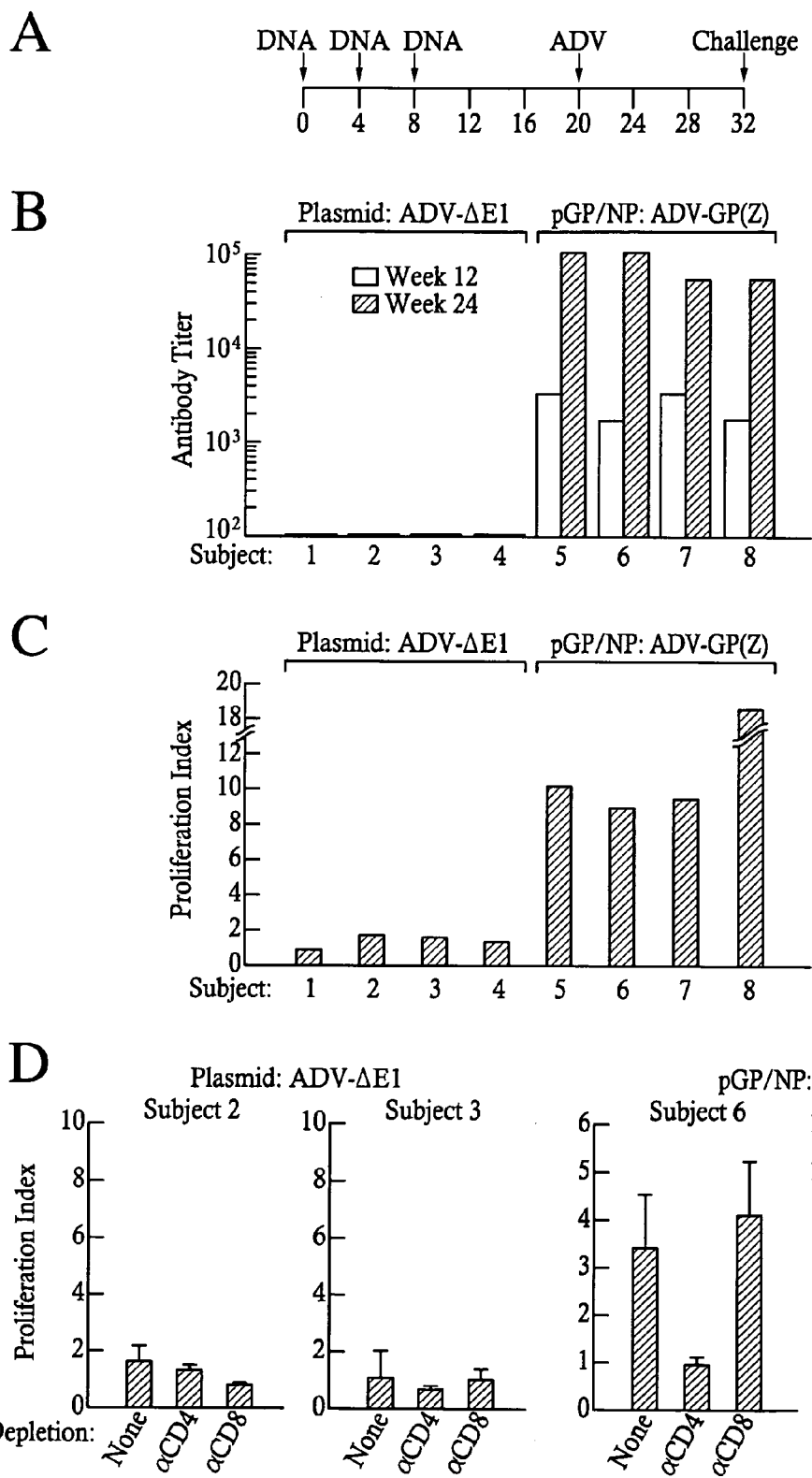
FIGS. 48(A–D) shows. DNA-Adenovirus immunization of cynomolgus macaques. A) Immunization schedule for DNA and/or adenovirus injections, and challenge with the wild-type Mayinga strain of the Zaire subtype of Ebola virus. B) Elisa titers of Ebola-specific antibodies in serum. Serum was collected at week 12 (open bar) and 2 days before the immunization at week 24 (closed bar). C) Lymphoproliferative responses to Ebola-secreted glycoprotein (SGP) following immunization. Bars represent the average fold-proliferation of all four blood samples for each subject. The standard deviation is not shown because the baseline level of induction varied between experiments. However, PBMC from all 8 animals were assayed within the same experiment for each time point, and the averages displayed in the figure are representative of the results obtained for any single time point. D) Lymphoproliferative responses to Ebola SGP in bulk PBMC following depletion of lymphocyte subsets. PBMC from week 24 were treated with Dynal magnetic beads coated with the indicated antibody to deplete $CD4^+$ or $CD8^+$ cell subsets. Cells remaining after depletion were normalized for input cell number and stimulated as described in the Example. Results are shown for two control (Subjects 2 and 3) and two vaccinated (Subjects 6 and 7) monkeys.

Whereas the rodent model has been useful in the development of a vaccine strategy, Ebola virus isolated directly from humans must first be adapted by multiple, sequential passage in rodents in order to produce a lethal infection in mice or guinea pigs (Connolly, B. M. et al. 1999 *J Infect Dis* 179:S203–S217; Bray, M. et al. 1998 *J Infect Dis* 178: 651–661). Primate models of Ebola infection are thought to have a stronger predictive value for human disease and immune protection. We therefore conducted studies in non-human primates using a bimodal DNA/ADV vaccine and the multiple plasmid strategy that correlated with protection in guinea pigs. Cynomolgus macaques (*Macaca fascicularis*) received 3 injections of naked DNA vectors at 4-week intervals (FIG. 48A) and, after several months of rest which has been shown to boost immune responses (Letvin, N. L. et al. 1997 *PNAS USA* 94:9378–9383), were boosted with recombinant adenovirus expressing only the Zaire glycoprotein (FIG. 48A). Control animals received empty vectors (plasmid DNA and ADV-ΔE1 recombinant adenovirus), and vaccinated animals received the multicomponent DNA vaccine containing NP and three subtypes of Ebola GP (pGP/NP), followed by ADV-GP(Z). As expected, anti-Ebola serum antibodies could not be detected in control animals, but in animals receiving the Ebola vaccine, an antigen-specific antibody response was detected at week 12, one month after the third DNA injection (FIG. 48B). After boosting with recombinant adenovirus, antibody titers increased 10- to 20-fold over the levels obtained with DNA alone. Three months after the final immunization, antibody levels remained high, except for one animal (subject 8) whose titer dropped slightly from $5\times10^4$ to $1.3\times10^4$.

Primate cellular responses to Ebola antigens were next examined with an in vitro lymphocyte proliferation assay. In control monkeys, antigen-specific lymphocyte proliferation, measured by $^3$H-thymidine uptake, was equivalent to that in matched, unstimulated cells, resulting in a proliferation index near 1.0 for each animal (FIG. 48C). In contrast, peripheral blood mononuclear cells (PBMC) from animals immunized with the multivalent vaccine showed 9- to 20-fold increased stimulation, demonstrating a robust immune response to Ebola antigen at the cellular level. Depletion of CD4-positive lymphocytes reduced the antigen-stimulated proliferative response of PBMC from vaccinated monkeys to the level observed in control animals (FIG. 48D). Depletion of CD8-positive lymphocytes, however, did not affect Ebola antigen-specific lymphocyte proliferation. Therefore, the CD4-positive subset of lymphocytes, which provide the T cell help required for high antibody titers, contributes to the vaccine-induced cellular immune response.

Figure 49:
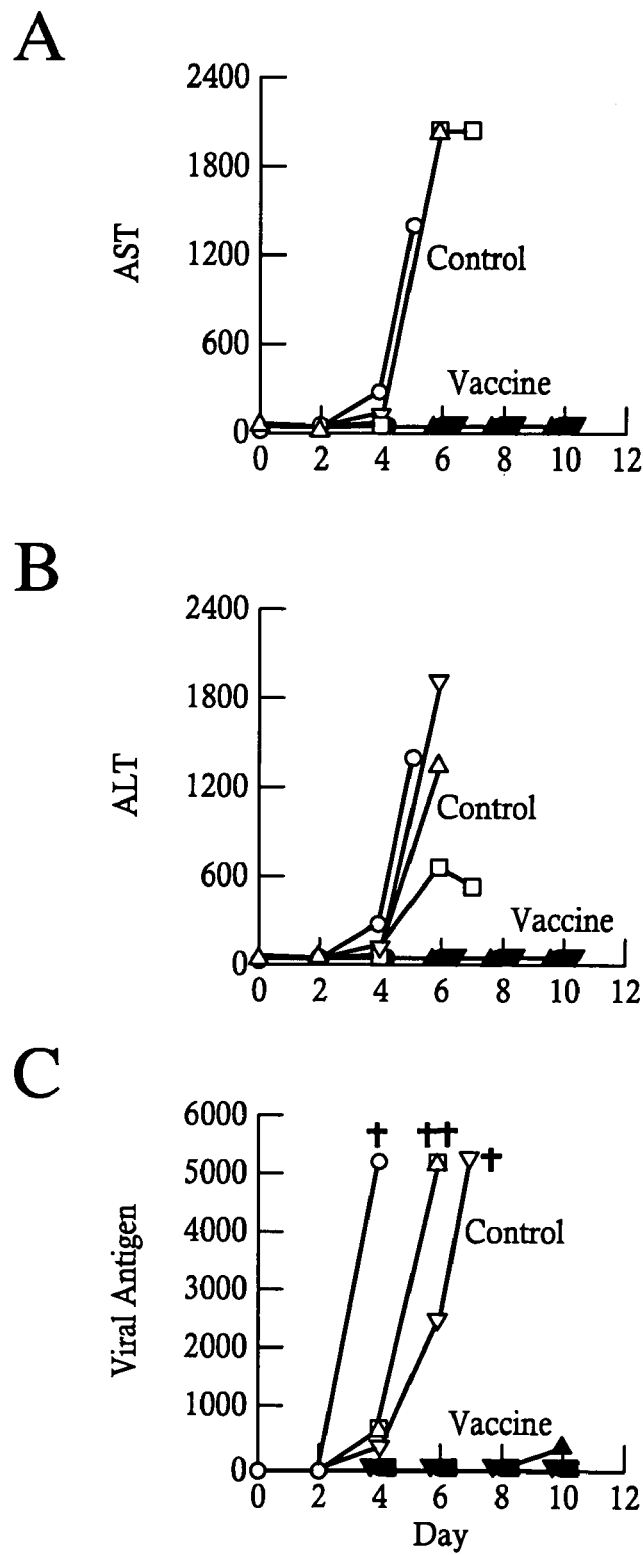
FIGS. 49(A–C) shows protection of cynomolgus macaques against lethal challenge with Ebola virus after DNA-adenovirus immunization. A, B) Hepatic enzyme levels in monkeys after challenge with Ebola virus. Liver enzymes [alanine aminotransferase (ALT) and aspartate aminotransferase (AST)] levels in the non-human primate sera were measured by standard recommended procedures using General chemistry 12 reagent disk for the Piccolo™ Analyzer (Abaxis, Inc., Sunnyvale, Calif.). Results are shown for four immunized (closed symbols) and four control (open symbols) monkeys. C) Plasma viraemia in monkeys following infection with Ebola virus. Crosses represent time of death in control animals [days 5 (subject 1) and 6 (subjects 2 and 4)]. One control animal, subject 3, was euthanized on day 7 when it was moribund. One vaccinated animal that was resistant to infection, subject 5, was euthanized on day 10 for histological examination of tissues. By day 17, none of the animals had detectable viraemia, and they remained aviraemic for the duration of the observation period (6 months). Data are the reciprocal endpoint dilution of serum for each monkey. Results are shown for four immunized (closed symbols) and four control (open symbols) monkeys.

To determine the protective efficacy of this vaccination regimen, monkeys were challenged with a lethal dose of the wild-type Mayinga strain from the Zaire subtype of Ebola virus. In the control monkeys, blood chemistry revealed an increase in hepatic enzymes (FIG. 49A, B) that is characteristic for Ebola virus infection (Fisher-Hoch, S. P. et al. 1985 *J Infect Dis* 152:887–894). No such increase was observed in vaccinated subjects. The elevation of serum alanine aminotransferase (ALT) and aspartate aminotransferase (AST) was parallel to a dramatic increase in viraemia in all of the control animals (FIG. 49C). In contrast, no substantial increase in viral load was observed in vaccinated monkeys. The kinetics of disease progression was similar among the control animals, and the disease incidence was 100% in this group. Death occurred between days 5 and 6 for 3 animals, and the last monkey, moribund, was euthanized on day 7. In contrast, 4 out of 4 monkeys immunized with the combination DNA-adenovirus vaccine survived this lethal challenge of Ebola virus, and sterilizing immunity was achieved in 3 out of 4 subjects. The remaining animal showed a small transient rise in viral antigen; however, when followed long-term, all vaccinated animals showed no signs or symptoms of infection, and there was no detectable viraemia for more than 6 months after infection, as measured by ELISA detection of viral antigen (FIG. 49A) and end point titration analysis of cultured virus. The vaccine recipient (subject 8) that exhibited a transient low level of viraemia on day 10 returned to undetectable levels by day 17.

As the natural reservoir for Ebola virus is unknown, the potential for traditional public health measures to prevent future outbreaks is limited, thus increasing the urgency for the development of a vaccine and therapeutics in humans. The present findings demonstrate that primates can be immunized against the lethal effects of Ebola virus infection, and that sterilizing immunity can be achieved using a heterologous prime-boost strategy. A multicomponent genetic vaccine expressing Ebola virus structural proteins from diverse geographic isolates generated a strong antigen-specific immune response and resulted in the survival of immunized primates after challenge with a lethal dose of Ebola Zaire, the subtype of this virus associated with the highest number of deaths in human infections. The results of this study suggest that T-cell mediated and humoral immunity contribute to virus clearance in non-human primates, consistent with previous studies in rodents (Xu, L. et al. 1998 *Nat Med* 4:37–42; Wilson, J. et al. 2000 *Science* 287:1664–1666). Two immune parameters, antibody titer (1:75,000 vs.<1:100, P=0.001) and the cellular proliferative response (~12-fold vs. 1.4-fold, P=0.0014), provided highly significant immune correlates of protection. Studies investigating the correlates of immune protection from Ebola virus infection in humans are hampered by the aggressive nature of the virus and necessarily high level of biosafety containment. With the model of primate immunity presented here, it is envisioned as now being possible to elucidate the mechanisms of immune protection from Ebola virus infection, to advance immune-based anti-viral therapies, and to develop a human vaccine for this pathogen and even other infectious causes of hemorrhagic fever.

DESCRIPTIONS OF EBOLA, MARBURG, AND LASSA CONSTRUCTS

VRC 6000  VRC6000 (pVR1012-GP(Z)).
Backbone, pVR1012 (#450) expressing Ebola Glycoprotein of Zaire Subtype. Orientation is BamHI/EcoRI/EcoRV/EcoRI/BglII)

VRC 6001  VRC6001 (pVR1012x/s-GP(Z)) No other description.
This is the same as 6000, with the addition of an Sfi restriction site to the pVR1012 backbone.

VRC 6002  VRC6002 (pVR1012-GP(Z) delta MUC).
The mucin-like domain of GP(Z) was deleted. 530 bp in the backbone, pVR1012 GP(Z) were deleted from EarI(2844) to BfaI(3374). This mutant can bind to the Ebola receptor.

VRC 6003  VRC6003 (pVR1012-GP(Z) delta MUC delta FUR).
The mucin-like domain and furin-cleavage site of CP(Z) were deleted. 593 bp in the backbone, pVR1012 GP (Z) were deleted, from EarI(2844) to EarI(3437). The protein has properties similar to pVR1012-GP(Z) delta MUC.

VRC 6004  VRC6004 (pVR1012-GP(Z) delta GP2).
A majority of the GP2 region in GP(Z) was deleted. 430 bp from the backbone, pVR1012-GP (Z) were deleted from BclI(3414) to BspEI(3844).
The TM (transmembrane) region was retained.

VRC 6005  VRC6005 (pVR1012-GP(Z) delta GP2 delta C-term A).
This is a C-terminal deletion of GP2. 267 bp were deleted from the pVR1012-GP (Z) backbone, from MscI(3623) to BspMI(3890).

VRC 6006  VRC6006 (pVR1012-GP(Z) delta GP2 delta C-term B).
This is a smaller deletion of GP2 C-terminal. 110 bp of backbone pVR1012-GP(Z) were deleted from BstXI(3780) to BspMI(3890).

VRC 6007  VRC6007 (pVR1012-GP(Z) delta GP2 delta FUS).
The fusion peptide in GP2 of GP(Z) was deleted in this mutant, using PCR. 47 bp from the backbone, pVR1012-GP(Z), was deleted from (3508–3555).

VRC 6008  VRC6008 (pVR1012-GP(Z) delta TM).
The TM region of GP(Z) was truncated in this mutant. A stop codon (TGA) was added downstream of the BspMI site (3889). This protein is secreted and doesn't form a trimer.

VRC 6052  VRC 6052 (pVR1012-GP(Z) delta sGP).
The majority of the SGP/GP homology region was deleted. 687 bp from the backbone, pVR1012-GP(Z), were deleted from HincII(2083) to HincII(2270).

VRC 6101  VRC 6101 (pVR1012x/s Ebola GP(R) (dTM)).
The vector expresses Ebola glycoprotein (subtype Reston) without its transmembrane and intracellular domains. Using PCR, a stop codon was generated downstream of a.a. 650 of GP(R), followed by an XbaI site. This protein can be secreted and is termed GP(R)(dTM).

-continued

DESCRIPTIONS OF EBOLA, MARBURG, AND LASSA CONSTRUCTS

VRC 6110  VRC 6110 (pAdApt Ebola GP(R) (dTM)).
An adenoviral shuttle vector expressing Ebola virus glycoprotein (Reston subtype) without its transmembrane and intracellular domains. Using PCR, a stop codon was generated downstream of a.a. 651 of GP(Reston), followed by an XbaI site. The resulting recombinant adenovirus expresses a 651 a.a. secreted glycoprotein termed GP(R)(dTM).

VRC 6200  VRC6200 (pVR1012-GP(S)).
Backbone, pVR1012(#450), expressing Ebola Glycoprotein of the Sudan Subtype. Orientation is EcoRI/EcoRV/BamHI/BamHI/BamHI/XbaI.

VRC 6201  VRC 6201 (pVR1012x/s Ebola GP(S)).
No other description, but this is the same as 6200 with the addition of an Sfi site to the 1012 backbone.

VRC 6202  VRC6202 (pVR1012-GP(S) delta TM).
The TM region of GP(S) was truncated in this mutant. A stop codon (TGA) was added downstream of the BspMI site(xxx). This protein is secreted and doesn't form a trimer.

VRC 6300  VRC6300 (pVR1012-GP(IC)).
Backbone, pVR1012(#450), expressing Ebola Glycoprotein of the Ivory Coast Subtype. Orientation is EcoRI/EcoRV/BamHI/BamHI/BamHI/XbaI.

VRC 6301  VRC6301 (pVR1012x/s-GP(IC)).
No other description, but this is the same as 6300 with the addition of an Sfi site to the 1012 backbone.

VRC 6302  VRC6302 (pVR1012-GP(IC) delta TM).
The TM region of GP(IC) was truncated in this mutant. A stop codon (TGA) was added downstream of the BspMI site. This protein is secreted and doesn't form a trimer.

VRC 6303  VRC 6303 (pVR1012x/s Ebola GP (IC) (dTM)).
A pVRC2000 based vector expressing Ebola glycoprotein (Ivory Coast subtype) without transmembrane and intracellular domains. Using PCR, a stop codon was generated downstream of a.a. 650, followed by a BglII site. The vector expresses a 650 a.a. secreted glycoprotein (a.a. 1–a.a. 650).

VRC 6310  VRC 6310 (pAdApt Ebola GP (IC) (dTM)).
An adenoviral shuttle vector expressing Ebola glycoprotein (subtype Ivory Coast) without its transmembrane and intracellular domains. Using PCR, a stop codon was generated downstream of a.a. 651 of GP(IC). The resulting recombinant adenovirus expresses a 651 a.a secreted glycoprotein termed as GP(IC)(dTM).

VRC 6351  VRC6351 (pVR1012x/s-sGP(IC))). No other description.

VRC 6400  VRC6400 (pVR1012-NP).
Backbone, pVR1012(#450) expressing Ebola Nucleoprotein of the Ivory Coast Subtype.

VRC 6401  VRC6401 (pVR1012x/s-NP).
No other description, but this is the same as 6400 with the addition of an Sfi site to the 1012 backbone.

VRC 6500  VRC6500 (pVR1012-VP35).
The backbone is pVR1012(#450). The insert is VP35 from Ebola cloned from pGEM 3Zf(+)VP35(#1213).

VRC 6600  VRC6600 (pAD/CMV-GP(dTM)(Z-CITE-S).
No other description.

VRC 6601  VRC6601 (pAdApt Ebola GP(S)). No other description.

VRC 6602  VRC6602 (pAdApt Ebola GP(S)(dTM)).
An adenoviral shuttle vector expressing Ebola glycoprotein (Sudan subtype) without its transmembrane and intracellular domains. A stop codon was fused downstream of a.a. 650 of GP(S). The resulting recombinant adenovirus expresses a 654 a.a. secreted glycoprotein, termed as GP(S)(dTM).

VRC 6603  VRC6603 (pAdApt Ebola GP(Z)). No other description.

VRC 6604  VRC 6604 (pAdApt Ebola GP(Z)(dTM)).
Adenoviral shuttle vector expressing Ebola glycoprotein (subtype Zaire) without its transmembrane and intracellular domains. A stop codon was fused downstream of a.a. 651 of GP(Z). The resulting recombinant adenovirus expresses a 655 a.a. secreted glycoprotein termed as GP(Z)(dTM).

VRC 6701  VRC6701 (pVR1012-Marburg).
Marburg glycoprotein (GP) open reading frame, Musoke strain. Marburg was cloned into backbone #450(Bam(blunt)/XbaI) from VRC6700 (Xba/PvuII).

-continued

DESCRIPTIONS OF EBOLA,
MARBURG, AND LASSA CONSTRUCTS

VRC 6702   VRC 6702 (pVR1012x/s Marburg GP (dTM)).
           This vector expresses the Marburg virus glycoprotein
           without its transmembrane and intracellular domains.
           Using PCR, a stop codon was generated downstream of
           a.a. 650 of GP(Marburg), followed by a BglII site.
           This protein can be secreted and termed as
           GP(Marburg)(dTM).
VRC 6710   VRC 6710 (pAdApt Marburg GP (dTM)).
           Adenoviral shuttle vector (pVRC 1290) expressing
           Marburg virus glycoprotein without transmembrane and
           intracellular domains. Using PCR, a terminator codon was
           generated downstream of a.a. 650, followed by a BglII site.
           The resulting recombinant adenovirus expresses a 650 a.a.
           secreted protein (a.a. 1–a.a. 650).
VRC 6800   VRC6800 (pVR1012x/s Lassa GP). No other description.
VRC 6801   VRC6801 (pVR1012x/s Lassa GP (dTM).
           No other description.
VRC 6810   VRC6810 (pAdApt Lassa GP). No other description.
VRC 6811   VRC6811 (pAdApt Lassa GP (dTM)). No other description.

EXAMPLE 1

Vector construction. The construction of DNA vectors expressing Ebola Zaire glycoprotein (GP), secreted GP (SGP), and nucleoprotein (NP) has been described in Xu, L. et al. 1998 *Nat Med* 4:37–42. The GP Sudan and Ivory Coast expression vectors were constructed similarly. Briefly, GP open reading frames were generated from polymerase chain reaction after reverse transcription of RNA (RT-PCR) products of infected cell RNA using the following primers: 5' ATC TTC AGG ATC TCG CCA TGG A 3' (Sudan GP gene; NcoI>ATG; SEQ ID NO: 44), 5'GAT ATT CAA CAA AGC AGC TTG CAG 3' (Sudan GP gene; C-terminus GP stop; SEQ ID NO: 45), 5' CTA ATC ACA GTC ACC ATG GGA 3' (Ivory Coast GP gene; NcoI>ATG; SEQ ID NO: 46), 5' AAA GTA TGA TGC TAT ATT AGT TCA 3' (Ivory Coast GP gene; C-terminus GP stop; SEQ ID NO: 47) yielding the TA clones PCR2.1 Sudan and PCR2.1 Ivory Coast. The Sudan glycoprotein was digested from plasmid PCR2.1 with XbaI/HindIII, Klenow treated, and cloned into the XbaI site of p1012 (Xu, L. et al. 1998 *Nat Med* 4:37–42). Ivory Coast GP was digested from plasmid PCR2.1 with EcoRI, Klenow treated, and cloned into the XbaI site of p1012 (Xu, L. et al. 1998 *Nat Med* 4:37–42).

To make ADV-GP, the BamHI/EcoRI fragment of GP(Z) was digested from pGEM-3 Zf(-)-GP, treated with Klenow, and inserted into HindIII/XbaI/Kle/CIP treated pRc/CMV plasmid. The resulting plasmid (PRC/CMV-GP(Z)) was digested by NruI/DraIII and treated with Klenow. The NruI/DraIII/Kle fragment containing the CMV enhancer, GP(Z) DNA and bovine growth hormone polyadenylation signal was inserted into the BglII site of the adenoviral shuttle plasmid pAdBglII (Ohno, T. et al. 1994 Science 265:781–784). The adenovirus, a first generation dl 309-based Ad5 vector, contained a deletion in E1 to render the vector replication-defective and a partial deletion/substitution in E3, which disrupts the coding sequences for the E3 proteins with a relative molecular mass of 14.7 kD, 14.5 kD and 10.4 kD, respectively. The recombinant adenovirus expressing Zaire GP, ADV-GP(Z), was made according to previously published methods (Aoki, K. et al. 1999 *Mol Med* 5:224–231). The dose of adenovirus administered, $10^{10}$ plaque-forming units (PFU) per animal (approximately $3 \times 10^9$ PFU/kg), is within the range used safely in human gene therapy trials.

Animal study and safety. Eight cynomolgus macaques (*Macaca fascicularis*), 3 years of age and weighing 2–3 kg, obtained from Covance (Princeton, N.J.), were used for the immunization and challenge experiment. To obtain blood specimens and administer vaccines, the monkeys were anesthetized with Ketamine. The animals were housed singly and received regular enrichment according to the Guide for the Care and Use of Laboratory Animals (DHEW No. NIH 86-23). Just before the Ebola virus challenge and up to the end of the experiment, the animals were maintained in the Maximum Containment Laboratory (BSL-4) and fed and checked daily. One animal was euthanized that appeared moribund and was subsequently necropsied for pathologic examination. In addition, a single asymptomatic vaccinated animal was euthanized for pathologic and virologic analysis.

Mouse immunization. DNA and adenovirus vectors expressing Ebola Zaire GP or NP were constructed as described previously (Xu, L. et al. 1998 *Nat Med* 4:37–42; Ohno, T. et al. 1994 *Science* 265:781–784), with gene expression under the control of the cytomegalovirus enhancer and promoter. Mice were immunized intramuscularly with 100 μg of DNA (pGP or a p1012 plasmid control) or $10^8$ PFU of adenovirus (ADV-GP or ADV-ΔE1 control virus) on days 0, 14, and 28 and blood was collected on day 28. On day 42, mice received an intramuscular boost with DNA or adenovirus and titers were re-measured on day 56. ELISA IgG titers were determined using 96-well plates coated with a preparation of Ebola virus antigen derived from purified virions and enriched for membrane-associated proteins (GP, VP40 and VP24) (Ksiazek, T. G. et al. 1992 *J Clin Microbiol* 30:947–950). Specific antigen binding was detected using a goat anti-human IgG(H+L)—horseradish peroxidase conjugate and ABTS/Peroxide (substrate/indicator).

Macaque immunization. For the DNA immunizations, animals received 1 mg each of DNA expressing GP(Zaire) [GP(Z)], GP(Ivory Coast) [pGP(IC)], GP(Sudan) [pGP(S)] and NP(Zaire) administered as a mixture [pGP/NP], or 4 mg empty [pGP(Z)] control plasmid bilaterally (2 mg per side) in the deltoid muscle. Immunization at weeks 0 and 4 were by IM injection, and at week 8 by Biojector. For the adenovirus boost, animals received $10^{10}$ PFU of ADV-GP (Zaire subtype) or ADV-ΔE1 (empty vector) divided into two doses administered bilaterally in the deltoid muscle. At week 32, all animals received an intraperitoneal injection of approximately 6 PFUs of Ebola virus (Zaire 1976 isolate; Mayinga strain) (Kiley, M. P. et al. 1980 *J Gen Virol* 49:333–341) in 1 ml Hanks' buffered salt solution. The virus was isolated directly from patient blood and used after a single passage in Vero cells.

ELISA IgG titers were determined as above for control (Plasmid: ADV-ΔE1) and immunized [pGP/NP: ADV-GP (Z)] monkeys. The reciprocal endpoint of dilution for each subject was at week 12 and week 24. Serum antibody levels were measured by ELISA as described (Ksiazek, T. G. et al. 1992 *J Clin Microbiol* 30:947–950).

Blood was collected from control (plasmid: ADV-ΔE1) or immunized [pGP/NP: ADV-GP(Z)] animals 1–3 days prior to the immunizations at weeks 4, 8 and 20, and at week 24. Blood was separated over a Percoll gradient to obtain the lymphocyte enriched population. Lymphocytes were stimulated as described (Xu, L. et al. 1998 Nat Med 4:37–42) for 5 days in vitro using supernatant from cells transfected with either Ebola secreted glycoprotein (SGP) or empty plasmid, and proliferation was measured by ³H-thymidine uptake. The proliferation index was calculated as the proliferation in wells receiving SGP divided by proliferation in wells receiving control supernatant.

Viral detection in macaques. The presence of circulating Ebola virus antigen was detected as described (Ksiazek, T. G. et al. 1992 *J Clin Microbiol* 30:947–950) by capturing VP40 protein from serial dilutions of monkey plasma. 96-well plates coated with antiVP40 mAb were used to capture antigen, and detection was with a rabbit anti-Ebola virus serum.

EXAMPLE 2

The amino acid sequences of Ebola GP(Zaire) and NP (Zaire) were obtained from Genbank: GP(Zaire), Genbank accession no. P87666; NP(Zaire), Genbank accession no. NC_002549; while GP(Sudan/Gulu) was obtained from the CDC. The amino acid sequences were then back-translated to DNA sequences using mammalian preferred codons. Serial 75 bp oligos with 25 bp overlapping were prepared to cover the entire gene. The oligos were then assembled into intact mammalian genes containing preferred codons using PCR. In the design, a stop codon was introduced in front of the predicted transmembrane domains of GP(Zaire) (a.a. 648–676) and GP (Sudan/Gulu) (a. a. 648–676) so that this region was excluded from these synthetically created genes. The deletions also led to the loss of a 4 a.a. cytoplasmic region in both constructs. Final sequencing of the Ebola GP (Zaire) sequence revealed 10 divergent amino acids from the laboratory GP sequence, which was used in our animal studies and these were corrected by site-directed mutagenesis. These inserts were cloned into p1012 x/s by XbaI/SalI.

Construction of CMV/R-GP(S/G)(ΔTM)/h

The codon-modified, transmembrane domain deleted form of the Ebola GP (Sudan/Gulu) gene was excised from p1020(x/s)-GP(S/G)(ΔTM)/h using SalI/KpnI, and inserted into the SalI/KpnI digested CMV/R/MCS plasmid.

Construction of CMV/R GP(Z) (ΔTM)/h

The codon-modified, transmembrane domain deleted form of the Ebola GP (Zaire) gene was excised from p1012 x/s-GP (Z)(dTM)/h SalI/BglII sites and cloned into the SalI/BglII sites of the CMV/R plasmid.

Construction of CMV/R Ebola NP

The NotI-KpnI fragment from VRC6400 (pVR1012-NP) expressing Ebola nucleoprotein of Zaire Subtype was excised and cloned into the NotI/KpnI sites of the CMV/R plasmid.

EXAMPLE 3

Improved Non-Viral Mammalian Expression Vector

This invention provides an improved mammalian expression vector which generates a higher level of protein expression than vectors currently in use.

Initially, 3 new vectors, each containing a different enhancer, were developed and tested. The RSV enhancer, the mouse ubiquitin enhancer (mUBB), and the CMV enhancer (Xu et al. 1998 *Nature Med.* 4:37–42) were each combined with the HTLV-1 R region (Takebe et al. 1988 *Mol Cell Biol* 8:466–472) to create separate vectors. When these 3 vectors were compared to the backbone containing the CMV enhancer in combination with the CMV translational enhancer and intron (CMVint), which is currently the most effective vector, in vitro data showed that expression with the vector containing the CMV/R was increased 5–10 fold compared to CMV/int, and immunological studies showed induction of significantly higher CD4 and CD8 T cell responses compared to CMVint. Both in vivo and in vitro responses were markedly higher with this new vector. Neither of the other two vectors produced comparable results.

The expression vector is unique in that it uses a specific translational enhancer in combination with specific enhancer/promoters to yield high levels of expression and enhanced immunogenicity for DNA vaccines. This is particularly important because the potency of these vaccines in humans is marginal and generic improvements can serve as important platforms to make the technology practical for human use. The expression vector cassettes can be used in other gene based vaccines as well, or for production of recombinant proteins from eukaryotic expression vectors. The invention is useful in the production of genetic vaccines and gene therapies for a wide variety of diseases, including HIV and other viral diseases and cancer.

FIG. 50. Enhanced Expression of Modified CMV Expression Vector, CMV/R.

Mouse fibroblast 3 T3 cells were transfected with (A) vector alone (lane 1), CMVint-gp-145(dCFI) (lane 2), CMV/R-gp145(dCFI) (lane 3) or (B) mUBB-gp145(dCFI) (lane 4), mUBB/R-gp145(dCFI) (lane 5) in 6-well tissue culture dishes with 0.5 ug of the corresponding plasmids using calcium phosphate. 24 hours after transfection, cells were harvested and lysed in lysis buffer (50 mM HEPES, 150 mM NaCl, 1% NP-40, Mini Complete protease inhibitor cocktail (Roche)). 10 μg of total protein of each sample were separated on a 4–15% gradient gel using SDS-PAGE, followed by protein transfer and Western blot analysis. Human HIV-IgG (1:5000) was used as the primary antibody, and HRP-conjugated goat anti-human IgG (1:5000) as the secondary antibody. The membrane was developed using the ECL Western blot developing system. The arrow indicates the specific band for the HIV Env gp145(ΔCFI) polyprotein.

Figure 51:
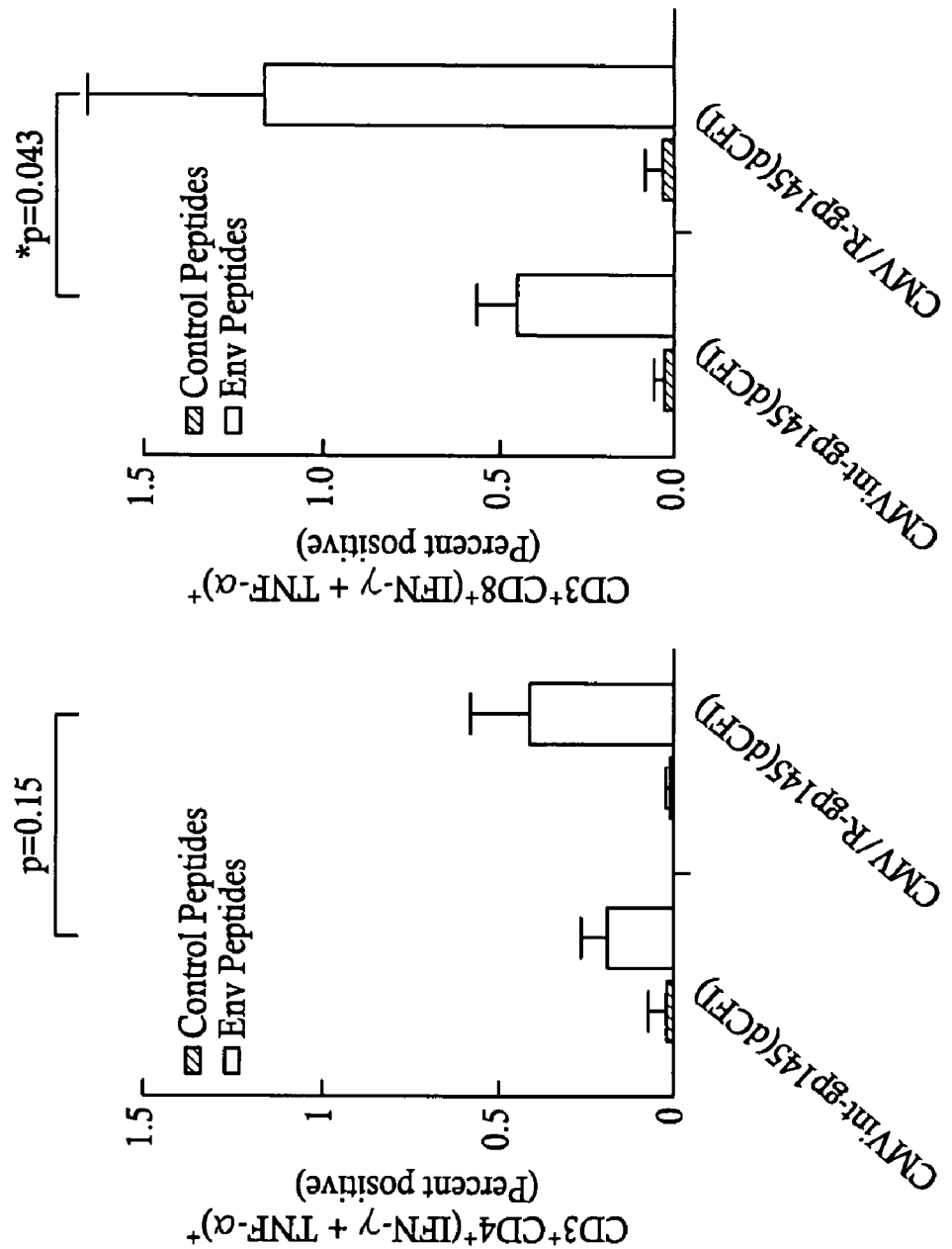
FIG. 51 shows enhanced immunogenicity of modified CMV expression vector, CMV/R, in mice.

FIG. 51. Enhanced Immunogenicity of Modified CMV Expression Vector, CMV/R, In Mice.

Five mice in each group were immunized with 50 μg of the indicated plasmid DNA at weeks 0, 2, and 6. 10 days after the last injection, splenocytes from each mouse were harvested and stimulated using a pool of control peptides (15 mer), or a pool of HIV Env peptides (15 mer) for 6 hours. The stimulated splenocytes were stained using a cocktail of antibodies containing PE-anti-mouse CD3, PerCP-anti-mouse CD4, APC-anti-mouse CD8, FITC-anti-mouse IFN-γ and FITC-anti-mouse TNF-α. The samples were analyzed by flow cytometry. CD3/CD4/IFN-γ/TNF-α and CD3/CD8/IFN-γ/TNF-α positive cell numbers were measured using FloJo software (Treestar).

The CMV Enhancer/Promoter, R Region (HTVL-1), CMV IE Splicing Acceptor sequence

CCATTGCATACGTTGTATCCATATCATAATATGTACATTTATATTGGCTCATGTCCAACAT (SEQ ID NO: 52):

TACCGCCATGTTGACATTGATTATTGACTAGTTATTAATAGTAATCAATTACGGGGTCATT

—continued

```
AGTTCATAGCCCATATATGGAGTTCCGCGTTACATAACTTACGGTAAATGGCCCGCCTGGC

TGACCGCCCAACGACCCCCGCCCATTGACGTCAATAATGACGTATGTTCCCATAGTAACGC

CAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGACGGTAAATGG

CCCGCCTGGCATTATGCCCAGTACATGACCTTATGGGACTTTCCTACTTGGCAGTACATCT

ACGTATTAGTCATCGCTATTACCATGGTGATGCGGTTTTGGCAGTACATCAATGGGCGTGG

ATAGCGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTGACGC

AAATGGGCGGTAGGCGTGTACGGTGGGAGGTCTATATAAGCAGAGCTCGTTTAGTGAACCG

TCAGATCGCCTGGAGACGCCATCCACGCTGTTTTGACCTCCATAGAAGACACCGGGACCGA

TCCAGCCTCCATCGGCTCGCATCTCTCCTTCACGCGCCCGCCGCCTTACCTGAGGCCGCCA

TCCACGCCGGTTGAGTCGCGTTCTGCCGCCTCCCGCCTGTGGTGCCTCCTGAACTACGTCC

GCCGTCTAGGTAAGTTTAGAGCTCAGGTCGAGACCGGGCCTTTGTCCGGCGCTCCCTTGGA

GCCTACCTAGACTCAGCCGGCTCTCCACGCTTTGCCTGACCCTGCTTGCTCAACTCTAGTT

AACGGTGGAGGGCAGTGTAGTCTGAGCAGTACTCGTTGCTGCCGCGCGCGCCACCAGACAT

AATAGCTGACAGACTAACAGACTGTTCCTTTCCATGGGTCTTTTCTGCAG
```

1–741: CMV Enhancer/Promoter
742–972: HTLV-1 R region
973–1095: CMV/IE Splicing Acceptor While the present invention has been described in some detail for purposes of clarity and understanding, one skilled in the art will appreciate that various changes in form and detail can be made without departing from the true scope of the invention. All figures, tables, and appendices, as well as patents, applications and publications referred to above are hereby incorporated by reference.

---

What is claimed is:

1. An expression vector comprising an enhancer with at least 95, 96, 97, 98, 99, or 100% sequence identity to SEQ ID NO: 52, wherein the enhancer mediates expression of a nucleic acid operably linked thereto.

2. The expression vector of claim 1 wherein the % identity is 95.

3. The expression vector of claim 1 wherein the % identity is 96.

4. The expression vector of claim 1 wherein the % identity is 97.

5. The expression vector of claim 1 wherein the % identity is 98.

6. The expression vector of claim 1 wherein the % identity is 99.

7. The expression vector of claim 1 wherein the % identity is 100.

* * * * *

SEQUENCE LISTING

```
<160> NUMBER OF SEQ ID NOS: 52

<210> SEQ ID NO 1
<211> LENGTH: 7154
<212> TYPE: DNA
<213> ORGANISM: Artificial Sequence
<220> FEATURE:
<223> OTHER INFORMATION: Synthetic Construct pVR1012 -GP(Z)

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
```

-continued

| | |
|---|---|
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccccttggc | 1080 |
| tcttatgcat gctatactgt ttttggcttg gggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tatttttaca | 1320 |
| ggatggggtc ccatttatta tttacaaatt cacatataca caacgccgt ccccgtgcc | 1380 |
| cgcagttttt attaaacata gcgtgggatc tccacgcgaa tctcgggtac gtgttccgga | 1440 |
| catgggctct tctccggtag cggcggagct tccacatccg agccctggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcggtagg gtatgtgtct | 1620 |
| gaaaatgagc gtggagattg ggctcgcacg gctgacgcag atggaagact taaggcagcg | 1680 |
| gcagaagaag atgcaggcag ctgagttgtt gtattctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgtcgaca cgtgtgatca gatatcgcgg ccgctctaga ccaggccctg | 1920 |
| gatcgatcca acaacacaat gggcgttaca ggaatattgc agttacctcg tgatcgattc | 1980 |
| aagaggacat cattctttct ttgggtaatt atccttttcc aaagaacatt ttccatccca | 2040 |
| cttggagtca tccacaatag cacattacag gttagtgatg tcgacaaact agtttgtcgt | 2100 |
| gacaaactgt catccacaaa tcaattgaga tcagttggac tgaatctcga agggaatgga | 2160 |
| gtggcaactg acgtgccatc tgcaactaaa agatggggct tcaggtccgg tgtcccacca | 2220 |
| aaggtggtca attatgaagc tggtgaatgg gctgaaaact gctacaatct tgaaatcaaa | 2280 |
| aaacctgacg ggagtgagtg tctaccagca gcgccagacg ggattcgggg cttccccgg | 2340 |
| tgccggtatg tgcacaaagt atcaggaacg ggaccgtgtg ccggagactt tgccttccat | 2400 |
| aaagagggtg ctttcttcct gtatgatcga cttgcttcca cagttatcta ccgaggaacg | 2460 |
| actttcgctg aaggtgtcgt tgcatttctg atactgcccc aagctaagaa ggacttcttc | 2520 |
| agctcacacc ccttgagaga gccggtcaat gcaacgagg accgtctag tggctactat | 2580 |
| tctaccacaa ttagatatca ggctaccggt tttggaacca atgagacaga gtacttgttc | 2640 |
| gaggttgaca atttgaccta cgtccaactt gaatcaagat tcacaccaca gtttctgctc | 2700 |
| cagctgaatg agacaatata tacaagtggg aaaaggagca ataccacggg aaaactaatt | 2760 |
| tggaaggtca accccgaaat tgatacaaca atcggggagt gggccttctg ggaaactaaa | 2820 |
| aaaaacctca ctagaaaaat tcgcagtgaa gagttgtctt tcacagttgt atcaaacgga | 2880 |
| gccaaaaaca tcagtggtca gagtccggcg cgaacttctt ccgacccagg gaccaacaca | 2940 |
| acaactgaag accacaaaat catggcttca gaaaattcct ctgcaatggt tcaagtgcac | 3000 |

```
agtcaaggaa gggaagctgc agtgtcgcat ctaacaaccc ttgccacaat ctccacgagt   3060
ccccaatccc tcacaaccaa accaggtccg gacaacagca cccataatac acccgtgtat   3120
aaacttgaca tctctgaggc aactcaagtt gaacaacatc accgcagaac agacaacgac   3180
agcacagcct ccgacactcc ctctgccacg accgcagccg gaccccccaaa agcagagaac   3240 accaacacga gcaagagcac tgacttcctg gaccccgcca ccacaacaag tccccaaaac   3300
cacagcgaga ccgctggcaa caacaacact catcaccaag ataccggaga agagagtgcc   3360
agcagcggga agctaggctt aattaccaat actattgctg gagtcgcagg actgatcaca   3420
ggcgggagaa gaactcgaag agaagcaatt gtcaatgctc aacccaaatg caaccctaat   3480
ttacattact ggactactca ggatgaaggt gctgcaatcg gactggcctg gataccatat   3540
ttcgggccag cagccgaggg aatttacata gaggggctaa tgcacaatca agatggttta   3600
atctgtgggt tgagacagct ggccaacgag acgactcaag ctcttcaact gttcctgaga   3660
gccacaactg agctacgcac cttttcaatc ctcaaccgta aggcaattga tttcttgctg   3720
cagcgatggg gcggcacatg ccacattctg ggaccggact gctgtatcga accacatgat   3780
tggaccaaga acataacaga caaaattgat cagattattc atgattttgt tgataaaacc   3840
cttccggacc aggggacaa tgacaattgg tggacaggat ggagacaatg gataccggca   3900
ggtattggag ttacaggcgt tgtaattgca gttatcgctt tattctgtat atgcaaattt   3960
gtcttttagt ttttcttcag attgcttcat ggaaaagctc agcctcaaat caatgaaacc   4020
aggatttaat tatatggatt acttgaatct aagattactt gacaaatgat aatataatac   4080
actggagctt taaacatagc caatgtgatt ctaactcctt taaactcaca gttaatcata   4140
aacaaggttt gaggtaccga gctcgaattg atctgctgtg ccttctagtt gccagccatc   4200
tgttgtttgc ccctcccccg tgccttcctt gaccctggaa ggtgccactc ccactgtcct   4260
ttcctaataa aatgaggaaa ttgcatcgca ttgtctgagt aggtgtcatt ctattctggg   4320
gggtggggtg gggcaggaca gcaaggggga ggattgggaa gacaatagca ggcatgctgg   4380
ggatgcggtg ggctctatgg gtacccaggt gctgaagaat tgacccggtt cctcctgggc   4440
cagaaagaag caggcacatc cccttctctg tgacacaccc tgtccacgcc cctggttctt   4500
agttccagcc ccactcatag gacactcata gctcaggagg gctccgcctt caatcccacc   4560
cgctaaagta cttggagcgg tctctcccctc cctcatcagc ccaccaaacc aaacctagcc   4620
tccaagagtg ggaagaaatt aaagcaagat aggctattaa gtgcagaggg agagaaaatg   4680
cctccaacat gtgaggaagt aatgagagaa atcatagaat ttcttccgct tcctcgctca   4740
ctgactcgct gcgctcggtc gttcggctgc ggcgagcggt atcagctcac tcaaaggcgg   4800
taatacggtt atccacagaa tcaggggata acgcaggaaa gaacatgtga gcaaaaggcc   4860
agcaaaaggc caggaaccgt aaaaaggccg cgttgctggc gttttccat aggctccgcc   4920 cccctgacga gcatcacaaa aatcgacgct caagtcagag gtggcgaaac ccgacaggac   4980
tataaagata ccaggcgttt ccccctggaa gctccctcgt gcgctctcct gttccgaccc   5040
tgccgcttac cggatacctg tccgcctttc tcccttcggg aagcgtggcg ctttctcata   5100
gctcacgctg taggtatctc agttcggtgt aggtcgttcg ctccaagctg ggctgtgtgc   5160
acgaaccccc cgttcagccc gaccgctgcg ccttatccgg taactatcgt cttgagtcca   5220
acccggtaag acacgactta tcgccactgg cagcagccac tggtaacagg attagcagag   5280
cgaggtatgt aggcggtgct acagagttct tgaagtggtg gcctaactac ggctacacta   5340
gaagaacagt atttggtatc tgcgctctgc tgaagccagt taccttcgga aaaagagttg   5400
```

-continued

```
gtagctcttg atccggcaaa caaaccaccg ctggtagcgg tggttttttt gtttgcaagc    5460
agcagattac gcgcagaaaa aaaggatctc aagaagatcc tttgatcttt tctacggggt    5520
ctgacgctca gtggaacgaa aactcacgtt aagggatttt ggtcatgaga ttatcaaaaa    5580
ggatcttcac ctagatcctt ttaaattaaa aatgaagttt aaatcaatc taaagtatat    5640 atgagtaaac ttggtctgac agttaccaat gcttaatcag tgaggcacct atctcagcga    5700
tctgtctatt tcgttcatcc atagttgcct gactcggggg ggggggcgc tgaggtctgc    5760 ctcgtgaaga aggtgttgct gactcatacc aggcctgaat cgccccatca tccagccaga    5820
aagtgaggga gccacggttg atgagagctt tgttgtaggt ggaccagttg gtgattttga    5880
acttttgctt tgccacggaa cggtctgcgt tgtcgggaag atgcgtgatc tgatccttca    5940
actcagcaaa agttcgattt attcaacaaa gccgccgtcc cgtcaagtca gcgtaatgct    6000
ctgccagtgt tacaaccaat taaccaattc tgattagaaa aactcatcga gcatcaaatg    6060
aaactgcaat ttattcatat caggattatc aataccatat ttttgaaaaa gccgtttctg    6120
taatgaagga gaaaactcac cgaggcagtt ccataggatg gcaagatcct ggtatcggtc    6180
tgcgattccg actcgtccaa catcaataca acctattaat ttccctcgt caaaaataag    6240 gttatcaagt gagaaatcac catgagtgac gactgaatcc ggtgagaatg gcaaaagctt    6300
atgcatttct ttccagactt gttcaacagg ccagccatta cgctcgtcat caaaatcact    6360
cgcatcaacc aaaccgttat tcattcgtga ttgcgcctga gcgagacgaa atacgcgatc    6420
gctgttaaaa ggacaattac aaacaggaat cgaatgcaac cggcgcagga acactgccag    6480
cgcatcaaca atattttcac ctgaatcagg atattcttct aatacctgga atgctgtttt    6540
cccggggatc gcagtggtga gtaaccatgc atcatcagga gtacggataa aatgcttgat    6600
ggtcggaaga ggcataaatt ccgtcagcca gtttagtctg accatctcat ctgtaacatc    6660
attggcaacg ctacctttgc catgtttcag aaacaactct ggcgcatcgg gcttcccata    6720
caatcgatag attgtcgcac ctgattgccc gacattatcg cgagcccatt tatacccata    6780
taaatcagca tccatgttgg aatttaatcg cggcctcgag caagacgttt cccgttgaat    6840
atggctcata acacccccttg tattactgtt tatgtaagca gacagttta ttgttcatga    6900 tgatatattt ttatcttgtg caatgtaaca tcagagattt tgagacacaa cgtggctttc    6960
cccccccccc cattattgaa gcatttatca gggttattgt ctcatgagcg gatacatatt    7020
tgaatgtatt tagaaaaata acaaataggg gttccgcgc acatttcccc gaaaagtgcc    7080
acctgacgtc taagaaacca ttattatcat gacattaacc tataaaaata ggcgtatcac    7140
gaggcccttt cgtc                                                     7154
```

<210> SEQ ID NO 2
<211> LENGTH: 7188
<212> TYPE: DNA
<213> ORGANISM: Artificial Sequence
<220> FEATURE:
<223> OTHER INFORMATION: Synthetic Construct pVR1012x/s Ebola GP(Z)

<400> SEQUENCE: 2

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
```

| | |
|---|---|
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgaccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg aacgcggat | 1020 |
| tccccgtgcc aagagtgacg taagtaccgc ctatagactc tataggcaca cccctttggc | 1080 |
| tcttatgcat gctatactgt ttttggcttg gggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tatttttaca | 1320 |
| ggatggggtc ccatttatta tttacaaatt cacatataca acaacgccgt cccccgtgcc | 1380 |
| cgcagttttt attaaacata gcgtgggatc tccacgcgaa tctcgggtac gtgttccgga | 1440 |
| catgggctct tctccggtag cggcggagct tccacatccg agccctggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcgtagg gtatgtgtct | 1620 |
| gaaaatgagc gtggagattg ggctcgcacg gctgacgcag atggaagact taaggcagcg | 1680 |
| gcagaagaag atgcaggcag ctgagttgtt gtattctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgtcgaca cgtgtgatca gatatcgcgg ccgctctaga ccaggccctg | 1920 |
| gatcgatcca acaacacaat gggcgttaca ggaatattgc agttacctcg tgatcgattc | 1980 |
| aagaggacat cattctttct ttgggtaatt atccttttcc aaagaacatt ttccatccca | 2040 |
| cttggagtca tccacaatag cacattacag gttagtgatg tcgacaaact agtttgtcgt | 2100 |
| gacaaactgt catccacaaa tcaattgaga tcagttggac tgaatctcga agggaatgga | 2160 |
| gtggcaactg acgtgccatc tgcaactaaa agatggggct tcaggtccgg tgtcccacca | 2220 |
| aaggtggtca attatgaagc tggtgaatgg gctgaaaact gctacaatct tgaaatcaaa | 2280 |
| aaacctgacg ggagtgagtg tctaccagca gcgccagacg ggattcgggg cttccccgg | 2340 |
| tgccggtatg tgcacaaagt atcaggaacg ggaccgtgtg ccggagactt tgccttccat | 2400 |
| aaagagggtg ctttcttcct gtatgatcga cttgcttcca cagttatcta ccgaggaacg | 2460 |
| actttcgctg aaggtgtcgt tgcatttctg tatactgcccc aagctaagaa ggacttcttc | 2520 |
| agctcacacc ccttgagaga gccggtcaat gcaacggagg accgtctag tggctactat | 2580 |
| tctaccacaa ttagatatca ggctaccgt tttggaacca atgagacaga gtacttgttc | 2640 |
| gaggttgaca atttgaccta cgtccaactt gaatcaagat tcacaccaca gtttctgctc | 2700 |

```
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg accccccaaa agcagagaac    3240
accaacacga gcaagagcac tgacttcctg gaccccgcca ccacaacaag tccccaaaac    3300
cacagcgaga ccgctggcaa caacaacact catcaccaag ataccggaga gagagtgcc     3360 agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540 tcgggccag cagccgaggg aatttacata gagggctaa tgcacaatca agatggttta     3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgat    3780
tggaccaaga acataacaga caaaattgat cagattattc atgattttgt tgataaaacc    3840
cttccggacc aggggacaa tgacaattgg tggacaggat ggagacaatg gataccggca     3900
ggtattggag ttacaggcgt tgtaattgca gttatcgctt tattctgtat atgcaaattt    3960 gtctttagt ttttcttcag attgcttcat ggaaaagctc agcctcaaat caatgaaacc     4020
aggatttaat tatatggatt acttgaatct aagattactt gacaaatgat aatataatac    4080
actggagctt taaacatagc caatgtgatt ctaactcctt taaactcaca gttaatcata    4140
aacaaggttt gaggtaccga gctcgaattg atctgctgtg ccttctagtt gccagccatc    4200
tgttgtttgc ccctcccccg tgccttcctt gaccctggaa ggtgccactc ccactgtcct    4260
ttcctaataa aatgaggaaa ttgcatcgca ttgtctgagt aggtgtcatt ctattctggg    4320
gggtggggtg gggcaggaca gcaaggggga ggattgggaa gacaatagca ggcatgctgg    4380
ggatgcggtg ggctctatgg gtacccaggt gctgaagaat tgacccggtt cctcctgggc    4440
cagaaagaag caggcacatc cccttctctg tgacacaccc tgtccacgcc cctggttctt    4500
agttccagcc ccactcatag gacactcata gctcaggagg gctccgcctt caatcccacc    4560
cgctaaagta cttggagcgg tctctcccct cctcatcagc ccaccaaacc aaacctagcc    4620
tccaagagtg ggaagaaatt aaagcaagat aggctattaa gtgcagaggg agagaaaatg    4680
cctccaacat gtgaggaagt aatgagagaa atcatagaat tttaaggcca tgatttaagg    4740
ccatcatggc cttaatcttc cgcttcctcg ctcactgact cgctgcgctc ggtcgttcgg    4800
ctgcggcgag cggtatcagc tcactcaaag gcggtaatac ggttatccac agaatcaggg    4860
gataacgcag gaaagaacat gtgagcaaaa ggccagcaaa aggccaggaa ccgtaaaaag    4920
gccgcgttgc tggcgttttt ccataggctc cgcccccctg acgagcatca caaaaatcga    4980
cgctcaagtc agaggtggcg aaacccgaca ggactataaa gataccaggc gtttccccct    5040
ggaagctccc tcgtgcgctc tcctgttccg accctgccgc ttaccggata cctgtccgcc    5100
```

```
tttctccctt cgggaagcgt ggcgctttct catagctcac gctgtaggta tctcagttcg    5160
gtgtaggtcg ttcgctccaa gctgggctgt gtgcacgaac ccccgttca gcccgaccgc     5220 tgcgccttat ccgtaacta tcgtcttgag tccaacccgg taagacacga cttatcgcca     5280
ctggcagcag ccactggtaa caggattagc agagcgaggt atgtaggcgg tgctacagag    5340
ttcttgaagt ggtggcctaa ctacggctac actagaagaa cagtatttgg tatctgcgct    5400
ctgctgaagc cagttacctt cggaaaaaga gttggtagct cttgatccgg caaacaaacc    5460
accgctggta gcggtggttt ttttgtttgc aagcagcaga ttacgcgcag aaaaaaagga    5520
tctcaagaag atcctttgat cttttctacg ggtctgacg ctcagtggaa cgaaaactca     5580
cgttaaggga ttttggtcat gagattatca aaaggatct caccctagat cctttttaaat    5640 taaaaatgaa gttttaaatc aatctaaagt atatatgagt aaacttggtc tgacagttac    5700
caatgcttaa tcagtgaggc acctatctca gcgatctgtc tatttcgttc atccatagtt    5760
gcctgactcg ggggggggg gcgctgaggt ctgcctcgtg aagaaggtgt tgctgactca     5820
taccaggcct gaatcgcccc atcatccagc cagaaagtga gggagccacg gttgatgaga    5880
gctttgttgt aggtggacca gttggtgatt ttgaactttt gctttgccac ggaacggtct    5940
gcgttgtcgg gaagatgcgt gatctgatcc ttcaactcag caaaagttcg atttattcaa    6000
caaagccgcc gtcccgtcaa gtcagcgtaa tgctctgcca gtgttacaac caattaacca    6060
attctgatta gaaaaactca tcgagcatca atgaaactg caatttattc atatcaggat     6120
tatcaataca atattttga aaagccgtt tctgtaatga aggagaaaac tcaccgaggc      6180
agttccatag gatggcaaga tcctggtatc ggtctgcgat tccgactcgt ccaacatcaa    6240
tacaacctat taatttcccc tcgtcaaaaa taaggttatc aagtgagaaa tcaccatgag    6300
tgacgactga atccggtgag aatggcaaaa gcttatgcat ttctttccag acttgttcaa    6360
caggccagcc attacgctcg tcatcaaaat cactcgcatc aaccaaaccg ttattcattc    6420
gtgattgcgc ctgagcgaga cgaaatacgc gatcgctgtt aaaaggacaa ttacaaacag    6480
gaatcgaatg caaccggcgc aggaacactg ccagcgcatc aacaatattt tcacctgaat    6540
caggatattc ttctaatacc tggaatgctg ttttcccggg gatcgcagtg gtgagtaacc    6600
atgcatcatc aggagtacgg ataaaatgct tgatggtcgg aagaggcata aattccgtca    6660
gccagtttag tctgaccatc tcatctgtaa catcattggc aacgctacct ttgccatgtt    6720
tcagaaacaa ctctggcgca tcgggcttcc catacaatcg atagattgtc gcacctgatt    6780
gcccgacatt atcgcgagcc catttatacc catataaatc agcatccatg ttggaattta    6840
atcgcggcct cgagcaagac gtttcccgtt gaatatggct cataacaccc cttgtattac    6900
tgtttatgta agcagacagt tttattgttc atgatgatat atttttatct gtgcaatgt     6960 aacatcagag attttgagac acaacgtggc tttccccccc ccccattat tgaagcattt     7020 atcagggtta ttgtctcatg agcggataca tatttgaatt tatttagaaa aataaacaaa    7080 tagggggttcc gcgcacattt ccccgaaaag tgccacctga cgtctaagaa accattatta   7140
tcatgacatt aacctataaa aataggcgta tcacgaggcc ctttcgtc                 7188
```

<210> SEQ ID NO 3  
<211> LENGTH: 6624  
<212> TYPE: DNA  
<213> ORGANISM: Artificial Sequence  
<220> FEATURE:  
<223> OTHER INFORMATION: Synthetic Construct pVR1012-GP(Z) delta MUC -continued

```
<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgaccccg cccattgacg tcaataatga cgtatgttcc      480
catagtaacg ccaataggga ctttccattg acgtcaatgg gtggagtatt tacgtaaac      540 tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960 tagaagacac cgggaccgat ccagcctccg cggccgggaa cggtgcattg gaacgcggat    1020
tccccgtgcc aagagtgacg taagtaccgc ctatagactc tataggcaca ccccttggc    1080 tcttatgcat gctatactgt ttttggcttg gggcctatac cccccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320 ggatggggtc ccatttatta tttacaaatt cacatataca caacgccgt cccccgtgcc    1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatggggct tcaggtccgg tgtcccacca    2220
aaggtggtca attatgaagc tggtgaatgg gctgaaaact gctacaatct tgaaatcaaa    2280
aaacctgacg ggagtgagtg tctaccagca gcgccagacg ggattcgggg cttcccccgg    2340
```

-continued

```
tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg tatactgccc aagctaagaa ggacttcttc   2520
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcgtaggctt aattaccaat actattgctg gagtcgcagg   2880
actgatcaca ggcgggagaa gaactcgaag agaagcaatt gtcaatgctc aacccaaatg   2940
caaccctaat ttacattact ggactactca ggatgaaggt gctgcaatcg gactggcctg   3000
gataccatat ttcgggccag cagccgaggg aatttacata gagggctaa tgcacaatca   3060 agatggttta atctgtgggt tgagacagct ggccaacgag acgactcaag ctcttcaact   3120
gttcctgaga gccacaactg agctacgcac cttttcaatc ctcaaccgta aggcaattga   3180
tttcttgctg cagcgatggg gcggcacatg ccacattctg ggaccggact gctgtatcga   3240
accacatgat tggaccaaga acataacaga caaaattgat cagattattc atgattttgt   3300
tgataaaacc cttccggacc aggggacaa tgacaattgg tggacaggat ggagacaatg   3360
gataccggca gtattggag ttacaggcgt tgtaattgca gttatcgctt tattctgtat   3420
atgcaaattt gtctttttagt ttttcttcag attgcttcat ggaaaagctc agcctcaaat   3480
caatgaaacc aggatttaat tatatggatt acttgaatct aagattactt gacaaatgat   3540
aatataatac actggagctt taaacatagc caatgtgatt ctaactcctt taaactcaca   3600
gttaatcata aacaaggttt gaggtaccga gctcgaattg atctgctgtg ccttctagtt   3660
gccagccatc tgttgtttgc ccctcccccg tgccttcctt gaccctggaa ggtgccactc   3720
ccactgtcct ttcctaataa aatgaggaaa ttgcatcgca ttgtctgagt aggtgtcatt   3780
ctattctggg gggtggggtg gggcaggaca gcaaggggga ggattgggaa gacaatagca   3840
ggcatgctgg ggatgcggtg ggctctatgg gtacccaggt gctgaagaat tgacccggtt   3900
cctcctgggc cagaaagaag caggcacatc cccttctctg tgacacaccc tgtccacgcc   3960
cctggttctt agttccagcc ccactcatag gacactcata gctcaggagg gctccgcctt   4020
caatcccacc cgctaaagta cttggagcgg tctctccctc cctcatcagc ccaccaaacc   4080
aaacctagcc tccaagagtg ggaagaaatt aaagcaagat aggctattaa gtgcagaggg   4140
agagaaaatg cctccaacat gtgaggaagt aatgagagaa atcatagaat tcttccgct   4200 tcctcgctca ctgactcgct gcgctcggtc gttcggctgc ggcgagcggt atcagctcac   4260
tcaaaggcgg taatacggtt atccacagaa tcaggggata cgcaggaaa gaacatgtga   4320 gcaaaaggcc agcaaaggc caggaaccgt aaaaaggccg cgttgctggc gtttttccat   4380
aggctccgcc cccctgacga gcatcacaaa aatcgacgct caagtcagag gtggcgaaac   4440
ccgacaggac tataaagata ccaggcgttt ccccctggaa gctccctcgt gcgctctcct   4500
gttccgaccc tgccgcttac cggatacctg tccgccttc tcccttcggg aagcgtggcg   4560
ctttctcata gctcacgctg taggtatctc agttcggtgt aggtcgttcg ctccaagctg   4620
ggctgtgtgc acgaaccccc cgttcagccc gaccgctgcg ccttatccgg taactatcgt   4680
cttgagtcca acccggtaag acacgactta tcgccactgg cagcagccac tggtaacagg   4740
```

```
attagcagag cgaggtatgt aggcggtgct acagagttct tgaagtggtg gcctaactac    4800
ggctacacta agaacagt atttggtatc tgcgctctgc tgaagccagt taccttcgga    4860
aaaagagttg gtagctcttg atccggcaaa caaaccaccg ctggtagcgg tggttttttt    4920
gtttgcaagc agcagattac gcgcagaaaa aaaggatctc aagaagatcc tttgatcttt    4980 tctacgggt ctgacgctca gtggaacgaa aactcacgtt aagggatttt ggtcatgaga    5040
ttatcaaaaa ggatcttcac ctagatcctt ttaaattaaa aatgaagttt taaatcaatc    5100
taaagtatat atgagtaaac ttggtctgac agttaccaat gcttaatcag tgaggcacct    5160
atctcagcga tctgtctatt tcgttcatcc atagttgcct gactcggggg ggggggggcgc    5220 tgaggtctgc ctcgtgaaga aggtgttgct gactcatacc aggcctgaat cgccccatca    5280
tccagccaga aagtgaggga gccacggttg atgagagctt gttgtaggt ggaccagttg    5340 gtgattttga acttttgctt tgccacggaa cggtctgcgt tgtcgggaag atgcgtgatc    5400
tgatccttca actcagcaaa agttcgattt attcaacaaa gccgccgtcc cgtcaagtca    5460
gcgtaatgct ctgccagtgt tacaaccaat taaccaattc tgattagaaa aactcatcga    5520
gcatcaaatg aaactgcaat ttattcatat caggattatc aataccatat ttttgaaaaa    5580
gccgtttctg taatgaagga gaaaactcac cgaggcagtt ccataggatg caagatcct    5640 ggtatcggtc tgcgattccg actcgtccaa catcaataca acctattaat ttcccctcgt    5700
caaaaataag gttatcaagt gagaaatcac catgagtgac gactgaatcc ggtgagaatg    5760
gcaaaagctt atgcatttct ttccagactt gttcaacagg ccagccatta cgctcgtcat    5820
caaaatcact cgcatcaacc aaaccgttat tcattcgtga ttgcgcctga gcgagacgaa    5880
atacgcgatc gctgttaaaa ggacaattac aaacaggaat cgaatgcaac cggcgcagga    5940
acactgccag cgcatcaaca atattttcac ctgaatcagg atattcttct aatacctgga    6000
atgctgtttt cccggggatc gcagtggtga gtaaccatgc atcatcagga gtacggataa    6060
aatgcttgat ggtcggaaga ggcataaatt ccgtcagcca gtttagtctg accatctcat    6120
ctgtaacatc attggcaacg ctacctttgc catgtttcag aaacaactct ggcgcatcgg    6180
gcttcccata caatcgatag attgtcgcac ctgattgccc gacattatcg cgagcccatt    6240
tatacccata taaatcagca tccatgttgg aatttaatcg cggcctcgag caagacgttt    6300
cccgttgaat atggctcata caccccttg tattactgtt tatgtaagca gacagttta    6360 ttgttcatga tgatatattt ttatcttgtg caatgtaaca tcagagattt tgagacacaa    6420
cgtggctttc ccccccccc cattattgaa gcatttatca gggttattgt ctcatgagcg    6480
gatacatatt tgaatgtatt tagaaaaata acaaatagg ggttccgcgc acatttcccc    6540
gaaaagtgcc acctgacgtc taagaaacca ttattatcat gacattaacc tataaaaata    6600
ggcgtatcac gaggcccttt cgtc                                          6624
```

<210> SEQ ID NO 4
<211> LENGTH: 6561
<212> TYPE: DNA
<213> ORGANISM: Artificial Sequence
<220> FEATURE:
<223> OTHER INFORMATION: Synthetic Construct pVR1012-GP(Z) deltaMUC
    delta FUR

<400> SEQUENCE: 4

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
```

| | |
|---|---|
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgaccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg aacgcggat | 1020 |
| tccccgtgcc aagagtgacg taagtaccgc ctatagactc tataggcaca ccctttggc | 1080 |
| tcttatgcat gctatactgt ttttggcttg gggcctatac acccccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tatttttaca | 1320 |
| ggatggggtc ccatttatta tttacaaatt cacatataca acaacgccgt ccccgtgcc | 1380 |
| cgcagttttt attaaacata gcgtgggatc tccacgcgaa tctcgggtac gtgttccgga | 1440 |
| catgggctct tctccggtag cggcggagct tccacatccg agccctggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcggtagg gtatgtgtct | 1620 |
| gaaaatgagc gtggagattg ggctcgcacg gctgacgcag atggaagact taaggcagcg | 1680 |
| gcagaagaag atgcaggcag ctgagttgtt gtattctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgtcgaca cgtgtgatca gatatcgcgg ccgctctaga ccaggccctg | 1920 |
| gatcgatcca acaacacaat gggcgttaca ggaatattgc agttacctcg tgatcgattc | 1980 |
| aagaggacat cattctttct ttgggtaatt atccttttcc aaagaacatt ttccatccca | 2040 |
| cttggagtca tccacaatag cacattacag gttagtgatg tcgacaaact agtttgtcgt | 2100 |
| gacaaactgt catccacaaa tcaattgaga tcagttggac tgaatctcga agggaatgga | 2160 |
| gtggcaactg acgtgccatc tgcaactaaa agatggggct tcaggtccgg tgtcccacca | 2220 |
| aaggtggtca attatgaagc tggtgaatgg gctgaaaact gctacaatct tgaaatcaaa | 2280 |
| aaacctgacg ggagtgagtg tctaccagca gcgccagacg ggattcgggg cttccccgg | 2340 |
| tgccggtatg tgcacaaagt atcaggaacg ggaccgtgtg ccggagactt tgccttccat | 2400 |
| aaagagggtc ctttcttcct gtatgatcga cttgcttcca cagttatcta ccgaggaacg | 2460 |
| actttcgctg aaggtgtcgt tgcatttctg atactgcccc aagctaagaa ggacttcttc | 2520 |

```
agctcacacc ccttgagaga gccggtcaat gcaacggagg acccgtctag tggctactat   2580
tctaccacaa ttagatatca ggctaccggt tttggaacca atgagacaga gtacttgttc   2640
gaggttgaca atttgaccta cgtccaactt gaatcaagat tcacaccaca gtttctgctc   2700
cagctgaatg agacaatata tacaagtggg aaaaggagca ataccacggg aaaactaatt   2760
tggaaggtca accccgaaat tgatacaaca atcggggagt gggccttctg ggaaactaaa   2820
aaaaacctca ctagaaaaat tcggaagaga agcaattgtc aatgctcaac ccaaatgcaa   2880
ccctaattta cattactgga ctactcagga tgaaggtgct gcaatcggac tggcctggat   2940
accatatttc gggccagcag ccgagggaat ttacatagag gggctaatgc acaatcaaga   3000
tggtttaatc tgtgggttga cagagctggc caacgagacg actcaagctc ttcaactgtt   3060
cctgagagcc acaactgagc tacgcacctt ttcaatcctc aaccgtaagg caattgattt   3120
cttgctgcag cgatggggcg gcacatgcca cattctggga ccggactgct gtatcgaacc   3180
acatgattgg accaagaaca taacagacaa aattgatcag attattcatg attttgttga   3240
taaaacccct ccggaccagg gggacaatga caattggtgg acaggatgga gacaatggat   3300
accggcaggt attggagtta caggcgttgt aattgcagtt atcgctttat tctgtatatg   3360
caaatttgtc ttttagtttt tcttcagatt gcttcatgga aaagctcagc ctcaaatcaa   3420
tgaaaccagg atttaattat atggattact tgaatctaag attacttgac aaatgataat   3480
ataatacact ggagctttaa acatagccaa tgtgattcta actcctttaa actcacagtt   3540
aatcataaac aaggtttgag gtaccgagct cgaattgatc tgctgtgcct tctagttgcc   3600
agccatctgt tgtttgcccc tcccccgtgc cttccttgac cctggaaggt gccactccca   3660 ctgtccttc ctaataaaat gaggaaattg catcgcattg tctgagtagg tgtcattcta   3720
ttctgggggg tgggtgggg caggacagca aggggggagga ttgggaagac aatagcaggc   3780
atgctgggga tgcggtgggc tctatgggta cccaggtgct gaagaattga cccggttcct   3840
cctgggccag aaagaagcag gcacatcccc ttctctgtga cacaccctgt ccacgcccct   3900
ggttcttagt tccagccca ctcataggac actcatagct caggagggct ccgccttcaa   3960
tcccacccgc taaagtactt ggagcggtct ctccctccct catcagccca ccaaaccaaa   4020
cctagcctcc aagagtggga agaaattaaa gcaagatagg ctattaagtg cagagggaga   4080
gaaaatgcct ccaacatgtg aggaagtaat gagagaaatc atagaatttc ttccgcttcc   4140
tcgctcactg actcgctgcg ctcggtcgtt cggctgcggc gagcggtatc agctcactca   4200
aaggcggtaa tacggttatc cacagaatca ggggataacg caggaaagaa catgtgagca   4260
aaaggccagc aaaaggccag gaaccgtaaa aaggccgcgt tgctggcgtt tttccatagg   4320
ctccgccccc ctgacgagca tcacaaaaat cgacgctcaa gtcagaggtg gcgaaacccg   4380
acaggactat aaagatacca ggcgtttccc cctggaagct ccctcgtgcg ctctcctgtt   4440
ccgaccctgc cgcttaccgg atacctgtcc gcctttctcc cttcgggaag cgtggcgctt   4500
tctcatagct cacgctgtag gtatctcagt tcggtgtagg tcgttcgctc caagctgggc   4560
tgtgtgcacg aaccccccgt tcagcccgac cgctgcgcct tatccggtaa ctatcgtctt   4620
gagtccaacc cggtaagaca cgacttatcg ccactggcag cagccactgg taacaggatt   4680
agcagagcga ggtatgtagg cggtgctaca gagttcttga agtggtggcc taactacggc   4740
tacactagaa gaacagtatt tggtatctgc gctctgctga agccagttac cttcggaaaa   4800
agagttggta gctcttgatc cggcaaacaa accaccgctg gtagcggtgg ttttttttgtt   4860 tgcaagcagc agattacgcg cagaaaaaaa ggatctcaag aagatccttt gatcttttct   4920
```

-continued

```
acggggtctg acgctcagtg gaacgaaaac tcacgttaag ggattttggt catgagatta   4980
tcaaaaagga tcttcaccta gatcctttta aattaaaaat gaagttttaa atcaatctaa   5040
agtatatatg agtaaacttg gtctgacagt taccaatgct taatcagtga ggcacctatc   5100
tcagcgatct gtctatttcg ttcatccata gttgcctgac tcgggggggg ggggcgctga   5160
ggtctgcctc gtgaagaagg tgttgctgac tcataccagg cctgaatcgc cccatcatcc   5220
agccagaaag tgagggagcc acggttgatg agagctttgt tgtaggtgga ccagttggtg   5280
attttgaact tttgctttgc cacggaacgg tctgcgttgt cgggaagatg cgtgatctga   5340
tccttcaact cagcaaaagt tcgatttatt caacaaagcc gccgtcccgt caagtcagcg   5400
taatgctctg ccagtgttac aaccaattaa ccaattctga ttagaaaaac tcatcgagca   5460
tcaaatgaaa ctgcaattta ttcatatcag gattatcaat accatatttt tgaaaaagcc   5520
gtttctgtaa tgaaggagaa aactcaccga ggcagttcca taggatggca agatcctggt   5580
atcggtctgc gattccgact cgtccaacat caatacaacc tattaatttc ccctcgtcaa   5640
aaataaggtt atcaagtgag aaatcaccat gagtgacgac tgaatccggt gagaatggca   5700
aaagcttatg catttctttc cagacttgtt caacaggcca gccattacgc tcgtcatcaa   5760
aatcactcgc atcaaccaaa ccgttattca ttcgtgattg cgcctgagcg agacgaaata   5820
cgcgatcgct gttaaaagga caattacaaa caggaatcga atgcaaccgg cgcaggaaca   5880
ctgccagcgc atcaacaata ttttcacctg aatcaggata ttcttctaat acctggaatg   5940
ctgttttccc ggggatcgca gtggtgagta accatgcatc atcaggagta cggataaaat   6000
gcttgatggt cggaagaggc ataaattccg tcagccagtt tagtctgacc atctcatctg   6060
taacatcatt ggcaacgcta cctttgccat gtttcagaaa caactctggc gcatcgggct   6120
tcccatacaa tcgatagatt gtcgcacctg attgcccgac attatcgcga gcccatttat   6180
acccatataa atcagcatcc atgttggaat ttaatcgcgg cctcgagcaa gacgtttccc   6240
gttgaatatg gctcataaca ccccttgtat tactgtttat gtaagcagac agttttattg   6300
ttcatgatga tatattttta tcttgtgcaa tgtaacatca gagattttga gacacaacgt   6360
ggctttcccc ccccccccat tattgaagca tttatcaggg ttattgtctc atgagcggat   6420
acatatttga atgtatttag aaaaataaac aaataggggt tccgcgcaca tttccccgaa   6480
aagtgccacc tgacgtctaa gaaaccatta ttatcatgac attaacctat aaaaataggc   6540
gtatcacgag gccctttcgt c                                             6561
```

<210> SEQ ID NO 5
<211> LENGTH: 6724
<212> TYPE: DNA
<213> ORGANISM: Artificial Sequence
<220> FEATURE:
<223> OTHER INFORMATION: Synthetic Construct pVR1012-GP(Z) delta GP2

<400> SEQUENCE: 5

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
```

```
cccgcctggc tgaccgccca acgaccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgccccta ttgacgtcaa      600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg gaacgcggat     1020
tccccgtgcc aagagtgacg taagtaccgc ctatagactc tataggcaca ccctttggc     1080
tcttatgcat gctatactgt ttttggcttg gggcctatac cccccgctt ccttatgcta     1140
taggtgatgg tatagcttag cctataggtg tgggttattg accattattg accactcccc     1200
tattggtgac gatactttcc attactaatc cataacatgg ctctttgcca caactatctc     1260
tattggctat atgccaatac tctgtccttc agagactgac acggactctg tattttaca     1320
ggatggggtc ccatttatta tttacaaatt cacatataca acaacgccgt ccccgtgcc     1380
cgcagttttt attaaacata gcgtgggatc tccacgcgaa tctcgggtac gtgttccgga     1440
catgggctct tctccggtag cggcggagct tccacatccg agccctggtc ccatgcctcc     1500
agcggctcat ggtcgctcgg cagctccttg ctcctaacag tggaggccag acttaggcac     1560
agcacaatgc ccaccaccac cagtgtgccg cacaaggccg tggcggtagg gtatgtgtct     1620
gaaaatgagc gtggagattg ggctcgcacg gctgacgcag atggaagact taaggcagcg     1680
gcagaagaag atgcaggcag ctgagttgtt gtattctgat aagagtcaga ggtaactccc     1740
gttgcggtgc tgttaacggt ggagggcagt gtagtctgag cagtactcgt tgctgccgcg     1800
cgcgccacca gacataatag ctgacagact aacagactgt tcctttccat gggtcttttc     1860
tgcagtcacc gtcgtcgaca cgtgtgatca gatatcgcgg ccgctctaga ccaggccctg     1920
gatcgatcca acaacacaat gggcgttaca ggaatattgc agttacctcg tgatcgattc     1980
aagaggacat cattctttct ttgggtaatt atccttttcc aaagaacatt ttccatccca     2040
cttggagtca tccacaatag cacattacag gttagtgatg tcgacaaact agtttgtcgt     2100
gacaaactgt catccacaaa tcaattgaga tcagttggac tgaatctcga agggaatgga     2160
gtggcaactg acgtgccatc tgcaactaaa agatggggct tcaggtccgg tgtcccacca     2220
aagtggtca attatgaagc tggtgaatgg gctgaaaact gctacaatct tgaaatcaaa     2280
aaacctgacg ggagtgagtg tctaccagca gcgccagacg ggattcgggg cttccccgg     2340
tgccggtatg tgcacaaagt atcaggaacg ggaccgtgtg ccgagacttg tgccttccat     2400
aaagagggtg ctttcttcct gtatgatcga cttgcttcca cagttatcta ccgaggaacg     2460
actttcgctg aagtgtcgt tgcatttctg tatactgcccc aagctaagaa ggacttcttc     2520
agctcacacc ccttgagaga gccggtcaat gcaacggagg accgtctag tggctactat     2580
tctaccacaa ttagatatca ggctaccggt tttggaacca atgagacaga gtacttgttc     2640
gaggttgaca atttgaccta cgtccaactt gaatcaagat tcacaccaca gtttctgctc     2700
cagctgaatg agacaatata tacaagtggg aaaaggagca ataccacggg aaaactaatt     2760
tggaaggtca accccgaaat tgatacaaca atcggggagt gggccttctg ggaaactaaa     2820
```

-continued

| | |
|---|---|
| aaaaacctca ctagaaaaat tcgcagtgaa gagttgtctt tcacagttgt atcaaacgga | 2880 |
| gccaaaaaca tcagtggtca gagtccggcg cgaacttctt ccgacccagg gaccaacaca | 2940 |
| acaactgaag accacaaaat catggcttca gaaaattcct ctgcaatggt tcaagtgcac | 3000 |
| agtcaaggaa gggaagctgc agtgtcgcat ctaacaaccc ttgccacaat ctccacgagt | 3060 |
| cccccaatccc tcacaaccaa accaggtccg acaacagca cccataatac acccgtgtat | 3120 |
| aaacttgaca tctctgaggc aactcaagtt gaacaacatc accgcagaac agacaacgac | 3180 |
| agcacagcct ccgacactcc ctctgccacg accgcagccg acccccaaa agcagagaac | 3240 |
| accaacacga gcaagagcac tgacttcctg gaccccgcca ccacaacaag tccccaaaac | 3300 |
| cacagcgaga ccgctggcaa caacaacact catcaccaag ataccggaga agagagtgcc | 3360 |
| agcagcggga agctaggctt aattaccaat actattgctg gagtcgcagg actccggacc | 3420 |
| aggggggacaa tgacaattgg tggacaggat ggagacaatg gataccggca ggtattggag | 3480 |
| ttacaggcgt tgtaattgca gttatcgctt tattctgtat atgcaaattt gtcttttagt | 3540 |
| ttttcttcag attgcttcat ggaaaagctc agcctcaaat caatgaaacc aggatttaat | 3600 |
| tatatggatt acttgaatct aagattactt gacaaatgat aatataatac actggagctt | 3660 |
| taaacatagc caatgtgatt ctaactcctt taaactcaca gttaatcata aacaaggttt | 3720 |
| gaggtaccga gctcgaattg atctgctgtg ccttctagtt gccagccatc tgttgtttgc | 3780 |
| ccctccccg tgccttcctt gaccctggaa ggtgccactc ccactgtcct ttcctaataa | 3840 |
| aatgaggaaa ttgcatcgca ttgtctgagt aggtgtcatt ctattctggg gggtggggtg | 3900 |
| gggcaggaca gcaagggga ggattgggaa gacaatagca ggcatgctgg ggatgcggtg | 3960 |
| ggctctatgg gtacccaggt gctgaagaat tgacccggtt cctcctgggc cagaaagaag | 4020 |
| caggcacatc cccttctctg tgacacaccc tgtccacgcc cctggttctt agttccagcc | 4080 |
| ccactcatag gacactcata gctcaggagg gctccgcctt caatcccacc cgctaaagta | 4140 |
| cttggagcgg tctctccctc cctcatcagc ccaccaaacc aaacctagcc tccaagagtg | 4200 |
| ggaagaaatt aaagcaagat aggctattaa gtgcagaggg agagaaaatg cctccaacat | 4260 |
| gtgaggaagt aatgagagaa atcatagaat ttcttccgct tcctcgctca ctgactcgct | 4320 |
| gcgctcggtc gttcggctgc ggcgagcggt atcagctcac tcaaaggcgg taatacggtt | 4380 |
| atccacagaa tcagggata acgcaggaaa gaacatgtga gcaaaaggcc agcaaaaggc | 4440 |
| caggaaccgt aaaaaggccg cgttgctggc gtttttccat aggctccgcc cccctgacga | 4500 |
| gcatcacaaa aatcgacgct caagtcagag gtggcgaaac ccgacaggac tataaagata | 4560 |
| ccaggcgttt cccctggaa gctccctcgt gcgctctcct gttccgaccc tgccgcttac | 4620 |
| cggatacctg tccgccttc tcccttcggg aagcgtggcg ctttctcata gctcacgctg | 4680 |
| taggtatctc agttcggtgt aggtcgttcg ctccaagctg ggctgtgtgc acgaaccccc | 4740 |
| cgttcagccc gaccgctgcg ccttatccgg taactatcgt cttgagtcca acccggtaag | 4800 |
| acacgactta tcgccactgg cagcagccac tggtaacagg attagcagag cgaggtatgt | 4860 |
| aggcggtgct acagagttct tgaagtggtg gcctaactac ggctacacta agaacagt | 4920 |
| atttggtatc tgcgctctgc tgaagccagt taccttcgga aaagagttg gtagctcttg | 4980 |
| atccggcaaa caaccaccg ctggtagcgg tggtttttt gtttgcaagc agcagattac | 5040 |
| gcgcagaaaa aaggatctc aagaagatcc tttgatcttt tctacggggt ctgacgctca | 5100 |
| gtggaacgaa aactcacgtt aagggatttt ggtcatgaga ttatcaaaaa ggatcttcac | 5160 |
| ctagatcctt ttaaattaaa aatgaagttt taaatcaatc taaagtatat atgagtaaac | 5220 |

```
ttggtctgac agttaccaat gcttaatcag tgaggcacct atctcagcga tctgtctatt      5280
tcgttcatcc atagttgcct gactcggggg ggggggcgc tgaggtctgc ctcgtgaaga      5340
aggtgttgct gactcatacc aggcctgaat cgccccatca tccagccaga agtgaggga      5400 gccacggttg atgagagctt tgttgtaggt ggaccagttg gtgattttga acttttgctt      5460
tgccacggaa cggtctgcgt tgtcgggaag atgcgtgatc tgatccttca actcagcaaa      5520
agttcgattt attcaacaaa gccgccgtcc cgtcaagtca gcgtaatgct ctgccagtgt      5580
tacaaccaat taaccaattc tgattagaaa aactcatcga gcatcaaatg aaactgcaat      5640
ttattcatat caggattatc aataccatat ttttgaaaaa gccgtttctg taatgaagga      5700
gaaaactcac cgaggcagtt ccataggatg gcaagatcct ggtatcggtc tgcgattccg      5760
actcgtccaa catcaataca acctattaat ttccctcgt caaaaataag gttatcaagt       5820
gagaaatcac catgagtgac gactgaatcc ggtgagaatg gcaaaagctt atgcatttct      5880
ttccagactt gttcaacagg ccagccatta cgctcgtcat caaaatcact cgcatcaacc      5940
aaaccgttat tcattcgtga ttgcgcctga gcgagacgaa atacgcgatc gctgttaaaa      6000
ggacaattac aaacaggaat cgaatgcaac cggcgcagga acactgccag cgcatcaaca      6060
atattttcac ctgaatcagg atattcttct aatacctgga atgctgtttt cccggggatc      6120
gcagtggtga gtaaccatgc atcatcagga gtacggataa aatgcttgat ggtcggaaga      6180
ggcataaatt ccgtcagcca gtttagtctg accatctcat ctgtaacatc attggcaacg      6240
ctacctttgc catgtttcag aaacaactct ggcgcatcgg gcttcccata caatcgatag      6300
attgtcgcac ctgattgccc gacattatcg cgagcccatt tatacccata taaatcagca      6360
tccatgttgg aatttaatcg cggcctcgag caagacgttt cccgttgaat atggctcata      6420
acaccccttg tattactgtt tatgtaagca gacagttta ttgttcatga tgatatattt        6480
ttatcttgtg caatgtaaca tcagagattt tgagacacaa cgtggctttc ccccccccc      6540 cattattgaa gcatttatca gggttattgt ctcatgagcg gatacatatt tgaatgtatt      6600
tagaaaaata acaaataggg gttccgcgc acatttcccc gaaaagtgcc acctgacgtc      6660
taagaaacca ttattatcat gacattaacc tataaaaata ggcgtatcac gaggcccttt      6720
cgtc                                                                   6724
```

<210> SEQ ID NO 6
<211> LENGTH: 6887
<212> TYPE: DNA
<213> ORGANISM: Artificial Sequence
<220> FEATURE:
<223> OTHER INFORMATION: Synthetic Construct pVR1012-GP(Z) delta GP2
    delta C-term A

<400> SEQUENCE: 6

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc        180
accatatgcg gtgtgaaata ccgcacagat gcgtaaggag aaaataccgc atcagattgg       240
ctattggcca ttgcatacgt tgtatccata tcataatatg tacatttata ttggctcatg      300
tccaacatta ccgccatgtt gacattgatt attgactagt tattaatagt aatcaattac       360
ggggtcatta gttcatagcc catatatgga gttccgcgtt acataactta cggtaaatgg      420
cccgcctggc tgaccgccca acgacccccg cccattgacg tcaataatga cgtatgttcc      480
```

-continued

| | | | | |
|---|---|---|---|---|
| catagtaacg | ccaataggga | ctttccattg | acgtcaatgg | gtggagtatt | tacggtaaac | 540 |
| tgcccacttg | gcagtacatc | aagtgtatca | tatgccaagt | acgccccta | ttgacgtcaa | 600 |
| tgacggtaaa | tggcccgcct | ggcattatgc | ccagtacatg | accttatggg | actttcctac | 660 |
| ttggcagtac | atctacgtat | tagtcatcgc | tattaccatg | gtgatgcggt | tttggcagta | 720 |
| catcaatggg | cgtggatagc | ggtttgactc | acggggattt | ccaagtctcc | accccattga | 780 |
| cgtcaatggg | agtttgtttt | ggcaccaaaa | tcaacgggac | tttccaaaat | gtcgtaacaa | 840 |
| ctccgcccca | ttgacgcaaa | tgggcggtag | gcgtgtacgg | tgggaggtct | atataagcag | 900 |
| agctcgttta | gtgaaccgtc | agatcgcctg | gagacgccat | ccacgctgtt | ttgacctcca | 960 |
| tagaagacac | cgggaccgat | ccagcctccg | cggccgggaa | cggtgcattg | gaacgcggat | 1020 |
| tccccgtgcc | aagagtgacg | taagtaccgc | ctatagactc | tataggcaca | ccccttggc | 1080 |
| tcttatgcat | gctatactgt | ttttggcttg | gggcctatac | accccgctt | ccttatgcta | 1140 |
| taggtgatgg | tatagcttag | cctataggtg | tgggttattg | accattattg | accactcccc | 1200 |
| tattggtgac | gatactttcc | attactaatc | cataacatgg | ctctttgcca | caactatctc | 1260 |
| tattggctat | atgccaatac | tctgtccttc | agagactgac | acggactctg | tatttttaca | 1320 |
| ggatggggtc | ccatttatta | tttacaaatt | cacatataca | acaacgccgt | ccccgtgcc | 1380 |
| cgcagttttt | attaaacata | gcgtgggatc | tccacgcgaa | tctcgggtac | gtgttccgga | 1440 |
| catgggctct | tctccggtag | cggcggagct | tccacatccg | agccctggtc | ccatgcctcc | 1500 |
| agcggctcat | ggtcgctcgg | cagctccttg | ctcctaacag | tggaggccag | acttaggcac | 1560 |
| agcacaatgc | ccaccaccac | cagtgtgccg | cacaaggccg | tggcggtagg | gtatgtgtct | 1620 |
| gaaaatgagc | gtggagattg | ggctcgcacg | gctgacgcag | atggaagact | taaggcagcg | 1680 |
| gcagaagaag | atgcaggcag | ctgagttgtt | gtattctgat | aagagtcaga | ggtaactccc | 1740 |
| gttgcggtgc | tgttaacggt | ggagggcagt | gtagtctgag | cagtactcgt | tgctgccgcg | 1800 |
| cgcgccacca | gacataatag | ctgacagact | aacagactgt | tcctttccat | gggtcttttc | 1860 |
| tgcagtcacc | gtcgtcgaca | cgtgtgatca | gatatcgcgg | ccgctctaga | ccaggccctg | 1920 |
| gatcgatcca | acaacacaat | gggcgttaca | ggaatattgc | agttacctcg | tgatcgattc | 1980 |
| aagaggacat | cattctttct | tgggtaatt | atcctttcc | aaagaacatt | ttccatccca | 2040 |
| cttggagtca | tccacaatag | cacattacag | gttagtgatg | tcgacaaact | agtttgtcgt | 2100 |
| gacaaactgt | catccacaaa | tcaattgaga | tcagttggac | tgaatctcga | agggaatgga | 2160 |
| gtggcaactg | acgtgccatc | tgcaactaaa | agatggggct | tcaggtccgg | tgtcccacca | 2220 |
| aaggtggtca | attatgaagc | tggtgaatgg | gctgaaaact | gctacaatct | tgaaatcaaa | 2280 |
| aaacctgacg | ggagtgagtg | tctaccagca | gcgccagacg | ggattcgggg | cttcccccgg | 2340 |
| tgccggtatg | tgcacaaagt | atcaggaacg | ggaccgtgtg | ccggagactt | gccttccat | 2400 |
| aaagagggtg | ctttcttcct | gtatgatcga | cttgcttcca | cagttatcta | ccgaggaacg | 2460 |
| actttcgctg | aaggtgtcgt | tgcatttctg | atactgcccc | aagctaagaa | ggacttcttc | 2520 |
| agctcacacc | ccttgagaga | gccggtcaat | gcaacgagg | acccgtctag | tggctactat | 2580 |
| tctaccacaa | ttagatatca | ggctaccggt | tttggaacca | atgagacaga | gtacttgttc | 2640 |
| gaggttgaca | atttgaccta | cgtccaactt | gaatcaagat | tcacaccaca | gtttctgctc | 2700 |
| cagctgaatg | agacaatata | tacaagtggg | aaaaggagca | ataccacggg | aaaactaatt | 2760 |
| tggaaggtca | accccgaaat | tgatacaaca | atcggggagt | gggccttctg | ggaaactaaa | 2820 |
| aaaaacctca | ctagaaaaat | tcgcagtgaa | gagttgtctt | tcacagttgt | atcaaacgga | 2880 |

-continued

```
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060 cccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg accccccaaa agcagagaac    3240
accaacacga gcaagagcac tgacttcctg accccgcca ccacaacaag tccccaaaac     3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggggataccg gcaggtattg gagttacagg cgttgtaatt    3660
gcagttatcg ctttattctg tatatgcaaa tttgtctttt agttttctt cagattgctt     3720 catggaaaag ctcagcctca aatcaatgaa accaggattt aattatatgg attacttgaa    3780
tctaagatta cttgacaaat gataaatata tacactggag cttaaacat agccaatgtg     3840 attctaactc ctttaaactc acagttaatc ataaacaagg tttgaggtac cgagctcgaa    3900
ttgatctgct gtgccttcta gttgccagcc atctgttgtt tgcccctccc ccgtgccttc    3960
cttgaccctg gaaggtgcca ctcccactgt cctttcctaa taaaatgagg aaattgcatc    4020
gcattgtctg agtaggtgtc attctattct ggggggtggg gtggggcagg acagcaaggg    4080
ggaggattgg gaagacaata gcaggcatgc tggggatgcg gtgggctcta tgggtaccca    4140
ggtgctgaag aattgacccg gttcctcctg ggccagaaag aagcaggcac atcccttct    4200 ctgtgacaca ccctgtccac gcccctggtt cttagttcca gccccactca taggacactc    4260
atagctcagg agggctccgc cttcaatccc cccgctaaa gtacttggag cggtctctcc     4320
ctccctcatc agcccaccaa accaaaccta gcctccaaga gtgggaagaa attaaagcaa    4380
gataggctat taagtgcaga gggagagaaa atgcctccaa catgtgagga agtaatgaga    4440
gaaatcatag aatttcttcc gcttcctcgc tcactgactc gctgcgctcg tcgttcggc    4500 tgcggcgagc ggtatcagct cactcaaagg cggtaatacg gttatccaca gaatcagggg    4560
ataacgcagg aaagaacatg tgagcaaaag gccagcaaaa ggccaggaac cgtaaaaagg    4620
ccgcgttgct ggcgtttttc cataggctcc gcccccctga cgagcatcac aaaaatcgac    4680
gctcaagtca gaggtggcga aacccgacag gactataaag ataccaggcg tttccccctg    4740
gaagctccct cgtgcgctct cctgttccga ccctgccgct taccggatac ctgtccgcct    4800
ttctcccttc gggaagcgtg gcgctttctc atagctcacg ctgtaggtat ctcagttcgg    4860
tgtaggtcgt tcgctccaag ctgggctgtg tgcacgaacc cccgttcag cccgaccgct     4920 gcgccttatc cggtaactat cgtcttgagt ccaacccggt aagacacgac ttatcgccac    4980
tggcagcagc cactggtaac aggattagca gagcgaggta tgtaggcggt gctacagagt    5040
tcttgaagtg gtggcctaac tacggctaca ctagaagaac agtatttggt atctgcgctc    5100
tgctgaagcc agttaccttc ggaaaaagag ttggtagctc ttgatccggc aaacaaacca    5160
ccgctggtag cggtggtttt tttgtttgca agcagcagat tacgcgcaga aaaaaggat    5220 ctcaagaaga tcctttgatc ttttctacgg ggtctgacgc tcagtggaac gaaaactcac    5280
```

```
gttaagggat tttggtcatg agattatcaa aaaggatctt cacctagatc cttttaaatt      5340
aaaaatgaag ttttaaatca atctaaagta tatatgagta aacttggtct gacagttacc      5400
aatgcttaat cagtgaggca cctatctcag cgatctgtct atttcgttca tccatagttg      5460
cctgactcgg ggggggggg cgctgaggtc tgcctcgtga agaaggtgtt gctgactcat      5520
accaggcctg aatcgcccca tcatccagcc agaaagtgag ggagccacgg ttgatgagag      5580
ctttgttgta ggtggaccag ttggtgattt tgaacttttg ctttgccacg gaacggtctg      5640
cgttgtcggg aagatgcgtg atctgatcct tcaactcagc aaaagttcga tttattcaac      5700
aaagccgccg tcccgtcaag tcagcgtaat gctctgccag tgttacaacc aattaaccaa      5760
ttctgattag aaaaactcat cgagcatcaa atgaaactgc aatttattca tatcaggatt      5820
atcaatacca tattttgaa aaagccgttt ctgtaatgaa ggagaaaact caccgaggca      5880
gttccatagg atggcaagat cctggtatcg gtctgcgatt ccgactcgtc aacatcaat       5940 acaacctatt aatttcccct cgtcaaaaat aaggttatca agtgagaaat caccatgagt      6000
gacgactgaa tccggtgaga atggcaaaag cttatgcatt tctttccaga cttgttcaac      6060
aggccagcca ttacgctcgt catcaaaatc actcgcatca accaaaccgt tattcattcg      6120
tgattgcgcc tgagcgagac gaaatacgcg atcgctgtta aaaggacaat acaaacagg       6180 aatcgaatgc aaccggcgca ggaacactgc cagcgcatca acaatatttt cacctgaatc      6240
aggatattct tctaatacct ggaatgctgt tttcccgggg atcgcagtgg tgagtaacca      6300
tgcatcatca ggagtacgga taaaatgctt gatggtcgga agaggcataa attccgtcag      6360
ccagtttagt ctgaccatct catctgtaac atcattggca acgctacctt tgccatgttt      6420
cagaaacaac tctggcgcat cgggcttccc atacaatcga tagattgtcg cacctgattg      6480
cccgacatta tcgcgagccc atttataccc atataaatca gcatccatgt tggaatttaa      6540
tcgcggcctc gagcaagacg tttcccgttg aatatggctc ataacacccc ttgtattact      6600
gtttatgtaa gcagacagtt ttattgttca tgatgatata ttttttatctt gtgcaatgta      6660 acatcagaga ttttgagaca caacgtggct ttccccccc ccccattatt gaagcattta      6720
tcagggttat tgtctcatga gcggatacat atttgaatgt atttagaaaa ataaacaaat      6780
aggggttccg cgcacatttc cccgaaaagt gccacctgac gtctaagaaa ccattattat      6840
catgacatta acctataaaa ataggcgtat cacgaggccc tttcgtc                    6887
```

<210> SEQ ID NO 7
<211> LENGTH: 7044
<212> TYPE: DNA
<213> ORGANISM: Artificial Sequence
<220> FEATURE:
<223> OTHER INFORMATION: Synthetic Construct pVR1012-GP(Z) delta GP2
    Delta C-term B

<400> SEQUENCE: 7

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
```

-continued

```
cccgcctggc tgaccgccca acgaccccccg cccattgacg tcaataatga cgtatgttcc      480
catagtaacg ccaataggga cttttccattg acgtcaatgg gtggagtatt tacggtaaac      540
tgcccacttg gcagtacatc aagtgtatca tatgccaagt acgccccccta ttgacgtcaa     600 tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg gaacgcggat     1020
tccccgtgcc aagagtgacg taagtaccgc ctatagactc tataggcaca ccccttttggc    1080 tcttatgcat gctatactgt ttttggcttg gggcctatac cccccgctt ccttatgcta      1140 taggtgatgg tatagcttag cctataggtg tgggttattg accattattg accactcccc     1200
tattggtgac gatactttcc attactaatc cataacatgg ctctttgcca caactatctc     1260
tattggctat atgccaatac tctgtccttc agagactgac acggactctg tatttttaca     1320
ggatggggtc ccatttatta tttacaaatt cacatataca acaacgccgt cccccgtgcc     1380
cgcagttttt attaaacata cgtgggatc tccacgcgaa tctcgggtac gtgttccgga      1440
catgggctct tctccggtag cggcggagct tccacatccg agccctggtc ccatgcctcc     1500
agcggctcat ggtcgctcgg cagctccttg ctcctaacag tggaggccag acttaggcac     1560
agcacaatgc ccaccaccac cagtgtgccg cacaaggccg tggcggtagg gtatgtgtct     1620
gaaaatgagc gtggagattg ggctcgcacg gctgacgcag atggaagact taaggcagcg     1680
gcagaagaag atgcaggcag ctgagttgtt gtattctgat aagagtcaga ggtaactccc     1740
gttgcggtgc tgttaacggt ggagggcagt gtagtctgag cagtactcgt tgctgccgcg     1800
cgcgccacca gacataatag ctgacagact aacagactgt tcctttccat gggtcttttc     1860
tgcagtcacc gtcgtcgaca cgtgtgatca gatatcgcgg ccgctctaga ccaggccctg     1920
gatcgatcca acaacacaat gggcgttaca ggaatattgc agttaccctg tgatcgattc     1980
aagaggacat cattctttct ttgggtaatt atccttttcc aaagaacatt ttccatccca     2040
cttggagtca tccacaatag cacattacag gttagtgatg tcgacaaact agtttgtcgt     2100
gacaaactgt catccacaaa tcaattgaga tcagttggac tgaatctcga agggaatgga    2160
gtggcaactg acgtgccatc tgcaactaaa agatggggct tcaggtccgg tgtcccacca     2220
aaggtggtca attatgaagc tggtgaatgg gctgaaaact gctacaatct tgaaatcaaa     2280
aaacctgacg ggagtgagtg tctaccagca gcgccagacg ggattcgggg cttccccccgg    2340 tgccggtatg tgcacaaagt atcaggaacg ggaccgtgtg ccgagacttt gccttccat     2400 aaagagggtg ctttcttcct gtatgatcga cttgcttcca cagttatcta ccgaggaacg     2460
actttcgctg aaggtgtcgt tgcatttctg atactgcccc aagctaagaa ggacttcttc     2520
agctcacacc ccttgagaga gccggtcaat gcaacggagg accgtctag tggctactat     2580 tctaccacaa ttagatatca ggctaccggt tttggaacca atgagacaga gtacttgttc     2640
gaggttgaca atttgaccta cgtccaactt gaatcaagat tcacaccaca gtttctgctc     2700
cagctgaatg agacaatata tacaagtggg aaaaggagca ataccacggg aaaactaatt     2760
tggaaggtca accccgaaat tgatacaaca atcggggagt gggccttctg ggaaactaaa     2820
```

-continued

```
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060 cccaatccc tcacaaccaa accaggtccg acaacagca cccataatac acccgtgtat     3120
aaacttgaca tctctgaggc aactcaagtt gaacaacatc accgcagaac agacaacgac    3180
agcacagcct ccgacactcc ctctgccacg accgcagccg acccccaaa agcagagaac     3240 accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgag    3780
gataccggca ggtattggag ttacaggcgt tgtaattgca gttatcgctt tattctgtat    3840
atgcaaattt gtcttttagt ttttcttcag attgcttcat ggaaaagctc agcctcaaat    3900
caatgaaacc aggatttaat tatatggatt acttgaatct aagattactt gacaaatgat    3960
aatataatac actggagctt taaacatagc caatgtgatt ctaactcctt taaactcaca    4020
gttaatcata aacaaggttt gaggtaccga gctcgaattg atctgctgtg ccttctagtt    4080
gccagccatc tgttgtttgc ccctcccccg tgccttcctt gacctggaa ggtgccactc     4140 ccactgtcct ttcctaataa aatgaggaaa ttgcatcgca ttgtctgagt aggtgtcatt    4200
ctattctggg gggtggggtg gggcaggaca gcaaggggga ggattgggaa gacaatagca    4260
ggcatgctgg ggatgcggtg ggctctatgg gtacccaggt gctgaagaat tgacccggtt    4320
cctcctgggc cagaaagaag caggcacatc cccttctctg tgacacaccc tgtccacgcc    4380
cctggttctt agttccagcc ccactcatag gacactcata gctcaggagg ctccgccttc    4440
caatcccacc cgctaaagta cttggagcgg tctctccctc cctcatcagc ccaccaaacc    4500
aaacctagcc tccaagagtg ggaagaaatt aaagcaagat aggctattaa gtgcagaggg    4560
agagaaaatg cctccaacat gtgaggaagt aatgagagaa atcatagaat ttcttccgct    4620
tcctcgctca ctgactcgct gcgctcggtc gttcggctgc ggcgagcggt atcagctcac    4680
tcaaaggcgg taatacggtt atccacagaa tcagggggata acgcaggaaa gaacatgtga    4740
gcaaaaggcc agcaaaaggc caggaaccgt aaaaaggccg cgttgctggc gttttttccat   4800 aggctccgcc cccctgacga gcatcacaaa aatcgacgct caagtcagag gtggcgaaac    4860
ccgacaggac tataaagata ccaggcgttt ccccctggaa gctccctcgt gcgctctcct    4920
gttccgaccc tgccgcttac cggatacctg tccgcctttc tcccttcggg aagcgtggcg    4980
ctttctcata gctcacgctg taggtatctc agttcggtgt aggtcgttcg ctccaagctg    5040
ggctgtgtgc acgaaccccc cgttcagccc gaccgctgcg ccttatccgg taactatcgt    5100
cttgagtcca acccggtaag acacgactta tcgccactgg cagcagccac tggtaacagg    5160
attagcagag cgaggtatgt aggcggtgct acagagttct tgaagtggtg gcctaactac    5220
```

-continued

```
ggctacacta aagaacagt atttggtatc tgcgctctgc tgaagccagt taccttcgga      5280
aaaagagttg gtagctcttg atccggcaaa caaaccaccg ctggtagcgg tggttttttt      5340
gtttgcaagc agcagattac gcgcagaaaa aaggatctc aagaagatcc tttgatcttt      5400
tctacggggt ctgacgctca gtggaacgaa aactcacgtt aagggatttt ggtcatgaga      5460
ttatcaaaaa ggatcttcac ctagatcctt taaattaaa aatgaagttt taaatcaatc      5520
taaagtatat atgagtaaac ttggtctgac agttaccaat gcttaatcag tgaggcacct      5580
atctcagcga tctgtctatt tcgttcatcc atagttgcct gactcggggg ggggggcgc      5640
tgaggtctgc ctcgtgaaga aggtgttgct gactcatacc aggcctgaat cgccccatca      5700
tccagccaga aagtgaggga gccacggttg atgagagctt tgttgtaggt ggaccagttg      5760
gtgattttga acttttgctt tgccacgaaa cggtctgcgt tgtcgggaag atgcgtgatc      5820
tgatccttca actcagcaaa agttcgattt attcaacaaa gccgccgtcc cgtcaagtca      5880
gcgtaatgct ctgccagtgt tacaaccaat taaccaattc tgattagaaa aactcatcga      5940
gcatcaaatg aaactgcaat ttattcatat caggattatc aataccatat ttttgaaaaa      6000
gccgtttctg taatgaagga gaaaactcac cgaggcagtt ccataggatg caagatcct      6060
ggtatcggtc tgcgattccg actcgtccaa catcaataca acctattaat ttcccctcgt      6120
caaaataag gttatcaagt gagaaatcac catgagtgac gactgaatcc ggtgagaatg      6180
gcaaaagctt atgcatttct ttccagactt gttcaacagg ccagccatta cgctcgtcat      6240
caaaatcact cgcatcaacc aaaccgttat tcattcgtga ttgcgcctga gcgagacgaa      6300
atacgcgatc gctgttaaaa ggacaattac aaacaggaat cgaatgcaac cggcgcagga      6360
acactgccag cgcatcaaca atattttcac ctgaatcagg atattcttct aatacctgga      6420
atgctgtttt cccggggatc gcagtggtga gtaaccatgc atcatcagga gtacggataa      6480
aatgcttgat ggtcggaaga ggcataaatt ccgtcagcca gtttagtctg accatctcat      6540
ctgtaacatc attggcaacg ctacctttgc catgtttcag aaacaactct ggcgcatcgg      6600
gcttcccata caatcgatag attgtcgcac ctgattgccc gacattatcg cgagcccatt      6660
tatacccata taaatcagca tccatgttgg aatttaatcg cggcctcgag caagacgttt      6720
cccgttgaat atggctcata acaccccttg tattactgtt tatgtaagca gacagtttta      6780
ttgttcatga tgatatattt ttatcttgtg caatgtaaca tcagagattt tgagacacaa      6840
cgtggctttc cccccccccc cattattgaa gcatttatca gggttattgt ctcatgagcg      6900
gatacatatt tgaatgtatt tagaaaaata acaaataggg gttccgcgc acatttcccc      6960
gaaaagtgcc acctgacgtc taagaaacca ttattatcat gacattaacc tataaaaata      7020
ggcgtatcac gaggcccttt cgtc                                            7044
```

<210> SEQ ID NO 8
<211> LENGTH: 7106
<212> TYPE: DNA
<213> ORGANISM: Artificial Sequence
<220> FEATURE:
<223> OTHER INFORMATION: Synthetic Construct pVR1012-GP(Z) delta GP2
    delta FUS

<400> SEQUENCE: 8

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
```

```
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga cttttccattg acgtcaatgg gtggagtatt tacggtaaac    540
tgcccacttg gcagtacatc aagtgtatca tatgccaagt acgccccta ttgacgtcaa     600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960 tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtctttc    1860 tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcgacaaact agtttgtcgt   2100
gacaaactgt catccacaaa tcaattgaga tcagttggac tgaatctcga agggaatgga   2160
gtggcaactg acgtgccatc tgcaactaaa agatgggct tcaggtccgg tgtcccacca    2220
aaggtggtca attatgaagc tggtgaatgg gctgaaaact gctacaatct tgaaatcaaa   2280
aaacctgacg ggagtgagtg tctaccagca gcgccagacg ggattcgggg cttccccgg    2340 tgccggtatg tgcacaaagt atcaggaacg ggaccgtgtg ccggagactt tgccttccat   2400
aaagagggtg ctttcttcct gtatgatcga cttgcttcca cagttatcta ccgaggaacg   2460
actttcgctg aaggtgtcgt tgcatttctg tatactgcccc aagctaagaa ggacttcttc   2520
agctcacacc ccttgagaga gccggtcaat gcaacggagg acccgtctag tggctactat   2580
```

```
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat tcgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg acccccaaa agcagagaac    3240 accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaagag ggaatttaca tagaggggct aatgcacaat    3540
caagatggtt taatctgtgg gttgagacag ctggccaacg agacgactca agctcttcaa    3600
ctgttcctga gagccacaac tgagctacgc accttttcaa tcctcaaccg taaggcaatt    3660
gatttcttgc tgcagcgatg gggcggcaca tgccacattc tgggaccgga ctgctgtatc    3720
gaaccacatg attggaccaa gaacataaca gacaaaattg atcagattat tcatgatttt    3780
gttgataaaa cccttccgga ccaggggac aatgacaatt ggtggacagg atggagacaa    3840
tggataccgg caggtattgg agttacaggc gttgtaattg cagttatcgc tttattctgt    3900
atatgcaaat ttgtctttta gtttttcttc agattgcttc atggaaaagc tcagcctcaa    3960
atcaatgaaa ccaggattta attatatgga ttacttgaat ctaagattac ttgacaaatg    4020
ataatataat acactggagc tttaaacata gccaatgtga ttctaactcc tttaaactca    4080
cagttaatca taaacaaggt ttgaggtacc gagctcgaat tgatctgctg tgccttctag    4140
ttgccagcca tctgttgttt gcccctcccc cgtgccttcc ttgaccctgg aagtgccac    4200 tcccactgtc ctttcctaat aaaatgagga aattgcatcg cattgtctga gtaggtgtca    4260
ttctattctg gggggtgggg tggggcagga cagcaagggg gaggattggg aagacaatag    4320
caggcatgct ggggatgcgg tgggctctat gggtacccag gtgctgaaga attgacccgg    4380
ttcctcctgg gccagaaaga agcaggcaca tccccttctc tgtgacacac cctgtccacg    4440
cccctggttc ttagttccag ccccactcat aggacactca tagctcagga gggctccgcc    4500
ttcaatccca cccgctaaag tacttggagc ggtctctccc tccctcatca gcccaccaaa    4560
ccaaacctag cctccaagag tgggaagaaa ttaaagcaag ataggctatt aagtgcagag    4620
ggagagaaaa tgcctccaac atgtgaggaa gtaatgagaa aaatcataga atttcttccg    4680
cttcctcgct cactgactcg ctgcgctcgg tcgttcggct gcggcgagcg gtatcagctc    4740
actcaaaggc ggtaatacgg ttatccacag aatcagggga taacgcagga agaacatgt    4800 gagcaaaagg ccagcaaaag gccaggaacc gtaaaaaggc cgcgttgctg gcgttttttcc    4860 ataggctccg cccccctgac gagcatcaca aaaatcgacg ctcaagtcag aggtggcgaa    4920
acccgacagg actataaaga taccaggcgt ttccccctgg aagctccctc gtgcgctctc    4980
```

-continued

```
ctgttccgac cctgccgctt accggatacc tgtccgcctt tctcccttcg ggaagcgtgg      5040
cgctttctca tagctcacgc tgtaggtatc tcagttcggt gtaggtcgtt cgctccaagc      5100
tgggctgtgt gcacgaaccc cccgttcagc ccgaccgctg cgccttatcc ggtaactatc      5160
gtcttgagtc caacccggta agacacgact tatcgccact ggcagcagcc actggtaaca      5220
ggattagcag agcgaggtat gtaggcggtg ctacagagtt cttgaagtgg tggcctaact      5280
acggctacac tagaagaaca gtatttggta tctgcgctct gctgaagcca gttaccttcg      5340
gaaaaagagt tggtagctct tgatccggca aacaaaccac cgctggtagc ggtggttttt      5400
ttgtttgcaa gcagcagatt acgcgcagaa aaaaggatc tcaagaagat cctttgatct      5460
tttctacggg gtctgacgct cagtggaacg aaaactcacg ttaagggatt ttggtcatga      5520
gattatcaaa aaggatcttc acctagatcc ttttaaatta aaaatgaagt tttaaatcaa      5580
tctaaagtat atatgagtaa acttggtctg acagttacca atgcttaatc agtgaggcac      5640
ctatctcagc gatctgtcta tttcgttcat ccatagttgc ctgactcggg gggggggggc      5700
gctgaggtct gcctcgtgaa gaaggtgttg ctgactcata ccaggcctga atcgccccat      5760
catccagcca gaaagtgagg gagccacggt tgatgagagc tttgttgtag gtggaccagt      5820
tggtgatttt gaacttttgc tttgccacgg aacggtctgc gttgtcggga agatgcgtga      5880
tctgatcctt caactcagca aaagttcgat ttattcaaca agccgccgt cccgtcaagt      5940 cagcgtaatg ctctgccagt gttacaacca attaaccaat tctgattaga aaaactcatc      6000
gagcatcaaa tgaaactgca atttattcat atcaggatta tcaataccat atttttgaaa      6060
aagccgtttc tgtaatgaag gagaaaactc accgaggcag ttccatagga tggcaagatc      6120
ctggtatcgg tctgcgattc cgactcgtcc aacatcaata caacctatta atttcccctc      6180
gtcaaaaata aggttatcaa gtgagaaatc accatgagtg acgactgaat ccggtgagaa      6240
tggcaaaagc ttatgcattt ctttccagac ttgttcaaca ggccagccat tacgctcgtc      6300
atcaaaatca ctcgcatcaa ccaaaccgtt attcattcgt gattgcgcct gagcgagacg      6360
aaatacgcga tcgctgttaa aaggacaatt acaaacagga tcgaatgca accggcgcag      6420 gaacactgcc agcgcatcaa caatatttc acctgaatca ggatattctt ctaatacctg      6480
gaatgctgtt ttcccgggga tcgcagtggt gagtaaccat gcatcatcag gagtacggat      6540
aaaatgcttg atggtcggaa gaggcataaa ttccgtcagc cagtttagtc tgaccatctc      6600
atctgtaaca tcattggcaa cgctacctt gccatgtttc agaaacaact ctggcgcatc      6660
gggcttccca tacaatcgat agattgtcgc acctgattgc ccgacattat cgcgagccca      6720
tttataccca tataaatcag catccatgtt ggaatttaat cgcggcctcg agcaagacgt      6780
ttcccgttga atatggctca taacacccct tgtattactg tttatgtaag cagacagttt      6840
tattgttcat gatgatatat ttttatcttg tgcaatgtaa catcagagat tttgagacac      6900
aacgtggctt ccccccccc cccattattg aagcatttat cagggttatt gtctcatgag      6960
cggatacata tttgaatgta tttagaaaaa taaacaaata ggggttccgc gcacatttcc      7020
ccgaaaagtg ccacctgacg tctaagaaac cattattatc atgacattaa cctataaaaa      7080
taggcgtatc acgaggccct ttcgtc                                          7106
```

<210> SEQ ID NO 9
<211> LENGTH: 6914
<212> TYPE: DNA
<213> ORGANISM: Artificial Sequence
<220> FEATURE:
<223> OTHER INFORMATION: Synthetic Construct pVR1012-GP(Z) delta TM -continued

<400> SEQUENCE: 9

```
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctcca     960 tagaagacac cgggaccgat ccagcctccg cggccgggaa cggtgcattg gaacgcggat    1020
tccccgtgcc aagagtgacg taagtaccgc ctatagactc tataggcaca cccctttggc    1080
tcttatgcat gctatactgt ttttggcttg gggcctatac accccgctt ccttatgcta     1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggccctg    1920
gatcgatcca acaacacaat gggcgttaca ggaatattgc agttacctcg tgatcgattc    1980
aagaggacat cattctttct ttgggtaatt atccttttcc aaagaacatt ttccatccca    2040
cttggagtca tccacaatag cacattacag gttagtgatg tcgacaaact agtttgtcgt    2100
gacaaactgt catccacaaa tcaattgaga tcagttggac tgaatctcga agggaatgga    2160
gtggcaactg acgtgccatc tgcaactaaa agatgggct tcaggtccgg tgtcccacca     2220
aaggtggtca attatgaagc tggtgaatgg gctgaaaact gctacaatct tgaaatcaaa    2280
aaacctgacg ggagtgagtg tctaccagca gcgccagacg ggattcgggg cttccccgg     2340
```

-continued

```
tgccggtatg tgcacaaagt atcaggaacg ggaccgtgtg ccggagactt tgccttccat    2400
aaagagggtg ctttcttcct gtatgatcga cttgcttcca cagttatcta ccgaggaacg    2460
actttcgctg aaggtgtcgt tgcatttctg tatactgccc aagctaagaa ggacttcttc    2520
agctcacacc ccttgagaga gccggtcaat gcaacggagg acccgtctag tggctactat    2580
tctaccacaa ttagatatca ggctaccggt tttggaacca atgagacaga gtacttgttc    2640
gaggttgaca atttgaccta cgtccaactt gaatcaagat tcacaccaca gtttctgctc    2700
cagctgaatg agacaatata tacaagtggg aaaaggagca ataccacggg aaaactaatt    2760
tggaaggtca accccgaaat tgatacaaca atcggggagt gggccttctg ggaaactaaa    2820
aaaaacctca ctagaaaaat cgcagtgaa gagttgtctt tcacagttgt atcaaacgga    2880
gccaaaaaca tcagtggtca gagtccggcg cgaacttctt ccgacccagg gaccaacaca    2940
acaactgaag accacaaaat catggcttca gaaaattcct ctgcaatggt tcaagtgcac    3000
agtcaaggaa gggaagctgc agtgtcgcat ctaacaaccc ttgccacaat ctccacgagt    3060
ccccaatccc tcacaaccaa accaggtccg gacaacagca cccataatac acccgtgtat    3120
aaacttgaca tctctgaggc aactcaagtt gaacaacatc accgcagaac agacaacgac    3180
agcacagcct ccgacactcc ctctgccacg accgcagccg gaccccaaa agcagagaac    3240 accaacacga gcaagagcac tgacttcctg gaccccgcca ccacaacaag tccccaaaac    3300
cacagcgaga ccgctggcaa caacaacact catcaccaag ataccggaga agagagtgcc    3360
agcagcggga agctaggctt aattaccaat actattgctg gagtcgcagg actgatcaca    3420
ggcgggagaa gaactcgaag agaagcaatt gtcaatgctc aacccaaatg caaccctaat    3480
ttacattact ggactactca ggatgaaggt gctgcaatcg gactggcctg gataccatat    3540
ttcgggccag cagccgaggg aatttacata gaggggctaa tgcacaatca agatggttta    3600
atctgtgggt tgagacagct ggccaacgag acgactcaag ctcttcaact gttcctgaga    3660
gccacaactg agctacgcac cttttcaatc ctcaaccgta aggcaattga tttcttgctg    3720
cagcgatggg gcggcacatg ccacattctg ggaccggact gctgtatcga accacatgat    3780
tggaccaaga acataacaga caaaattgat cagattattc atgattttgt tgataaaacc    3840
cttccggacc aggggacaa tgacaattgg tggacaggat ggagacaatg gatgccgca    3900 tcgtgactga ctgacgatct gcctcgcgag atctgctgtg ccttctagtt gccagccatc    3960
tgttgtttgc ccctccccg tgccttcctt gaccctggaa ggtgccactc ccactgtcct    4020
ttcctaataa aatgaggaaa ttgcatcgca ttgtctgagt aggtgtcatt ctattctggg    4080
gggtggggtg gggcaggaca gcaaggggga ggattgggaa gacaatagca ggcatgctgg    4140
ggatgcggtg ggctctatgg gtacccaggt gctgaagaat tgacccggtt cctcctgggc    4200
cagaaagaag caggcacatc cccttctctg tgacacaccc tgtccacgcc cctggttctt    4260
agttccagcc ccactcatag gacactcata gctcaggagg ctccgccttc aatcccacc    4320 cgctaaagta cttggagcgg tctctccctc cctcatcagc ccaccaaacc aaacctagcc    4380
tccaagagtg ggaagaaatt aaagcaagat aggctattaa gtgcagaggg agagaaaatg    4440
cctccaacat gtgaggaagt aatgagagaa atcatagaat tcttccgct cctcgctca    4500 ctgactcgct cgctcggtc gttcggctgc ggcgagcgt atcagctcac tcaaaggcgg    4560
taatacggtt atccacagaa tcaggggata acgcaggaaa gaacatgtga gcaaaaggcc    4620
agcaaaaggc caggaaccgt aaaaaggccg cgttgctggc gttttcccat aggctccgcc    4680
cccctgacga gcatcacaaa aatcgacgct caagtcagag gtggcgaaac ccgacaggac    4740
```

-continued

```
tataaagata ccaggcgttt cccctggaa gctccctcgt gcgctctcct gttccgaccc    4800
tgccgcttac cggatacctg tccgcctttc tcccttcggg aagcgtggcg ctttctcata    4860
gctcacgctg taggtatctc agttcggtgt aggtcgttcg ctccaagctg gctgtgtgc    4920 acgaaccccc cgttcagccc gaccgctgcg ccttatccgg taactatcgt cttgagtcca    4980
acccggtaag acacgactta tcgccactgg cagcagccac tggtaacagg attagcagag    5040
cgaggtatgt aggcggtgct acagagttct gaagtggtg gcctaactac ggctacacta    5100
gaagaacagt atttggtatc tgcgctctgc tgaagccagt taccttcgga aaagagttg    5160 gtagctcttg atccggcaaa caaaccaccg ctggtagcgg tggttttttt gtttgcaagc    5220
agcagattac gcgcagaaaa aaggatctc aagaagatcc tttgatcttt tctacggggt    5280
ctgacgctca gtggaacgaa aactcacgtt aagggatttt ggtcatgaga ttatcaaaaa    5340
ggatcttcac ctagatcctt ttaaattaaa aatgaagttt taaatcaatc taaagtatat    5400
atgagtaaac ttggtctgac agttaccaat gcttaatcag tgaggcacct atctcagcga    5460
tctgtctatt tcgttcatcc atagttgcct gactcggggg ggggggcgc tgaggtctgc    5520 ctcgtgaaga aggtgttgct gactcatacc aggcctgaat cgccccatca tccagccaga    5580
aagtgaggga gccacggttg atgagagctt tgttgtaggt ggaccagttg gtgattttga    5640
acttttgctt tgccacggaa cggtctgcgt tgtcggaag atgcgtgatc tgatccttca    5700
actcagcaaa agttcgattt attcaacaaa gccgccgtcc cgtcaagtca gcgtaatgct    5760
ctgccagtgt tacaaccaat taaccaattc tgattagaaa aactcatcga gcatcaaatg    5820
aaactgcaat ttattcatat caggattatc aataccatat ttttgaaaaa gccgtttctg    5880
taatgaagga gaaaactcac cgaggcagtt ccataggatg caagatcct ggtatcggtc    5940 tgcgattccg actcgtccaa catcaataca acctattaat ttccctcgt caaaaataag    6000 gttatcaagt gagaaatcac catgagtgac gactgaatcc ggtgagaatg gcaaaagctt    6060
atgcatttct ttccagactt gttcaacagg ccagccatta cgctcgtcat caaaatcact    6120
cgcatcaacc aaaccgttat tcattcgtga ttgcgcctga gcgagacgaa atacgcgatc    6180
gctgttaaaa ggacaattac aaacaggaat cgaatgcaac cggcgcagga acactgccag    6240
cgcatcaaca atattttcac ctgaatcagg atattcttct aatacctgga atgctgtttt    6300 cccgggggatc gcagtggtga gtaaccatgc atcatcagga gtacggataa aatgcttgat    6360
ggtcggaaga ggcataaatt ccgtcagcca gtttagtctg accatctcat ctgtaacatc    6420
attggcaacg ctacctttgc catgtttcag aaacaactct ggcgcatcgg gcttcccata    6480
caatcgatag attgtcgcac ctgattgccc gacattatcg cgagcccatt tatacccata    6540
taaatcagca tccatgttgg aatttaatcg cggcctcgag caagacgttt cccgttgaat    6600
atggctcata cacccccttg tattactgtt tatgtaagca gacagtttta ttgttcatga    6660
tgatatattt ttatcttgtg caatgtaaca tcagagattt tgagacacaa cgtggctttc    6720 ccccccccc cattattgaa gcatttatca gggttattgt ctcatgagcg gatacatatt    6780
tgaatgtatt tagaaaaata aacaaatagg ggttccgcgc acatttcccc gaaaagtgcc    6840
acctgacgtc taagaaacca ttattatcat gacattaacc tataaaaata ggcgtatcac    6900
gaggcccttt cgtc                                                      6914
```

<210> SEQ ID NO 10
<211> LENGTH: 6467
<212> TYPE: DNA
<213> ORGANISM: Artificial Sequence -continued
<220> FEATURE:
<223> OTHER INFORMATION: Synthetic Construct pVR1012-GP(Z) delta SGP

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatcgatcca acaacacaat gggcgttaca ggaatattgc agttacctcg tgatcgattc   1980
aagaggacat cattctttct ttgggtaatt atccttttcc aaagaacatt ttccatccca   2040
cttggagtca tccacaatag cacattacag gttagtgatg tcaaccccga aattgataca   2100
acaatcgggg agtgggcctt ctgggaaact aaaaaaaacc tcactagaaa aattcgcagt   2160
gaagagttgt ctttcacagt tgtatcaaac ggagccaaaa acatcagtgg tcagagtccg   2220
```

-continued

```
gcgcgaactt cttccgaccc agggaccaac acaacaactg aagaccacaa aatcatggct    2280
tcagaaaatt cctctgcaat ggttcaagtg cacagtcaag gaagggaagc tgcagtgtcg    2340
catctaacaa cccttgccac aatctccacg agtccccaat ccctcacaac caaaccaggt    2400
ccggacaaca gcacccataa tacacccgtg tataaacttg acatctctga ggcaactcaa    2460
gttgaacaac atcaccgcag aacagacaac gacagcacag cctccgacac tccctctgcc    2520
acgaccgcag ccggaccccc aaaagcagag aacaccaaca cgagcaagag cactgacttc    2580
ctggaccccg ccaccacaac aagtccccaa accacagcg agaccgctgg caacaacaac    2640
actcatcacc aagataccgg agaagagagt gccagcagcg ggaagctagg cttaattacc    2700
aatactattg ctggagtcgc aggactgatc acaggcggga gaagaactcg aagagaagca    2760
attgtcaatg ctcaacccaa atgcaaccct aatttacatt actggactac tcaggatgaa    2820
ggtgctgcaa tcggactggc ctggatacca tatttcgggc cagcagccga gggaatttac    2880 atagagggc taatgcacaa tcaagatggt ttaatctgtg ggttgagaca gctggccaac    2940
gagacgactc aagctcttca actgttcctg agagccacaa ctgagctacg cacctttca    3000 atcctcaacc gtaaggcaat tgatttcttg ctgcagcgat ggggcggcac atgccacatt    3060
ctgggaccgg actgctgtat cgaaccacat gattggacca agaacataac agacaaaatt    3120
gatcagatta ttcatgattt tgttgataaa acccttccgg accaggggga caatgacaat    3180
tggtggacag gatggagaca atggataccg gcaggtattg gagttacagg cgttgtaatt    3240
gcagttatcg ctttattctg tatatgcaaa tttgtcttt agttttctt cagattgctt    3300 catggaaaag ctcagcctca aatcaatgaa accaggattt aattatatgg attacttgaa    3360
tctaagatta cttgacaaat gataatataa tacactggag ctttaaacat agccaatgtg    3420
attctaactc ctttaaactc acagttaatc ataaacaagg tttgaggtac cgagctcgaa    3480
ttgatctgct gtgccttcta gttgccagcc atctgttgtt tgcccctcc ccgtgccttc    3540 cttgaccctg gaaggtgcca ctcccactgt cctttcctaa taaaatgagg aaattgcatc    3600
gcattgtctg agtaggtgtc attctattct ggggggtggg gtggggcagg acagcaaggg    3660
ggaggattgg gaagacaata gcaggcatgc tggggatgcg gtgggctcta tgggtaccca    3720
ggtgctgaag aattgacccg gttcctcctg ggccagaaag aagcaggcac atccccttct    3780
ctgtgacaca ccctgtccac gccctggtt cttagttcca gccccactca taggacactc    3840
atagctcagg agggctccgc cttcaatccc acccgctaaa gtacttggag cggtctctcc    3900
ctccctcatc agcccaccaa accaaaccta gcctccaaga gtgggaagaa attaaagcaa    3960
gataggctat taagtgcaga gggagagaaa atgcctccaa catgtgagga agtaatgaga    4020
gaaatcatag aatttcttcc gcttcctcgc tcactgactc gctgcgctcg gtcgttcggc    4080
tgcggcgagc ggtatcagct cactcaaagg cggtaatacg gttatccaca gaatcagggg    4140
ataacgcagg aaagaacatg tgagcaaaag gccagcaaaa ggccaggaac cgtaaaaagg    4200
ccgcgttgct ggcgtttttc cataggctcc gcccccctga cgagcatcac aaaaatcgac    4260
gctcaagtca gaggtggcga aacccgacag gactataaag ataccaggcg tttcccctg    4320 gaagctccct cgtgcgctct cctgttccga ccctgccgct taccggatac ctgtccgcct    4380
ttctcccttc gggaagcgtg gcgctttctc atagctcacg ctgtaggtat ctcagttcgg    4440
tgtaggtcgt tcgctccaag ctgggctgtg tgcacgaacc cccgttcag cccgaccgct    4500 gcgccttatc cggtaactat cgtcttgagt ccaacccgt aagacacgac ttatcgccac    4560
tggcagcagc cactggtaac aggattagca gagcgaggta tgtaggcggt gctacagagt    4620
```

| | |
|---|---|
| tcttgaagtg gtggcctaac tacggctaca ctagaagaac agtatttggt atctgcgctc | 4680 |
| tgctgaagcc agttaccttc ggaaaaagag ttggtagctc ttgatccggc aaacaaacca | 4740 |
| ccgctggtag cggtggtttt tttgtttgca agcagcagat tacgcgcaga aaaaaaggat | 4800 |
| ctcaagaaga tcctttgatc ttttctacgg ggtctgacgc tcagtggaac gaaaactcac | 4860 |
| gttaagggat tttggtcatg agattatcaa aaaggatctt cacctagatc cttttaaatt | 4920 |
| aaaaatgaag ttttaaatca atctaaagta tatatgagta acttggtct gacagttacc | 4980 |
| aatgcttaat cagtgaggca cctatctcag cgatctgtct atttcgttca tccatagttg | 5040 |
| cctgactcgg ggggggggg cgctgaggtc tgcctcgtga agaaggtgtt gctgactcat | 5100 |
| accaggcctg aatcgcccca tcatccagcc agaaagtgag ggagccacgg ttgatgagag | 5160 |
| ctttgttgta ggtggaccag ttggtgattt tgaacttttg ctttgccacg gaacggtctg | 5220 |
| cgttgtcggg aagatgcgtg atctgatcct tcaactcagc aaaagttcga tttattcaac | 5280 |
| aaagccgccg tcccgtcaag tcagcgtaat gctctgccag tgttacaacc aattaaccaa | 5340 |
| ttctgattag aaaaactcat cgagcatcaa atgaaactgc aatttattca tatcaggatt | 5400 |
| atcaataccca tattttttgaa aaagccgttt ctgtaatgaa ggagaaaact caccgaggca | 5460 |
| gttccatagg atggcaagat cctggtatcg gtctgcgatt ccgactcgtc aacatcaat | 5520 |
| acaacctatt aatttcccct cgtcaaaaat aaggttatca agtgagaaat caccatgagt | 5580 |
| gacgactgaa tccggtgaga atggcaaaag cttatgcatt tctttccaga cttgttcaac | 5640 |
| aggccagcca ttacgctcgt catcaaaatc actcgcatca accaaaccgt tattcattcg | 5700 |
| tgattgcgcc tgagcgagac gaaatacgcg atcgctgtta aaaggacaat tacaaacagg | 5760 |
| aatcgaatgc aaccggcgca ggaacactgc cagcgcatca acaatatttt cacctgaatc | 5820 |
| aggatattct tctaatacct ggaatgctgt tttcccgggg atcgcagtgg tgagtaacca | 5880 |
| tgcatcatca ggagtacgga taaaatgctt gatggtcgga agaggcataa attccgtcag | 5940 |
| ccagtttagt ctgaccatct catctgtaac atcattggca acgctacctt tgccatgttt | 6000 |
| cagaaacaac tctggcgcat cgggcttccc atacaatcga tagattgtcg cacctgattg | 6060 |
| cccgacatta tcgcgagccc atttataccc atataaatca gcatccatgt tggaatttaa | 6120 |
| tcgcggcctc gagcaagacg tttcccgttg aatatggctc ataacacccc ttgtattact | 6180 |
| gtttatgtaa gcagacagtt ttattgttca tgatgatata tttttatctt gtgcaatgta | 6240 |
| acatcagaga ttttgagaca caacgtggct ttcccccccc ccccattatt gaagcattta | 6300 |
| tcagggttat tgtctcatga gcggatacat atttgaatgt atttagaaaa ataaacaaat | 6360 |
| aggggttccg cgcacatttc cccgaaaagt gccacctgac gtctaagaaa ccattattat | 6420 |
| catgacatta acctataaaa ataggcgtat cacgaggccc tttcgtc | 6467 |

<210> SEQ ID NO 11
<211> LENGTH: 6913
<212> TYPE: DNA
<213> ORGANISM: Artificial Sequence
<220> FEATURE:
<223> OTHER INFORMATION: Synthetic Construct pVR1012x/s Ebola GP(R)(dTM)

<400> SEQUENCE: 11

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |

```
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgaccccg cccattgacg tcaataatga cgtatgttcc        480
catagtaacg ccaataggga cttttccattg acgtcaatgg gtggagtatt tacggtaaac      540
tgcccacttg gcagtacatc aagtgtatca tatgccaagt acgccccta ttgacgtcaa        600 tgacggtaaa tggcccgcct ggcattatgc ccagtacatg accttatggg actttcctac       660
ttggcagtac atctacgtat tagtcatcgc tattaccatg gtgatgcggt tttggcagta       720
catcaatggg cgtggatagc ggtttgactc acggggattt ccaagtctcc accccattga       780
cgtcaatggg agtttgtttt ggcaccaaaa tcaacgggac tttccaaaat gtcgtaacaa       840
ctccgcccca ttgacgcaaa tgggcggtag cgtgtacgg tgggaggtct atataagcag        900
agctcgttta gtgaaccgtc agatcgcctg gagacgccat ccacgctgtt ttgacctcca       960
tagaagacac cgggaccgat ccagcctccg cggccgggaa cggtgcattg aacgcggat       1020 tccccgtgcc aagagtgacg taagtaccgc ctatagactc tataggcaca cccctttggc      1080
tcttatgcat gctatactgt ttttggcttg ggcctatac accccgctt ccttatgcta        1140 taggtgatgg tatagcttag cctataggtg tgggttattg accattattg accactcccc      1200
tattggtgac gatactttcc attactaatc cataacatgg ctctttgcca caactatctc      1260
tattggctat atgccaatac tctgtccttc agagactgac acggactctg tatttttaca      1320
ggatggggtc ccatttatta tttacaaatt cacatataca acaacgccgt cccccgtgcc      1380
cgcagttttt attaaacata gcgtgggatc tccacgcgaa tctcgggtac gtgttccgga      1440 catggctct tctccggtag cggcggagct tccacatccg agccctggtc ccatgcctcc       1500
agcggctcat ggtcgctcgg cagctccttg ctcctaacag tggaggccag acttaggcac      1560
agcacaatgc ccaccaccac cagtgtgccg cacaaggccg tggcggtagg gtatgtgtct      1620
gaaaatgagc gtggagattg ggctcgcacg gctgacgcag atggaagact taaggcagcg      1680
gcagaagaag atgcaggcag ctgagttgtt gtattctgat aagagtcaga ggtaactccc      1740
gttgcggtgc tgttaacggt ggagggcagt gtagtctgag cagtactcgt tgctgccgcg      1800
cgcgccacca gacataatag ctgacagact aacagactgt tcctttccat gggtcttttc      1860
tgcagtcacc gtcgtcgaca cgtgtgatca gatccccaaa ttacctatac aacatggggt      1920
caggatatca acttctccaa ttgcctcggg aacgttttcg taaaacttcg ttcttagtat      1980
gggtaatcat cctcttccag cgagcaatct ccatgccgct tggtatagtg acaaatagca      2040
ctctcaaagc aacagaaatt gatcaattgg tttgtcggga caaactgtca tcaaccagtc      2100
agctcaagtc tgtggggctg aatctggaag gaaatggaat tgcaaccgat gtcccatcag      2160
caacaaaacg ctgggganttt cgttcaggtg tgcctcccaa ggtggtcagc tatgaagccg      2220
gagaatgggc agaaaattgc tacaatctgg agatcaaaaa gtcagacgga agtgaatgcc      2280
tccctctccc tcccgacggt gtacgaggat tccctagatg tcgctatgtc acaaagttc       2340 aaggaacagg tccttgtccc ggtgacttag ctttccataa aaatggggct ttttcttgt       2400 atgatagatt ggcctcaact gtcatctacc gagggacaac ttttgctgaa ggtgtcgtag      2460
cttttttaat tctgtcagag cccaagaagc atttttggaa ggctacacca gctcatgaac      2520
cggtgaacac aacagatgat tccacaagct actacatgac cctgacactc agctacgaga      2580
tgtcaaattt tgggggcaat gaaagtaaca ccctttttaa ggtagacaac cacacatatg      2640
```

```
tgcaactaga tcgtccacac actccgcagt tccttgttca gctcaatgaa acacttcgaa   2700
gaaataatcg ccttagcaac agtacaggga gattgacttg acattggat cctaaaattg    2760 aaccagatgt tggtgagtgg gccttctggg aaactaaaaa aacttttccc aacaacttca   2820
tggagaaaac ttgcatttcc aaattctatc aacccacacc aacaactcct cagatcagag   2880
cccggcggga actgtccaag gaaaaattag ctaccaccca cccgccaaca actccgagct   2940
ggttccaacg gattcccctc cagtggtttc agtgctcact gcaggacgga cagaggaaat   3000
gtcgacccaa ggtctaacca acggagagac aatcacaggt ttcaccgcga acccaatgac   3060
aaccaccatt gccccaagtc aaccatgac aagcgaggtt gataacaatg taccaagtga     3120
acaaccgaac aacacagcat ccattgaaga ctccccccca tcggcaagca acgagacaat   3180
ttaccactcc gagatggatc cgatccaagg ctcgaacaac tccgcccaga gcccacagac   3240
caagaccacg ccagcaccca aacatcccc gatgacccag acccgcaag agacggccaa      3300 cagcagcaaa ccaggaacca gcccaggaag cgcagccgga ccaagtcagc ccggactcac   3360
tataaataca gtaagtaagg tagctgattc actgagtccc accaggaaac aaaagcgatc   3420
ggttcgacaa acaccgcta ataaatgtaa cccagatctt tactattgga cagctgttga     3480
tgagggggca gcagtaggat tggcatggat tccatatttc ggacctgcag cagaaggcat   3540
ctacattgag ggtgtaatgc ataatcagaa tgggcttatt tgcgggctac gtcagctagc   3600
caatgaaact acccaggctc ttcaattatt tctgcgggcc acaacagaac tgaggactta   3660
ctcacttctt aacagaaaag ctattgattt tcttcttcaa cgatggggag gtacctgtcg   3720
aatcctagga ccatcttgtt gcattgagcc acatgattgg acaaaaaata ttactgatga   3780
aattaaccaa attaaacatg actttattga caatccccta ccagaccacg agatgatct     3840 taatctatgg acaggttgga gacaatggtg aatctagacc aggccctgga tccagatctg   3900
ctgtgccttc tagttgccag ccatctgttg tttgccccct ccccgtgcct tccttgaccc   3960
tggaaggtgc cactcccact gtcctttcct aataaaatga ggaaattgca tcgcattgtc   4020
tgagtaggtg tcattctatt ctgggggtg gggtggggca ggacagcaag ggggaggatt     4080
gggaagacaa tagcaggcat gctggggatg cggtgggctc tatgggtacc caggtgctga   4140
agaattgacc cggttcctcc tgggccagaa agaagcaggc acatcccctt ctctgtgaca    4200
caccctgtcc acgcccctgg ttcttagttc cagcccact cataggacac tcatagctca     4260
ggagggctcc gccttcaatc ccacccgcta agtacttgg agcggtctct ccctccctca     4320
tcagcccacc aaaccaaacc tagcctccaa gagtgggaag aaattaaagc aagataggct   4380
attaagtgca gagggagaga aaatgcctcc aacatgtgag gaagtaatga gagaaatcat   4440
agaattttaa ggccatgatt taaggccatc atggccttaa tcttccgctt cctcgctcac   4500
tgactcgctg cgctcggtcg ttcggctgcg gcgagcggta tcagctcact caaaggcggt   4560
aatacggtta tccacagaat cagggataa cgcaggaaa acatgtgag caaaaggcca      4620 gcaaaggcc aggaaccgta aaaaggccgc gttgctggcg ttttttccata ggctccgccc     4680 ccctgacgag catcacaaaa atcgacgctc aagtcagagg tggcgaaacc cgacaggact   4740
ataaagatac caggcgtttc ccctggaag ctccctcgtg cgctctcctg ttccgaccct     4800
gccgcttacc ggatacctgt ccgcctttct cccttcggga agcgtggcgc tttctcatag   4860
ctcacgctgt aggtatctca gttcggtgta ggtcgttcgc tccaagctgg gctgtgtgca   4920
cgaacccccc gttcagcccg accgctgcgc cttatccggt aactatcgtc ttgagtccaa   4980
cccggtaaga cacgacttat cgccactggc agcagccact ggtaacagga ttagcagagc   5040
```

```
gaggtatgta ggcggtgcta cagagttctt gaagtggtgg cctaactacg gctacactag    5100
aagaacagta tttggtatct gcgctctgct gaagccagtt accttcggaa aaagagttgg    5160
tagctcttga tccggcaaac aaaccaccgc tggtagcggt ggttttttg tttgcaagca     5220 gcagattacg cgcagaaaaa aaggatctca agaagatcct ttgatctttt ctacggggtc    5280
tgacgctcag tggaacgaaa actcacgtta agggattttg gtcatgagat tatcaaaaag    5340
gatcttcacc tagatccttt taaattaaaa atgaagtttt aaatcaatct aaagtatata    5400
tgagtaaact tggtctgaca gttaccaatg cttaatcagt gaggcaccta tctcagcgat    5460
ctgtctattt cgttcatcca tagttgcctg actcggggg gggggggcgct gaggtctgcc    5520 tcgtgaagaa ggtgttgctg actcatacca ggcctgaatc gccccatcat ccagccagaa    5580
agtgagggag ccacggttga tgagagcttt gttgtaggtg gaccagttgg tgattttgaa    5640
cttttgcttt gccacggaac ggtctgcgtt gtcgggaaga tgcgtgatct gatccttcaa    5700
ctcagcaaaa gttcgattta ttcaacaaag ccgccgtccc gtcaagtcag cgtaatgctc    5760
tgccagtgtt acaaccaatt aaccaattct gattagaaaa actcatcgag catcaaatga    5820
aactgcaatt tattcatatc aggattatca ataccatatt tttgaaaaag ccgtttctgt    5880
aatgaaggag aaaactcacc gaggcagttc cataggatgg caagatcctg gtatcggtct    5940
gcgattccga ctcgtccaac atcaatacaa cctattaatt tcccctcgtc aaaaataagg    6000
ttatcaagtg agaaatcacc atgagtgacg actgaatccg gtgagaatgg caaaagctta    6060
tgcatttctt tccagacttg ttcaacaggc cagccattac gctcgtcatc aaaatcactc    6120
gcatcaacca aaccgttatt cattcgtgat tgcgcctgag cgagacgaaa tacgcgatcg    6180
ctgttaaaag gacaattaca aacaggaatc gaatgcaacc ggcgcaggaa cactgccagc    6240
gcatcaacaa tattttcacc tgaatcagga tattcttcta atacctggaa tgctgttttc    6300
ccggggatcg cagtggtgag taaccatgca tcatcaggag tacggataaa atgcttgatg    6360
gtcggaagag gcataaattc cgtcagccag tttagtctga ccatctcatc tgtaacatca    6420
ttggcaacgc tacctttgcc atgtttcaga aacaactctg gcgcatcggg cttcccatac    6480
aatcgataga ttgtcgcacc tgattgcccg acattatcgc gagcccattt atacccatat    6540
aaatcagcat ccatgttgga atttaatcgc ggcctcgagc aagacgtttc ccgttgaata    6600
tggctcataa caccccttgt attactgttt atgtaagcag acagttttat tgttcatgat    6660
gatatatttt tatcttgtgc aatgtaacat cagagatttt gagacacaac gtggctttcc    6720
cccccccccc attattgaag catttatcag ggttattgtc tcatgagcgg atacatattt    6780
gaatgtattt agaaaaataa acaaataggg gttccgcgca catttccccg aaaagtgcca    6840
cctgacgtct aagaaaccat tattatcatg acattaacct ataaaaatag gcgtatcacg    6900
aggccctttc gtc                                                       6913
```

<210> SEQ ID NO 12
<211> LENGTH: 8131
<212> TYPE: DNA
<213> ORGANISM: Artificial Sequence
<220> FEATURE:
<223> OTHER INFORMATION: Synthetic Construct pAdApt Ebola GP(R)(dTM)

<400> SEQUENCE: 12

```
ttaattaacc gcaattctca tgtttgacag cttatcatca tcaataatat accttatttt     60
ggattgaagc caatatgata atgaggggt ggagtttgtg acgtggcgcg ggcgtggga     120 acggggcggg tgacgtagta gtgtggcgga agtgtgatgt tgcaagtgtg gcggaacaca    180
```

```
tgtaagcgac ggatgtggca aaagtgacgt ttttggtgtg cgccggtgta cacaggaagt      240
gacaattttc gcgcggtttt aggcggatgt tgtagtaaat ttgggcgtaa ccgagtaaga      300
tttggccatt ttcgcgggaa aactgaataa gaggaagtga atctgaata attttgtgtt       360 actcatagcg cgtaatattt gtctagggcc gcggggactt tgaccgttta cgtggagact      420
cgcccaggtg ttttctcag gtgttttccg cgttccgggt caaagttggc gttttattat       480
tatagtcagt acgtaccagt gcactggcct agagcggccc cattgcatac gttgtatcca      540
tatcataata tgtacattta tattggctca tgtccaacat taccgccatg ttgacattga      600
ttattgacta gttattaata gtaatcaatt acggggtcat tagttcatag cccatatatg      660
gagttccgcg ttacataact tacggtaaat ggcccgcctg gctgaccgcc caacgacccc      720
cgcccattga cgtcaataat gacgtatgtt cccatagtaa cgccaatagg actttccat      780 tgacgtcaat gggtggagta tttacggtaa actgcccact tggcagtaca tcaagtgtat      840
catatgccaa gtacgccccc tattgacgtc aatgacggta atggcccgc ctggcattat       900 gcccagtaca tgaccttatg gactttcct acttggcagt acatctacgt attagtcatc       960
gctattacca tggtgatgcg gttttggcag tacatcaatg ggcgtggata gcggtttgac      1020
tcacggggat ttccaagtct ccaccccatt gacgtcaatg ggagtttgtt ttggcaccaa      1080
aatcaacggg actttccaaa atgtcgtaac aactccgccc cattgacgca aatgggcggt      1140
aggcgtgtac ggtgggaggt ctatataagc agagctcgtt tagtgaaccg tcagatcgcc      1200
tggagacgcc atccacgctg ttttgacctc catagaagac accgggaccg atccagcctc      1260
cgtcaccgtc gtcgacacgt gtgatcagat atcaacttct ccaattgcct cgggaacgtt      1320
ttcgtaaaac ttcgttctta gtatgggtaa tcatcctctt ccagcgagca atctccatgc      1380
cgcttggtat agtgacaaat agcactctca aagcaacaga aattgatcaa ttggtttgtc      1440 gggacaaaact gtcatcaacc agtcagctca agtctgtggg gctgaatctg aaggaaatg      1500 gaattgcaac cgatgtccca tcagcaacaa aacgctgggg atttcgttca ggtgtgcctc      1560
ccaaggtggt cagctatgaa gccggagaat gggcagaaaa ttgctacaat ctggagatca      1620
aaaagtcaga cggaagtgaa tgcctccctc tccctcccga cggtgtacga ggattcccta      1680
gatgtcgcta tgtccacaaa gttcaaggaa caggtccttg tcccggtgac ttagcttttcc     1740 ataaaaatgg ggcttttttc ttgtatgata gattggcctc aactgtcatc taccgaggga      1800
caacttttgc tgaaggtgtc gtagcttttt taattctgtc agagcccaag aagcattttt      1860
ggaaggctac accagctcat gaaccggtga acacaacaga tgattccaca agctactaca      1920
tgaccctgac actcagctac gagatgtcaa attttggggg caatgaaagt aacacccttt      1980
ttaaggtaga caaccacaca tatgtgcaac tagatcgtcc acacactccg cagttccttg      2040
ttcagctcaa tgaaacactt cgaagaaata atcgccttag caacagtaca gggagattga      2100
cttggacatt ggatcctaaa attgaaccag atgttggtga gtgggccttc tgggaaacta      2160
aaaaaacttt tcccaacaac ttcatggaga aaacttgcat ttccaaattc tatcaacccca     2220 caccaacaac tcctcagatc agagcccggc gggaactgtc caaggaaaaa ttagctacca      2280
cccacccgcc aacaactccg agctggttcc aacggattcc cctccagtgg tttcagtgct      2340
cactgcagga cggacagagg aaatgtcgac ccaaggtcta accaacgag agacaatcac       2400 aggtttcacc gcgaacccaa tgacaaccac cattgcccca agtccaacca tgacaagcga      2460
ggttgataac aatgtaccaa gtgaacaacc gaacaacaca gcatccattg aagactcccc      2520
cccatcggca agcaacgaga caatttacca ctccgagatg gatccgatcc aaggctcgaa      2580
```

-continued

```
caactccgcc cagagcccac agaccaagac cacgccagca cccacaacat ccccgatgac    2640
ccaggacccg caagagacgg ccaacagcag caaaccagga accagcccag gaagcgcagc    2700
cggaccaagt cagcccggac tcactataaa tacagtaagt aaggtagctg attcactgag    2760
tcccaccagg aaacaaaagc gatcggttcg acaaaacacc gctaataaat gtaacccaga    2820
tctttactat tggacagctg ttgatgaggg ggcagcagta ggattggcat ggattccata    2880
tttcggacct gcagcagaag gcatctacat tgagggtgta atgcataatc agaatgggct    2940
tatttgcggg ctacgtcagc tagccaatga aactacccag gctcttcaat tatttctgcg    3000
ggccacaaca gaactgagga cttactcact tcttaacaga aaagctattg attttcttct    3060
tcaacgatgg ggaggtacct gtcgaatcct aggaccatct tgttgcattg agccacatga    3120
ttggacaaaa atattactg atgaaattaa ccaaattaaa catgacttta ttgacaatcc     3180
cctaccagac cacggagatg atcttaatct atggacaggt tggagacaat ggtgaatcta    3240
gaccaggccc tggatccaga tctgctgtgc cttctagttg ccagccatct gttgtttgcc    3300
cctcccccgt gccttccttg accctggaag gtgccactcc cactgtcctt tcctaataaa    3360
atgaggaaat tgcatcgcat tgtctgagta ggtgtcattc tattctgggg ggtgggggtgg   3420 ggcagcacag caaggggggag gattgggaag acaatagcag gcatgctggg gatgcggtgg   3480
gctctatggg tacccagggc cgcataactt cgtataatgt atgctatacg aagttataag    3540
atctgtactg aaatgtgtgg gcgtggctta agggtgggaa agaatatata aggtgggggt    3600
cttatgtagt tttgtatctg ttttgcagca gccgccgccg ccatgagcac caactcgttt    3660
gatggaagca ttgtgagctc atatttgaca acgcgcatgc ccccatgggc cggggtgcgt    3720
cagaatgtga tgggctccag cattgatggt cgcccccgtcc tgcccgcaaa ctctactacc    3780
ttgacctacg agaccgtgtc tggaacgccg ttggagactg cagcctccgc cgccgcttca    3840
gccgctgcag ccaccgcccg cgggattgtg actgactttg cttttcctgag cccgcttgca    3900 agcagtgcag cttcccgttc atccgcccgc gatgacaagt tgacggctct tttggcacaa    3960
ttggattctt tgacccggga acttaatgtc gtttctcagc agctgttgga tctgcgccag    4020
caggtttctg ccctgaaggc ttcctcccct cccaatgcgg tttaaaacat aaataaaaaa    4080
ccagactctg tttggatttg gatcaagcaa gtgtcttgct gtctttattt aggggttttg    4140
cgcgcgcggt aggcccggga ccagcggtct cggtcgttga gggtcctgtg tatttttttcc   4200 aggacgtggt aaaggtgact ctggatgttc agatacatgg gcataagccc gtctctgggg    4260
tggaggtagc accactgcag agcttcatgc tgcggggtgg tgttgtagat gatccagtcg    4320
tagcaggagc gctgggcgtg gtgcctaaaa atgtctttca gtagcaagct gattgccagg    4380
ggcaggccct tggtgtaagt gttttacaaag cggttaagct gggatgggtg catacgtggg   4440
gatatgagat gcatcttgga ctgtattttt aggttggcta tgttcccagc catatccctc    4500
cggggattca tgttgtgcag aaccaccagc acagtgtatc cggtgcactt gggaaatttg    4560
tcatgtagct tagaaggaaa tgcgtggaag aacttggaga cgcccttgtg acctccaaga    4620
ttttccatgc attcgtccat aatgatggca atgggcccac gggcggcggc ctgggcgaag    4680
atatttctgg gatcactaac gtcatagttg tgttccagga tgagatcgtc ataggccatt    4740
tttacaaagc gcgggcggag ggtgccgaca tgcggtataa tggttccatc cggcccaggg    4800
gcgtagttac cctcacagat ttgcatttcc cacgctttga gttcagatgg ggggatcatg    4860
tctacctgcg gggcgatgaa gaaaacggtt tccggggtag gggagatcag ctgggaagaa    4920
agcaggttcc tgagcagctg cgacttaccg cagccggtgg gcccgtaaat cacacctatt    4980
```

```
accggctgca actggtagtt aagagagctg cagctgccgt catccctgag caggggggcc    5040
acttcgttaa gcatgtccct gactcgcatg ttttccctga ccaaatccgc cagaaggcgc    5100
tcgccgccca gcgatagcag ttcttgcaag gaagcaaagt ttttcaacgg tttgagaccg    5160
tccgccgtag gcatgctttt gagcgtttga ccaagcagtt ccaggcggtc ccacagctcg    5220
gtcacctgct ctacggcatc tcgatccagc atatctcctc gtttcgcggg ttggggcggc    5280
tttcgctgta cggcagtagt cggtgctcgt ccagacgggc caggtcatg tctttccacg     5340
ggcgcagggt cctcgtcagc gtagtctggg tcacggtgaa ggggtgcgct ccgggctgcg    5400
cgctggccag ggtgcgcttg aggctggtcc tgctggtgct gaagcgctgc cggtcttcgc    5460
cctgcgcgtc ggccaggtag catttgacca tggtgtcata gtccagcccc tccgcggcgt    5520
ggcccttggc gcgcagcttg cccttggagg aggcgccgca cgaggggcag tgcagacttt    5580
tgagggcgta gagcttgggc gcgagaaata ccgattccgg ggagtaggca tccgcgccgc    5640
aggccccgca gacggtctcg cattccacga gccaggtgag ctctggccgt tcggggtcaa    5700
aaaccaggtt tccccatgc ttttgatgc gtttcttacc tctggtttcc atgagccggt      5760
gtccacgctc ggtgacgaaa aggctgtccg tgtccccgta tacagacttg agaggcctgt    5820
cctcgagcgg tgttccgcgg tcctcctcgt atagaaactc ggaccactct gagacaaagg    5880
ctcgcgtcca ggccagcacg aaggaggcta agtgggaggg gtagcggtcg ttgtccacta    5940
gggggtccac tcgctccagg gtgtgaagac acatgtcgcc ctcttcggca tcaaggaagg    6000
tgattggttt gtaggtgtag gccacgtgac cgggtgttcc tgaagggggg ctataaaagg    6060
gggtggggc gcgttcgtcc tcactctctt ccgcatcgct gtctgcgagg ccagctgtt     6120
ggggtgagtc gacgcgaggc tggatggcct tccccattat gattcttctc gcttccggcg    6180
gcatcgggat gcccgcgttg caggccatgc tgtccaggca ggtagatgac gaccatcagg    6240
gacagcttca aggccagcaa aaggccagga ccgtaaaaa ggccgcgttg ctggcgtttt     6300
tccataggct ccgccccct gacgagcatc acaaaaatcg acgctcaagt cagaggtggc     6360
gaaacccgac aggactataa agataccagg cgtttccccc tggaagctcc ctcgtgcgct    6420
ctcctgttcc gaccctgccg cttaccggat acctgtccgc ctttctccct cgggaagcg     6480
tggcgctttc tcatagctca cgctgtaggt atctcagttc ggtgtaggtc gttcgctcca    6540
agctgggctg tgtgcacgaa ccccccgttc agcccgaccg ctgcgcctta ccggtaact     6600
atcgtcttga gtccaacccg gtaagacacg acttatcgcc actggcagca gccactggta    6660
acaggattag cagagcgagg tatgtaggcg gtgctacaga gttcttgaag tggtggccta    6720
actacggcta cactagaagg acagtatttg gtatctgcgc tctgctgaag ccagttacct    6780
tcggaaaaag agttggtagc tcttgatccg gcaaacaaac caccgctggt agcggtggtt    6840
ttttgtttg caagcagcag attacgcgca gaaaaaagg atctcaagaa gatcctttga      6900
tcttttctac gggtctgac gctcagtgga acgaaaactc acgttaaggg attttggtca     6960
tgagattatc aaaaggatc ttcacctaga tccttttaaa ttaaaaatga gttttaaat      7020
caatctaaag tatatatgag taaacttggt ctgacagtta ccaatgctta atcagtgagg    7080
cacctatctc agcgatctgt ctatttcgtt catccatagt tgcctgactc cccgtcgtgt    7140
agataactac gatacgggag ggcttaccat ctggccccag tgctgcaatg ataccgcgag    7200
acccacgctc accggctcca gatttatcag caataaacca gccagccgga agggccgagc    7260
gcagaagtgg tcctgcaact ttatccgcct ccatccagtc tattaattgt tgccgggaag    7320
ctagagtaag tagttcgcca gttaatagtt tgcgcaacgt tgttgccatt gctgcaggca    7380
```

| | |
|---|---|
| tcgtggtgtc acgctcgtcg tttggtatgg ctttcattcag ctccggttcc caacgatcaa | 7440 |
| ggcgagttac atgatccccc atgttgtgca aaaaagcggt tagctccttc ggtcctccga | 7500 |
| tcgttgtcag aagtaagttg gccgcagtgt tatcactcat ggttatggca gcactgcata | 7560 |
| attctcttac tgtcatgcca tccgtaagat gcttttctgt gactggtgag tactcaacca | 7620 |
| agtcattctg agaatagtgt atgcggcgac cgagttgctc ttgcccggcg tcaacacggg | 7680 |
| ataataccgc gccacatagc agaactttaa aagtgctcat cattggaaaa cgttcttcgg | 7740 |
| ggcgaaaact ctcaaggatc ttaccgctgt tgagatccag ttcgatgtaa cccactcgtg | 7800 |
| cacccaactg atcttcagca tcttttactt tcaccagcgt ttctgggtga gcaaaaacag | 7860 |
| gaaggcaaaa tgccgcaaaa aagggaataa gggcgacacg gaaatgttga atactcatac | 7920 |
| tcttcctttt tcaatattat tgaagcattt atcagggtta ttgtctcatg agcggataca | 7980 |
| tatttgaatg tatttagaaa aataaacaaa tagggggttcc gcgcacattt ccccgaaaag | 8040 |
| tgccacctga cgtctaagaa accattatta tcatgacatt aacctataaa aataggcgta | 8100 |
| tcacgaggcc ctttcgtctt caagaattgt t | 8131 |

<210> SEQ ID NO 13
<211> LENGTH: 7082
<212> TYPE: DNA
<213> ORGANISM: Artificial Sequence
<220> FEATURE:
<223> OTHER INFORMATION: Synthetic Construct pVR1012-GP(S)

<400> SEQUENCE: 13

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaatagggga ctttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |
| tcttatgcat gctatactgt ttttggcttg gggcctatac cccccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tattttaca | 1320 |

-continued

```
ggatggggtc ccatttatta tttacaaatt cacatataca acaacgccgt cccccgtgcc      1380
cgcagttttt attaaacata gcgtgggatc tccacgcgaa tctcgggtac gtgttccgga      1440
catgggctct tctccggtag cggcggagct tccacatccg agccctggtc ccatgcctcc      1500
agcggctcat ggtcgctcgg cagctccttg ctcctaacag tggaggccag acttaggcac      1560
agcacaatgc ccaccaccac cagtgtgccg cacaaggccg tggcggtagg gtatgtgtct      1620
gaaaatgagc gtggagattg ggctcgcacg gctgacgcag atggaagact taaggcagcg      1680
gcagaagaag atgcaggcag ctgagttgtt gtattctgat aagagtcaga ggtaactccc      1740
gttgcggtgc tgttaacggt ggagggcagt gtagtctgag cagtactcgt tgctgccgcg      1800
cgcgccacca gacataatag ctgacagact aacagactgt tcctttccat gggtcttttc      1860
tgcagtcacc gtcgtcgaca cgtgtgatca gatatcgcgg ccgctctagc tagatgcatg      1920
ctcgagcggc cgccagtgtg atggatatct gcagaattcg gcttatcttc aggatctcgc      1980
catggagggt cttagcctac tccaattgcc cagagataaa tttcgaaaaa gctcttcctt      2040
tgtttgggtc atcatcttat ttcaaaggc cttttccatg cctttgggtg ttgtgaccaa       2100 cagcactta gaagtaacag agattgacca gctagtctgc aaggatcatc ttgcatccac       2160
tgaccagctg aaatcagttg gtctcaacct cgaggggagc ggagtatcta ctgatatccc      2220
atctgcgaca aagcgttggg gcttcagatc tggtgtgcct cccaaggtgg tcagctatga      2280
agcaggagaa tgggctgaaa attgctacaa tcttgaaata agaagccgg acgggagcga       2340 atgcttaccc ccaccgccgg atggtgtcag aggctttcca aggtgccgct atgttcacaa      2400
agcccaagga accgggccct gcccgggtga ctatgccttt cacaaggatg gagctttctt      2460
cctctatgac aggctggctt caactgtaat ttacagagga gtcaattttg ctgagggggt      2520
aattgcattc ttgatattgg ctaaaccaaa ggaaacgttc cttcaatcac cccccattcg      2580
agaggcagta aactcactg aaaatacatc aagttactat gccacatcct acttggagta      2640
cgaaatcgaa aattttggtg ctcaacactc cacgacccctt ttcaaaatta acaataatac     2700
ttttgttctt ctggacaggc cccacacgcc tcagttcctt ttccagctga atgataccat      2760
tcaccttcac caacagttga gcaacacaac tgggaaacta atttggacac tagatgctaa      2820
tatcaatgct gatattggtg aatgggcttt ttgggaaaat aaaaaaaatc tctccgaaca      2880
actacgtgga gaagagctgt cttcgaaac tttatcgctc aacgagacag aagacgatga      2940
tgcgacatcg tcgagaacta caaagggaag aatctccgac cgggccacca ggaagtattc      3000
ggacctggtt ccaaaggatt cccctgggat ggtttcattg cacgtaccag aagggggaaac      3060 aacattgccg tctcagaatt cgacagaagg tcgaagagta gatgtgaata ctcaggaaac      3120
tatcacagag acaactgcaa caatcatagg cactaacggt aacaacatgc agatctccac      3180
catcgggaca ggactgagct ccagccaaat cctgagttcc tcaccgacca tggcaccaag      3240
ccctgagact cagacctcca caacctacac accaaaacta ccagtgatga ccaccgagga      3300
accaacaaca ccaccgagaa actctcctgg ctcaacaaca gaagcaccca ctctcaccac      3360
cccagagaat ataacaacag cggttaaaac tgttttgcca caagagtcca caagcaacgg      3420
tctaataact tcaacagtaa caggattct tgggagcctt ggacttcgaa aacgcagcag      3480
aagacaagtt aacaccaggg ccacgggtaa atgcaatccc aacttacact actgactgc       3540 acaagaacaa cataatgctg ctgggattgc ctggatcccg tactttggac cgggtgcaga      3600
aggcatatac actgaaggcc ttatgcacaa ccaaaatgcc ttagtctgtg gactcagaca      3660
acttgcaaat gaaacaactc aagctctgca gctttttctta agggccacga cggagctgcg      3720
```

```
gacatatacc atactcaata ggaaggccat agatttcctt ctgcgacgat ggggcgggac    3780
atgtaggatc ctgggaccag attgttgcat tgagccacat gattggacca aaaacatcac    3840
tgataaaatc aaccaaatca tccatgattt catcgacaac cctttaccca atcaggataa    3900
tgatgataat tggtggacgg gctggagaca gtggatccct gcaggaatag gcattactgg    3960
aattattatt gcaatcattg ctcttctttg cgtctgcaag ctgctttgtt gaatatcaag    4020
ccgaattcca gcacactggc ggccgttact agtggatccg agctcggatc caagctctag    4080
accaggccct ggatccagat ctgctgtgcc ttctagttgc cagccatctg ttgtttgccc    4140
ctcccccgtg ccttccttga ccctggaagg tgccactccc actgtccttt cctaataaaa    4200
tgaggaaatt gcatcgcatt gtctgagtag gtgtcattct attctggggg gtggggtggg    4260
gcaggacagc aaggggggagg attgggaaga caatagcagg catgctgggg atgcggtggg    4320
ctctatgggt acccaggtgc tgaagaattg acccggttcc tcctgggcca gaaagaagca    4380
ggcacatccc cttctctgtg acacccctg tccacgcccc tggttcttag ttccagcccc    4440
actcatagga cactcatagc tcaggagggc tccgccttca atcccacccg ctaaagtact    4500
tggagcggtc tctccctccc tcatcagccc accaaaccaa acctagcctc caagagtggg    4560
aagaaattaa agcaagatag gctattaagt gcagagggag agaaaatgcc tccaacatgt    4620
gaggaagtaa tgagagaaat catagaattt cttccgcttc ctcgctcact gactcgctgc    4680
gctcggtcgt tcggctgcgg cgagcggtat cagctcactc aaaggcggta atacggttat    4740
ccacagaatc aggggataac gcaggaaaga acatgtgagc aaaaggccag caaaaggcca    4800
ggaaccgtaa aaaggccgcg ttgctggcgt ttttccatag gctccgcccc cctgacgagc    4860
atcacaaaaa tcgacgctca agtcagaggt ggcgaaaccc gacaggacta taaagatacc    4920
aggcgtttcc ccctggaagc tccctcgtgc gctctcctgt tccgaccctg ccgcttaccg    4980
gatacctgtc cgcctttctc ccttcgggaa gcgtggcgct ttctcatagc tcacgctgta    5040
ggtatctcag ttcggtgtag gtcgttcgct ccaagctggg ctgtgtgcac gaaccccccg    5100
ttcagcccga ccgctgcgcc ttatccggta actatcgtct tgagtccaac ccggtaagac    5160
acgacttatc gccactggca gcagccactg gtaacaggat tagcagagcg aggtatgtag    5220
gcggtgctac agagttcttg aagtggtggc ctaactacgg ctacactaga agaacagtat    5280
ttggtatctg cgctctgctg aagccagtta ccttcggaaa aagagttggt agctcttgat    5340
ccggcaaaca aaccaccgct ggtagcggtg gtttttttgt ttgcaagcag cagattacgc    5400
gcagaaaaaa aggatctcaa gaagatcctt tgatcttttc tacggggtct gacgctcagt    5460
ggaacgaaaa ctcacgttaa gggattttgg tcatgagatt atcaaaaagg atcttcacct    5520
agatcctttt aaattaaaaa tgaagtttta atcaatcta aagtatatat gagtaaactt    5580
ggtctgacag ttaccaatgc ttaatcagtg aggcacctat ctcagcgatc tgtctatttc    5640
gttcatccat agttgcctga ctcggggggg ggggcgctg aggtctgcct cgtgaagaag    5700
gtgttgctga ctcataccag gcctgaatcg ccccatcatc cagccagaaa gtgagggagc    5760
cacggttgat gagagctttg ttgtaggtgg accagttggt gattttgaac ttttgctttg    5820
ccacggaacg gtctgcgttg tcgggaagat gcgtgatctg atccttcaac tcagcaaaag    5880
ttcgatttat tcaacaaagc cgccgtcccg tcaagtcagc gtaatgctct gccagtgtta    5940
caaccaatta accaattctg attagaaaaa ctcatcgagc atcaaatgaa actgcaattt    6000
attcatatca ggattatcaa taccatattt ttgaaaagc cgtttctgta atgaaggaga    6060
aaactcaccg aggcagttcc ataggatggc aagatcctgg tatcggtctg cgattccgac    6120
```

-continued

| | |
|---|---|
| tcgtccaaca tcaatacaac ctattaattt ccctcgtca aaataaggt tatcaagtga | 6180 |
| gaaatcacca tgagtgacga ctgaatccgg tgagaatggc aaaagcttat gcatttcttt | 6240 |
| ccagacttgt tcaacaggcc agccattacg ctcgtcatca aaatcactcg catcaaccaa | 6300 |
| accgttattc attcgtgatt gcgcctgagc gagacgaaat acgcgatcgc tgttaaaagg | 6360 |
| acaattacaa acaggaatcg aatgcaaccg gcgcaggaac actgccagcg catcaacaat | 6420 |
| attttcacct gaatcaggat attcttctaa tacctggaat gctgttttcc cggggatcgc | 6480 |
| agtggtgagt aaccatgcat catcaggagt acggataaaa tgcttgatgg tcggaagagg | 6540 |
| cataaattcc gtcagccagt ttagtctgac catctcatct gtaacatcat ggcaacgct | 6600 |
| acctttgcca tgtttcagaa acaactctgg cgcatcgggc ttcccataca atcgatagat | 6660 |
| tgtcgcacct gattgcccga cattatcgcg agcccattta tacccatata aatcagcatc | 6720 |
| catgttggaa tttaatcgcg gcctcgagca agacgtttcc cgttgaatat ggctcataac | 6780 |
| accccttgta ttactgttta tgtaagcaga cagtttatt gttcatgatg atatattttt | 6840 |
| atcttgtgca atgtaacatc agagattttg agacacaacg tggctttccc cccccccca | 6900 |
| ttattgaagc atttatcagg gttattgtct catgagcgga tacatatttg aatgtattta | 6960 |
| gaaaaataaa caaataggg ttccgcgcac atttccccga aaagtgccac ctgacgtcta | 7020 |
| agaaaccatt attatcatga cattaaccta taaaaatagg cgtatcacga ggccctttcg | 7080 |
| tc | 7082 |

<210> SEQ ID NO 14
<211> LENGTH: 7087
<212> TYPE: DNA
<213> ORGANISM: Artificial Sequence
<220> FEATURE:
<223> OTHER INFORMATION: Synthetic Construct pVR1012x/s Ebola GP(S)

<400> SEQUENCE: 14

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |

```
tcttatgcat gctatactgt ttttggcttg gggcctatac accccccgctt ccttatgcta    1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca     1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgccagtgt gatggatatc    1920
tgcagaattc ggcttatctt caggatctcg ccatggaggg tcttagccta ctccaattgc    1980
ccagagataa atttcgaaaa agctctttct ttgtttgggt catcatctta tttcaaaagg    2040
cctttttccat gcctttgggt gttgtgacca acagcacttt agaagtaaca gagattgacc    2100
agctagtctg caaggatcat cttgcatcca ctgaccagct gaaatcagtt ggtctcaacc    2160
tcgaggggag cggagtatct actgatatcc catctgcgac aaagcgttgg ggcttcagat    2220
ctggtgtgcc tcccaaggtg gtcagctatg aagcaggaga atgggctgaa aattgctaca    2280
atcttgaaat aaagaagccg gacgggagcg aatgcttacc cccaccgccg gatggtgtca    2340
gaggcttttcc aaggtgccgc tatgttcaca agcccaagg aaccgggccc tgcccggggtg    2400
actatgcctt tcacaaggat ggagcttttct tcctctatga caggctggct tcaactgtaa    2460
tttacagagg agtcaatttt gctgaggggg taattgcatt cttgatattg ctaaaccaa     2520
aggaaacgtt ccttcaatca ccccccattc gagaggcagt aaactacact gaaaatacat    2580
caagttacta tgccacatcc tacttggagt acgaaatcga aaattttggt gctcaacact    2640
ccacgaccct tttcaaaatt aacaataata cttttgttct tctggacagg ccccacacgc    2700
ctcagttcct tttccagctg aatgatacca ttcaccttca ccaacagttg agcaacacaa    2760
ctgggaaact aatttggaca ctagatgcta atatcaatgc tgatattggt gaatgggctt    2820
tttgggaaaa taaaaaaaat ctctccgaac aactacgtgg agaagagctg tctttcgaaa    2880
ctttatcgct caacgagaca gaagacgatg atgcgcatc gtcgagaact acaaagggaa     2940
gaatctccga ccgggccacc aggaagtatt cggacctggt tccaaggat tcccctggga    3000
tggtttcatt gcacgtacca gaaggggaaa caacattgcc gtctcagaat cgacagaag    3060
gtcgaagagt agatgtgaat actcaggaaa ctatcacaga gacaactgca acaatcatag    3120
gcactaacgg taacaacatg cagatctcca ccatcgggac aggactgagc tccagccaaa    3180
tcctgagttc ctcaccgacc atggcaccaa gccctgagac tcagacctcc acaacctaca    3240
caccaaaact accagtgatg accaccgagg aatcaacaac accaccgaga aactctcctg    3300
gctcaacaac agaagcaccc actctcacca ccccagagaa tataacaaca gcggttaaaa    3360
ctgttttgcc acaagagtcc acaagcaacg gtctaataac ttcaacagta acagggattc    3420
ttgggagcct tggacttcga aaacgcagca gaagacaagt taacaccagg gccacgggta    3480
```

```
aatgcaatcc caacttacac tactggactg cacaagaaca acataatgct gctgggattg   3540
cctggatccc gtactttgga ccgggtgcag aaggcatata cactgaaggc cttatgcaca   3600
accaaaatgc cttagtctgt ggactcagac aacttgcaaa tgaaacaact caagctctgc   3660
agcttttctt aagggccacg acggagctgc ggacatatac catactcaat aggaaggcca   3720
tagatttcct tctgcgacga tggggcggga catgtaggat cctgggacca gattgttgca   3780
ttgagccaca tgattggacc aaaaacatca ctgataaaat caaccaaatc atccatgatt   3840
tcatcgacaa cccttaccc aatcaggata atgatgataa ttggtggacg ggctggagac   3900
agtggatccc tgcaggaata ggcattactg gaattattat tgcaatcatt gctcttcttt   3960
gcgtctgcaa gctgctttgt tgaatatcaa gccgaattcc agcacactgg cggccgttac   4020
tagtggatcc gagctcggta ccaagctcta gaccaggccc tggatccaga tctgctgtgc   4080
cttctagttg ccagccatct gttgtttgcc ctcccccgt gccttccttg accctggaag   4140
gtgccactcc cactgtcctt tcctaataaa atgaggaaat tgcatcgcat tgtctgagta   4200
ggtgtcattc tattctgggg ggtgggtgg ggcaggacag caaggggag gattgggaag   4260 acaatagcag gcatgctggg gatgcggtgg gctctatggg tacccaggtg ctgaagaatt   4320
gacccggttc ctcctgggcc agaaagaagc aggcacatcc ccttctctgt gacacaccct   4380
gtccacgccc ctggttctta gttccagccc cactcatagg acactcatag ctcaggaggg   4440
ctccgccttc aatcccaccc gctaaagtac ttggagcggt ctctccctcc ctcatcagcc   4500
caccaaacca aacctagcct ccaagagtgg aagaaatta aagcaagata ggctattaag   4560
tgcagaggga gagaaaatgc ctccaacatg tgaggaagta atgagagaaa tcatagaatt   4620
ttaaggccat gatttaaggc catcatggcc ttaatcttcc gcttcctcgc tcactgactc   4680
gctgcgctcg gtcgttcggc tgcggcgagc ggtatcagct cactcaaagg cggtaatacg   4740
gttatccaca gaatcagggg ataacgcagg aagaacatg tgagcaaaag gccagcaaaa   4800
ggccaggaac cgtaaaaagg ccgcgttgct ggcgtttttc cataggctcc gcccccctga   4860
cgagcatcac aaaaatcgac gctcaagtca gaggtggcga acccgacag gactataaag   4920 ataccaggcg tttcccctg aagctccct cgtgcgctct cctgttccga ccctgccgct   4980
taccggatac ctgtccgcct ttctcccttc gggaagcgtg gcgctttctc atagctcacg   5040
ctgtaggtat ctcagttcgg tgtaggtcgt tcgctccaag ctgggctgtg tgcacgaacc   5100
ccccgttcag cccgaccgct gcgccttatc cggtaactat cgtcttgagt ccaacccggt   5160
aagacacgac ttatcgccac tggcagcagc cactggtaac aggattagca gagcgaggta   5220
tgtaggcggt gctacagagt tcttgaagtg gtggcctaac tacggctaca ctagaagaac   5280
agtatttggt atctgcgctc tgctgaagcc agttaccttc ggaaaaagag ttggtagctc   5340
ttgatccggc aaacaaacca ccgctggtag cggtggtttt tttgtttgca agcagcagat   5400
tacgcgcaga aaaaaggat ctcaagaaga tcctttgatc ttttctacgg gtctgacgc   5460 tcagtggaac gaaaactcac gttaagggat tttggtcatg agattatcaa aaaggatctt   5520
cacctagatc cttttaaatt aaaaatgaag ttttaaatca atctaaagta tatatgagta   5580
aacttggtct gacagttacc aatgcttaat cagtgaggca cctatctcag cgatctgtct   5640
atttcgttca tccatagttg cctgactcgg gggggggg cgctgaggtc tgcctcgtga   5700
agaaggtgtt gctgactcat accaggcctg aatcgcccca tcatccagcc agaaagtgag   5760
ggagccacgg ttgatgagag ctttgttgta ggtggaccag ttggtgattt tgaacttttg   5820
ctttgccacg gaacggtctg cgttgtcggg aagatgcgtg atctgatcct tcaactcagc   5880
```

```
aaaagttcga tttattcaac aaagccgccg tcccgtcaag tcagcgtaat gctctgccag      5940
tgttacaacc aattaaccaa ttctgattag aaaaactcat cgagcatcaa atgaaactgc      6000
aatttattca tatcaggatt atcaatacca tattttgaa aaagccgttt ctgtaatgaa       6060
ggagaaaact caccgaggca gttccatagg atggcaagat cctggtatcg gtctgcgatt      6120
ccgactcgtc caacatcaat acaacctatt aatttcccct cgtcaaaaat aaggttatca      6180
agtgagaaat caccatgagt gacgactgaa tccggtgaga atggcaaaag cttatgcatt      6240
tctttccaga cttgttcaac aggccagcca ttacgctcgt catcaaaatc actcgcatca      6300
accaaaccgt tattcattcg tgattgcgcc tgagcgagac gaaatacgcg atcgctgtta      6360
aaaggacaat tacaaacagg aatcgaatgc aaccggcgca ggaacactgc cagcgcatca      6420
acaatatttt cacctgaatc aggatattct tctaatacct ggaatgctgt tttcccgggg      6480
atcgcagtgg tgagtaacca tgcatcatca ggagtacgga taaaatgctt gatggtcgga      6540
agaggcataa attccgtcag ccagtttagt ctgaccatct catctgtaac atcattggca      6600
acgctacctt tgccatgttt cagaaacaac tctggcgcat cgggcttccc atacaatcga      6660
tagattgtcg cacctgattg cccgacatta tcgcgagccc atttataccc atataaatca      6720
gcatccatgt tggaatttaa tcgcggcctc gagcaagacg tttcccgttg aatatggctc      6780
ataacacccc ttgtattact gtttatgtaa gcagacagtt ttattgttca tgatgatata      6840
tttttatctt gtgcaatgta acatcagaga ttttgagaca aacgtggct tcccccccc       6900 ccccattatt gaagcattta tcagggttat tgtctcatga gcggatacat atttgaatgt      6960
atttagaaaa ataaacaaat aggggttccg cgcacatttc cccgaaaagt gccacctgac      7020
gtctaagaaa ccattattat catgacatta acctataaaa ataggcgtat cacgaggccc      7080
tttcgtc                                                                7087

<210> SEQ ID NO 15
<211> LENGTH: 6940
<212> TYPE: DNA
<213> ORGANISM: Artificial Sequence
<220> FEATURE:
<223> OTHER INFORMATION: Synthetic Construct pVR1012-GP(S) delta TM

<400> SEQUENCE: 15
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac      360
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaatagga cttttccattg acgtcaatgg gtggagtatt tacgtaaac       540 tgcccacttg gcagtacatc aagtgtatca tatgccaagt acgccccta ttgacgtcaa       600 tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggcaccaaaa tcaacgggac tttccaaaat gtcgtaacaa      840
```

```
ctccgcccca ttgacgcaaa tgggcggtag gcgtgtacgg tgggaggtct atataagcag      900
agctcgttta gtgaaccgtc agatcgcctg gagacgccat ccacgctgtt ttgacctcca      960
tagaagacac cgggaccgat ccagcctccg cggccgggaa cggtgcattg aacgcggat      1020 tccccgtgcc aagagtgacg taagtaccgc ctatagactc tataggcaca ccccttggc      1080 tcttatgcat gctatactgt ttttggcttg gggcctatac accccgctt ccttatgcta      1140 taggtgatgg tatagcttag cctataggtg tgggttattg accattattg accactcccc      1200
tattggtgac gatactttcc attactaatc cataacatgg ctctttgcca caactatctc      1260
tattggctat atgccaatac tctgtccttc agagactgac acggactctg tattttaca      1320 ggatggggtc ccatttatta tttacaaatt cacatataca acaacgccgt cccccgtgcc      1380
cgcagttttt attaaacata gcgtgggatc tccacgcgaa tctcgggtac gtgttccgga      1440
catgggctct tctccggtag cggcggagct tccacatccg agccctggtc ccatgcctcc      1500
agcggctcat ggtcgctcgg cagctccttg ctcctaacag tggaggccag acttaggcac      1560
agcacaatgc ccaccaccac cagtgtgccg cacaaggccg tggcggtagg gtatgtgtct      1620
gaaaatgagc gtggagattg ggctcgcacg gctgacgcag atggaagact taaggcagcg      1680
gcagaagaag atgcaggcag ctgagttgtt gtattctgat aagagtcaga ggtaactccc      1740
gttgcggtgc tgttaacggt ggagggcagt gtagtctgag cagtactcgt tgctgccgcg      1800
cgcgccacca gacataatag ctgacagact aacagactgt tcctttccat gggtcttttc      1860
tgcagtcacc gtcgtcgact ctagctagat gcatgctcga gcggccgcca gtgtgatgga      1920
tatctgcaga attcggctta tcttcaggat ctcgccatgg agggtcttag cctactccaa      1980
ttgcccagag ataaatttcg aaaaagctct ttctttgttt gggtcatcat cttatttcaa      2040
aaggcctttt ccatgccttt gggtgttgtg accaacagca ctttagaagt aacagagatt      2100
gaccagctag tctgcaagga tcatcttgca tccactgacc agctgaaatc agttggtctc      2160
aacctcgagg ggagcggagt atctactgat atcccatctg cgacaaagcg ttggggcttc      2220
agatctggtg tgcctcccaa ggtggtcagc tatgaagcag gagaatgggc tgaaaattgc      2280
tacaatcttg aaataaagaa gccggacggg agcgaatgct taccccacc gccggatggt      2340 gtcagaggct ttccaaggtg ccgctatgtt cacaaagccc aaggaaccgg gccctgcccg      2400
ggtgactatg cctttcacaa ggatggagct ttcttcctct atgacaggct ggcttcaact      2460
gtaatttaca gaggagtcaa ttttgctgag ggggtaattg cattcttgat attggctaaa      2520
ccaaaggaaa cgttccttca atcacccccc attgagagg cagtaaacta cactgaaaat      2580
acatcaagtt actatgccac atcctacttg gagtacgaaa tcgaaaattt tggtgctcaa      2640
cactccacga cccttttcaa aattaacaat aatactttg ttcttctgga caggccccac      2700
acgcctcagt tccttttcca gctgaatgat accattcacc ttcaccaaca gttgagcaac      2760
acaactggga aactaattg gacactagat gctaatatca atgctgatat tggtgaatgg      2820
gcttttgggg aaaataaaaa aaatctctcc gaacaactac gtggagaaga gctgtctttc      2880
gaaactttat cgctcaacga gacagaagac gatgatgcga catcgtcgag aactacaaag      2940
ggaagaatct ccgaccgggc caccaggaag tattcggacc tggttccaaa ggattcccct      3000
gggatggttt cattgcacgt accagaaggg gaaacaacat tgccgtctca gaattcgaca      3060
gaaggtcgaa gagtagatgt gaatactcag gaaactatca cagagacaac tgcaacaatc      3120
ataggcacta acggtaacaa catgcagatc tccaccatcg ggacaggact gagctccagc      3180
caaatcctga gttcctcacc gaccatggca ccaagccctg agactcagac ctccacaacc      3240
```

```
tacacaccaa aactaccagt gatgaccacc gaggaaccaa caacaccacc gagaaactct    3300
cctggctcaa caacagaagc acccactctc accaccccag agaatataac aacagcggtt    3360
aaaactgttt tgccacaaga gtccacaagc aacggtctaa taacttcaac agtaacaggg    3420
attcttggga gccttggact tcgaaaacgc agcagaagac aagttaacac cagggccacg    3480
ggtaaatgca atcccaactt acactactgg actgcacaag aacaacataa tgctgctggg    3540
attgcctgga tcccgtactt tggaccgggt gcagaaggca tatacactga aggccttatg    3600
cacaaccaaa atgccttagt ctgtggactc agacaacttg caaatgaaac aactcaagct    3660
ctgcagcttt tcttaagggc cacgacggag ctgcggacat ataccatact caataggaag    3720
gccatagatt tccttctgcg acgatggggc gggacatgta ggatcctggg accagattgt    3780
tgcattgagc cacatgattg gaccaaaaac atcactgata aaatcaacca aatcatccat    3840
gatttcatcg acaaccettt acccaatcag gataatgatg ataattggtg gacgggctgg    3900
agacagtgga tcccggccgc atcgtgactg actgacgatc tgcctcgcgg atccagatct    3960
gctgtgcctt ctagttgcca gccatctgtt gtttgccect ccccgtgcc ttccttgacc    4020 ctggaaggtg ccactcccac tgtcctttcc taataaaatg aggaaattgc atcgcattgt    4080
ctgagtaggt gtcattctat tctgggggt ggggtggggc aggacagcaa ggggaggat    4140 tgggaagaca atagcaggca tgctggggat gcggtgggct ctatgggtac ccaggtgctg    4200
aagaattgac ccggttcctc ctgggccaga agaagcagg cacatcccct tctctgtgac    4260
acaccctgtc cacgccectg gttcttagtt ccagccccac tcataggaca ctcatagctc    4320
aggagggctc cgccttcaat cccacccgct aaagtacttg gagcggtctc tccctccctc    4380
atcagcccac caaccaaac ctagcctcca agagtgggaa gaaattaaag caagataggc    4440
tattaagtgc agagggagag aaaatgcctc caacatgtga ggaagtaatg agagaaatca    4500
tagaatttct tccgcttcct cgctcactga ctcgctgcgc tcgtcgttc ggctgcggcg    4560 agcggtatca gctcactcaa aggcggtaat acggttatcc acagaatcag gggataacgc    4620
aggaaagaac atgtgagcaa aaggccagca aaaggccagg aaccgtaaaa aggccgcgtt    4680
gctggcgttt ttccataggc tccgcccccc tgacgagcat cacaaaaatc gacgctcaag    4740
tcagaggtgg cgaaacccga caggactata aagataccag gcgtttcccc ctggaagctc    4800
cctcgtgcgc tctcctgttc cgaccctgcc gcttaccgga tacctgtccg cctttctccc    4860
ttcgggaagc gtggcgcttt ctcatagctc acgctgtagg tatctcagtt cggtgtaggt    4920
cgttcgctcc aagctgggct gtgtgcacga accccccgtt cagcccgacc gctgcgcctt    4980
atccggtaac tatcgtcttg agtccaaccc ggtaagacac gacttatcgc cactggcagc    5040
agccactggt aacaggatta gcagagcgag gtatgtaggc ggtgctacag agttcttgaa    5100
gtggtggcct aactacggct acactagaag aacagtattt ggtatctgcg ctctgctgaa    5160
gccagttacc ttcggaaaaa gagttggtag ctcttgatcc ggcaaacaaa ccaccgctgg    5220
tagcggtggt ttttttgttt gcaagcagca gattacgcgc agaaaaaaag gatctcaaga    5280
agatcctttg atcttttcta cggggtctga cgctcagtgg aacgaaaact cacgttaagg    5340
gattttggtc atgagattat caaaaaggat cttcacctag atccttttaa attaaaaatg    5400
aagttttaaa tcaatctaaa gtatatatga gtaaacttgg tctgacagtt accaatgctt    5460
aatcagtgag gcacctatct cagcgatctg tctatttcgt tcatccatag ttgcctgact    5520 cgggggggg gggcgctgag gtctgcctcg tgaagaaggt gttgctgact cataccaggc    5580
ctgaatcgcc ccatcatcca gccagaaagt gagggagcca cggttgatga gagctttgtt    5640
```

-continued

```
gtaggtggac cagttggtga ttttgaactt ttgctttgcc acggaacggt ctgcgttgtc    5700
gggaagatgc gtgatctgat ccttcaactc agcaaaagtt cgatttattc aacaaagccg    5760
ccgtcccgtc aagtcagcgt aatgctctgc cagtgttaca accaattaac caattctgat    5820
tagaaaaact catcgagcat caaatgaaac tgcaatttat tcatatcagg attatcaata    5880 ccatatttt gaaaaagccg tttctgtaat gaaggagaaa actcaccgag gcagttccat    5940
aggatggcaa gatcctggta tcggtctgcg attccgactc gtccaacatc aatacaacct    6000
attaatttcc cctcgtcaaa ataaggtta tcaagtgaga atcaccatg agtgacgact    6060 gaatccggtg agaatggcaa aagcttatgc atttctttcc agacttgttc aacaggccag    6120
ccattacgct cgtcatcaaa atcactcgca tcaaccaaac cgttattcat cgtgattgc    6180 gcctgagcga gacgaaatac gcgatcgctg ttaaaaggac aattacaaac aggaatcgaa    6240
tgcaaccggc gcaggaacac tgccagcgca tcaacaatat tttcacctga atcaggatat    6300
tcttctaata cctggaatgc tgttttccg gggatcgcag tggtgagtaa ccatgcatca    6360
tcaggagtac ggataaaatg cttgatggtc ggaagaggca taaattccgt cagccagttt    6420
agtctgacca tctcatctgt aacatcattg gcaacgctac ctttgccatg tttcagaaac    6480
aactctggcg catcgggctt cccatacaat cgatagattg tcgcacctga ttgcccgaca    6540
ttatcgcgag cccatttata cccatataaa tcagcatcca tgttggaatt taatcgcggc    6600
ctcgagcaag acgtttcccg ttgaatatgg ctcataacac cccttgtatt actgtttatg    6660
taagcagaca gttttattgt tcatgatgat atatttttat cttgtgcaat gtaacatcag    6720
agattttgag acacaacgtg gctttccccc ccccccatt attgaagcat ttatcagggt    6780
tattgtctca tgagcggata catatttgaa tgtatttaga aaataaaaca aataggggtt    6840
ccgcgcacat ttccccgaaa agtgccacct gacgtctaag aaaccattat tatcatgaca    6900
ttaacctata aaataggcg tatcacgagg ccctttcgtc                           6940
```

<210> SEQ ID NO 16
<211> LENGTH: 7002
<212> TYPE: DNA
<213> ORGANISM: Artificial Sequence
<220> FEATURE:
<223> OTHER INFORMATION: Synthetic Construct pVR1012-GP(IC)

<400> SEQUENCE: 16

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
```

-continued

```
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttggc    1080 tcttatgcat gctatactgt ttttggcttg ggcctatac accccgctt ccttatgcta    1140 taggtgatgg tatagcttag cctataggtg tgggttattg accattattg accactcccc   1200
tattggtgac gatactttcc attactaatc cataacatgg ctcttgcca caactatctc    1260 tattggctat atgccaatac tctgtccttc agagactgac acggactctg tatttttaca    1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtcttttca atcccgttgg    2040
gggttgtaca caacaatacc ctacaagtga gtgatattga caagtttgtg tgccgagaca    2100
aactctcttc aactagccaa ttgaagtcag tcggttgaa cttggagggc aatggagtag    2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
aaggagcctt cttcctgtat gaccgactcg catcaacaat catttatcgg ggtacaacct    2460
ttgccgaagg agttattgca tttctgatct tgcctaaggc gcgaaaggat ttttccagt     2520 ctcctccatt gcatgagcct gccaacatga ccacgatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
accaggtcct tgacacgaca gcgacggtct ctcctcccat ctccgcccac aaccacgcag    2940
ccgaagacca caagaattg gtttcagagg attccactcc agtggttcag atgcaaaaca    3000
tcaagggaaa ggacacaatg ccaaccacag tgacgggtgt accaacaacc acccctctc    3060 catttccaat caatgctcgc aacactgatc ataccaaatc atttatcggc ctggagggc     3120 cccaagaaga ccacagcacc acacagcctg ccaagaccac cagccaacca accaacagca    3180
```

```
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac ccgacgaac     3360 tcagtggacc tggcttcctg acgaacacaa tacgggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720 gatgggagg aacatgtcac attctagggc ctgattgttg cattgaaccc caagattgga    3780
ccaaaaatat cactgataaa attgatcaaa taatccatga ctttgtcgat aataatcttc    3840
caaatcagaa tgatggcagc aactggtgga ctggatggaa acaatgggtt cctgctggaa    3900
taggaatcac aggagtaatc attgctatta ttgctttgct gtgcatttgc aaattcatgc    3960
tttgaactaa tatagcatca tactttaagc cgaattctag accaggccct ggatccagat    4020
ctgctgtgcc ttctagttgc cagccatctg ttgtttgccc ctccccgtg ccttccttga     4080 ccctggaagg tgccactccc actgtccttt cctaataaaa tgaggaaatt gcatcgcatt    4140
gtctgagtag gtgtcattct attctggggg gtggggtggg gcaggacagc aaggggagg    4200 attgggaaga caatagcagg catgctgggg atgcggtggg ctctatgggt acccaggtgc    4260
tgaagaattg acccggttcc tcctgggcca gaaagaagca ggcacatccc cttctctgtg    4320
acacaccctg tccacgcccc tggttcttag ttccagcccc actcatagga cactcatagc    4380
tcaggagggc tccgccttca atcccacccg ctaaagtact tggagcggtc tctccctccc    4440
tcatcagccc accaaaccaa acctagcctc caagagtggg aagaaattaa agcaagatag    4500
gctattaagt gcagagggag agaaaatgcc tccaacatgt gaggaagtaa tgagagaaat    4560
catagaattt cttccgcttc ctcgctcact gactcgctgc gctcggtcgt tcggctgcgg    4620
cgagcggtat cagctcactc aaaggcggta atacggttat ccacagaatc agggggataac    4680 gcaggaaaga acatgtgagc aaaaggccag caaaaggcca ggaaccgtaa aaaggccgcg    4740
ttgctggcgt ttttccatag gctccgcccc cctgacgagc atcacaaaaa tcgacgctca    4800
agtcagaggt ggcgaaaccc gacaggacta taaagatacc aggcgtttcc ccctggaagc    4860
tccctcgtgc gctctcctgt tccgaccctg ccgcttaccg gatacctgtc cgcctttctc    4920
ccttcgggaa gcgtggcgct ttctcatagc tcacgctgta ggtatctcag ttcggtgtag    4980
gtcgttcgct ccaagctggg ctgtgtgcac gaaccccccg ttcagcccga ccgctgcgcc    5040
ttatccggta actatcgtct tgagtccaac ccggtaagac acgacttatc gccactggca    5100
gcagccactg gtaacaggat tagcagagcg aggtatgtag cgtgctac agagttcttg     5160 aagtggtggc ctaactacgg ctacactaga agaacagtat ttggtatctg cgctctgctg    5220
aagccagtta ccttcggaaa aagagttggt agctcttgat ccggcaaaca aaccaccgct    5280
ggtagcggtg gtttttttgt ttgcaagcag cagattacgc gcagaaaaaa aggatctcaa    5340
gaagatcctt tgatcttttc tacgggtct gacgctcagt ggaacgaaaa ctcacgttaa     5400
gggattttgg tcatgagatt atcaaaaagg atcttcacct agatcctttt aaattaaaaa    5460
tgaagtttta aatcaatcta agtatatat gagtaaactt ggtctgacag ttaccaatgc     5520
ttaatcagtg aggcacctat ctcagcgatc tgtctatttc gttcatccat agttgcctga    5580
```

```
ctcgggggggg gggggcgctg aggtctgcct cgtgaagaag gtgttgctga ctcataccag    5640
gcctgaatcg ccccatcatc cagccagaaa gtgagggagc cacggttgat gagagctttg    5700
ttgtaggtgg accagttggt gattttgaac ttttgctttg ccacggaacg gtctgcgttg    5760
tcgggaagat gcgtgatctg atccttcaac tcagcaaaag ttcgatttat tcaacaaagc    5820
cgccgtcccg tcaagtcagc gtaatgctct gccagtgtta caaccaatta accaattctg    5880
attagaaaaa ctcatcgagc atcaaatgaa actgcaattt attcatatca ggattatcaa    5940
taccatattt ttgaaaaagc cgtttctgta atgaaggaga aaactcaccg aggcagttcc    6000
ataggatggc aagatcctgg tatcggtctg cgattccgac tcgtccaaca tcaatacaac    6060
ctattaattt cccctcgtca aaataaggt tatcaagtga gaaatcacca tgagtgacga    6120
ctgaatccgg tgagaatggc aaaagcttat gcatttcttt ccagacttgt tcaacaggcc    6180
agccattacg ctcgtcatca aaatcactcg catcaaccaa accgttattc attcgtgatt    6240
gcgcctgagc gagacgaaat acgcgatcgc tgttaaaagg acaattacaa acaggaatcg    6300
aatgcaaccg gcgcaggaac actgccagcg catcaacaat attttcacct gaatcaggat    6360
attcttctaa tacctggaat gctgttttcc cggggatcgc agtggtgagt aaccatgcat    6420
catcaggagt acggataaaa tgcttgatgg tcggaagagg cataaattcc gtcagccagt    6480
ttagtctgac catctcatct gtaacatcat tggcaacgct acctttgcca tgtttcagaa    6540
acaactctgg cgcatcgggc ttcccataca atcgatagat tgtcgcacct gattgcccga    6600
cattatcgcg agcccattta tacccatata atcagcatc catgttggaa tttaatcgcg    6660
gcctcgagca agacgtttcc cgttgaatat ggctcataac ccccttgta ttactgttta    6720 tgtaagcaga cagttttatt gttcatgatg atatatttt atcttgtgca atgtaacatc    6780
agagattttg agacacaacg tggctttccc cccccccca ttattgaagc atttatcagg    6840
gttattgtct catgagcgga tacatatttg aatgtatttta gaaaataaa caaatagggg    6900 ttccgcgcac atttccccga aaagtgccac ctgacgtcta agaaaccatt attatcatga    6960
cattaaccta taaaaatagg cgtatcacga ggccctttcg tc                       7002
```

<210> SEQ ID NO 17
<211> LENGTH: 7036
<212> TYPE: DNA
<213> ORGANISM: Artificial Sequence
<220> FEATURE:
<223> OTHER INFORMATION: Synthetic Construct pVR1012 x/s Ebola GP(IC)

<400> SEQUENCE: 17

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
```

-continued

```
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca ccccttttggc   1080 tcttatgcat gctatactgt ttttggcttg ggcctatac accccgctt ccttatgcta   1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga attcggcttc   1920
taatcacagt caccatggga gcgtcaggga ttctgcaatt gccccgtgag cgcttcagga   1980
aaacatcttt cttttgtttgg gtaataatcc tattccataa agtcttttca atcccgttgg   2040
gggttgtaca caacaatacc ctacaagtga gtgatattga caagtttgtg tgccgagaca   2100
aactctcttc aactagccaa ttgaagtcag tcgggttgaa cttggagggc aatggagtag   2160
caactgatgt accaacggca accaaaagat ggggttttcg agctggtgtt ccaccaaagg   2220
tggtaaattg cgaagctgga gaatgggctg agaactgtta taacctggct ataaagaaag   2280
ttgatggtag tgagtgccta ccagaagccc ctgagggagt gagggatttt ccccgttgcc   2340
gctatgtaca caaagtctca ggaactggac catgcccagg aggactcgcc tttcacaaag   2400
aaggagcctt cttcctgtat gaccgactcg catcaacaat catttatcgg ggtacaacct   2460
ttgccgaagg agttattgca tttctgatct tgcctaaggc gcgaaaggat ttttttccagt   2520 ctcctccatt gcatgagcct gccaacatga ccacggatcc ctccagttac tatcacacga   2580
caacaataaa ctacgtggtt gataattttg aaccaacac cacagagttt ctgttccaag   2640
tcgatcattt gacgtatgtg cagctcgagg caagattcac accacaattc cttgtcctcc   2700
taaatgaaac catctactct gataaccgca gaagtaacac aacaggaaaa ctaatctgga   2760
aaataaatcc cactgttgat accagcatgg gtgagtgggc tttctgggaa aataaaaaaa   2820
acttcacaaa aacccttttca agtgaagagt tgtcttttcgt acctgtacca gaacccaga   2880 accaggtcct tgacacgaca gcgacggtct ctcctcccat ctccgcccac aaccacgcag   2940
ccgaagacca caaagaattg gtttcagagg attccactcc agtggttcag atgcaaaaca   3000
tcaagggaaa ggacacaatg ccaaccacag tgacgggtgt accaacaacc acaccctctc   3060
```

```
catttccaat caatgctcgc aacactgatc ataccaaatc atttatcggc ctggaggggc    3120
cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtg ccattccaag agccgtgcac cccgacgaac    3360
tcagtggacc tggcttcctg acgaacacaa tacgggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720
gatggggagg aacatgtcac attctagggc ctgattgttg cattgaaccc caagattgga    3780
ccaaaaatat cactgataaa attgatcaaa taatccatga cttttgtcgat aataatcttc    3840 caaatcagaa tgatggcagc aactggtgga ctggatggaa acaatgggtt cctgctggaa    3900
taggaatcac aggagtaatc attgctatta ttgcttttgct gtgcatttgc aaattcatgc    3960
tttgaactaa tatagcatca tactttaagc cgaattctag accaggccct ggatccagat    4020
ctgctgtgcc ttctagttgc cagccatctg ttgtttgccc ctccccgtg ccttccttga    4080 ccctggaagg tgccactccc actgtccttt cctaataaaa tgaggaaatt gcatcgcatt    4140
gtctgagtag gtgtcattct attctggggg gtggggtggg gcaggacagc aagggggagg    4200
attgggaaga caatagcagg catgctgggg atgcggtggg ctctatgggt acccaggtgc    4260
tgaagaattg acccggttcc tcctgggcca gaaagaagca ggcacatccc cttctctgtg    4320
acacaccctg tccacgcccc tggttcttag ttccagcccc actcatagga cactcatagc    4380
tcaggagggc tccgccttca atcccacccg ctaaagtact tggagcggtc tctccctccc    4440
tcatcagccc accaaaccaa acctagcctc caagagtggg aagaaattaa agcaagatag    4500
gctattaagt gcagagggag agaaaatgcc tccaacatgt gaggaagtaa tgagagaaat    4560
catagaattt taaggccatg atttaaggcc atcatggcct taatcttccg cttcctcgct    4620
cactgactcg ctgcgctcgg tcgttcggct gcggcgagcg tatcagctc actcaaaggc    4680 ggtaatacgg ttatccacag aatcagggga taacgcagga agaacatgt gagcaaaagg    4740 ccagcaaaag gccaggaacc gtaaaaaggc cgcgttgctg gcgttttttcc ataggctccg    4800 cccccctgac gagcatcaca aaaatcgacg ctcaagtcag aggtggcgaa acccgacagg    4860
actataaaga taccaggcgt ttccccctgg aagctccctc gtgcgctctc ctgttccgac    4920
cctgccgctt accggatacc tgtccgcctt tctcccttcg ggaagcgtgg cgctttctca    4980
tagctcacgc tgtaggtatc tcagttcggt gtaggtcgtt cgctccaagc tgggctgtgt    5040
gcacgaaccc cccgttcagc ccgaccgctg cgccttatcc ggtaactatc gtcttgagtc    5100
caacccggta agacacgact tatcgccact ggcagcagcc actggtaaca ggattagcag    5160
agcgaggtat gtaggcggtg ctacagagtt cttgaagtgg tggcctaact acggctacac    5220
tagaagaaca gtatttggta tctgcgctct gctgaagcca gttaccttcg gaaaaagagt    5280
tggtagctct tgatccggca aacaaaccac cgctggtagc ggtggttttt tgtttgcaa    5340 gcagcagatt acgcgcagaa aaaaaggatc tcaagaagat cctttgatct tttctacggg    5400
gtctgacgct cagtggaacg aaaactcacg ttaagggatt ttggtcatga gattatcaaa    5460
```

-continued

```
aaggatcttc acctagatcc ttttaaatta aaaatgaagt tttaaatcaa tctaaagtat    5520
atatgagtaa acttggtctg acagttacca atgcttaatc agtgaggcac ctatctcagc    5580
gatctgtcta tttcgttcat ccatagttgc ctgactcggg gggggggggc gctgaggtct    5640
gcctcgtgaa gaaggtgttg ctgactcata ccaggcctga atcgccccat catccagcca    5700
gaaagtgagg gagccacggt tgatgagagc tttgttgtag gtggaccagt tggtgatttt    5760
gaacttttgc tttgccacgg aacggtctgc gttgtcggga gatgcgtga tctgatcctt    5820 caactcagca aaagttcgat ttattcaaca agccgccgt cccgtcaagt cagcgtaatg    5880
ctctgccagt gttacaacca attaaccaat tctgattaga aaaactcatc gagcatcaaa    5940
tgaaactgca atttattcat atcaggatta tcaataccat attttttgaaa agccgtttc    6000 tgtaatgaag gagaaaactc accgaggcag ttccatagga tggcaagatc ctggtatcgg    6060
tctgcgattc cgactcgtcc aacatcaata aaccctatta atttcccctc gtcaaaaata    6120
aggttatcaa gtgagaaatc accatgagtg acgactgaat ccgtgagaa tggcaaaagc    6180 ttatgcattt ctttccagac ttgttcaaca ggccagccat tacgctcgtc atcaaaatca    6240
ctcgcatcaa ccaaaccgtt attcattcgt gattgcgcct gagcgagacg aaatacgcga    6300
tcgctgttaa aaggacaatt acaaacagga atcgaatgca accggcgcag gaacactgcc    6360
agcgcatcaa caatattttc acctgaatca ggatattctt ctaatacctg gaatgctgtt    6420
ttcccgggga tcgcagtggt gagtaaccat gcatcatcag gagtacggat aaaatgcttg    6480
atggtcggaa gaggcataaa ttccgtcagc cagtttagtc tgaccatctc atctgtaaca    6540
tcattggcaa cgctaccttt gccatgtttc agaaacaact ctggcgcatc gggcttccca    6600
tacaatcgat agattgtcgc acctgattgc ccgacattat cgcgagccca tttatcccca    6660
tataaatcag catccatgtt ggaatttaat cgcggcctcg agcaagacgt ttcccgttga    6720
atatggctca taacacccct tgtattactg tttatgtaag cagacagttt tattgttcat    6780
gatgatatat ttttatcttg tgcaatgtaa catcagagat tttgagacac aacgtggctt    6840 tcccccccccc cccattattg aagcatttat cagggttatt gtctcatgag cggatacata    6900
tttgaatgta tttagaaaaa taaacaaata ggggttccgc gcacatttcc ccgaaaagtg    6960
ccacctgacg tctaagaaac cattattatc atgacattaa cctataaaaa taggcgtatc    7020
acgaggccct ttcgtc                                                    7036
```

<210> SEQ ID NO 18
<211> LENGTH: 6885
<212> TYPE: DNA
<213> ORGANISM: Artificial Sequence
<220> FEATURE:
<223> OTHER INFORMATION: Synthetic Construct pVR1012-GP(IC) delta TM

<400> SEQUENCE: 18

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
```

```
catagtaacg ccaatuggga ctttccattg acgtcaatgg gtggagtatt tacggtaaac    540
tgcccacttg gcagtacatc aagtgtatca tatgccaagt acgccccta ttgacgtcaa    600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg gggcctatac accccgctt ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtcttttca atcccgttgg    2040
gggttgtaca caacaatacc ctacaagtga gtgatattga caagtttgtg tgccgagaca    2100
aactctcttc aactagccaa ttgaagtcag tcgggttgaa cttggagggc aatggagtag    2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
aaggagcctt cttcctgtat gaccgactcg catcaacaat catttatcgg ggtacaacct    2460
ttgccgaagg agttattgca tttctgatct tgcctaaggc gcgaaaggat ttttccagt    2520 ctcctccatt gcatgagcct gccaacatga ccacggatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttca agtgaagagt tgtctttcgt acctgtacca gaaacccaga    2880
```

```
accaggtcct tgacacgaca gcgacggtct ctcctcccat ctccgcccac aaccacgcag   2940
ccgaagacca caaagaattg gtttcagagg attccactcc agtggttcag atgcaaaaca   3000
tcaagggaaa ggacacaatg ccaaccacag tgacgggtgt accaacaacc acaccctctc   3060
catttccaat caatgctcgc aacactgatc ataccaaatc atttatcggc ctggaggggc   3120
cccaagaaga ccacagcacc acacagcctg ccaagaccac cagccaacca accaacagca   3180
cagaatcgac gacactaaac ccaacatcag agccctccag tagaggcacg ggaccatcca   3240
gccccacggt ccccaacacc acagaaagcc acgccgaact tggcaagaca accccaacca   3300
cactcccaga acagcacact gccgccagtg ccattccaag agccgtgcac cccgacgaac   3360
tcagtggacc tggcttcctg acgaacacaa tacgggggt acaaatctc ctgacaggat   3420 ccagaagaaa gcgaagggat gtcactccca atacacaacc caaatgcaac caaacctgc   3480 actattggac agccttggat gagggtgctg ccataggttt agcctggata ccatacttcg   3540
ggccagcagc tgagggaatt tacactgaag gcataatgga gaatcaaaat ggattgatct   3600
gtggattgag gcagctggcc aacgaaacga cacaagctct tcaattgttc ttaagggcaa   3660
ctactgagtt gcgtacattc tctatactaa atcggaaagc aatagacttc ttgctccaaa   3720 gatgggagg aacatgtcac attctagggc ctgattgttg cattgaaccc caagattgga   3780
ccaaaaatat cactgataaa attgatcaaa taatccatga ctttgtcgat aataatcttc   3840
caaatcagaa tgatggcagg gccgcatcgt gactgactga cgatctgcct cgcggatcca   3900
gatctgctgt gccttctagt tgccagccat ctgttgtttg cccctccccc gtgccttcct   3960
tgaccctgga aggtgccact cccactgtcc tttcctaata aaatgaggaa attgcatcgc   4020
attgtctgag taggtgtcat tctattctgg ggggtgggt ggggcaggac agcaagggg   4080 aggattggga agacaatagc aggcatgctg gggatgcggt gggctctatg ggtacccagg   4140
tgctgaagaa ttgacccggt tcctcctggg ccagaaagaa gcaggcacat ccccttctct   4200
gtgacacacc ctgtccacgc ccctggttct tagttccagc cccactcata ggacactcat   4260
agctcaggag ggctccgcct tcaatcccac ccgctaaagt acttggagcg gtctctccct   4320
ccctcatcag cccaccaaac caaacctagc ctccaagagt gggaagaaat taaagcaaga   4380
taggctatta agtgcagagg gagagaaaat gcctccaaca tgtgaggaag taatgagaga   4440
aatcatagaa tttcttccgc ttcctcgctc actgactcgc tgcgctcggt cgttcggctg   4500
cggcgagcgg tatcagctca ctcaaaggcg gtaatacggt tatccacaga atcaggggat   4560
aacgcaggaa agaacatgtg agcaaaaggc cagcaaaagg ccaggaaccg taaaaaggcc   4620
gcgttgctgg cgtttttcca taggctccgc cccctgacg agcatcacaa aatcgacgc   4680 tcaagtcaga ggtggcgaaa cccgacagga ctataaagat accaggcgtt cccccctgga   4740
agctccctcg tgcgctctcc tgttccgacc ctgccgctta ccggatacct gtccgccttt   4800
ctcccttcgg gaagcgtggc gctttctcat agctcacgct gtaggtatct cagttcggtg   4860
taggtcgttc gctccaagct gggctgtgtg cacgaacccc ccgttcagcc cgaccgctgc   4920
gccttatccg gtaactatcg tcttgagtcc aacccggtaa gacacgactt atcgccactg   4980
gcagcagcca ctggtaacag gattagcaga gcgaggtatg taggcggtgc tacagagttc   5040
ttgaagtggt ggcctaacta cggctacact agaagaacag tatttggtat ctgcgctctg   5100
ctgaagccag ttaccttcgg aaaaagagtt ggtagctctt gatccggcaa acaaaccacc   5160
gctggtagcg gtggtttttt tgtttgcaag cagcagatta cgcgcagaaa aaaggatct   5220 caagaagatc ctttgatctt ttctacgggg tctgacgctc agtggaacga aaactcacgt   5280
```

| | | | | |
|---|---|---|---|---|
| taagggattt | tggtcatgag | attatcaaaa | aggatcttca | cctagatcct tttaaattaa | 5340 |
| aaatgaagtt | ttaaatcaat | ctaaagtata | tatgagtaaa | cttggtctga cagttaccaa | 5400 |
| tgcttaatca | gtgaggcacc | tatctcagcg | atctgtctat | ttcgttcatc catagttgcc | 5460 |
| tgactcgggg | gggggggcg | ctgaggtctg | cctcgtgaag | aaggtgttgc tgactcatac | 5520 |
| caggcctgaa | tcgccccatc | atccagccag | aaagtgaggg | agccacggtt gatgagagct | 5580 |
| tgttgtagg | tggaccagtt | ggtgattttg | aacttttgct | ttgccacgga acggtctgcg | 5640 |
| ttgtcgggaa | gatgcgtgat | ctgatccttc | aactcagcaa | aagttcgatt tattcaacaa | 5700 |
| agccgccgtc | ccgtcaagtc | agcgtaatgc | tctgccagtg | ttacaaccaa ttaaccaatt | 5760 |
| ctgattagaa | aaactcatcg | agcatcaaat | gaaactgcaa | tttattcata tcaggattat | 5820 |
| caataccata | tttttgaaaa | agccgtttct | gtaatgaagg | agaaaactca ccgaggcagt | 5880 |
| tccataggat | ggcaagatcc | tggtatcggt | ctgcgattcc | gactcgtcca acatcaatac | 5940 |
| aacctattaa | tttcccctcg | tcaaaaataa | ggttatcaag | tgagaaatca ccatgagtga | 6000 |
| cgactgaatc | cggtgagaat | ggcaaaagct | tatgcatttc | tttccagact tgttcaacag | 6060 |
| gccagccatt | acgctcgtca | tcaaaatcac | tcgcatcaac | caaaccgtta ttcattcgtg | 6120 |
| attgcgcctg | agcgagacga | aatacgcgat | cgctgttaaa | aggacaatta caaacaggaa | 6180 |
| tcgaatgcaa | ccgcgcagg | aacactgcca | gcgcatcaac | aatattttca cctgaatcag | 6240 |
| gatattcttc | taatacctgg | aatgctgttt | tcccggggat | cgcagtggtg agtaaccatg | 6300 |
| catcatcagg | agtacggata | aaatgcttga | tggtcggaag | aggcataaat tccgtcagcc | 6360 |
| agtttagtct | gaccatctca | tctgtaacat | cattggcaac | gctacctttg ccatgtttca | 6420 |
| gaaacaactc | tggcgcatcg | ggcttcccat | acaatcgata | gattgtcgca cctgattgcc | 6480 |
| cgacattatc | gcgagcccat | ttatacccat | ataaatcagc | atccatgttg gaatttaatc | 6540 |
| gcggcctcga | gcaagacgtt | tcccgttgaa | tatggctcat | aacacccctt gtattactgt | 6600 |
| ttatgtaagc | agacagtttt | attgttcatg | atgatatatt | tttatcttgt gcaatgtaac | 6660 |
| atcagagatt | ttgagacaca | acgtggcttt | ccccccccc | ccattattga agcatttatc | 6720 |
| agggttattg | tctcatgagc | ggatacatat | ttgaatgtat | ttagaaaaat aaacaaatag | 6780 |
| gggttccgcg | cacatttccc | cgaaaagtgc | cacctgacgt | ctaagaaacc attattatca | 6840 |
| tgacattaac | ctataaaaat | aggcgtatca | cgaggccctt | tcgtc | 6885 |

<210> SEQ ID NO 19
<211> LENGTH: 6889
<212> TYPE: DNA
<213> ORGANISM: Artificial Sequence
<220> FEATURE:
<223> OTHER INFORMATION: Synthetic Construct pVR1012x/s Ebola
    GP(IC)(dTM)

<400> SEQUENCE: 19

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcaggcgcg tcagcgggtg | 120 |
| ttggcgggtg | tcggggctgg | cttaactatg | cggcatcaga | gcagattgta ctgagagtgc | 180 |
| accatatgcg | gtgtgaaata | ccgcacagat | gcgtaaggag | aaaataccgc atcagattgg | 240 |
| ctattggcca | ttgcatacgt | tgtatccata | tcataatatg | tacatttata ttggctcatg | 300 |
| tccaacatta | ccgccatgtt | gacattgatt | attgactagt | tattaatagt aatcaattac | 360 |
| ggggtcatta | gttcatagcc | catatatgga | gttccgcgtt | acataactta cggtaaatgg | 420 |

```
cccgcctggc tgaccgccca acgaccccg cccattgacg tcaataatga cgtatgttcc    480
catagtaacg ccaataggga cttcccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg ggcctatac accccgctt ccttatgcta    1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca    1320
ggatggggtc ccatttatta tttacaaatt cacatataca acaacgccgt ccccgtgcc    1380
cgcagttttt attaaacata cgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gataattctc taatcacagt catcatggga   1920
gcgtcaggga ttctgcaatt gccccgtgag cgcttcagga aaacatcttt ctttgtttgg   1980
gtaataatcc tattccataa agtcttttca atcccgttgg gggttgtaca caacaatacc   2040
ctacaagtga gtgatattga caagtttgtg tgccgagaca aactctcttc aactagccaa   2100
ttgaagtcag tcgggttgaa cttggagggc aatggagtag caactgatgt accaacggca   2160
accaaaagat gggttttcg agctggtgtt ccaccaaagg tggtaaatta cgaagctgga   2220
gaatgggctg agaactgtta taacctggct ataaagaaag ttgatggtag tgagtgccta   2280
ccagaagccc ctgagggagt gagggatttt ccccgttgcc gctatgtaca caaagtctca   2340
ggaactggac catgcccagg aggactcgcc tttcacaaag aaggagcctt cttcctgtat   2400
gaccgactcg catcaacaat catttatcgg ggtacaacct ttgccgaagg agttattgca   2460
tttctgatct tgcctaaggc gcgaaaggat ttttccagt ctcctccatt gcatgagcct   2520
gccaacatga ccacggatcc ctccagttac tatcacacga caacaataaa ctacgtggtt   2580
gataattttg gaaccaacac cacagagttt ctgttccaag tcgatcattt gacgtatgtg   2640
cagctcgagg caagattcac accacaattc cttgtcctcc taaatgaaac catctactct   2700
gataaccgca gaagtaacac aacaggaaaa ctaatctgga aaataaatcc cactgttgat   2760
accagcatgg gtgagtgggc tttctgggaa aataaaaaaa cttcacaaaa acccttcaa    2820
```

-continued

| | |
|---|---|
| gtgaagagtt gtctttcgta cctgtaccag aaacccagaa ccaggtcctt gacacgacag | 2880 |
| cgacggtctc tcctcccatc tccgcccaca accacgcagg cgaagaccac aaagaattgg | 2940 |
| tttcagagga ttccactcca gtggttcaga tgcaaaacat caagggaaag gacacaatgc | 3000 |
| caaccacagt gacgggtgta ccaacaacca caccctctcc atttccaatc aatgctcgca | 3060 |
| acactgatca taccaaatca tttatcggcc tggaggggcc ccaagaagac cacagcacca | 3120 |
| cacagcctgc caagaccacc agccaaccaa ccaacagcac agaatcgacg acactaaacc | 3180 |
| caacatcaga gccctccagt agaggcacgg gaccatccag ccccacggtc cccaacacca | 3240 |
| cagaaagcca cgccgaactt ggcaagacaa ccccaaccac actcccagaa cagcacactg | 3300 |
| ccgccagtgc cattccaaga gccgtgcacc ccgacgaact cagtggacct ggcttcctga | 3360 |
| cgaacacaat acgggggtg acaaatctcc tgacaggatc cagaagaaag cgaagggatg | 3420 |
| tcactcccaa tacacaaccc aaatgcaacc caaacctgca ctattggaca gccttggatg | 3480 |
| agggtgctgc cataggttta gcctggatac catacttcgg gccagcagct gagggaattt | 3540 |
| acactgaagg cataatggag aatcaaaatg gattgatctg tggattgagg cagctggcca | 3600 |
| acgaaacgac acaagctctt caattgttct aagggcaac tactgagttg cgtacattct | 3660 |
| ctatactaaa tcggaaagca atagacttct tgctccaaag atggggagga acatgtcaca | 3720 |
| ttctagggcc tgattgttgc attgaacccc aagattggac caaaaatatc actgataaaa | 3780 |
| ttgatcaaat aatccatgac tttgtcgata taatcttcc aaatcagaat gatggcagca | 3840 |
| actggtggac tggatggaaa caatggtgaa gatctgctgt gccttctagt tgccagccat | 3900 |
| ctgttgtttg cccctccccc gtgccttcct tgaccctgga aggtgccact cccactgtcc | 3960 |
| tttcctaata aaatgaggaa attgcatcgc attgtctgag taggtgtcat tctattctgg | 4020 |
| ggggtggggt ggggcaggac agcaagggg aggattggga agacaatagc aggcatgctg | 4080 |
| gggatgcggt gggctctatg ggtacccagg tgctgaagaa ttgacccggt tcctcctggg | 4140 |
| ccagaaagaa gcaggcacat cccctttctct gtgacacacc ctgtccacgc ccctggttct | 4200 |
| tagttccagc cccactcata ggacactcat agctcaggag ggctccgcct tcaatcccac | 4260 |
| ccgctaaagt acttggagcg gtctctccct ccctcatcag cccaccaaac caaacctagc | 4320 |
| ctccaagagt gggaagaaat taaagcaaga taggctatta agtgcagagg gagagaaaat | 4380 |
| gcctccaaca tgtgaggaag taatgagaga aatcatagaa ttttaaggcc atgatttaag | 4440 |
| gccatcatgg ccttaatctt ccgcttcctc gctcactgac tcgctgcgct cggtcgttcg | 4500 |
| gctgcggcga gcggtatcag ctcactcaaa ggcggtaata cggttatcca cagaatcagg | 4560 |
| ggataacgca ggaaagaaca tgtgagcaaa aggccagcaa aaggccagga accgtaaaaa | 4620 |
| ggccgcgttg ctggcgtttt tccataggct ccgcccccct gacgagcatc acaaaaatcg | 4680 |
| acgctcaagt cagaggtggc gaaacccgac aggactataa agataccagg cgtttccccc | 4740 |
| tggaagctcc ctcgtgcgct ctcctgttcc gaccctgccg cttaccggat acctgtccgc | 4800 |
| ctttctccct tcgggaagcg tggcgctttc tcatagctca cgctgtaggt atctcagttc | 4860 |
| ggtgtaggtc gttcgctcca agctgggctg tgtgcacgaa ccccccgttc agcccgaccg | 4920 |
| ctgcgcctta tccggtaact atcgtcttga gtccaacccg gtaagacacg acttatcgcc | 4980 |
| actggcagca gccactggta acaggattag cagagcgagg tatgtaggcg gtgctacaga | 5040 |
| gttcttgaag tggtggccta actacggcta cactagaaga acagtatttg gtatctgcgc | 5100 |
| tctgctgaag ccagttacct tcggaaaaag agttggtagc tcttgatccg gcaaacaaac | 5160 |
| caccgctggt agcggtggtt tttttgtttg caagcagcag attacgcgca gaaaaaaagg | 5220 |

```
atctcaagaa gatcctttga tcttttctac ggggtctgac gctcagtgga acgaaaactc    5280
acgttaaggg attttggtca tgagattatc aaaaaggatc ttcacctaga tccttttaaa    5340
ttaaaaatga agttttaaat caatctaaag tatatatgag taaacttggt ctgacagtta    5400
ccaatgctta atcagtgagg cacctatctc agcgatctgt ctatttcgtt catccatagt    5460
tgcctgactc ggggggggggg ggcgctgagg tctgcctcgt gaagaaggtg ttgctgactc    5520
ataccaggcc tgaatcgccc catcatccag ccagaaagtg agggagccac ggttgatgag    5580
agctttgttg taggtggacc agttggtgat tttgaacttt tgctttgcca cggaacggtc    5640
tgcgttgtcg ggaagatgcg tgatctgatc cttcaactca gcaaaagttc gatttattca    5700
acaaagccgc cgtcccgtca agtcagcgta atgctctgcc agtgttacaa ccaattaacc    5760
aattctgatt agaaaaactc atcgagcatc aaatgaaact gcaatttatt catatcagga    5820
ttatcaatac catatttttg aaaaagccgt ttctgtaatg aaggagaaaa ctcaccgagg    5880
cagttccata ggatggcaag atcctggtat cggtctgcga ttccgactcg tccaacatca    5940
atacaaccta ttaatttccc ctcgtcaaaa ataaggttat caagtgagaa atcaccatga    6000
gtgacgactg aatccggtga agtggcaaa agcttatgca tttctttcca gacttgttca    6060
acaggccagc cattacgctc gtcatcaaaa tcactcgcat caaccaaacc gttattcatt    6120
cgtgattgcg cctgagcgag acgaaatacg cgatcgctgt taaaaggaca attacaaaca    6180
ggaatcgaat gcaaccggcg caggaacact gccagcgcat caacaatatt ttcacctgaa    6240
tcaggatatt cttctaatac ctggaatgct gttttcccgg ggatcgcagt ggtgagtaac    6300
catgcatcat caggagtacg gataaaatgc ttgatggtcg aagaggcat aaattccgtc    6360 agccagttta gtctgaccat ctcatctgta acatcattgg caacgctacc tttgccatgt    6420
ttcagaaaca actctggcgc atcgggcttc ccatacaatc gatagattgt cgcacctgat    6480
tgcccgacat tatcgcgagc ccatttatac ccatataaat cagcatccat gttggaattt    6540
aatcgcggcc tcgagcaaga cgtttcccgt tgaatatggc tcataacacc ccttgtatta    6600
ctgtttatgt aagcagacag ttttattgtt catgatgata tatttttatc ttgtgcaatg    6660
taacatcaga gattttgaga cacaacgtgg ctttccccc ccccccatta ttgaagcatt    6720
tatcagggtt attgtctcat gagcggatac atatttgaat gtatttagaa aaataaacaa    6780 atagggttc cgcgcacatt tccccgaaaa gtgccacctg acgtctaaga aaccattatt    6840
atcatgacat aacctataa aaataggcgt atcacgaggc cctttcgtc              6889
```

<210> SEQ ID NO 20
<211> LENGTH: 8146
<212> TYPE: DNA
<213> ORGANISM: Artificial Sequence
<220> FEATURE:
<223> OTHER INFORMATION: Synthetic Construct pAdApt EbolaGP(IC)(dTM)

<400> SEQUENCE: 20

```
ttaattaacc gcaattctca tgtttgacag cttatcatca tcaataatat accttatttt      60
ggattgaagc caatatgata atgaggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
```

-continued

```
cgcccaggtg ttttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg actttccat    780
tgacgtcaat gggtggagta tttacggtaa actgcccact tggcagtaca tcaagtgtat    840
catatgccaa gtacgccccc tattgacgtc aatgacggta atggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat aattctctaa tcacagtcat catgggagcg   1320
tcagggattc tgcaattgcc ccgtgagcgc ttcaggaaaa catctttctt tgtttgggta   1380
ataatcctat tccataaagt cttttcaatc ccgttggggg ttgtacacaa caataccta   1440
caagtgagtg atattgacaa gtttgtgtgc cgagacaaac tctcttcaac tagccaattg   1500
aagtcagtcg ggttgaactt ggagggcaat ggagtagcaa ctgatgtacc aacggcaacc   1560
aaaagatggg gttttcgagc tggtgttcca ccaaaggtgg taaattacga agctggagaa   1620
tgggctgaga actgttataa cctggctata agaaagttg atggtagtga gtgcctacca   1680
gaagcccctg agggagtgag ggattttccc cgttgccgct atgtacacaa agtctcagga   1740
actggaccat gcccaggagg actcgccttt cacaaagaag gagccttctt cctgtatgac   1800
cgactcgcat caacaatcat ttatcggggt acaacctttg ccgaaggagt tattgcattt   1860
ctgatcttgc ctaaggcgcg aaaggatttt ttccagtctc ctccattgca tgagcctgcc   1920
aacatgacca cggatccctc cagttactat cacacgacaa caataaacta cgtggttgat   1980
aattttggaa ccaacaccac agagtttctg ttccaagtcg atcatttgac gtatgtgcag   2040
ctcgaggcaa gattcacacc acaattcctt gtcctcctaa atgaaaccat ctactctgat   2100
aaccgcagaa gtaacacaac aggaaaacta atctggaaaa taaatcccac tgttgatacc   2160
agcatgggtg agtgggcttt ctgggaaaat aaaaaaactt cacaaaaacc ctttcaagtg   2220
aagagttgtc tttcgtacct gtaccagaaa cccagaacca ggtccttgac acgacagcga   2280
cggtctctcc tcccatctcc gcccacaacc acgcaggcga agaccacaaa gaattggttt   2340
cagaggattc cactccagtg gttcagatgc aaaacatcaa gggaaaggac acaatgccaa   2400
ccacagtgac gggtgtacca acaaccacac cctctccatt tccaatcaat gctcgcaaca   2460
ctgatcatac caaatcattt atcggcctgg aggggcccca agaagaccac agcaccacac   2520
agcctgccaa gaccaccagc caaccaacca acagcacaga atcgacgaca ctaaacccaa   2580
catcagagcc ctccagtaga ggcacgggac catccagccc cacggtcccc aacaccacag   2640
aaagccacgc cgaacttggc aagacaaccc caaccacact cccagaacag cacactgccg   2700
ccagtgccat tccaagagcc gtgcaccccg acgaactcag tggacctggc ttcctgacga   2760
acacaatacg gggggtgaca aatctcctga caggatccag aagaaagcga agggatgtca   2820
```

```
ctcccaatac acaacccaaa tgcaacccaa acctgcacta ttggacagcc ttggatgagg   2880
gtgctgccat aggtttagcc tggataccat acttcgggcc agcagctgag ggaatttaca   2940
ctgaaggcat aatggagaat caaaatggat tgatctgtgg attgaggcag ctggccaacg   3000
aaacgacaca agctcttcaa ttgttcttaa gggcaactac tgagttgcgt acattctcta   3060
tactaaatcg gaaagcaata gacttcttgc tccaaagatg gggaggaaca tgtcacattc   3120
tagggcctga ttgttgcatt gaaccccaag attggaccaa aaatatcact gataaaattg   3180
atcaaataat ccatgacttt gtcgataata atcttccaaa tcagaatgat ggcagcaact   3240
ggtggactgg atggaaacaa tggtgaagat ccagatctgc tgtgccttct agttgccagc   3300
catctgttgt ttgcccctcc cccgtgcctt ccttgaccct ggaaggtgcc actcccactg   3360
tcctttccta ataaaatgag gaaattgcat cgcattgtct gagtaggtgt cattctattc   3420
tggggggtgg ggtggggcag cacagcaagg gggaggattg gaagacaat agcaggcatg   3480 ctggggatgc ggtgggctct atgggtaccc agggccgcat aacttcgtat aatgtatgct   3540
atacgaagtt ataagatctg tactgaaatg tgtgggcgtg gcttaagggt gggaaagaat   3600
atataaggtg ggggtcttat gtagttttgt atctgttttg cagcagccgc cgccgccatg   3660
agcaccaact cgtttgatgg aagcattgtg agctcatatt tgacaacgcg catgccccca   3720
tgggccgggg tgcgtcagaa tgtgatgggc tccagcattg atggtcgccc cgtcctgccc   3780
gcaaactcta ctaccttgac ctacgagacc gtgtctggaa cgccgttgga gactgcagcc   3840
tccgccgccg cttcagccgc tgcagccacc gcccgcggga ttgtgactga ctttgctttc   3900
ctgagcccgc ttgcaagcag tgcagcttcc cgttcatccg cccgcgatga caagttgacg   3960
gctcttttgg cacaattgga ttctttgacc cgggaactta atgtcgtttc tcagcagctg   4020
ttggatctgc gccagcaggt ttctgccctg aaggcttcct cccctcccaa tgcggtttaa   4080
aacataaata aaaaaccaga ctctgtttgg atttggatca agcaagtgtc ttgctgtctt   4140
tatttagggg ttttgcgcgc gcggtaggcc cgggaccagc ggtctcggtc gttgagggtc   4200
ctgtgtattt tttccaggac gtggtaaagg tgactctgga tgttcagata catgggcata   4260
agcccgtctc tggggtggag gtagcaccac tgcagagctt catgctgcgg ggtggtgttg   4320
tagatgatcc agtcgtagca ggagcgctgg gcgtggtgcc taaaaatgtc tttcagtagc   4380
aagctgattg ccaggggcag gcccttggtg taagtgttta caaagcggtt aagctgggat   4440
gggtgcatac gtggggatat gagatgcatc ttggactgta tttttaggtt ggctatgttc   4500
ccagccatat ccctccgggg attcatgttg tgcagaacca ccagcacagt gtatccggtg   4560
cacttgggaa atttgtcatg tagcttagaa ggaaatgcgt ggaagaactt ggagacgccc   4620
ttgtgacctc caagattttc catgcattcg tccataatga tggcaatggg cccacgggcg   4680
gcggcctggg cgaagatatt tctgggatca ctaacgtcat agttgtgttc caggatgaga   4740
tcgtcatagg ccatttttac aaagcgcggg cggagggtgc cagactgcgg tataatggtt   4800
ccatccggcc cagggcgta gttaccctca cagatttgca tttcccacgc tttgagttca   4860 gatggggga tcatgtctac ctgcggggcg atgaagaaaa cggtttccgg ggtaggggag   4920
atcagctggg aagaaagcag gttcctgagc agctgcgact taccgcagcc ggtgggcccg   4980
taaatcacac ctattaccgg ctgcaactgg tagttaagag agctgcagct gccgtcatcc   5040
ctgagcaggg gggccacttc gttaagcatg tccctgactc gcatgttttc cctgaccaaa   5100
tccgccagaa ggcgctcgcc gcccagcgat agcagttctt gcaaggaagc aaagttttc   5160 aacggtttga gaccgtccgc cgtaggcatg cttttgagcg tttgaccaag cagttccagg   5220
```

```
cggtcccaca gctcggtcac ctgctctacg gcatctcgat ccagcatatc tcctcgtttc    5280
gcgggttggg gcggctttcg ctgtacggca gtagtcggtg ctcgtccaga cgggccaggg    5340
tcatgtcttt ccacgggcgc agggtcctcg tcagcgtagt ctgggtcacg gtgaaggggt    5400
gcgctccggg ctgcgcgctg gccagggtgc gcttgaggct ggtcctgctg gtgctgaagc    5460
gctgccggtc ttcgccctgc gcgtcggcca ggtagcattt gaccatggtg tcatagtcca    5520 gccctccgc ggcgtggccc ttggcgcgca gcttgcccct tggaggaggcg ccgcacgagg    5580 ggcagtgcag acttttgagg gcgtagagct tgggcgcgag aaataccgat tccggggagt    5640
aggcatccgc gccgcaggcc ccgcagacgg tctcgcattc cacgagccag gtgagctctg    5700
gccgttcggg gtcaaaaacc aggttttcccc catgcttttt gatgcgtttc ttacctctgg    5760
tttccatgag ccggtgtcca cgctcggtga cgaaaaggct gtccgtgtcc ccgtatacag    5820
acttgagagg cctgtcctcg agcggtgttc cgcggtcctc ctcgtataga aactcggacc    5880
actctgagac aaaggctcgc gtccaggcca gcacgaagga ggctaagtgg gaggggtagc    5940
ggtcgttgtc cactagggggt tccactcgct ccagggtgtg aagacacatg tcgccctctt    6000
cggcatcaag gaaggtgatt ggtttgtagg tgtaggccac gtgaccgggt gttcctgaag    6060
gggggctata aaggggggtg ggggcgcgtt cgtcctcact ctcttccgca tcgctgtctg    6120
cgagggccag ctgttggggt gagtcgacgc gaggctggat ggccttcccc attatgattc    6180
ttctcgcttc cggcggcatc gggatgcccg cgttgcaggc catgctgtcc aggcaggtag    6240
atgacgacca tcaggacag cttcaaggcc agcaaaaggc caggaaccgt aaaaaggccg    6300
cgttgctggc gttttttccat aggctccgcc ccctgacga gcatcacaaa aatcgacgct    6360
caagtcagag gtggcgaaac ccgacaggac tataaagata ccaggcgttt ccccctggaa    6420
gctccctcgt gcgctctcct gttccgaccc tgccgcttac cggatacctg tccgcctttc    6480
tcccttcggg aagcgtggcg ctttctcata gctcacgctg taggtatctc agttcggtgt    6540
aggtcgttcg ctccaagctg ggctgtgtgc acgaaccccc cgttcagccc gaccgctgcg    6600
ccttatccgg taactatcgt cttgagtcca acccggtaag acacgactta tcgccactgg    6660
cagcagccac tggtaacagg attagcagag cgaggtatgt aggcggtgct acagagttct    6720
tgaagtggtg gcctaactac ggctacacta aaggacagt atttggtatc tgcgctctgc    6780
tgaagccagt taccttcgga aaagagttg gtagctcttg atccggcaaa caaaccaccg    6840
ctggtagcgg tggttttttt gtttgcaagc agcagattac gcgcagaaaa aaaggatctc    6900
aagaagatcc tttgatcttt tctacggggt ctgacgctca gtggaacgaa aactcacgtt    6960
aagggatttt ggtcatgaga ttatcaaaaa ggatcttcac ctagatcctt ttaaattaaa    7020
aatgaagttt taaatcaatc taaagtatat atgagtaaac ttggtctgac agttaccaat    7080
gcttaatcag tgaggcacct atctcagcga tctgtctatt tcgttcatcc atagttgcct    7140
gactccccgt cgtgtagata actacgatac gggagggctt accatctggc cccagtgctg    7200
caatgatacc gcgagaccca cgctcaccgg ctccagattt atcagcaata aaccagccag    7260
ccggaagggc cgagcgcaga agtggtcctg caactttatc cgcctccatc cagtctatta    7320
attgttgccg ggaagctaga gtaagtagtt cgccagttaa tagtttgcgc aacgttgttg    7380
ccattgctgc aggcatcgtg gtgtcacgct cgtcgtttgg tatggcttca ttcagctccg    7440
gttcccaacg atcaaggcga gttacatgat cccccatgtt gtgcaaaaaa gcggttagct    7500
ccttcggtcc tccgatcgtt gtcagaagta agttggccgc agtgttatca ctcatggtta    7560
tggcagcact gcataattct cttactgtca tgccatccgt aagatgcttt tctgtgactg    7620
```

-continued

| | |
|---|---|
| gtgagtactc aaccaagtca ttctgagaat agtgtatgcg gcgaccgagt tgctcttgcc | 7680 |
| cggcgtcaac acgggataat accgcgccac atagcagaac tttaaaagtg ctcatcattg | 7740 |
| gaaaacgttc ttcggggcga aaactctcaa ggatcttacc gctgttgaga tccagttcga | 7800 |
| tgtaacccac tcgtgcaccc aactgatctt cagcatcttt tactttcacc agcgtttctg | 7860 |
| ggtgagcaaa aacaggaagg caaaatgccg caaaaaaggg aataagggcg acacggaaat | 7920 |
| gttgaatact catactcttc ctttttcaat attattgaag catttatcag ggttattgtc | 7980 |
| tcatgagcgg atacatattt gaatgtattt agaaaaataa acaataggg gttccgcgca | 8040 |
| catttccccg aaaagtgcca cctgacgtct aagaaaccat tattatcatg acattaacct | 8100 |
| ataaaaatag gcgtatcacg aggccctttc gtcttcaaga attgtt | 8146 |

<210> SEQ ID NO 21
<211> LENGTH: 7023
<212> TYPE: DNA
<213> ORGANISM: Artificial Sequence
<220> FEATURE:
<223> OTHER INFORMATION: Synthetic Construct pVR1012x/s-SGP(IC)

<400> SEQUENCE: 21

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcagattgg | 240 |
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga cttccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccctttggc | 1080 |
| tcttatgcat gctatactgt ttttggcttg ggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tattttaca | 1320 |
| ggatggggtc ccattattta tttacaaatt cacatataca acaacgccgt ccccgtgcc | 1380 |
| cgcagttttt attaaacata gcgtgggatc tccacgcgaa tctcgggtac gtgttccgga | 1440 |
| catgggctct tctccggtag cggcggagct tccacatccg agccctggtc ccatgcctcc | 1500 |
| agcggctcat ggtcgctcgg cagctccttg ctcctaacag tggaggccag acttaggcac | 1560 |

-continued

```
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga attcggcttc    1920
taatcacagt caccatggga gcgtcaggga ttctgcaatt gccccgtgag cgcttcagga    1980
aaacatcttt ctttgtttgg gtaataatcc tattccataa agtcttttca atcccgttgg    2040
gggttgtaca caacaatacc ctacaagtga gtgatattga caagtttgtg tgccgagaca    2100
aactctcttc aactagccaa ttgaagtcag tcgggttgaa cttggagggc aatggagtag    2160
caactgatgt accaacggca accaaaagat ggggttttcg agctggtgtt ccaccaaagg    2220
tggtaaattg cgaagctgga gaatgggctg agaactgtta taacctggct ataaagaaag    2280
ttgatggtag tgagtgccta ccagaagccc ctgagggagt gagggatttt ccccgttgcc    2340
gctatgtaca caaagtctca ggaactggac catgcccagg aggactcgcc tttcacaaag    2400
aaggagcctt cttcctgtat gaccgactcg catcaacaat catttatcgg ggtacaacct    2460
ttgccgaagg agttattgca tttctgatct tgcctaaggc gcgaaaggat tttttccagt    2520
ctcctccatt gcatgagcct gccaacatga ccacggatcc ctccagttac tatcacacga    2580
caacaataaa ctacgtggtt gataattttg gaaccaacac cacagagttt ctgttccaag    2640
tcgatcattt gacgtatgtg cagctcgagg caagattcac accacaattc cttgtcctcc    2700
taaatgaaac catctactct gataaccgca gaagtaacac aacaggaaaa ctaatctgga    2760
aaataaatcc cactgttgat accagcatgg gtgagtgggc tttctgggaa aataaaaaaa    2820
acttcacaaa aacccttcca agtgaagagt tgtctttcgt acctgtacca gaaacccaga    2880
accaggtcct tgacacgaca gcgacggtct ctcctcccat ctccgcccac aaccacgcag    2940
ccgaagacca caaagaattg gtttcagagg attccactcc agtggttcag atgcaaaaca    3000
tcaagggaaa ggacacaatg ccaaccacag tgacgggtgt accaacaacc acaccctctc    3060
catttccaat caatgctcgc aacactgatc ataccaaatc attttatcgg ctggaggggc    3120
cccaagaaga ccacagcacc acacagcctg ccaagaccac cagccaacca accaacagca    3180
cagaatcgac gacactaaac ccaacatcag agccctccag tagaggcacg ggaccatcca    3240
gccccacggt ccccaacacc acagaaagcc acgccgaact tggcaagaca accccaacca    3300
cactcccaga acagcacact gccgccagtc ccattccaag agccgtgcac cccgacgaac    3360
tcagtggacc tggcttcctg acgaacacaa tacgggggt tacaaatctc ctgacaggat    3420
ccagaagaaa gcgaagggat gtcactccca atacacaacc caaatgcaac ccaaacctgc    3480
actattggac agccttggat gagggtgctg ccataggttt agcctggata ccatacttcg    3540
ggccagcagc tgagggaatt tacactgaag gcataatgga gaatcaaaat ggattgatct    3600
gtggattgag gcagctggcc aacgaaacga cacaagctct tcaattgttc ttaagggcaa    3660
ctactgagtt gcgtacattc tctatactaa atcggaaagc aatagacttc ttgctccaaa    3720 gatgggagg aacatgtcac attctagggc ctgattgttg cattgaaccc caagattgga    3780
ccaaaaatat cactgataaa attgatcaaa taatccatga ctttgtcgat aataatcttc    3840
caaatcagaa tgatgcagc aactggtgga ctggatggaa acaatggggtt cctgctggaa    3900 taggaatcac aggagtaatc attgctatta ttgctttgct gtgcatttgc aaattcatgc    3960
```

```
tttgaactaa tatagcatca tactttaagc cgaattctag accaggccct ggatccagat   4020
ctgctgtgcc ttctagttgc cagccatctg ttgtttgccc ctcccccgtg ccttccttga   4080
ccctggaagg tgccactccc actgtccttt cctaataaaa tgaggaaatt gcatcgcatt   4140
gtctgagtag gtgtcattct attctggggg gtggggtggg gcaggacagc aaggggagg    4200 attgggaaga caatagcagg catgctgggg atgcggtggg ctctatgggt acccaggtgc   4260
tgaagaattg acccggttcc tcctgggcca gaaagaagca ggcacatccc cttctctgtg   4320
acacaccctg tccacgcccc tggttcttag ttccagcccc actcatagga cactcatagc   4380
tcaggagggc tccgccttca atcccacccg ctaaagtact tggagcggtc tctccctccc   4440
tcatcagccc accaaaccaa acctagcctc caagagtggg aagaaattaa agcaagatag   4500
gctattaagt gcagagggag agaaaatgcc tccaacatgt gaggaagtaa tgagagaaat   4560
catagaattt taaggccatc atggccttaa tcttccgctt cctcgctcac tgactcgctg   4620
cgctcggtcg ttcggctgcg gcgagcggta tcagctcact caaaggcggt aatacggtta   4680
tccacagaat caggggataa cgcaggaaag aacatgtgag caaaaggcca gcaaaaggcc   4740
aggaaccgta aaaaggccgc gttgctggcg tttttccata ggctccgccc ccctgacgag   4800
catcacaaaa atcgacgctc aagtcagagg tggcgaaacc cgacaggact ataaagatac   4860
caggcgtttc cccctggaag ctccctcgtg cgctctcctg ttccgaccct gccgcttacc   4920
ggatacctgt ccgcctttct cccttcggga agcgtggcgc tttctcatag ctcacgctgt   4980
aggtatctca gttcggtgta ggtcgttcgc tccaagctgg gctgtgtgca cgaaccccc    5040 gttcagcccg accgctgcgc cttatccggt aactatcgtc ttgagtccaa cccggtaaga   5100
cacgacttat cgccactggc agcagccact ggtaacagga ttagcagagc gaggtatgta   5160
ggcggtgcta cagagttctt gaagtggtgg cctaactacg gctacactag aagaacagta   5220
tttggtatct gcgctctgct gaagccagtt accttcggaa aaagagttgg tagctcttga   5280
tccggcaaac aaaccaccgc tggtagcggt ggtttttttg tttgcaagca gcagattacg   5340
cgcagaaaaa aaggatctca agaagatcct ttgatctttt ctacggggtc tgacgctcag   5400
tggaacgaaa actcacgtta agggattttg gtcatgagat tatcaaaaag gatcttcacc   5460
tagatccttt taaattaaaa atgaagtttt aaatcaatct aaagtatata tgagtaaact   5520
tggtctgaca gttaccaatg cttaatcagt gaggcaccta tctcagcgat ctgtctattt   5580
cgttcatcca tagttgcctg actccggggg gggggcgct gaggtctgcc tcgtgaagaa    5640
ggtgttgctg actcatacca ggcctgaatc gccccatcat ccagccagaa agtgagggag   5700
ccacggttga tgagagcttt gttgtaggtg gaccagttgg tgattttgaa cttttgcttt   5760
gccacggaac ggtctgcgtt gtcgggaaga tgcgtgatct gatccttcaa ctcagcaaaa   5820
gttcgattta ttcaacaaag ccgccgtccc gtcaagtcag cgtaatgctc tgccagtgtt   5880
acaaccaatt aaccaattct gattagaaaa actcatcgag catcaaatga actgcaatt    5940 tattcatatc aggattatca ataccatatt tttgaaaaag ccgtttctgt aatgaaggag   6000
aaaactcacc gaggcagttc cataggatgg caagatcctg gtatcggtct gcgattccga   6060
ctcgtccaac atcaatacaa cctattaatt tcccctcgtc aaaaataagg ttatcaagtg   6120
agaaatcacc atgagtgacg actgaatccg gtgagaatgg caaaagctta tgcatttctt   6180
tccagacttg ttcaacaggc cagccattac gctcgtcatc aaaatcactc gcatcaacca   6240
aaccgttatt cattcgtgat tgcgcctgag cgagacgaaa tacgcgatcg ctgttaaaag   6300
gacaattaca acaggaatc gaatgcaacc ggcgcaggaa cactgccagc gcatcaacaa    6360
```

-continued

```
tattttcacc tgaatcagga tattcttcta atacctggaa tgctgttttc ccggggatcg    6420
cagtggtgag taaccatgca tcatcaggag tacggataaa atgcttgatg gtcggaagag    6480
gcataaattc cgtcagccag tttagtctga ccatctcatc tgtaacatca ttggcaacgc    6540
tacctttgcc atgtttcaga acaactctg  gcgcatcggg cttcccatac aatcgataga    6600
ttgtcgcacc tgattgcccg acattatcgc gagcccattt atacccatat aaatcagcat    6660
ccatgttgga atttaatcgc ggcctcgagc aagacgtttc ccgttgaata tggctcataa    6720
caccccttgt attactgttt atgtaagcag acagttttat tgttcatgat gatatatttt    6780
tatcttgtgc aatgtaacat cagagatttt gagacacaac gtggctttcc cccccccccc    6840
attattgaag catttatcag ggttattgtc tcatgagcgg atacatattt gaatgtattt    6900
agaaaaataa acaaataggg gttccgcgca catttccccg aaaagtgcca cctgacgtct    6960
aagaaaccat tattatcatg acattaacct ataaaaatag gcgtatcacg aggccctttc    7020
gtc                                                                  7023
```

<210> SEQ ID NO 22
<211> LENGTH: 7295
<212> TYPE: DNA
<213> ORGANISM: Artificial Sequence
<220> FEATURE:
<223> OTHER INFORMATION: Synthetic Construct pVR1012-NP

<400> SEQUENCE: 22

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta  ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt tgacctccat     960 agaagacac  cgggaccgat ccagcctccg cggccgggaa cggtgcattg gaacgcggat    1020
tccccgtgcc aagagtgacg taagtaccgc ctatagactc tataggcaca ccccttggc    1080 tcttatgcat gctatactgt ttttggcttg gggcctatac accccgcttc cttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt cccccgtgcc    1380
```

-continued

```
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccagccctg   1920
gatccagatc gatccgagta tggattctcg tcctcagaaa atctggatgg cgccgagtct   1980
cactgaatct gacatggatt accacaagat cttgacagca ggtctgtccg ttcaacaggg   2040
gattgttcgg caaagagtca tcccagtgta tcaagtaaac aatcttgaag aaatttgcca   2100
acttatcata caggcctttg aagcaggtgt tgattttcaa gagagtgcgg acagtttcct   2160
tctcatgctt tgtcttcatc atgcgtacca gggagattac aaactttct tggaaagtgg   2220
cgcagtcaag tatttggaag ggcacgggtt ccgttttgaa gtcaagaagc gtgatggagt   2280
gaagcgcctt gaggaattgc tgccagcagt atctagtgga aaaacatta agagaacact   2340
tgctgccatg ccggaagagg agacaactga agctaatgcc ggtcagtttc tctcctttgc   2400
aagtctattc cttccgaaat tggtagtagg agaaaaggct tgccttgaga aggttcaaag   2460
gcaaattcaa gtacatgcag agcaaggact gatacaatat ccaacagctt ggcaatcagt   2520
aggacacatg atggtgattt ccgtttgat gcgaacaaat tttctgatca aatttctcct   2580
aatacaccaa gggatgcaca tggttgccgg gcatgatgcc aacgatgctg tgatttcaaa   2640
ttcagtggct caagctcgtt tttcaggctt attgattgtc aaaacagtac ttgatcatat   2700
cctacaaaag acagaacgag gagttcgtct ccatcctctt gcaaggaccg ccaaggtaaa   2760
aaatgaggtg aactccttta aggctgcact cagctccctg gccaagcatg gagagtatgc   2820
tcctttcgcc cgacttttga acctttctgg agtaaataat cttgagcatg gtcttttccc   2880
tcaactatcg gcaattgcac tcggagtcgc cacagcacac gggagtaccc tcgcaggagt   2940
aaatgttgga gaacagtatc aacaactcag agaggctgcc actgaggctg agaagcaact   3000
ccaacaatat gcagagtctc gcgaacttga ccatcttgga cttgatgatc aggaaaagaa   3060
aattcttatg aacttccatc agaaaaagaa cgaaatcagc ttccagcaaa caaacgctat   3120
ggtaactcta agaaaagagc gcctggccaa gctgacagaa gctatcactg ctgcgtcact   3180
gcccaaaaca agtggacatt acgatgatga tgacgacatt ccctttccag gacccatcaa   3240
tgatgacgac aatcctggcc atcaagatga tgatccgact gactcacagg atacgaccat   3300
tcccgatgtg gtggttgatc ccgatgatgg aagctacggc gaataccaga gttactcgga   3360
aaacggcatg aatgcaccag atgacttggt cctattcgat ctagacgagg acgacgagga   3420
cactaagcca gtgcctaata gatcgaccaa gggtggacaa cagaagaaca gtcaaaaggg   3480
ccagcatata gagggcagac agacacaatc caggccaatt caaaatgtcc caggccctca   3540
cagaacaatc caccacgcca gtgcgccact acggacaat gacagaagaa atgaaccctc   3600
cggctcaacc agccctcgca tgctgacacc aattaacgaa gaggcagacc cactggacga   3660
tgccgacgac gagacgtcta gccttccgcc cttggagtca gatgatgaag agcaggacag   3720
ggacggaact tccaaccgca cacccactgt cgccccaccg gctcccgtat acagagatca   3780
```

-continued

```
ctctgaaaag aaagaactcc cgcaagacga gcaacaagat caggaccaca ctcaagaggc    3840
caggaaccag gacagtgaca acacccagtc agaacactct tttgaggaga tgtatcgcca    3900
cattctaaga tcacaggggc catttgatgc tgttttgtat tatcatatga tgaaggatga    3960
gcctgtagtt ttcagtacca gtgatggcaa agagtacacg tatccagact cccttgaaga    4020
ggaatatcca ccatggctca ctgaaaaaga ggctatgaat gaagagaata gatttgttac    4080
attggatggt caacaatttt attggccggt gatgaatcac aagaataaat tcatggcaat    4140
cctgcaacat catcagtgaa tgagcatgga acaatgggat gattcaaccg acaaatagct    4200
aacattaagt agtcaaggaa cgaaaacagg aagaattttt gatgtctaag gtgtgaatta    4260
ttatcacaat aaaagtgatt cttatttttg aatttgggcg agctcgaatt gatctgctgt    4320
gccttctagt tgccagccat ctgttgtttg ccctccccc gtgccttcct tgaccctgga    4380
aggtgccact cccactgtcc tttcctaata aaatgaggaa attgcatcgc attgtctgag    4440
taggtgtcat tctattctgg ggggtggggt gggcaggac agcaagggg aggattggga    4500 agacaatagc aggcatgctg gggatgcggt gggctctatg ggtacccagg tgctgaagaa    4560
ttgacccggt tcctcctggg ccagaaagaa gcaggcacat ccccttctct gtgacacacc    4620
ctgtccacgc ccctggttct tagttccagc cccactcata ggacactcat agctcaggag    4680
ggctccgcct tcaatcccac ccgctaaagt acttggagcg gtctctccct ccctcatcag    4740
cccaccaaac caaacctagc ctccaagagt gggaagaaat taaagcaaga taggctatta    4800
agtgcagagg gagagaaaat gcctccaaca tgtgaggaag taatgagaga atcatagaa     4860 tttcttccgc ttcctcgctc actgactcgc tgcgctcggt cgttcggctg cggcgagcgg    4920
tatcagctca ctcaaaggcg gtaatacggt tatccacaga atcaggggat aacgcaggaa    4980
agaacatgtg agcaaaaggc cagcaaaagg ccaggaaccg taaaaaggcc gcgttgctgg    5040
cgttttccca taggctccgc cccctgacg agcatcacaa aaatcgacgc tcaagtcaga    5100
ggtggcgaaa cccgacagga ctataaagat accaggcgtt tcccctgga agctccctcg     5160 tgcgctctcc tgttccgacc ctgccgctta ccggatacct gtccgccttt ctccttcgg     5220 gaagcgtggc gctttctcat agctcacgct gtaggtatct cagttcggtg taggtcgttc    5280
gctccaagct gggctgtgtg cacgaacccc ccgttcagcc cgaccgctgc gccttatccg    5340
gtaactatcg tcttgagtcc aacccggtaa gacacgactt atcgccactg gcagcagcca    5400
ctggtaacag gattagcaga gcgaggtatg taggcggtgc tacagagttc ttgaagtggt    5460
ggcctaacta cggctacact agaagaacag tatttggtat ctgcgctctg ctgaagccag    5520
ttaccttcgg aaaaagagtt ggtagctctt gatccggcaa acaaaccacc gctggtagcg    5580
gtggtttttt tgtttgcaag cagcagatta cgcgcagaaa aaaaggatct caagaagatc    5640
ctttgatctt ttctacgggg tctgacgctc agtggaacga aaactcacgt taagggattt    5700
tggtcatgag attatcaaaa aggatcttca cctagatcct ttaaattaa aaatgaagtt     5760 ttaaatcaat ctaaagtata tatgagtaaa cttggtctga cagttaccaa tgcttaatca    5820
gtgaggcacc tatctcagcg atctgtctat ttcgttcatc catagttgcc tgactcgggg    5880
ggggggggcg ctgaggtctg cctcgtgaag aaggtgttgc tgactcatac caggcctgaa    5940
tcgccccatc atccagccag aaagtgaggg agccacggtt gatgagagct tgttgtagg     6000 tggaccagtt ggtgattttg aacttttgct ttgccacgga acggtctgcg ttgtcgggaa    6060
gatgcgtgat ctgatccttc aactcagcaa agttcgatt tattcaacaa agccgccgtc     6120
ccgtcaagtc agcgtaatgc tctgccagtg ttacaaccaa ttaaccaatt ctgattagaa    6180
```

```
aaactcatcg agcatcaaat gaaactgcaa tttattcata tcaggattat caataccata   6240
tttttgaaaa agccgtttct gtaatgaagg agaaaactca ccgaggcagt tccataggat   6300
ggcaagatcc tggtatcggt ctgcgattcc gactcgtcca acatcaatac aacctattaa   6360
tttcccctcg tcaaaaataa ggttatcaag tgagaaatca ccatgagtga cgactgaatc   6420
cggtgagaat ggcaaaagct tatgcatttc tttccagact tgttcaacag gccagccatt   6480
acgctcgtca tcaaaatcac tcgcatcaac caaaccgtta ttcattcgtg attgcgcctg   6540
agcgagacga atacgcgat cgctgttaaa aggacaatta caaacaggaa tcgaatgcaa   6600
ccggcgcagg aacactgcca gcgcatcaac aatattttca cctgaatcag gatattcttc   6660
taatacctgg aatgctgttt tcccggggat cgcagtggtg agtaaccatg catcatcagg   6720
agtacggata aaatgcttga tggtcggaag aggcataaat tccgtcagcc agtttagtct   6780
gaccatctca tctgtaacat cattggcaac gctacctttg ccatgtttca gaaacaactc   6840
tggcgcatcg gcttcccat acaatcgata gattgtcgca cctgattgcc cgacattatc   6900
gcgagcccat ttatacccat ataaatcagc atccatgttg gaatttaatc gcggcctcga   6960
gcaagacgtt tcccgttgaa tatggctcat aacacccctt gtattactgt ttatgtaagc   7020
agacagtttt attgttcatg atgatatatt tttatcttgt gcaatgtaac atcagagatt   7080
ttgagacaca acgtggcttt cccccccccc ccattattga agcatttatc agggttattg   7140
tctcatgagc ggatacatat ttgaatgtat ttagaaaaat aaacaaatag gggttccgcg   7200
cacatttccc cgaaaagtgc cacctgacgt ctaagaaacc attattatca tgacattaac   7260
ctataaaaat aggcgtatca cgaggccctt tcgtc                             7295
```

<210> SEQ ID NO 23
<211> LENGTH: 7329
<212> TYPE: DNA
<213> ORGANISM: Artificial Sequence
<220> FEATURE:
<223> OTHER INFORMATION: Synthetic Construct pVR1012x/s Ebola-NP

<400> SEQUENCE: 23

```
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120 ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acaacttaa cggtaaatgg   420 cccgcctggc tgaccgccca acgacccccg cccattgacg tcaataatga cgtatgttcc   480
catagtaacg ccaatagggga cttttccattg acgtcaatgg gtggagtatt tacggtaaac   540
tgcccacttg gcagtacatc aagtgtatca tatgccaagt acgccccta ttgacgtcaa   600 tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
```

```
tagaagacac cgggaccgat ccagcctccg cggccgggaa cggtgcattg gaacgcggat    1020
tccccgtgcc aagagtgacg taagtaccgc ctatagactc tataggcaca ccccctttggc   1080 tcttatgcat gctatactgt ttttggcttg gggcctatac accccgctt ccttatgcta    1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga ccaggccctg   1920
gatccagatc gatccgagta tggattctcg tcctcagaaa atctggatgg cgccgagtct   1980
cactgaatct gacatggatt accacaagat cttgacagca ggtctgtccg ttcaacaggg   2040
gattgttcgg caaagagtca tcccagtgta tcaagtaaac aatcttgaag aaatttgcca   2100
acttatcata caggcctttg aagcaggtgt tgattttcaa gagagtgcgg acagtttcct   2160
tctcatgctt tgtcttcatc atgcgtacca gggagattac aaacttttct tggaaagtgg   2220
cgcagtcaag tatttggaag ggcacggggtt ccgttttgaa gtcaagaagc gtgatggagt   2280
gaagcgcctt gaggaattgc tgccagcagt atctagtgga aaaaacatta agagaacact   2340
tgctgccatg ccggaagagg agacaactga agctaatgcc ggtcagtttc tctccttgc    2400 aagtctattc cttccgaaat tggtagtagg agaaaaggct tgccttgaga aggttcaaag   2460
gcaaattcaa gtacatgcag agcaaggact gatacaatat ccaacagctt ggcaatcagt   2520
aggacacatg atggtgattt ccgtttgat gcgaacaaat tttctgatca aatttctcct    2580
aatacaccaa gggatgcaca tggttgccgg gcatgatgcc aacgatgctg tgatttcaaa   2640
ttcagtggct caagctcgtt tttcaggctt attgattgtc aaaacagtac ttgatcatat   2700
cctacaaaag acagaacgag gagttcgtct ccatcctctt gcaaggaccg ccaaggtaaa   2760
aaatgaggtg aactccttta aggctgcact cagctccctg gccaagcatg gagagtatgc   2820
tcctttcgcc cgactttttga acctttctgg agtaaataat cttgagcatg gtcttttccc   2880
tcaactatcg gcaattgcac tcggagtcgc cacagcacac gggagtaccc tcgcaggagt   2940
aaatgttgga gaacagtatc aacaactcag agaggctgcc actgaggctg agaagcaact   3000
ccaacaatat gcagagtctc gcgaacttga ccatcttgga cttgatgatc aggaaaagaa   3060
aattcttatg aacttccatc agaaaaagaa cgaaatcagc ttccagcaaa caaacgctat   3120
ggtaactcta agaaaagagc gcctggccaa gctgacagaa gctatcactg ctgcgtcact   3180
gcccaaaaca agtggacatt cgatgatga tgacgacatt cccttttcag gacccatcaa   3240
tgatgacgac aatcctggcc atcaagatga tgatccgact gactcacagg atacgaccat   3300
tcccgatgtg gtggttgatc ccgatgatgg aagctacggc gaataccaga gttactcgga   3360
```

```
aaacggcatg aatgcaccag atgacttggt cctattcgat ctagacgagg acgacgagga    3420
cactaagcca gtgcctaata gatcgaccaa gggtggacaa cagaagaaca gtcaaaaggg    3480
ccagcatata gagggcagac agacacaatc caggccaatt caaaatgtcc caggccctca    3540
cagaacaatc caccacgcca gtgcgccact cacggacaat gacagaagaa atgaaccctc    3600
cggctcaacc agccctcgca tgctgacacc aattaacgaa gaggcagacc cactggacga    3660
tgccgacgac gagacgtcta gccttccgcc cttggagtca gatgatgaag agcaggacag    3720
ggacggaact tccaaccgca cacccactgt cgccccaccg gctcccgtat acagagatca    3780
ctctgaaaag aaagaactcc cgcaagacga gcaacaagat caggaccaca ctcaagaggc    3840
caggaaccag gacagtgaca acacccagtc agaacactct tttgaggaga tgtatcgcca    3900
cattctaaga tcacagggc catttgatgc tgttttgtat tatcatatga tgaaggatga    3960
gcctgtagtt ttcagtacca gtgatggcaa agagtacacg tatccagact cccttgaaga    4020
ggaatatcca ccatggctca ctgaaaaaga ggctatgaat aagagaata gatttgttac    4080
attggatggt caacaatttt attggccggt gatgaatcac aagaataaat tcatggcaat    4140
cctgcaacat catcagtgaa tgagcatgga acaatgggat gattcaaccg acaaatagct    4200
aacattaagt agtcaaggaa cgaaaacagg aagaatttt gatgtctaag gtgtgaatta    4260
ttatcacaat aaaagtgatt cttatttttg aatttgggcg agctcgaatt gatctgctgt    4320
gccttctagt tgccagccat ctgttgtttg cccctccccc gtgccttcct tgaccctgga    4380
aggtgccact cccactgtcc tttcctaata aaatgaggaa attgcatcgc attgtctgag    4440
taggtgtcat tctattctgg ggggtggggt ggggcaggac agcaagggggg aggattggga    4500
agacaatagc aggcatgctg gggatgcggt gggctctatg ggtacccagg tgctgaagaa    4560
ttgacccggt tcctcctggg ccagaaagaa gcaggcacat ccccttctct gtgacacacc    4620
ctgtccacgc ccctggttct tagttccagc cccactcata ggacactcat agctcaggag    4680
ggctccgcct tcaatcccac ccgctaaagt acttggagcg gtctctccct ccctcatcag    4740
cccaccaaac caaacctagc ctccaagagt gggaagaaat taaagcaaga taggctatta    4800
agtgcagagg gagagaaaat gcctccaaca tgtgaggaag taatgagaga aatcatgaaa    4860
ttttaaggcc atgatttaag gccatcatgg ccttaatctt ccgcttcctc gctcactgac    4920
tcgctgcgct cggtcgttcg gctgcggcga gcggtatcag ctcactcaaa ggcggtaata    4980
cggttatcca cagaatcagg ggataacgca ggaaagaaca tgtgagcaaa aggccagcaa    5040
aaggccagga accgtaaaaa ggccgcgttg ctggcgtttt tccataggct ccgcccccct    5100
gacgagcatc acaaaaatcg acgctcaagt cagaggtggc gaaacccgac aggactataa    5160
agataccagg cgtttccccc tggaagctcc ctcgtgcgct ctcctgttcc gaccctgccg    5220
cttaccggat acctgtccgc ctttctccct tcgggaagcg tggcgctttc tcatagctca    5280
cgctgtaggt atctcagttc ggtgtaggtc gttcgctcca agctgggctg tgtgcacgaa    5340
ccccccgttc agcccgaccg ctgcgcctta tccggtaact atcgtcttga gtccaacccg    5400
gtaagacacg acttatcgcc actggcagca gccactggta acaggattag cagagcgagg    5460
tatgtaggcg gtgctacaga gttcttgaag tggtggccta actacggcta cactagaaga    5520
acagtatttg gtatctgcgc tctgctgaag ccagttacct tcggaaaaag agttggtagc    5580
tcttgatccg gcaaacaaac caccgctggt agcggtggtt ttttgtttg caagcagcag    5640
attacgcgca gaaaaaaagg atctcaagaa gatcctttga tcttttctac ggggtctgac    5700
gctcagtgga acgaaaactc acgttaaggg attttggtca tgagattatc aaaaaggatc    5760
```

-continued

| | |
|---|---|
| ttcacctaga tccttttaaa ttaaaaatga agttttaaat caatctaaag tatatatgag | 5820 |
| taaacttggt ctgacagtta ccaatgctta atcagtgagg cacctatctc agcgatctgt | 5880 |
| ctatttcgtt catccatagt tgcctgactc ggggggggg ggcgctgagg tctgcctcgt | 5940 |
| gaagaaggtg ttgctgactc ataccaggcc tgaatcgccc catcatccag ccagaaagtg | 6000 |
| agggagccac ggttgatgag agctttgttg taggtggacc agttggtgat tttgaacttt | 6060 |
| tgctttgcca cggaacggtc tgcgttgtcg gaagatgcg tgatctgatc cttcaactca | 6120 |
| gcaaaagttc gatttattca acaaagccgc cgtcccgtca agtcagcgta atgctctgcc | 6180 |
| agtgttacaa ccaattaacc aattctgatt agaaaaactc atcgagcatc aaatgaaact | 6240 |
| gcaatttatt catatcagga ttatcaatac catattttg aaaaagccgt ttctgtaatg | 6300 |
| aaggagaaaa ctcaccgagg cagttccata ggatggcaag atcctggtat cggtctgcga | 6360 |
| ttccgactcg tccaacatca atacaaccta ttaatttccc ctcgtcaaaa ataaggttat | 6420 |
| caagtgagaa atcaccatga gtgacgactg aatccggtga agtggcaaa agcttatgca | 6480 |
| tttctttcca gacttgttca acaggccagc cattacgctc gtcatcaaaa tcactcgcat | 6540 |
| caaccaaacc gttattcatt cgtgattgcg cctgagcgag acgaaatacg cgatcgctgt | 6600 |
| taaaaggaca attacaaaca ggaatcgaat gcaaccggcg caggaacact gccagcgcat | 6660 |
| caacaatatt ttcacctgaa tcaggatatt cttctaatac ctggaatgct gttttcccgg | 6720 |
| ggatcgcagt ggtgagtaac catgcatcat caggagtacg gataaaatgc ttgatggtcg | 6780 |
| gaagaggcat aaattccgtc agccagttta gtctgaccat ctcatctgta acatcattgg | 6840 |
| caacgctacc tttgccatgt ttcagaaaca actctggcgc atcgggcttc ccatacaatc | 6900 |
| gatagattgt cgcacctgat tgcccgacat tatcgcgagc ccatttatac ccatataaat | 6960 |
| cagcatccat gttggaattt aatcgcggcc tcgagcaaga cgtttcccgt tgaatatggc | 7020 |
| tcataacacc ccttgtatta ctgtttatgt aagcagacag ttttattgtt catgatgata | 7080 |
| tatttttatc ttgtgcaatg taacatcaga gattttgaga cacaacgtgg ctttcccccc | 7140 |
| cccccccatta ttgaagcatt tatcagggtt attgtctcat gagcggatac atatttgaat | 7200 |
| gtatttagaa aaataaacaa ataggggttc cgcgcacatt tccccgaaaa gtgccacctg | 7260 |
| acgtctaaga aaccattatt atcatgacat taacctataa aaataggcgt atcacgaggc | 7320 |
| cctttcgtc | 7329 |

<210> SEQ ID NO 24
<211> LENGTH: 6148
<212> TYPE: DNA
<213> ORGANISM: Artificial Sequence
<220> FEATURE:
<223> OTHER INFORMATION: Synthetic Construct pVR1012-VP35

<400> SEQUENCE: 24

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
```

-continued

| | |
|---|---|
| catagtaacg ccaataggga cttcccattg acgtcaatgg gtggagtatt tacggtaaac | 540 |
| tgcccacttg gcagtacatc aagtgtatca tatgccaagt acgccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctccg cggccgggaa cggtgcattg gaacgcggat | 1020 |
| tccccgtgcc aagagtgacg taagtaccgc ctatagactc tataggcaca ccccttggc | 1080 |
| tcttatgcat gctatactgt ttttggcttg gggcctatac accccgctt ccttatgcta | 1140 |
| taggtgatgg tatagcttag cctataggtg tgggttattg accattattg accactcccc | 1200 |
| tattggtgac gatactttcc attactaatc cataacatgg ctctttgcca caactatctc | 1260 |
| tattggctat atgccaatac tctgtccttc agagactgac acggactctg tatttttaca | 1320 |
| ggatggggtc ccatttatta tttacaaatt cacatataca acaacgccgt ccccgtgcc | 1380 |
| cgcagttttt attaaacata gcgtgggatc tccacgcgaa tctcgggtac gtgttccgga | 1440 |
| catgggctct tctccggtag cggcggagct tccacatccg agccctggtc ccatgcctcc | 1500 |
| agcggctcat ggtcgctcgg cagctccttg ctcctaacag tggaggccag acttaggcac | 1560 |
| agcacaatgc ccaccaccac cagtgtgccg cacaaggccg tggcggtagg gtatgtgtct | 1620 |
| gaaaatgagc gtggagattg ggctcgcacg gctgacgcag atggaagact taaggcagcg | 1680 |
| gcagaagaag atgcaggcag ctgagttgtt gtattctgat aagagtcaga ggtaactccc | 1740 |
| gttgcggtgc tgttaacggt ggagggcagt gtagtctgag cagtactcgt tgctgccgcg | 1800 |
| cgcgccacca gacataatag ctgacagact aacagactgt tcctttccat gggtcttttc | 1860 |
| tgcagtcacc gtcgaattct ctagcactcg aagcttattg tcttcaatgt aaaagaaaag | 1920 |
| ctggtctaac aagatgacaa ctagaacaaa gggcaggggc catactgcgg ccacgactca | 1980 |
| aaacgacaga atgccaggcc ctgagctttc gggctggatc tctgagcagc taatgaccgg | 2040 |
| aagaattcct gtaagcgaca tcttctgtga tattgagaac aatccaggat tatgctacgc | 2100 |
| atcccaaatg caacaaacga agccaaaccc gaagacgcgc aacagtcaaa cccaaacgga | 2160 |
| cccaatttgc aatcatagtt ttgaggaggt agtacaaaca ttggcttcat tggctactgt | 2220 |
| tgtgcaacaa caaccatcg catcagaatc attagaacaa cgcattacga gtcttgagaa | 2280 |
| tggtctaaag ccagtttatg atatggcaaa aacaatctcc tcattgaaca gggtttgtgc | 2340 |
| tgagatggtt gcaaaatatg atcttctggt gatgacaacc ggtcgggcaa cagcaaccgc | 2400 |
| tgcggcaact gaggcttatt gggccgaaca tggtcaacca ccacctggac catcacttta | 2460 |
| tgaagaaagt gcgattcggg gtaagattga atctagagat gagaccgtcc ctcaaagtgt | 2520 |
| tagggaggca ttcaacaatc taaacagtac cacttcacta actgaggaaa attttgggaa | 2580 |
| acctgacatt tcggcaaagg atttgagaaa cattatgtat gatcacttgc ctggttttgg | 2640 |
| aactgctttc caccaattag tacaagtgat ttgtaaattg ggaaaagata gcaactcatt | 2700 |
| ggacatcatt catgctgagt tccaggccag cctggctgaa ggagactctc ctcaatgtgc | 2760 |
| cctaattcaa attacaaaaa gagttccaat cttccaagat gctgctccat ctgtcatcca | 2820 |
| catccgcttt cgaggtgaca ttccccgagc ttgccagaaa agcttgcgtc cagtcccacc | 2880 |

```
atcgcccaag attgatcgag gttgggatgt gtttttcagc ttcaagatgg taaaacactt   2940
ggactcaaaa tttgagccaa tctcccttcc ctccgaaaga ggcgaataat agcagaggct   3000
tcaactgctg aactataggg tacgttacat taatgataca cttgtgagta tcagccctgg   3060
ataatataag tcaattaaac gaccaagata aaattgttca tatctcgcta gcagcttaaa   3120
atataaatgt aataggagct atatctctga caggggatc cagatctgct gtgccttcta   3180
gttgccagcc atctgttgtt tgcccctccc ccgtgccttc cttgaccctg aaggtgcca   3240 ctcccactgt cctttcctaa taaaatgagg aaattgcatc gcattgtctg agtaggtgtc   3300
attctattct gggggtggg gtggggcagc acagcaaggg ggaggattgg gaagacaata   3360
gcaggcatgc tggggatgcg gtgggctcta tgggtaccca ggtgctgaag aattgacccg   3420
gttcctcctg ggccagaaag aagcaggcac atcccttct ctgtgacaca ccctgtccac   3480
gcccctggtt cttagttcca gccccactca taggacactc atagctcagg agggctccgc   3540
cttcaatccc acccgctaaa gtacttggag cggtctctcc ctccctcatc agcccaccaa   3600
accaaaccta gcctccaaga gtgggaagaa attaaagcaa gataggctat taagtgcaga   3660
gggagagaaa atgcctccaa catgtgagga agtaatgaga gaaatcatag aatttcttcc   3720
gcttcctcgc tcactgactc gctgcgctcg gtcgttcggc tgcggcgagc ggtatcagct   3780
cactcaaagg cggtaatacg gttatccaca gaatcagggg ataacgcagg aaagaacatg   3840
tgagcaaaag gccagcaaaa ggccaggaac cgtaaaaagg ccgcgttgct ggcgttttc   3900 cataggctcc gcccccctga cgagcatcac aaaaatcgac gctcaagtca gaggtggcga   3960
aacccgacag gactataaag ataccaggcg tttccccctg gaagctccct cgtgcgctct   4020
cctgttccga ccctgccgct taccggatac ctgtccgcct ttctcccttc gggaagcgtg   4080
gcgctttctc aatgctcacg ctgtaggtat ctcagttcgg tgtaggtcgt tcgctccaag   4140
ctgggctgtg tgcacgaacc ccccgttcag cccgaccgct cgccttatc cggtaactat   4200 cgtcttgagt ccaacccggt aagacacgac ttatcgccac tggcagcagc cactggtaac   4260
aggattagca gagcgaggta tgtaggcggt gctacagagt tcttgaagtg gtggcctaac   4320
tacggctaca ctagaaggac agtatttggt atctgcgctc tgctgaagcc agttaccttc   4380
ggaaaaagag ttggtagctc ttgatccggc aaacaaacca ccgctggtag cggtggtttt   4440
tttgtttgca agcagcagat tacgcgcaga aaaaaggat ctcaagaaga tcctttgatc   4500
ttttctacgg ggtctgacgc tcagtggaac gaaaactcac gttaagggat tttggtcatg   4560
agattatcaa aaaggatctt cacctagatc cttttaaatt aaaaatgaag ttttaaatca   4620
atctaaagta tatatgagta aacttggtct gacagttacc aatgcttaat cagtgaggca   4680
cctatctcag cgatctgtct atttcgttca tccatagttg cctgactccg gggggggggg   4740
gcgctgaggt ctgcctcgtg aagaaggtgt tgctgactca taccaggcct gaatcgcccc   4800
atcatccagc cagaaagtga gggagccacg gttgatgaga gctttgttgt aggtggacca   4860
gttggtgatt ttgaacttt gctttgccac ggaacggtct gcgttgtcgg aagatgcgt   4920 gatctgatcc ttcaactcag caaaagttcg atttattcaa caaagccgcc gtcccgtcaa   4980
gtcagcgtaa tgctctgcca gtgttacaac caattaacca attctgatta gaaaaactca   5040
tcgagcatca aatgaaactg caatttattc atatcaggat tatcaatacc atattttga   5100 aaaagccgtt tctgtaatga aggagaaaac tcaccgaggc agttccatag gatggcaaga   5160
tcctggtatc ggtctgcgat tccgactcgt ccaacatcaa tacaacctat taatttcccc   5220
tcgtcaaaaa taaggttatc aagtgagaaa tcaccatgag tgacgactga atccggtgag   5280
```

```
aatggcaaaa gcttatgcat ttctttccag acttgttcaa caggccagcc attacgctcg      5340
tcatcaaaat cactcgcatc aaccaaaccg ttattcattg gtgattgcgc ctgagcgaga      5400
cgaaatacgc gatcgctgtt aaaaggacaa ttacaaacag gaatcgaatg caaccggcgc      5460
aggaacactg ccagcgcatc aacaatattt tcacctgaat caggatattc ttctaatacc      5520
tggaatgctg ttttcccggg gatcgcagtg gtgagtaacc atgcatcatc aggagtacgg      5580
ataaaatgct tgatggtcgg aagaggcata aattccgtca gccagtttag tctgaccatc      5640
tcatctgtaa catcattggc aacgctacct tgccatgttt cagaaacaa ctctggcgca       5700 tcgggcttcc catacaatcg atagattgtc gcacctgatt gcccgacatt atcgcgagcc      5760
catttatacc catataaatc agcatccatg ttggaattta atcgcggcct cgagcaagac      5820
gtttcccgtt gaatatggct cataacaccc cttgtattac tgtttatgta agcagacagt      5880
tttattgttc atgatgatat attttttatct tgtgcaatgt aacatcagag attttgagac     5940
acaacgtggc tttccccccc cccccattat tgaagcattt atcagggtta ttgtctcatg      6000
agcggataca tatttgaatg tatttagaaa ataaacaaa taggggttcc gcgcacattt       6060
ccccgaaaag tgccacctga cgtctaagaa accattatta tcatgacatt aacctataaa      6120
aataggcgta tcacgaggcc ctttcgtc                                         6148

<210> SEQ ID NO 25
<211> LENGTH: 10783
<212> TYPE: DNA
<213> ORGANISM: Artificial Sequence
<220> FEATURE:
<223> OTHER INFORMATION: Synthetic Construct pAD/CMV-GP(dTM)(Z-CITE-S)

<400> SEQUENCE: 25
ttaattaacc gcaattctca tgtttgacag cttatcatca tcaataatat accttatttt        60
ggattgaagc caatatgata atgaggggggt ggagtttgtg acgtggcgcg gggcgtggga      120
acggggcggg tgacgtagta gtgtggcgga agtgtgatgt tgcaagtgtg gcggaacaca      180
tgtaagcgac ggatgtggca aaagtgacgt ttttggtgtg cgccggtgta cacaggaagt      240
gacaattttc gcgcggtttt aggcggatgt tgtagtaaat ttgggcgtaa ccgagtaaga      300
tttggccatt ttcgcgggaa aactgaataa gaggaagtga atctgaata attttgtgtt       360 actcatagcg cgtaatattt gtctagggcc gcggggactt tgaccgttta cgtggagact      420
cgcccaggtg tttttctcag gtgttttccg cgttccgggt caaagttggc gttttattat      480
tatagtcagt acgtaccagt gcactggcct agagcggccc cattgcatac gttgtatcca      540
tatcataata tgtacattta tattggctca tgtccaacat taccgccatg ttgacattga      600
ttattgacta gttattaata gtaatcaatt acggggtcat tagttcatag cccatatatg      660
gagttccgcg ttacataact tacggtaaat ggcccgcctg gctgaccgcc caacgacccc      720
cgcccattga cgtcaataat gacgtatgtt cccatagtaa cgccaatagg gactttccat      780
tgacgtcaat gggtggagta tttacggtaa actgcccact tggcagtaca tcaagtgtat      840
catatgccaa gtacgccccc tattgacgtc aatgacggta aatggcccgc ctggcattat      900
gcccagtaca tgaccttatg ggactttcct acttggcagt acatctacgt attagtcatc      960
gctattacca tggtgatgcg gttttggcag tacatcaatg ggcgtggata gcggtttgac     1020
tcacggggat ttccaagtct ccaccccatt gacgtcaatg ggagtttgtt ttggcaccaa     1080
aatcaacggg actttccaaa atgtcgtaac aactccgccc cattgacgca atgggcggt      1140 aggcgtgtac ggtgggaggt ctatataagc agagctcgtt tagtgaaccg tcagatcgcc     1200
```

```
tggagacgcc atccacgctg ttttgacctc catagaagac accgggaccg atccagcctc    1260
cgtcaccgtc gtcgacacgt gtgatcagat ctagaccagg ccctggatcg atccaacaac    1320
acaatgggcg ttacaggaat attgcagtta cctcgtgatc gattcaagag gacatcattc    1380
tttctttggg taattatcct tttccaaaga acatttccta tcccacttgg agtcatccac    1440
aatagcacat tacaggttag tgatgtcgac aaactagttt gtcgtgacaa actgtcatcc    1500
acaaatcaat tgagatcagt tggactgaat ctcgaaggga atggagtggc aactgacgtg    1560
ccatctgcaa ctaaaagatg gggcttcagg tccggtgtcc caccaaaggt ggtcaattat    1620
gaagctggtg aatgggctga aaactgctac aatcttgaaa tcaaaaaacc tgacgggagt    1680
gagtgtctac cagcagcgcc agacgggatt cggggcttcc cccggtgccg gtatgtgcac    1740
aaagtatcag gaacgggacc gtgtgccgga gactttgcct tccataaaga gggtgctttc    1800
ttcctgtatg atcgacttgc ttccacagtt atctaccgag gaacgacttt cgctgaaggt    1860
gtcgttgcat ttctgatact gccccaagct aagaaggact tcttcagctc acaccccttg    1920
agagagccgg tcaatgcaac ggaggacccg tctagtggct actattctac cacaattaga    1980
tatcaggcta ccggttttgg aaccaatgag acagagtact tgttcgaggt tgacaatttg    2040
acctacgtcc aacttgaatc aagattcaca ccacagtttc tgctccagct gaatgagaca    2100
atatatacaa gtgggaaaag gagcaatacc acgggaaaac taatttggaa ggtcaaccc    2160
gaaattgata caacaatcgg ggagtgggcc ttctgggaaa ctaaaaaaaa cctcactaga    2220
aaaattcgca gtgaagagtt gtctttcaca gttgtatcaa acggagccaa aaacatcagt    2280
ggtcagagtc cggcgcgaac ttcttccgac ccagggacca acacaacaac tgaagaccac    2340
aaaatcatgg cttcagaaaa ttcctctgca atggttcaag tgcacagtca aggaagggaa    2400
gctgcagtgt cgcatctaac aacccttgcc acaatctcca cgagtcccca atccctcaca    2460
accaaaccag gtccggacaa cagccacccat aatacacccg tgtataaact tgacatctct    2520
gaggcaactc aagttgaaca acatcaccgc agaacagaca acgacagcac agcctccgac    2580
actccctctg ccacgaccgc agccggaccc ccaaaagcag agaacaccaa cacgagcaag    2640
agcactgact tcctggaccc cgccaccaca acaagtcccc aaaaccacag cgagaccgct    2700
ggcaacaaca acactcatca ccaagatacc ggagaagaga gtgccagcag cgggaagcta    2760
ggcttaatta ccaatactat tgctggagtc gcaggactga tcacaggcgg gagaagaact    2820
cgaagagaag caattgtcaa tgctcaaccc aaatgcaacc ctaatttaca ttactggact    2880
actcaggatg aaggtgctgc aatcggactg gcctggatac catatttcgg gccagcagcc    2940
gagggaattt acatagaggg gctaatgcac aatcaagatg gtttaatctg tgggttgaga    3000
cagctggcca acgagacgac tcaagctctt caactgttcc tgagagccac aactgagcta    3060
cgcacctttt caatcctcaa ccgtaaggca attgatttct tgctgcagcg atgggcggc    3120
acatgccaca ttctgggacc ggactgctgt atcgaaccac atgattggac caagaacata    3180
acagacaaaa ttgatcagat tattcatgat tttgttgata aaaccccttcc ggaccagggg    3240
gacaatgaca attggtggac aggatggaga caatggatgg ccgcatcgtg actgactgac    3300
gatctgcctc gcgagatcaa ttccgcccct ctccctcccc cccccctaac gttactggcc    3360
gaagccgctt ggaataaggc cggtgtgcgt ttgtctatat gttatttttcc accatattgc    3420
cgtcttttgg caatgtgagg gcccggaaac ctggccctgt cttcttgacg agcattccta    3480
ggggtctttc ccctctcgcc aaaggaatgc aaggtctgtt gaatgtcgtg aaggaagcag    3540
ttcctctgga agcttcttga agacaaacaa cgtctgtagc gaccctttgc aggcagcgga    3600
```

```
acccccccacc tggcgacagg tgcctctgcg gccaaaagcc acgtgtataa gatacacctg   3660
caaaggcggc acaaccccag tgccacgttg tgagttggat agttgtggaa agagtcaaat   3720
ggctctcctc aagcgtattc aacaaggggc tgaaggatgc ccagaaggta ccccattgta   3780
tgggatctga tctggggcct cggtgcacat gctttacatg tgtttagtcg aggttaaaaa   3840
acgtctaggc cccccgaacc acggggacgt ggttttcctt tgaaaaacac gatgataata   3900
tggccacaac catggagggt cttagcctac tccaattgcc cagagataaa tttcgaaaaa   3960
gctctttctt tgtttgggtc atcatcttat ttcaaaaggc cttttccatg cctttgggtg   4020
ttgtgaccaa cagcacttta gaagtaacag agattgacca gctagtctgc aaggatcatc   4080
ttgcatccac tgaccagctg aaatcagttg gtctcaacct cgaggggagc ggagtatcta   4140
ctgatatccc atctgcgaca aagcgttggg gcttcagatc tggtgtgcct cccaaggtgg   4200
tcagctatga agcaggagaa tgggctgaaa attgctacaa tcttgaaata agaagccgg   4260 acgggagcga atgcttaccc ccaccgccgg atggtgtcag aggctttcca aggtgccgct   4320
atgttcacaa agcccaagga accgggccct gcccgggtga ctatgccttt cacaaggatg   4380
gagctttctt cctctatgac aggctggctt caactgtaat ttacagagga gtcaattttg   4440
ctgagggggt aattgcattc ttgatattgg ctaaaccaaa ggaaacgttc cttcaatcac   4500
cccccattcg agaggcagta aactacactg aaaatacatc aagttactat gccacatcct   4560
acttggagta cgaaatcgaa aattttggtg ctcaacactc cacgacccct ttcaaaatta   4620
acaataatac ttttgttctt ctggacaggc cccacacgcc tcagttcctt ttccagctga   4680
atgataccat tcaccttcac caacagttga gcaacacaac tgggaaacta atttggacac   4740
tagatgctaa tatcaatgct gatattggtg aatgggcttt ttgggaaaat aaaaaaaatc   4800
tctccgaaca actacgtgga gaagagctgt cttttcgaaac tttatcgctc aacgagacag   4860
aagacgatga tgcgacatcg tcgagaacta caaagggaag aatctccgac cgggccacca   4920
ggaagtattc ggacctggtt ccaaaggatt cccctgggat ggtttcattg cacgtaccag   4980
aaggggaaac aacattgccg tctcagaatt cgacagaagg tcgaagagta gatgtgaata   5040
ctcaggaaac tatcacagag acaactgcaa caatcatagg cactaacggt aacaacatgc   5100
agatctccac catcgggaca ggactgagct ccagccaaat cctgagttcc tcaccgacca   5160
tggcaccaag ccctgagact cagacctcca caacctacac accaaaacta ccagtgatga   5220
ccaccgagga accaacaaca ccaccgagaa actctcctgg ctcaacaaca gaagcaccca   5280
ctctcaccac cccagagaat ataacaacag cggttaaaac tgttttgcca caagagtcca   5340
caagcaacgg tctaataact tcaacagtaa cagggattct tgggagcctt ggacttcgaa   5400
aacgcagcag aagacaagtt aacaccaggg ccacgggtaa atgcaatccc aacttacact   5460
actggactgc acaagaacaa cataatgctg ctgggattgc ctggatcccg tactttggac   5520
cgggtgcaga aggcatatac actgaaggcc ttatgcacaa ccaaaatgcc ttagtctgtg   5580
gactcagaca acttgcaaat gaaacaactc aagctctgca gcttttctta agggccacga   5640
cggagctgcg gacatatacc atactcaata ggaaggccat agatttcctt ctgcgacgat   5700
ggggcgggac atgtaggatc ctgggaccag attgttgcat tgagccacat gattggacca   5760
aaaacatcac tgataaaatc aaccaaatca tccatgattt catcgacaac cctttaccca   5820
atcaggataa tgatgataat tggtggacgg gctggagaca gtggatcccg ccgcatcgt   5880 gactgactga cgatctgcct cgcggatcca gatctgctgt gccttctagt tgccagccat   5940
ctgttgtttg ccccteccccc gtgccttcct tgaccctgga aggtgccact cccactgtcc   6000
```

-continued

```
tttcctaata aaatgaggaa attgcatcgc attgtctgag taggtgtcat tctattctgg    6060 ggggtgggt ggggcagcac agcaaggggg aggattggga agacaatagc aggcatgctg     6120 gggatgcgt gggctctatg ggtacccagg gccgcataac ttcgtataat gtatgctata    6180
cgaagttata agatctgtac tgaaatgtgt gggcgtggct taagggtggg aaagaatata    6240
taaggtgggg gtcttatgta gttttgtatc tgttttgcag cagccgccgc cgccatgagc    6300
accaactcgt ttgatggaag cattgtgagc tcatatttga caacgcgcat gccccatgg     6360 gccggggtgc gtcagaatgt gatgggctcc agcattgatg gtcgccccgt cctgcccgca    6420
aactctacta ccttgaccta cgagaccgtg tctggaacgc cgttggagac tgcagcctcc    6480
gccgccgctt cagccgctgc agccaccgcc cgcgggattg tgactgactt tgctttcctg    6540
agcccgcttg caagcagtgc agcttcccgt tcatccgccc gcgatgacaa gttgacggct    6600
cttttggcac aattggattc tttgacccgg gaacttaatg tcgtttctca gcagctgttg    6660
gatctgcgcc agcaggtttc tgccctgaag gcttcctccc ctcccaatgc ggtttaaaac    6720
ataaataaaa aaccagactc tgtttggatt tggatcaagc aagtgtcttg ctgtctttat    6780
ttaggggttt tgcgcgcgcg gtaggccgg gaccagcggt ctcggtcgtt gagggtcctg     6840
tgtatttttt ccaggacgtg gtaaaggtga ctctggatgt tcagatacat gggcataagc    6900
ccgtctctgg ggtggaggta gcaccactgc agagcttcat gctgcggggt ggtgttgtag    6960
atgatccagt cgtagcagga gcgctgggcg tggtgcctaa aaatgtcttt cagtagcaag    7020
ctgattgcca ggggcaggcc cttggtgtaa gtgtttacaa agcggttaag ctgggatggg    7080
tgcatacgtg gggatatgag atgcatcttg gactgtattt ttaggttggc tatgttccca    7140
gccatatccc tccggggatt catgttgtgc agaaccacca gcacagtgta tccggtgcac    7200
ttgggaaatt tgtcatgtag cttagaagga aatgcgtgga agaacttgga gacgcccttg    7260
tgacctccaa gattttccat gcattcgtcc ataatgatgg caatgggccc acgggcggcg    7320
gcctgggcga agatatttct gggatcacta acgtcatagt tgtgttccag gatgagatcg    7380
tcataggcca ttttttacaaa gcgcgggcgg agggtgccag actgcggtat aatggttcca    7440
tccggcccag gggcgtagtt accctcacag atttgcattt cccacgcttt gagttcagat    7500 gggggggatca tgtctacctg cggggcgatg aagaaaacgg tttccggggt agggagatc    7560 agctgggaag aaagcaggtt cctgagcagc tgcgacttac cgcagccggt gggcccgtaa    7620
atcacaccta ttaccggctg caactggtag ttaagagagc tgcagctgcc gtcatccctg    7680
agcagggggg ccacttcgtt aagcatgtcc ctgactcgca tgttttccct gaccaaatcc    7740
gccagaaggc gctcgccgcc cagcgatagc agttcttgca aggaagcaaa gttttttcaac    7800 ggtttgagac cgtccgccgt aggcatgctt ttgagcgttt gaccaagcag ttccaggcgg    7860
tcccacagct cggtcacctg ctctacggca tctcgatcca gcatatctcc tcgtttcgcg    7920
ggttggggcg gctttcgctg tacgcagta gtcggtgctc gtccagacgg ccagggtca    7980 tgtctttcca cgggcgcagg gtcctcgtca gcgtagtctg ggtcacggtg aagggtgcg    8040 ctccgggctg cgcgctggcc agggtgcgct tgaggctggt cctgctggtg ctgaagcgct    8100
gccggtcttc gccctgcgcg tcggccaggt agcatttgac catggtgtca tagtccagcc    8160
cctccgcggc gtgccccttg gcgcgcagct tgcccttgga ggaggcgccg cacgaggggc    8220
agtgcagact tttgagggcg tagagcttgg gcgcgagaaa taccgattcc ggggagtagg    8280
catccgcgcc gcaggccccg cagacggtct cgcattccac gagccaggtg agctctggcc    8340
gttcggggtc aaaaaccagg tttccccccat gcttttttgat gcgtttctta cctctggttt    8400
```

```
ccatgagccg gtgtccacgc tcggtgacga aaaggctgtc cgtgtccccg tatacagact    8460
tgagaggcct gtcctcgagc ggtgttccgc ggtcctcctc gtatagaaac tcggaccact    8520
ctgagacaaa ggctcgcgtc caggccagca cgaaggaggc taagtgggag gggtagcggt    8580
cgttgtccac taggggtcc actcgctcca gggtgtgaag acacatgtcg ccctcttcgg     8640
catcaaggaa ggtgattggt ttgtaggtgt aggccacgtg accgggtgtt cctgaagggg    8700
ggctataaaa ggggtgggg gcgcgttcgt cctcactctc ttccgcatcg ctgtctgcga     8760
gggccagctg ttggggtgag tcgacgcgag gctggatggc cttccccatt atgattcttc    8820
tcgcttccgg cggcatcggg atgcccgcgt tgcaggccat gctgtccagg caggtagatg    8880
acgaccatca gggacagctt caaggccagc aaaaggccag gaaccgtaaa aaggccgcgt    8940
tgctggcgtt tttccatagg ctccgccccc ctgacgagca tcacaaaaat cgacgctcaa    9000
gtcagaggtg gcgaaacccg acaggactat aaagatacca ggcgtttccc cctggaagct    9060
ccctcgtgcg ctctcctgtt ccgacccgtc cgcttaccgg atacctgtcc gcctttctcc    9120
cttcgggaag cgtggcgctt tctcatagct cacgctgtag gtatctcagt tcggtgtagg    9180
tcgttcgctc caagctgggc tgtgtgcacg aaccccccgt tcagcccgac cgctgcgcct    9240
tatccggtaa ctatcgtctt gagtccaacc cggtaagaca cgacttatcg ccactggcag    9300
cagccactgg taacaggatt agcagagcga ggtatgtagg cggtgctaca gagttcttga    9360
agtggtggcc taactacggc tacactagaa ggacagtatt tggtatctgc gctctgctga    9420
agccagttac cttcggaaaa agagttggta gctcttgatc cggcaaacaa accaccgctg    9480
gtagcggtgg tttttttgtt tgcaagcagc agattacgcg cagaaaaaaa ggatctcaag    9540
aagatccttt gatcttttct acggggtctg acgctcagtg gaacgaaaac tcacgttaag    9600
ggattttggt catgagatta tcaaaaagga tcttcaccta gatccttta aattaaaaat     9660 gaagttttaa atcaatctaa agtatatatg agtaaacttg gtctgacagt taccaatgct    9720
taatcagtga ggcacctatc tcagcgatct gtctatttcg ttcatccata gttgcctgac    9780
tccccgtcgt gtagataact acgatacggg agggcttacc atctggcccc agtgctgcaa    9840
tgataccgcg agacccacgc tcaccggctc cagatttatc agcaataaac cagccagccg    9900
gaagggccga gcgcagaagt ggtcctgcaa ctttatccgc ctccatccag tctattaatt    9960
gttgccggga agctagagta agtagttcgc cagttaatag tttgcgcaac gttgttgcca   10020
ttgctgcagg catcgtggtg tcacgctcgt cgtttggtat ggcttcattc agctccggtt   10080
cccaacgatc aaggcgagtt acatgatccc ccatgttgtg caaaaaagcg gttagctcct   10140
tcggtcctcc gatcgttgtc agaagtaagt tggccgcagt gttatcactc atggttatgg   10200
cagcactgca taattctctt actgtcatgc catccgtaag atgcttttct gtgactggtg   10260
agtactcaac caagtcattc tgagaatagt gtatgcggcg accgagttgc tcttgcccgg   10320
cgtcaacacg ggataatacc gcgccacata gcagaacttt aaaagtgctc atcattggaa   10380
aacgttcttc gggcgaaaa ctctcaagga tcttaccgct gttgagatcc agttcgatgt     10440
aacccactcg tgcacccaac tgatcttcag catcttttac tttcaccagc gtttctgggt   10500
gagcaaaaac aggaaggcaa atgccgcaa aaagggaat aagggcgaca cggaaatgtt      10560
gaatactcat actcttcctt tttcaatatt attgaagcat ttatcagggt tattgtctca   10620
tgagcggata catatttgaa tgtatttaga aaaataaaca aataggggtt ccgcgcacat   10680
ttccccgaaa agtgccacct gacgtctaag aaaccattat tatcatgaca ttaacctata   10740
aaaataggcg tatcacgagg ccctttcgtc ttcaagaatt gtt                     10783
```

-continued

<210> SEQ ID NO 26
<211> LENGTH: 8338
<212> TYPE: DNA
<213> ORGANISM: Artificial Sequence
<220> FEATURE:
<223> OTHER INFORMATION: Synthetic Construct pAdApt Ebola GP(S)

<400> SEQUENCE: 26

| | | | | | |
|---|---|---|---|---|---|
| ttaattaacc | gcaattctca | tgtttgacag | cttatcatca | tcaataatat | accttatttt | 60 |
| ggattgaagc | caatatgata | atgaggggggt | ggagtttgtg | acgtggcgcg | ggcgtggga | 120 |
| acggggcggg | tgacgtagta | gtgtggcgga | agtgtgatgt | tgcaagtgtg | gcggaacaca | 180 |
| tgtaagcgac | ggatgtggca | aaagtgacgt | ttttggtgtg | cgccggtgta | cacaggaagt | 240 |
| gacaattttc | gcgcggtttt | aggcggatgt | tgtagtaaat | ttgggcgtaa | ccgagtaaga | 300 |
| tttggccatt | ttcgcgggaa | aactgaataa | gaggaagtga | atctgaata | attttgtgtt | 360 |
| actcatagcg | cgtaatattt | gtctagggcc | gcggggactt | tgaccgttta | cgtggagact | 420 |
| cgcccaggtg | tttttctcag | gtgttttccg | cgttccgggt | caaagttggc | gttttattat | 480 |
| tatagtcagt | acgtaccagt | gcactggcct | agagcggccc | cattgcatac | gttgtatcca | 540 |
| tatcataata | tgtacattta | tattggctca | tgtccaacat | taccgccatg | ttgacattga | 600 |
| ttattgacta | gttattaata | gtaatcaatt | acgggtcat | tagttcatag | cccatatatg | 660 |
| gagttccgcg | ttacataact | tacggtaaat | ggcccgcctg | gctgaccgcc | caacgacccc | 720 |
| cgcccattga | cgtcaataat | gacgtatgtt | cccatagtaa | cgccaatagg | gactttccat | 780 |
| tgacgtcaat | gggtggagta | tttacggtaa | actgcccact | tggcagtaca | tcaagtgtat | 840 |
| catatgccaa | gtacgccccc | tattgacgtc | aatgacggta | aatggcccgc | ctggcattat | 900 |
| gcccagtaca | tgaccttatg | ggactttcct | acttggcagt | acatctacgt | attagtcatc | 960 |
| gctattacca | tggtgatgcg | gttttggcag | tacatcaatg | ggcgtggata | gcggtttgac | 1020 |
| tcacggggat | ttccaagtct | ccaccccatt | gacgtcaatg | ggagtttgtt | ttggcaccaa | 1080 |
| aatcaacggg | actttccaaa | atgtcgtaac | aactccgccc | cattgacgca | aatgggcggt | 1140 |
| aggcgtgtac | ggtgggaggt | ctatataagc | agagctcgtt | tagtgaaccg | tcagatcgcc | 1200 |
| tggagacgcc | atccacgctg | ttttgacctc | catagaagac | accgggaccg | atccagcctc | 1260 |
| cgtcaccgtc | gtcgacacgt | gtgatcagat | atcgcggccg | ccagtgtgat | ggatatctgc | 1320 |
| agaattcggc | ttatcttcag | gatctcgcca | tggagggtct | tagcctactc | caattgccca | 1380 |
| gagataaatt | tcgaaaaagc | tctttctttg | tttgggtcat | catcttattt | caaaaggcct | 1440 |
| tttccatgcc | tttgggtgtt | gtgaccaaca | gcactttaga | agtaacagag | attgaccagc | 1500 |
| tagtctgcaa | ggatcatctt | gcatccactg | accagctgaa | atcagttggt | ctcaacctcg | 1560 |
| aggggagcgg | agtatctact | gatatcccat | ctgcgacaaa | gcgttgggc | ttcagatctg | 1620 |
| gtgtgcctcc | caaggtggtc | agctatgaag | caggagaatg | ggctgaaaat | tgctacaatc | 1680 |
| ttgaaataaa | gaagccggac | gggagcgaat | gcttaccccc | accgccggat | ggtgtcagag | 1740 |
| gctttccaag | gtgccgctat | gttcacaaag | cccaaggaac | cgggccctgc | ccgggtgact | 1800 |
| atgcctttca | caaggatgga | gctttcttcc | tctatgacag | gctggcttca | actgtaattt | 1860 |
| acagaggagt | caattttgct | gagggggtaa | ttgcattctt | gatattggct | aaaccaaagg | 1920 |
| aaacgttcct | tcaatcaccc | cccattcgag | aggcagtaaa | ctacactgaa | atacatcaa | 1980 |
| gttactatgc | cacatcctac | ttggagtacg | aaatcgaaaa | ttttggtgct | caacactcca | 2040 |
| cgacccttttt | caaaattaac | aataatactt | ttgttcttct | ggacaggccc | cacacgcctc | 2100 |

```
agttcctttt ccagctgaat gataccattc accttcacca acagttgagc aacacaactg   2160
ggaaactaat ttggacacta gatgctaata tcaatgctga tattggtgaa tgggcttttt   2220
gggaaaataa aaaaaatctc tccgaacaac tacgtggaga agagctgtct ttcgaaactt   2280
tatcgctcaa cgagacagaa gacgatgatg cgacatcgtc gagaactaca aagggaagaa   2340
tctccgaccg ggccaccagg aagtattcgg acctggttcc aaaggattcc cctgggatgg   2400
tttcattgca cgtaccagaa ggggaaacaa cattgccgtc tcagaattcg acagaaggtc   2460
gaagagtaga tgtgaatact caggaaacta tcacagagac aactgcaaca atcataggca   2520
ctaacggtaa caacatgcag atctccacca tcgggacagg actgagctcc agccaaatcc   2580
tgagttcctc accgaccatg gcaccaagcc ctgagactca gacctccaca acctacacac   2640
caaaactacc agtgatgacc accgaggaac caacaacacc accgagaaac tctcctggct   2700
caacaacaga agcacccact ctcaccaccc cagagaatat aacaacagcg gttaaaactg   2760
ttttgccaca agagtccaca agcaacggtc taataacttc aacagtaaca gggattcttg   2820
ggagccttgg acttcgaaaa cgcagcagaa gacaagttaa caccagggcc acgggtaaat   2880
gcaatcccaa cttacactac tggactgcac aagaacaaca taatgctgct gggattgcct   2940
ggatcccgta ctttggaccg ggtgcagaag gcatatacac tgaaggcctt atgcacaacc   3000
aaaatgcctt agtctgtgga ctcagacaac ttgcaaatga acaactcaa gctctgcagc   3060 ttttcttaag ggccacgacg gagctgcgga catataccat actcaatagg aaggccatag   3120
atttccttct gcgacgatgg ggcgggacat gtaggatcct gggaccagat tgttgcattg   3180
agccacatga ttggaccaaa aacatcactg ataaaatcaa ccaaatcatc catgatttca   3240
tcgacaaccc tttacccaat caggataatg atgataattg gtggacgggc tggagacagt   3300
ggatccctgc aggaataggc attactggaa ttattattgc aatcattgct cttctttgcg   3360
tctgcaagct gctttgttga atatcaagcc gaattccagc acactggcgg ccgttactag   3420
tggatccgag ctcggatcca agctctagac caggccctgg atccagatct gctgtgcctt   3480
ctagttgcca gccatctgtt gtttgccct cccccgtgcc ttccttgacc ctggaaggtg   3540
ccactcccac tgtcctttcc taataaaatg aggaaattgc atcgcattgt ctgagtaggt   3600
gtcattctat tctgggggggt ggggtggggc aggacagcaa gggggaggat tgggaagaca   3660
atagcaggca tgctggggat gcggtgggct ctatgggtac ccaggccgc ataacttcgt   3720 ataatgtatg ctatacgaag ttataagatc tgtactgaaa tgtgtgggcg tggcttaagg   3780
gtgggaaaga atatataagg tggggtctt atgtagttttt gtatctgttt tgcagcagcc   3840
gccgccgcca tgagcaccaa ctcgtttgat ggaagcattg tgagctcata tttgacaacg   3900
cgcatgcccc catgggccgg ggtgcgtcag aatgtgatgg gctccagcat tgatggtcgc   3960
cccgtcctgc ccgcaaactc tactaccttg acctacgaga ccgtgtctgg aacgccgttg   4020
gagactgcag cctccgccgc cgcttcagcc gctgcagcca ccgcccgcgg gattgtgact   4080
gactttgctt tcctgagccc gcttgcaagc agtgcagctt cccgttcatc cgcccgcgat   4140
gacaagttga cggctctttt ggcacaattg gattctttga cccgggaact taatgtcgtt   4200
tctcagcagc tgttggatct gcgccagcag gtttctgccc tgaaggcttc ctcccctccc   4260
aatgcggttt aaaacataaa taaaaaacca gactctgttt ggatttggat caagcaagtg   4320
tcttgctgtc tttatttagg ggttttgcgc gcgcggtagg cccgggacca gcggtctcgg   4380
tcgttgaggg tcctgtgtat ttttttccagg acgtggtaaa ggtgactctg gatgttcaga   4440
tacatgggca taagcccgtc tctggggtgg aggtagcacc actgcagagc ttcatgctgc   4500
```

```
ggggtggtgt tgtagatgat ccagtcgtag caggagcgct gggcgtggtg cctaaaaatg   4560
tctttcagta gcaagctgat tgccaggggc aggcccttgg tgtaagtgtt tacaaagcgg   4620
ttaagctggg atgggtgcat acgtggggat atgagatgca tcttggactg tattttagg    4680 ttggctatgt tcccagccat atccctccgg ggattcatgt tgtgcagaac caccagcaca   4740
gtgtatccgg tgcacttggg aaatttgtca tgtagcttag aaggaaatgc gtggaagaac   4800
ttggagacgc ccttgtgacc tccaagattt tccatgcatt cgtccataat gatggcaatg   4860
ggcccacggg cggcggcctg gcgaagata  tttctgggat cactaacgtc atagttgtgt   4920
tccaggatga gatcgtcata ggccattttt acaaagcgcg ggcggagggt gccagactgc   4980
ggtataatgg ttccatccgg cccaggggcg tagttaccct cacagatttg catttcccac   5040
gctttgagtt cagatggggg gatcatgtct acctgcgggg cgatgaagaa aacgtttcc    5100 ggggtagggg agatcagctg ggaagaaagc aggttcctga gcagctgcga cttaccgcag   5160
ccggtgggcc cgtaaatcac acctattacc ggctgcaact ggtagttaag agagctgcag   5220
ctgccgtcat ccctgagcag gggggccact tcgttaagca tgtccctgac tcgcatgttt   5280
tccctgacca aatccgccag aaggcgctcg ccgcccagcg atagcagttc ttgcaaggaa   5340
gcaaagtttt tcaacggttt gagaccgtcc gccgtaggca tgcttttgag cgtttgacca   5400
agcagttcca ggcggtccca cagctcggtc acctgctcta cggcatctcg atccagcata   5460
tctcctcgtt tcgcggggttg gggcggcttt cgctgtacgg cagtagtcgg tgctcgtcca   5520
gacgggccag ggtcatgtct ttccacgggc gcagggtcct cgtcagcgta gtctgggtca   5580
cggtgaaggg gtgcgctccg ggctgcgcgc tggccagggt gcgcttgagg ctggtcctgc   5640
tggtgctgaa gcgctgccgg tcttcgccct gcgcgtcggc caggtagcat ttgaccatgg   5700
tgtcatagtc cagcccctcc gcggcgtggc ccttggcgcg cagcttgccc ttggaggagg   5760
cgccgcacga ggggcagtgc agactttga  gggcgtagag cttgggcgcg agaaataccg   5820
attccgggga gtaggcatcc gcgccgcagg ccccgcagac ggtctcgcat ccacgagcc    5880 aggtgagctc tggccgttcg gggtcaaaaa ccaggtttcc cccatgcttt ttgatgcgtt   5940
tcttacctct ggtttccatg agccggtgtc cacgctcggt gacgaaaagg ctgtccgtgt   6000
ccccgtatac agacttgaga ggcctgtcct cgagcggtgt tccgcggtcc tcctcgtata   6060
gaaactcgga ccactctgag acaaaggctc gcgtccaggc cagcacgaag gaggctaagt   6120
gggaggggta gcggtcgttg tccactaggg ggtccactcg ctccagggtg tgaagacaca   6180
tgtcgccctc ttcggcatca aggaaggtga ttggtttgta ggtgtaggcc acgtgaccgg   6240
gtgttcctga aggggggcta taaagggggg tgggggcgcg ttcgtcctca ctctcttccg   6300
catcgctgtc tgcgagggcc agctgttggg gtgagtcgac gcgaggctgg atggccttcc   6360
ccattatgat tcttctcgct tccggcggca tcgggatgcc cgcgttgcag gccatgctgt   6420
ccaggcaggt agatgacgac catcagggac agcttcaagg ccagcaaaag gccaggaacc   6480
gtaaaaaggc cgcgttgctg gcgttttttcc ataggctccg ccccctgac  gagcatcaca   6540 aaaatcgacg ctcaagtcag aggtggcgaa acccgacagg actataaaga taccaggcgt   6600
ttccccctgg aagctccctc gtgcgctctc ctgttccgac cctgccgctt accggatacc   6660
tgtccgcctt tctcccttcg ggaagcgtgg cgctttctca tagctcacgc tgtaggtatc   6720
tcagttcggt gtaggtcgtt cgctccaagc tgggctgtgt gcacgaaccc cccgttcagc   6780
ccgaccgctg cgccttatcc ggtaactatc gtcttgagtc caacccggta agacacgact   6840
tatcgccact ggcagcagcc actggtaaca ggattagcag agcgaggtat gtaggcggtg   6900
```

-continued

```
ctacagagtt cttgaagtgg tggcctaact acggctacac tagaaggaca gtatttggta    6960
tctgcgctct gctgaagcca gttaccttcg gaaaaagagt tggtagctct tgatccggca    7020
aacaaaccac cgctggtagc ggtggttttt ttgtttgcaa gcagcagatt acgcgcagaa    7080
aaaaggatc tcaagaagat cctttgatct tttctacggg gtctgacgct cagtggaacg    7140
aaaactcacg ttaagggatt ttggtcatga gattatcaaa aaggatcttc acctagatcc    7200
ttttaaatta aaaatgaagt tttaaatcaa tctaaagtat atatgagtaa acttggtctg    7260
acagttacca atgcttaatc agtgaggcac ctatctcagc gatctgtcta tttcgttcat    7320
ccatagttgc ctgactcccc gtcgtgtaga taactacgat acgggagggc ttaccatctg    7380
gccccagtgc tgcaatgata ccgcgagacc cacgctcacc ggctccagat ttatcagcaa    7440
taaaccagcc agccggaagg gccgagcgca gaagtggtcc tgcaacttta tccgcctcca    7500
tccagtctat taattgttgc cgggaagcta gagtaagtag ttcgccagtt aatagtttgc    7560
gcaacgttgt tgccattgct gcaggcatcg tggtgtcacg ctcgtcgttt ggtatggctt    7620
cattcagctc cggttcccaa cgatcaaggc gagttacatg atcccccatg ttgtgcaaaa    7680
aagcggttag ctccttcggt cctccgatcg ttgtcagaag taagttggcc gcagtgttat    7740
cactcatggt tatggcagca ctgcataatt ctcttactgt catgccatcc gtaagatgct    7800
tttctgtgac tggtgagtac tcaaccaagt cattctgaga atagtgtatg cggcgaccga    7860
gttgctcttg cccggcgtca acacgggata ataccgcgcc acatagcaga actttaaaag    7920
tgctcatcat tggaaaacgt tcttcggggc gaaaactctc aaggatctta ccgctgttga    7980
gatccagttc gatgtaaccc actcgtgcac ccaactgatc ttcagcatct tttactttca    8040
ccagcgtttc tgggtgagca aaaacaggaa ggcaaaatgc cgcaaaaaag ggaataaggg    8100
cgacacggaa atgttgaata ctcatactct tcctttttca atattattga agcatttatc    8160
agggttattg tctcatgagc ggatacatat ttgaatgtat ttagaaaaat aaacaaatag    8220
gggttccgcg cacatttccc cgaaaagtgc cacctgacgt ctaagaaacc attattatca    8280
tgacattaac ctataaaaat aggcgtatca cgaggccctt tcgtcttcaa gaattgtt      8338
```

<210> SEQ ID NO 27
<211> LENGTH: 8221
<212> TYPE: DNA
<213> ORGANISM: Artificial Sequence
<220> FEATURE:
<223> OTHER INFORMATION: Synthetic Construct pAdApt Ebola GP(S)(dTM)

<400> SEQUENCE: 27

```
ttaattaacc gcaattctca tgtttgacag cttatcatca tcaataatat accttatttt      60
ggattgaagc caatatgata atgagggggt ggagtttgtg acgtggcgcg gggcgtggga     120
acggggcggg tgacgtagta gtgtggcgga agtgtgatgt tgcaagtgtg gcggaacaca     180
tgtaagcgac ggatgtggca aaagtgacgt ttttggtgtg cgccggtgta cacaggaagt     240
gacaattttc gcgcggtttt aggcggatgt tgtagtaaat ttgggcgtaa ccgagtaaga     300
tttggccatt ttcgcgggaa aactgaataa gaggaagtga atctgaata attttgtgtt      360
actcatagcg cgtaatattt gtctagggcc gcggggactt tgaccgttta cgtggagact     420
cgcccaggtg ttttttctcag gtgttttccg cgttccgggt caaagttggc gttttattat     480
tatagtcagt acgtaccagt gcactggcct agagcggccc cattgcatac gttgtatcca     540
tatcataata tgtacatttta tattggctca tgtccaacat taccgccatg ttgacattga     600
ttattgacta gttattaata gtaatcaatt acggggtcat tagttcatag cccatatatg     660
```

```
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta atggcccgc ctggcattat    900 gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca atgggcggt    1140 aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ccagtgtgat ggatatctgc   1320
agaattcggc ttatcttcag gatctcgcca tggaggtct tagcctactc caattgccca   1380
gagataaatt tcgaaaagc tctttctttg tttgggtcat catcttattt caaaaggcct   1440
tttccatgcc tttgggtgtt gtgaccaaca gcactttaga agtaacagag attgaccagc   1500
tagtctgcaa ggatcatctt gcatccactg accagctgaa atcagttggt ctcaacctcg   1560
aggggagcgg agtatctact gatatcccat ctgcgacaaa gcgttgggc ttcagatctg    1620 gtgtgcctcc caaggtggtc agctatgaag caggagaatg ggctgaaaat tgctacaatc   1680
ttgaaataaa gaagccggac gggagcgaat gcttacccc accgccggat ggtgtcagag    1740
gctttccaag gtgccgctat gttcacaaag cccaaggaac cgggccctgc ccgggtgact   1800
atgcctttca caaggatgga gctttcttcc tctatgacag gctggcttca actgtaattt   1860
acagaggagt caattttgct gaggggtaa ttgcattctt gatattggct aaaccaaagg    1920
aaacgttcct tcaatcaccc cccattcgag aggcagtaaa ctacactgaa atacatcaa    1980 gttactatgc cacatcctac ttggagtacg aaatcgaaaa ttttggtgct caacactcca   2040 cgacccttt caaaattaac aataatactt tgttcttct ggacaggccc cacacgcctc     2100
agttcctttt ccagctgaat gataccattc accttcacca acagttgagc aacacaactg   2160
ggaaactaat ttggacacta gatgctaata tcaatgctga tattggtgaa tgggcttttt   2220
gggaaaataa aaaaatctc tccgaacaac tacgtggaga gagctgtct ttcgaaactt     2280 tatcgctcaa cgagacagaa gacgatgatg cgacatcgtc gagaactaca aagggaagaa   2340
tctccgaccg ggccaccagg aagtattcgg acctggttcc aaaggattcc cctgggatgg   2400
tttcattgca cgtaccagaa ggggaaacaa cattgccgtc tcagaattcg acagaaggtc   2460
gaagagtaga tgtgaatact caggaaacta tcacagagac aactgcaaca atcataggca   2520
ctaacggtaa caacatgcag atctccacca tcgggacagg actgagctcc agccaaatcc   2580
tgagttcctc accgaccatg gcaccaagcc ctgagactca gacctccaca acctacacac   2640
caaaactacc agtgatgacc accgaggaac caacaacacc accgagaaac tctcctggct   2700
caacaacaga agcaccccact ctcaccaccc cagagaatat aacaacagcg gttaaaactg   2760
ttttgccaca agagtccaca agcaacggtc taataacttc aacagtaaca gggattcttg   2820
ggagccttgg acttcgaaaa cgcagcagaa gacaagttaa caccagggcc acgggtaaat   2880
gcaatcccaa cttacactac tggactgcac aagaacaaca taatgctgct gggattgcct   2940
ggatcccgta ctttggaccg ggtgcagaag gcatatacac tgaaggcctt atgcacaacc   3000
aaaatgcctt agtctgtgga ctcagacaac ttgcaaatga aacaactcaa gctctgcagc   3060
```

```
ttttcttaag ggccacgacg gagctgcgga catataccat actcaatagg aaggccatag     3120
atttccttct gcgacgatgg ggcgggacat gtaggatcct gggaccagat tgttgcattg     3180
agccacatga ttggaccaaa aacatcactg ataaaatcaa ccaaatcatc catgatttca     3240
tcgacaaccc tttacccaat caggataatg atgataattg gtggacgggc tggagacagt     3300
ggatcccggc cgcatcgtga ctgactgacg atctgcctcg cggatccaga tctgctgtgc     3360
cttctagttg ccagccatct gttgtttgcc cctcccccgt gccttccttg accctggaag     3420
gtgccactcc cactgtcctt tcctaataaa atgaggaaat tgcatcgcat tgtctgagta     3480
ggtgtcattc tattctgggg gtgggggtgg ggcaggacag caaggggggag gattgggaag     3540 acaatagcag gcatgctggg gatgcggtgg gctctatggg tacccagggc cgcataactt     3600
cgtataatgt atgctatacg aagttataag atctgtactg aaatgtgtgg gcgtggctta     3660
agggtgggaa agaatatata aggtgggggt cttatgtagt tttgtatctg ttttgcagca     3720
gccgccgccg ccatgagcac caactcgttt gatggaagca ttgtgagctc atatttgaca     3780
acgcgcatgc ccccatgggc cggggtgcgt cagaatgtga tgggctccag cattgatggt     3840
cgccccgtcc tgcccgcaaa ctctactacc ttgacctacg agaccgtgtc tggaacgccg     3900
ttggagactg cagcctccgc cgccgcttca gccgctgcag ccaccgcccg cgggattgtg     3960
actgactttg ctttcctgag cccgcttgca agcagtgcag cttcccgttc atccgcccgc     4020
gatgacaagt tgacggctct tttggcacaa ttggattctt tgacccggga acttaatgtc     4080
gtttctcagc agctgttgga tctgcgccag caggtttctg ccctgaaggc ttcctcccct     4140
cccaatgcgg tttaaaacat aaataaaaaa ccagactctg tttggatttg gatcaagcaa     4200
gtgtcttgct gtctttatttt aggggttttg cgcgcgcggt aggcccggga ccagcggtct     4260
cggtcgttga gggtcctgtg tattttttcc aggacgtggt aaaggtgact ctggatgttc     4320
agatacatgg gcataagccc gtctctgggg tggaggtagc accactgcag agcttcatgc     4380
tgcggggtgg tgttgtagat gatccagtcg tagcaggagc gctgggcgtg gtgcctaaaa     4440
atgtctttca gtagcaagct gattgccagg ggcaggccct tggtgtaagt gtttacaaag     4500
cggttaagct gggatgggtg catacgtggg gatatgagat gcatcttgga ctgtattttt     4560
aggttggcta tgttcccagc catatccctc cggggattca tgttgtgcag aaccaccagc     4620
acagtgtatc cggtgcactt gggaaatttg tcatgtagct tagaaggaaa tgcgtggaag     4680
aacttggaga cgcccttgtg acctccaaga ttttccatgc attcgtccat aatgatggca     4740
atgggcccac gggcggcggc ctgggcgaag atatttctgg gatcactaac gtcatagttg     4800
tgttccagga tgagatcgtc ataggccatt tttacaaagc gcgggcgagg ggtgccagac     4860
tgcggtataa tggttccatc cggcccaggg gcgtagttac cctcacagat ttgcatttcc     4920
cacgctttga gttcagatgg ggggatcatg tctacctgcg gggcgatgaa gaaaacggtt     4980
tccggggtag gggagatcag ctgggaagaa agcaggttcc tgagcagctg cgacttaccg     5040
cagccggtgg gcccgtaaat cacacctatt accggctgca actggtagtt aagagagctg     5100
cagctgccgt catccctgag cagggggggcc acttcgttaa gcatgtccct gactcgcatg     5160 ttttcctga ccaaatccgc cagaaggcgc tcgccgccca gcgatagcag ttcttgcaag     5220
gaagcaaagt ttttcaacgg tttgagaccg tccgccgtag gcatgctttt gagcgtttga     5280
ccaagcagtt ccaggcggtc ccacagctcg gtcacctgct ctacggcatc tcgatccagc     5340
atatctcctc gtttcgcggg ttggggcggc tttcgctgta cggcagtagt cggtgctcgt     5400
ccagacgggc cagggtcatg tcttttccacg ggcgcagggt cctcgtcagc gtagtctggg     5460
```

| | |
|---|---|
| tcacggtgaa ggggtgcgct ccgggctgcg cgctggccag ggtgcgcttg aggctggtcc | 5520 |
| tgctggtgct gaagcgctgc cggtcttcgc cctgcgcgtc ggccaggtag catttgacca | 5580 |
| tggtgtcata gtccagcccc tccgcggcgt ggcccttggc gcgcagcttg cccttggagg | 5640 |
| aggcgccgca cgagggcag tgcagacttt tgagggcgta gagcttgggc gcgagaaata | 5700 |
| ccgattccgg ggagtaggca tccgcgccgc aggccccgca gacggtctcg cattccacga | 5760 |
| gccaggtgag ctctggccgt tcgggtcaa aaaccaggtt tccccatgc tttttgatgc | 5820 |
| gtttcttacc tctggtttcc atgagccggt gtccacgctc ggtgacgaaa aggctgtccg | 5880 |
| tgtccccgta tacagacttg agaggcctgt cctcgagcgg tgttccgcgg tcctcctcgt | 5940 |
| atagaaactc ggaccactct gagacaaagg ctcgcgtcca ggccagcacg aaggaggcta | 6000 |
| agtgggaggg gtagcggtcg ttgtccacta ggggtccac tcgctccagg gtgtgaagac | 6060 |
| acatgtcgcc ctcttcggca tcaaggaagg tgattggttt gtaggtgtag gccacgtgac | 6120 |
| cgggtgttcc tgaaggggg ctataaaagg gggtgggggc gcgttcgtcc tcactctctt | 6180 |
| ccgcatcgct gtctgcgagg gccagctgtt ggggtgagtc gacgcgaggc tggatggcct | 6240 |
| tccccattat gattcttctc gcttccggcg gcatcgggat gccgcgttg caggccatgc | 6300 |
| tgtccaggca ggtagatgac gaccatcagg gacagcttca aggccagcaa aaggccagga | 6360 |
| accgtaaaaa ggccgcgttg ctggcgtttt tccataggct ccgcccccct gacgagcatc | 6420 |
| acaaaaatcg acgctcaagt cagaggtggc gaaacccgac aggactataa agataccagg | 6480 |
| cgtttccccc tggaagctcc ctcgtgcgct ctcctgttcc gaccctgccg cttaccggat | 6540 |
| acctgtccgc ctttctccct tcgggaagcg tggcgctttc tcatagctca cgctgtaggt | 6600 |
| atctcagttc ggtgtaggtc gttcgctcca agctgggctg tgtgcacgaa ccccccgttc | 6660 |
| agcccgaccg ctgcgcctta tccggtaact atcgtcttga gtccaacccg gtaagacacg | 6720 |
| acttatcgcc actggcagca gccactggta acaggattag cagagcgagg tatgtaggcg | 6780 |
| gtgctacaga gttcttgaag tggtggccta actacggcta cactagaagg acagtatttg | 6840 |
| gtatctgcgc tctgctgaag ccagttacct tcggaaaaag agttggtagc tcttgatccg | 6900 |
| gcaaacaaac caccgctggt agcggtggtt ttttgtttg caagcagcag attacgcgca | 6960 |
| gaaaaaagg atctcaagaa gatcctttga tcttttctac ggggtctgac gctcagtgga | 7020 |
| acgaaaactc acgttaaggg attttggtca tgagattatc aaaaaggatc ttcacctaga | 7080 |
| tccttttaaa ttaaaaatga agttttaaat caatctaaag tatatatgag taaacttggt | 7140 |
| ctgacagtta ccaatgctta atcagtgagg cacctatctc agcgatctgt ctatttcgtt | 7200 |
| catccatagt tgcctgactc cccgtcgtgt agataactac gatacgggag ggcttaccat | 7260 |
| ctggccccag tgctgcaatg ataccgcgag acccacgctc accggctcca gatttatcag | 7320 |
| caataaacca gccagccgga agggccgagc gcagaagtgg tcctgcaact ttatccgcct | 7380 |
| ccatccagtc tattaattgt tgccgggaag ctagagtaag tagttcgcca gttaatagtt | 7440 |
| tgcgcaacgt tgttgccatt gctgcaggca tcgtggtgtc acgctcgtcg tttggtatgg | 7500 |
| cttcattcag ctccggttcc caacgatcaa ggcgagttac atgatccccc atgttgtgca | 7560 |
| aaaaagcggt tagctccttc ggtcctccga tcgttgtcag aagtaagttg gccgcagtgt | 7620 |
| tatcactcat ggttatggca gcactgcata attctcttac tgtcatgcca tccgtaagat | 7680 |
| gcttttctgt gactggtgag tactcaacca agtcattctg agaatagtgt atgcggcgac | 7740 |
| cgagttgctc ttgcccggcg tcaacacggg ataataccgc gccacatagc agaactttaa | 7800 |
| aagtgctcat cattggaaaa cgttcttcgg ggcgaaaact ctcaaggatc ttaccgctgt | 7860 |

-continued

| | |
|---|---|
| tgagatccag ttcgatgtaa cccactcgtg cacccaactg atcttcagca tcttttactt | 7920 |
| tcaccagcgt ttctgggtga gcaaaaacag gaaggcaaaa tgccgcaaaa aagggaataa | 7980 |
| gggcgacacg gaaatgttga atactcatac tcttcctttt tcaatattat tgaagcattt | 8040 |
| atcagggtta ttgtctcatg agcggataca tatttgaatg tatttagaaa aataaacaaa | 8100 |
| taggggttcc gcgcacattt ccccgaaaag tgccacctga cgtctaagaa accattatta | 8160 |
| tcatgacatt aacctataaa aataggcgta tcacgaggcc ctttcgtctt caagaattgt | 8220 |
| t | 8221 |

<210> SEQ ID NO 28
<211> LENGTH: 8439
<212> TYPE: DNA
<213> ORGANISM: Artificial Sequence
<220> FEATURE:
<223> OTHER INFORMATION: Synthetic Construct pAdApt Ebola GP(Z)

<400> SEQUENCE: 28

| | |
|---|---|
| ttaattaacc gcaattctca tgtttgacag cttatcatca tcaataatat accttatttt | 60 |
| ggattgaagc caatatgata atgagggggt ggagtttgtg acgtggcgcg gggcgtggga | 120 |
| acggggcggg tgacgtagta gtgtggcgga agtgtgatgt tgcaagtgtg gcggaacaca | 180 |
| tgtaagcgac ggatgtggca aaagtgacgt ttttggtgtg cgccggtgta cacaggaagt | 240 |
| gacaattttc gcgcggtttt aggcggatgt tgtagtaaat ttgggcgtaa ccgagtaaga | 300 |
| tttggccatt tcgcgggaa aactgaataa gaggaagtga atctgaata attttgtgtt | 360 |
| actcatagcg cgtaatattt gtctagggcc gcggggactt tgaccgttta cgtggagact | 420 |
| cgcccaggtg tttttctcag gtgttttccg cgttccgggt caaagttggc gttttattat | 480 |
| tatagtcagt acgtaccagt gcactggcct agagcggccc cattgcatac gttgtatcca | 540 |
| tatcataata tgtacattta tattggctca tgtccaacat taccgccatg ttgacattga | 600 |
| ttattgacta gttattaata gtaatcaatt acggggtcat tagttcatag cccatatatg | 660 |
| gagttccgcg ttacataact tacggtaaat ggcccgcctg gctgaccgcc caacgacccc | 720 |
| cgcccattga cgtcaataat gacgtatgtt cccatagtaa cgccaatagg gactttccat | 780 |
| tgacgtcaat gggtggagta tttacggtaa actgcccact tggcagtaca tcaagtgtat | 840 |
| catatgccaa gtacgccccc tattgacgtc aatgacggta aatggcccgc ctggcattat | 900 |
| gcccagtaca tgaccttatg ggactttcct acttggcagt acatctacgt attagtcatc | 960 |
| gctattacca tggtgatgcg gttttggcag tacatcaatg ggcgtggata gcggtttgac | 1020 |
| tcacggggat ttccaagtct ccaccccatt gacgtcaatg ggagtttgtt ttggcaccaa | 1080 |
| aatcaacggg actttccaaa atgtcgtaac aactccgccc cattgacgca aatgggcggt | 1140 |
| aggcgtgtac ggtgggaggt ctatataagc agagctcgtt tagtgaaccg tcagatcgcc | 1200 |
| tggagacgcc atccacgctg ttttgacctc catagaagac accgggaccg atccagcctc | 1260 |
| cgtcaccgtc gtcgacacgt gtgatcagat atcgcggccg ctctagacca ggccctggat | 1320 |
| cgatccaaca acacaatggg cgttacagga atattgcagt tacctcgtga tcgattcaag | 1380 |
| aggacatcat tctttctttg ggtaattatc cttttccaaa gaacattttc catcccactt | 1440 |
| ggagtcatcc acaatagcac attacaggtt agtgatgtcg acaaactagt ttgtcgtgac | 1500 |
| aaactgtcat ccacaaatca attgagatca gttggactga atctcgaagg gaatgagtg | 1560 |
| gcaactgacg tgccatctgc aactaaaaga tggggcttca ggtccggtgt cccaccaaag | 1620 |
| gtggtcaatt atgaagctgg tgaatgggct gaaaactgct acaatcttga aatcaaaaaa | 1680 |

```
cctgacggga gtgagtgtct accagcagcg ccagacggga ttcggggctt ccccgtgc    1740 cggtatgtgc acaaagtatc aggaacggga ccgtgtgccg agactttgc cttccataaa    1800 gagggtgctt tcttcctgta tgatcgactt gcttccacag ttatctaccg aggaacgact    1860
ttcgctgaag gtgtcgttgc atttctgata ctgccccaag ctaagaagga cttcttcagc    1920
tcacacccct tgagagagcc ggtcaatgca acggaggacc cgtctagtgg ctactattct    1980
accacaatta gatatcaggc taccggtttt ggaaccaatg agacagagta cttgttcgag    2040
gttgacaatt tgacctacgt ccaacttgaa tcaagattca caccacagtt tctgctccag    2100
ctgaatgaga caatatatac aagtgggaaa aggagcaata ccacgggaaa actaatttgg    2160
aaggtcaacc ccgaaattga tacaacaatc ggggagtggg ccttctggga aactaaaaaa    2220
aacctcacta gaaaaattcg cagtgaagag ttgtctttca cagttgtatc aaacggagcc    2280
aaaaacatca gtggtcagag tccggcgcga acttcttccg acccagggac caacacaaca    2340
actgaagacc acaaaatcat ggcttcagaa aattcctctg caatggttca agtgcacagt    2400
caaggaaggg aagctgcagt gtcgcatcta acaacccttg ccacaatctc cacgagtccc    2460
caatccctca caaccaaacc aggtccggac aacagcaccc ataatacacc cgtgtataaa    2520
cttgacatct ctgaggcaac tcaagttgaa caacatcacc gcagaacaga caacgacagc    2580
acagcctccg acactccctc tgccacgacc gcagccggac cccaaaagc agagaacacc    2640 aacacgagca agagcactga cttcctggac cccgccacca caacaagtcc caaaaccac    2700 agcgagaccg ctggcaacaa caacactcat caccaagata ccggagaaga gagtgccagc    2760
agcgggaagc taggcttaat taccaatact attgctggag tcgcaggact gatcacaggc    2820
gggagaagaa ctcgaagaga agcaattgtc aatgctcaac ccaaatgcaa ccctaattta    2880
cattactgga ctactcagga tgaaggtgct gcaatcggac tggcctggat accatatttc    2940
gggccagcag ccgagggaat ttacatagag gggctaatgc acaatcaaga tggtttaatc    3000
tgtgggttga gacagctggc caacgagacg actcaagctc ttcaactgtt cctgagagcc    3060
acaactgagc tacgcacctt ttcaatcctc aaccgtaagg caattgattt cttgctgcag    3120
cgatggggcg gcacatgcca cattctggga ccggactgct gtatcgaacc acatgattgg    3180
accaagaaca aacagacaa aattgatcag attattcatg atttgttga taaaccctt    3240 ccggaccagg gggacaatga caattggtgg acaggatgga gacaatggat accggcaggt    3300
attggagtta caggcgttgt aattgcagtt atcgctttat tctgtatatg caaatttgtc    3360
ttttagtttt tcttcagatt gcttcatgga aaagctcagc ctcaaatcaa tgaaaccagg    3420
atttaattat atggattact gaatctaag attacttgac aaatgataat ataatacact    3480
ggagctttaa acatagccaa tgtgattcta actccttaaa actcacagtt aatcataaac    3540
aaggtttgag gtaccgagct cgaattgatc tgctgtgcct tctagttgcc agccatctgt    3600
tgtttgcccc tcccccgtgc cttccttgac cctggaaggt gccactccca ctgtccttc    3660 ctaataaaat gaggaaattg catcgcattg tctgagtagg tgtcattcta ttctgggggg    3720
tggggtgggg caggacagca agggggagga ttgggaagac aatagcaggc atgctgggga    3780
tgcggtgggc tctatgggta cccagggccg cataacttcg tataatgtat gctatacgaa    3840
gttataagat ctgtactgaa atgtgtggc gtggcttaag ggtgggaaag aatatataag    3900
gtgggggtct tatgtagttt tgtatctgtt ttgcagcagc cgccgccgcc atgagcacca    3960
actcgtttga tggaagcatt gtgagctcat atttgacaac gcgcatgccc ccatgggccg    4020
gggtgcgtca gaatgtgatg ggctccagca ttgatggtcg ccccgtcctg cccgcaaact    4080
```

```
ctactaccctt gacctacgag accgtgtctg gaacgccgtt ggagactgca gcctccgccg    4140
ccgcttcagc cgctgcagcc accgcccgcg ggattgtgac tgactttgct ttcctgagcc    4200
cgcttgcaag cagtgcagct tcccgttcat ccgcccgcga tgacaagttg acggctcttt    4260
tggcacaatt ggattctttg acccgggaac ttaatgtcgt ttctcagcag ctgttggatc    4320
tgcgccagca ggtttctgcc ctgaaggctt cctcccctcc caatgcggtt taaaacataa    4380
ataaaaaacc agactctgtt tggatttgga tcaagcaagt gtcttgctgt ctttatttag    4440
gggttttgcg cgcgcggtag gcccgggacc agcggtctcg gtcgttgagg gtcctgtgta    4500
tttttttccag gacgtggtaa aggtgactct ggatgttcag atacatgggc ataagcccgt    4560
ctctggggtg gaggtagcac cactgcagag cttcatgctg cggggtggtg ttgtagatga    4620
tccagtcgta gcaggagcgc tgggcgtggt gcctaaaaat gtctttcagt agcaagctga    4680
ttgccagggg caggcccttg gtgtaagtgt ttacaaagcg gttaagctgg gatgggtgca    4740
tacgtgggga tatgagatgc atcttggact gtattttag gttggctatg ttcccagcca    4800
tatccctccg gggattcatg ttgtgcagaa ccaccagcac agtgtatccg gtgcacttgg    4860
gaaatttgtc atgtagctta aaggaaatg cgtggaagaa cttggagacg cccttgtgac    4920
ctccaagatt ttccatgcat tcgtccataa tgatggcaat gggcccacgg gcggcggcct    4980
gggcgaagat atttctggga tcactaacgt catagttgtg ttccaggatg agatcgtcat    5040
aggccatttt tacaaagcgc gggcggaggg tgccagactg cggtataatg gttccatccg    5100
gcccaggggc gtagttaccc tcacagattt gcatttccca cgctttgagt tcagatgggg    5160
ggatcatgtc tacctgcggg gcgatgaaga aaacggtttc cggggtaggg gagatcagct    5220
gggaagaaag caggttcctg agcagctgcg acttaccgca gccggtgggc ccgtaaatca    5280
cacctattac cggctgcaac tggtagttaa gagagctgca gctgccgtca tccctgagca    5340
gggggggccac ttcgttaagc atgtccctga ctcgcatgtt ttccctgacc aaatccgcca    5400
gaaggcgctc gccgcccagc gatagcagtt cttgcaagga agcaaagttt ttcaacggtt    5460
tgagaccgtc cgccgtaggc atgcttttga gcgtttgacc aagcagttcc aggcggtccc    5520
acagctcggt cacctgctct acggcatctc gatccagcat atctcctcgt ttcgcgggtt    5580
ggggcggctt tcgctgtacg gcagtagtcg gtgctcgtcc agacgggcca gggtcatgtc    5640
tttccacggg cgcagggtcc tcgtcagcgt agtctgggtc acggtgaagg ggtgcgctcc    5700
gggctgcgcg ctggccaggg tgcgcttgag gctggtcctg ctggtgctga agcgctgccg    5760
gtcttcgccc tgcgcgtcgg ccaggtagca tttgaccatg tgtcatagt ccagcccctc    5820
cgcggcgtgg cccttggcgc gcagcttgcc cttggaggag gcgccgcacg aggggcagtg    5880
cagactttg agggcgtaga gcttgggcgc gagaaatacc gattccgggg agtaggcatc    5940
cgcgccgcag gccccgcaga cggtctcgca ttccacgagc caggtgagct ctggccgttc    6000
ggggtcaaaa accaggtttc ccccatgctt tttgatgcgt ttcttacctc tggtttccat    6060
gagccggtgt ccacgctcgg tgacgaaaag gctgtccgtg tccccgtata cagacttgag    6120
aggcctgtcc tcgagcggtg ttccgcggtc tcctcgtat agaaactcgg accactctga    6180
gacaaaggct cgcgtccagg ccagcacgaa ggaggctaag tgggagggt agcggtcgtt    6240
gtccactagg gggtccactc gctccagggt gtgaagacac atgtcgccct cttcggcatc    6300
aaggaaggtg attggtttgt aggtgtaggc cacgtgaccg ggtgttcctg aagggggct    6360
ataaaggggg gtggggcgc gttcgtcctc actctcttcc gcatcgctgt ctgcgagggc    6420
cagctgttgg ggtgagtcga cgcgaggctg gatggccttc cccattatga ttcttctcgc    6480
```

```
ttccggcggc atcgggatgc ccgcgttgca ggccatgctg tccaggcagg tagatgacga     6540
ccatcaggga cagcttcaag gccagcaaaa ggccaggaac cgtaaaaagg ccgcgttgct     6600
ggcgtttttc cataggctcc gccccctga cgagcatcac aaaaatcgac gctcaagtca     6660
gaggtggcga aacccgacag gactataaag ataccaggcg tttcccctg gaagctccct     6720
cgtgcgctct cctgttccga ccctgccgct taccggatac ctgtccgcct ttctcccttc     6780
gggaagcgtg gcgctttctc atagctcacg ctgtaggtat ctcagttcgg tgtaggtcgt     6840
tcgctccaag ctgggctgtg tgcacgaacc ccccgttcag cccgaccgct gcgccttatc     6900
cggtaactat cgtcttgagt ccaacccggt aagacacgac ttatcgccac tggcagcagc     6960
cactggtaac aggattagca gagcgaggta tgtaggcggt gctacagagt tcttgaagtg     7020
gtggcctaac tacggctaca ctagaaggac agtatttggt atctgcgctc tgctgaagcc     7080
agttaccttc ggaaaaagag ttggtagctc ttgatccggc aaacaaacca ccgctggtag     7140
cggtggtttt tttgtttgca agcagcagat tacgcgcaga aaaaaggat ctcaagaaga     7200
tcctttgatc ttttctacgg ggtctgacgc tcagtggaac gaaaactcac gttaagggat     7260
tttggtcatg agattatcaa aaaggatctt cacctagatc cttttaaatt aaaaatgaag     7320
ttttaaatca atctaaagta tatatgagta aacttggtct gacagttacc aatgcttaat     7380
cagtgaggca cctatctcag cgatctgtct atttcgttca tccatagttg cctgactccc     7440
cgtcgtgtag ataactacga tacgggaggg cttaccatct ggccccagtg ctgcaatgat     7500
accgcgagac ccacgctcac cggctccaga tttatcagca ataaaccagc cagccggaag     7560
ggccgagcgc agaagtggtc ctgcaacttt atccgcctcc atccagtcta ttaattgttg     7620
ccgggaagct agagtaagta gttcgccagt taatagtttg cgcaacgttg ttgccattgc     7680
tgcaggcatc gtggtgtcac gctcgtcgtt tggtatggct tcattcagct ccggttccca     7740
acgatcaagg cgagttacat gatcccccat gttgtgcaaa aaagcggtta gctccttcgg     7800
tcctccgatc gttgtcagaa gtaagttggc cgcagtgtta tcactcatgg ttatggcagc     7860
actgcataat tctcttactg tcatgccatc cgtaagatgc ttttctgtga ctggtgagta     7920
ctcaaccaag tcattctgag aatagtgtat gcggcgaccg agttgctctt gcccggcgtc     7980
aacacgggat aataccgcgc cacatagcag aactttaaaa gtgctcatca ttggaaaacg     8040
ttcttcgggg cgaaaactct caaggatctt accgctgttg agatccagtt cgatgtaacc     8100
cactcgtgca cccaactgat cttcagcatc ttttactttc accagcgttt ctgggtgagc     8160
aaaaacagga aggcaaaatg ccgcaaaaaa gggaataagg gcgacacgga aatgttgaat     8220
actcatactc ttcctttttc aatattattg aagcatttat cagggttatt gtctcatgag     8280
cggatacata tttgaatgta tttagaaaaa taaacaaata ggggttccgc gcacatttcc     8340
ccgaaaagtg ccacctgacg tctaagaaac cattattatc atgacattaa cctataaaaa     8400
taggcgtatc acgaggccct ttcgtcttca agaattgtt                            8439
```

<210> SEQ ID NO 29
<211> LENGTH: 8199
<212> TYPE: DNA
<213> ORGANISM: Artificial Sequence
<220> FEATURE:
<223> OTHER INFORMATION: Synthetic Construct pAdApt Ebola GP(Z)(dTM)

<400> SEQUENCE: 29

```
ttaattaacc gcaattctca tgtttgacag cttatcatca tcaataatat accttatttt      60
ggattgaagc caatatgata atgaggggt ggagtttgtg acgtggcgcg gggcgtggga     120
```

-continued

| | |
|---|---|
| acggggcggg tgacgtagta gtgtggcgga agtgtgatgt tgcaagtgtg gcggaacaca | 180 |
| tgtaagcgac ggatgtggca aaagtgacgt ttttggtgtg cgccggtgta cacaggaagt | 240 |
| gacaattttc gcgcggtttt aggcggatgt tgtagtaaat ttgggcgtaa ccgagtaaga | 300 |
| tttggccatt ttcgcgggaa aactgaataa gaggaagtga aatctgaata attttgtgtt | 360 |
| actcatagcg cgtaatattt gtctagggcc gcggggactt tgaccgttta cgtggagact | 420 |
| cgcccaggtg ttttttctcag gtgttttccg cgttccgggt caaagttggc gttttattat | 480 |
| tatagtcagt acgtaccagt gcactggcct agagcggccc cattgcatac gttgtatcca | 540 |
| tatcataata tgtacattta tattggctca tgtccaacat taccgccatg ttgacattga | 600 |
| ttattgacta gttattaata gtaatcaatt acgggtcat tagttcatag cccatatatg | 660 |
| gagttccgcg ttacataact tacggtaaat ggcccgcctg gctgaccgcc caacgacccc | 720 |
| cgcccattga cgtcaataat gacgtatgtt cccatagtaa cgccaatagg gactttccat | 780 |
| tgacgtcaat gggtggagta tttacggtaa actgcccact tggcagtaca tcaagtgtat | 840 |
| catatgccaa gtacgccccc tattgacgtc aatgacggta aatggcccgc ctggcattat | 900 |
| gcccagtaca tgaccttatg gactttcct acttggcagt acatctacgt attagtcatc | 960 |
| gctattacca tggtgatgcg gttttggcag tacatcaatg ggcgtggata gcggtttgac | 1020 |
| tcacgggat ttccaagtct ccaccccatt gacgtcaatg ggagtttgtt ttggcaccaa | 1080 |
| aatcaacggg actttccaaa atgtcgtaac aactccgccc cattgacgca aatgggcggt | 1140 |
| aggcgtgtac ggtgggaggt ctatataagc agagctcgtt tagtgaaccg tcagatcgcc | 1200 |
| tggagacgcc atccacgctg ttttgacctc catagaagac accgggaccg atccagcctc | 1260 |
| cgtcaccgtc gtcgacacgt gtgatcagat atcgcggccg ctctagacca ggccctggat | 1320 |
| cgatccaaca acacaatggg cgttacagga atattgcagt tacctcgtga tcgattcaag | 1380 |
| aggacatcat tctttctttg ggtaattatc cttttccaaa gaacattttc catcccactt | 1440 |
| ggagtcatcc acaatagcac attacaggtt agtgatgtcg acaaactagt ttgtcgtgac | 1500 |
| aaactgtcat ccacaaatca attgagatca gttggactga atctcgaagg gaatggagtg | 1560 |
| gcaactgacg tgccatctgc aactaaaaga tggggcttca ggtccggtgt cccaccaaag | 1620 |
| gtggtcaatt atgaagctgg tgaatgggct gaaaactgct acaatcttga atcaaaaaaa | 1680 |
| cctgacggga gtgagtgtct accagcagcg ccagacggga ttcggggctt ccccggtgc | 1740 |
| cggtatgtgc acaaagtatc aggaacggga ccgtgtgccg gagactttgc cttccataaa | 1800 |
| gagggtgctt tcttcctgta tgatcgactt gcttccacag ttatctaccg aggaacgact | 1860 |
| ttcgctgaag gtgtcgttgc atttctgata ctgccccaag ctaagaagga cttcttcagc | 1920 |
| tcacacccct tgagagagcc ggtcaatgca acggaggacc cgtctagtgg ctactattct | 1980 |
| accacaatta gatatcaggc taccggtttt ggaaccaatg agacagagta cttgttcgag | 2040 |
| gttgacaatt tgacctacgt ccaacttgaa tcaagattca caccacagtt tctgctccag | 2100 |
| ctgaatgaga caatatatac aagtgggaaa aggagcaata ccacgggaaa actaatttgg | 2160 |
| aaggtcaacc ccgaaattga tacaacaatc ggggagtggg ccttctggga aactaaaaaa | 2220 |
| aacctcacta gaaaaattcg cagtgaagag ttgtctttca cagttgtatc aaacggagcc | 2280 |
| aaaaacatca gtggtcagag tccggcgcga acttcttccg acccagggac caacacaaca | 2340 |
| actgaagacc acaaaatcat ggcttcagaa aattcctctg caatggttca agtgcacagt | 2400 |
| caaggaaggg aagctgcagt gtcgcatcta acaacccttg ccacaatctc cacgagtccc | 2460 |
| caatccctca caaccaaacc aggtccggac aacagcaccc ataatacacc cgtgtataaa | 2520 |

```
cttgacatct ctgaggcaac tcaagttgaa caacatcacc gcagaacaga caacgcagc   2580 acagcctccg acactccctc tgccacgacc gcagccggac ccccaaaagc agagaacacc  2640
aacacgagca agagcactga cttcctggac cccgccacca aacaagtcc ccaaaaccac   2700 agcgagaccg ctggcaacaa caacactcat caccaagata ccggagaaga gagtgccagc  2760
agcgggaagc taggcttaat taccaatact attgctggag tcgcaggact gatcacaggc  2820
gggagaagaa ctcgaagaga agcaattgtc aatgctcaac ccaaatgcaa ccctaattta  2880
cattactgga ctactcagga tgaaggtgct gcaatcggac tggcctggat accatatttc  2940
gggccagcag ccgagggaat ttacatagag gggctaatgc acaatcaaga tggtttaatc  3000
tgtgggttga gacagctggc caacgagacg actcaagctc ttcaactgtt cctgagagcc  3060
acaactgagc tacgcacctt tcaatcctc aaccgtaagg caattgattt cttgctgcag   3120
cgatggggcg gcacatgcca cattctggga ccggactgct gtatcgaacc acatgattgg  3180
accaagaaca taacagacaa aattgatcag attattcatg attttgttga taaaacccctt 3240 ccggaccagg gggacaatga caattggtgg acaggatgga gacaatggat ggccgcatcg  3300
tgactgactg acgatctgcc tcgcgagatc tgctgtgcct tctagttgcc agccatctgt  3360
tgtttgcccc tcccccgtgc cttccttgac cctggaaggt gccactccca ctgtcctttc  3420
ctaataaaat gaggaaattg catcgcattg tctgagtagg tgtcattcta ttctgggggg  3480
tggggtgggg caggacagca aggggagga ttgggaagac aatagcaggc atgctgggga   3540
tgcggtgggc tctatgggta cccagggccg cataacttcg tataatgtat gctatacgaa  3600
gttataagat ctgtactgaa atgtgtgggc gtggcttaag ggtgggaaag aatatataag  3660
gtgggggtct tatgtagttt tgtatctgtt ttgcagcagc cgccgccgcc atgagcacca  3720
actcgtttga tggaagcatt gtgagctcat atttgacaac gcgcatgccc ccatgggccg  3780
gggtgcgtca gaatgtgatg ggctccagca ttgatggtcg ccccgtcctg cccgcaaact  3840
ctactacctt gacctacgag accgtgtctg gaacgccgtt ggagactgca gcctccgccg  3900
ccgcttcagc cgctgcagcc accgcccgcg ggattgtgac tgactttgct ttcctgagcc  3960
cgcttgcaag cagtgcagct tcccgttcat ccgcccgcga tgacaagttg acggctcttt  4020
tggcacaatt ggattctttg acccgggaac ttaatgtcgt ttctcagcag ctgttggatc  4080
tgcgccagca ggtttctgcc ctgaaggctt cctcccctcc caatgcggtt taaaacataa  4140
ataaaaaacc agactctgtt tggatttgga tcaagcaagt gtcttgctgt ctttatttag  4200
gggttttgcg cgcgcggtag gcccgggacc agcggtctcg gtcgttgagg gtcctgtgta  4260 tttttttccag gacgtggtaa aggtgactct ggatgttcag atacatgggc ataagcccgt  4320
ctctggggtg gaggtagcac cactgcagag cttcatgctg cggggtggtg ttgtagatga  4380
tccagtcgta gcaggagcgc tgggcgtggt gcctaaaaat gtctttcagt agcaagctga  4440
ttgccagggg caggcccttg gtgtaagtgt ttacaaagcg gttaagctgg atgggtgca   4500 tacgtgggga tatgagatgc atcttggact gtattttag gttggctatg ttcccagcca   4560
tatccctccg gggattcatg ttgtgcagaa ccaccagcac agtgtatccg gtgcacttgg  4620
gaaatttgtc atgtagctta aaggaaatg cgtggaagaa cttggagacg cccttgtgac   4680
ctccaagatt ttccatgcat tcgtccctaa tgatggcaat gggcccacgg gcggcggcct  4740
gggcgaagat atttctggga tcactaacgt catagttgtg ttccaggatg agatcgtcat  4800
aggccatttt tacaaagcgc gggcggaggg tgccagactg cggtataatg ttccatccg   4860 gcccaggggc gtagttaccc tcacagattt gcatttccca cgctttgagt tcagatgggg  4920
```

```
ggatcatgtc tacctgcggg gcgatgaaga aaacggtttc cggggtaggg gagatcagct    4980
gggaagaaag caggttcctg agcagctgcg acttaccgca gccggtgggc ccgtaaatca    5040
cacctattac cggctgcaac tggtagttaa gagagctgca gctgccgtca tccctgagca    5100 gggggggccac ttcgttaagc atgtccctga ctcgcatgtt ttccctgacc aaatccgcca    5160
gaaggcgctc gccgcccagc gatagcagtt cttgcaagga agcaaagttt ttcaacggtt    5220
tgagaccgtc cgccgtaggc atgcttttga gcgtttgacc aagcagttcc aggcggtccc    5280
acagctcggt cacctgctct acggcatctc gatccagcat atctcctcgt ttcgcgggtt    5340
ggggcggctt tcgctgtacg gcagtagtcg gtgctcgtcc agacgggcca gggtcatgtc    5400
tttccacggg cgcagggtcc tcgtcagcgt agtctgggtc acggtgaagg ggtgcgctcc    5460
gggctgcgcg ctggccaggg tgcgcttgag gctggtcctg ctggtgctga agcgctgccg    5520
gtcttcgccc tgcgcgtcgg ccaggtagca tttgaccatg gtgtcatagt ccagcccctc    5580
cgcggcgtgg cccttggcgc gcagcttgcc cttggaggag gcgccgcacg aggggcagtg    5640 cagactttg agggcgtaga gcttgggcgc gagaaatacc gattccgggg agtaggcatc    5700
cgcgccgcag gccccgcaga cggtctcgca ttccacgagc caggtgagct ctggccgttc    5760
ggggtcaaaa accaggtttc ccccatgctt tttgatgcgt ttcttacctc tggtttccat    5820
gagccggtgt ccacgctcgg tgacgaaaag gctgtccgtg tccccgtata cagacttgag    5880
aggcctgtcc tcgagcggtg ttccgcggtc ctcctcgtat agaaactcgg accactctga    5940
gacaaaggct cgcgtccagg ccagcacgaa ggaggctaag tgggaggggt agcggtcgtt    6000
gtccactagg gggtccactc gctccagggt gtgaagacac atgtcgccct cttcggcatc    6060
aaggaaggtg attggtttgt aggtgtaggc cacgtgaccg ggtgttcctg aagggggggct    6120 ataaagggg gtggggcgc gttcgtcctc actctcttcc gcatcgctgt ctgcgagggc    6180
cagctgttgg ggtgagtcga cgcgaggctg gatggccttc cccattatga ttcttctcgc    6240
ttccggcggc atcgggatgc ccgcgttgca ggccatgctg tccaggcagg tagatgacga    6300
ccatcaggga cagcttcaag gccagcaaaa ggccaggaac cgtaaaaagg ccgcgttgct    6360 ggcgttttc cataggctcc gccccctga cgagcatcac aaaaatcgac gctcaagtca    6420
gaggtggcga acccgacag gactataaag ataccaggcg tttccccctg gaagctccct    6480
cgtgcgctct cctgttccga ccctgccgct taccggatac ctgtccgcct ttctcccttc    6540
gggaagcgtg gcgctttctc atagctcacg ctgtaggtat ctcagttcgg tgtaggtcgt    6600
tcgctccaag ctgggctgtg tgcacgaacc ccccgttcag cccgaccgct gcgccttatc    6660
cggtaactat cgtcttgagt ccaacccggt aagacacgac ttatcgccac tggcagcagc    6720
cactggtaac aggattagca gagcgaggta tgtaggcggt gctacagagt tcttgaagtg    6780
gtggcctaac tacggctaca ctagaaggac agtatttggt atctgcgctc tgctgaagcc    6840
agttaccttc ggaaaaagag ttggtagctc ttgatccggc aaacaaacca ccgctggtag    6900
cggtggtttt tttgtttgca agcagcagat tacgcgcaga aaaaaaggat ctcaagaaga    6960
tcctttgatc ttttctacgg ggtctgacgc tcagtggaac gaaaactcac gttaagggat    7020
tttggtcatg agattatcaa aaaggatctt cacctagatc cttttaaatt aaaaatgaag    7080
ttttaaatca atctaaagta tatatgagta aacttggtct gacagttacc aatgcttaat    7140
cagtgaggca cctatctcag cgatctgtct atttcgttca tccatagttg cctgactccc    7200
cgtcgtgtag ataactacga tacgggaggg cttaccatct ggccccagtg ctgcaatgat    7260
accgcgagac ccacgctcac cggctccaga tttatcagca ataaaccagc cagccggaag    7320
```

```
ggccgagcgc agaagtggtc ctgcaacttt atccgcctcc atccagtcta ttaattgttg    7380
ccgggaagct agagtaagta gttcgccagt taatagtttg cgcaacgttg ttgccattgc    7440
tgcaggcatc gtggtgtcac gctcgtcgtt tggtatggct tcattcagct ccggttccca    7500
acgatcaagg cgagttacat gatcccccat gttgtgcaaa aaagcggtta gctccttcgg    7560
tcctccgatc gttgtcagaa gtaagttggc cgcagtgtta tcactcatgg ttatggcagc    7620
actgcataat tctcttactg tcatgccatc cgtaagatgc ttttctgtga ctggtgagta    7680
ctcaaccaag tcattctgag aatagtgtat gcggcgaccg agttgctctt gcccggcgtc    7740
aacacgggat aataccgcgc cacatagcag aactttaaaa gtgctcatca ttggaaaacg    7800
ttcttcgggg cgaaaactct caaggatctt accgctgttg agatccagtt cgatgtaacc    7860
cactcgtgca cccaactgat cttcagcatc ttttactttc accagcgttt ctgggtgagc    7920
aaaaacagga aggcaaaatg ccgcaaaaaa gggaataagg gcgacacgga aatgttgaat    7980
actcatactc ttcctttttc aatattattg aagcatttat cagggttatt gtctcatgag    8040
cggatacata tttgaatgta tttagaaaaa taaacaaata ggggttccgc gcacatttcc    8100
ccgaaaagtg ccacctgacg tctaagaaac cattattatc atgacattaa cctataaaaa    8160
taggcgtatc acgaggccct ttcgtcttca agaattgtt                           8199

<210> SEQ ID NO 30
<211> LENGTH: 7778
<212> TYPE: DNA
<213> ORGANISM: Artificial Sequence
<220> FEATURE:
<223> OTHER INFORMATION: Synthetic Construct pVR1012 Marburg

<400> SEQUENCE: 30
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc    1080 tcttatgcat gctatactgt ttttggcttg gggcctatac accccgcttc cttatgcta    1140 taggtgatgg tatagcttag cctataggtg tgggttattg accattattg accactcccc    1200
```

```
tattggtgac gatactttcc attactaatc cataacatgg ctctttgcca caactatctc   1260
tattggctat atgccaatac tctgtccttc agagactgac acggactctg tattttaca   1320 ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga gtcgaatgaa   1920
gaacattaat tgctgggtaa aagtgattaa tttctttaaa tttgaccaga ataatatttt   1980
gtcagtgaat atattctcat atcacttgat taaaaacaga aaattaccct aacatgaaga   2040
ccacatgttt ccttatcagt cttatcttaa ttcaagggac aaaaaatctc cccattttag   2100
agatagctag taataatcaa ccccaaaatg tggattcggt atgctccgga actctccaga   2160
agacagaaga cgtccatctg atgggattca cactgagtgg gcaaaaagtt gctgattccc   2220
ctttggaggc atccaagcga tgggctttca ggacaggtgt acctcccaag aatgttgagt   2280
acacagaggg ggaggaagcc aaaacatgct acaatataag tgtaacggat ccctctggaa   2340
aatccttgct gttagatcct cctaccaaca tccgtgacta tcctaaatgc aaaactatcc   2400
atcatattca aggtcaaaac cctcatgcac aggggatcgc ccttcattta tggggagcat   2460
tttttctgta tgatcgcatt gcctccacaa caatgtaccg aggcaaagtc ttcactgaag   2520
ggaacatagc agctatgatt gtcaataaga cagtgcacaa aatgattttc tcgcggcaag   2580
gacaagggta ccgtcatatg aatctgactt ctactaataa atattggaca agtagtaacg   2640
gaacgcaaac gaatgacact ggatgtttcg gcgctcttca agaatacaat tctacaaaga   2700
accaaacatg tgctccgtcc aaaataccatc caccactgcc cacagcccgt ccggagatca   2760
aactcacaag caccccaact gatgccacca aactcaatac cacggaccca agcagtgatg   2820
atgaggacct cgcaacatcc ggctcagggt ccggagaacg agaacccac acaacttctg   2880 atgcggtcac caagcaaggg ctttcatcaa caatgccacc cactccctca ccacaaccaa   2940
gcacgccaca gcaaggagga acaacacaca accattccca agatgctgtg actgaactag   3000
acaaaaataa cacaactgca caaccgtcca tgccccctca taacactacc acaatctcta   3060
ctaacaacac ctccaaacac aacttcagca ctctctctgc accattacaa acaccacca   3120 atgacaacac acagagcaca atcactgaaa atgagcaaac cagtgccccc tcgataacaa   3180
ccctgcctcc aacgggaaat cccaccacag caaagagcac cagcagcaaa aaggccccg   3240 ccacaacggc accaaacacg acaaatgagc atttcaccag tcctccccc accccagct   3300 cgactgcaca acatcttgta tatttcagaa gaaagcgaag tatcctctgg agggaaggcg   3360
acatgttccc ttttctggat gggttaataa atgctccaat tgattttgac ccagttccaa   3420
atacaaaaac aatctttgat gaatcctcta gttctggtgc ctcggctgag gaagatcaac   3480
atgcctcccc caatattagt ttaacttat cttattttcc taatataaat gagaacactg   3540
cctactctgg agaaaatgag aatgattgtg atgcagagtt aagaatttgg agcgttcagg   3600
```

```
aggatgacct ggccgcaggg ctcagttgga taccgttttt tggccctgga attgaaggac    3660
tttacactgc tgttttaatt aaaaatcaaa acaatttggt ctgcaggttg aggcgtctag    3720
ccaatcaaac tgccaaatcc ttggaactct tattgagagt cacaactgag gaaagaacat    3780
tctccttaat caatagacat gctattgact ttctactcac aagatgggga ggaacatgca    3840
aagtgcttgg acctgattgt tgcatcggga tagaagactt gtccaaaaat atttcagagc    3900
aaattgacca aattaaaaag gacgaacaaa agaggggac tggttggggt ctgggtggta    3960
aatggtggac atccgactgg ggtgttctta ctaacttggg cattttgcta ctattatcca    4020
tagctgtctt gattgctcta tcctgtattt gtcgtatctt tactaaatat atcggataac    4080
gttaaatgtg taatgattag gactttagga caattgctac tgagcccttt tctaatctac    4140
tgaaatcaac ttgggagatt tttaagaagc tgataactta atgtgaatca atagtttatg    4200
tattatcgat tattatggtt tgatattcaa ttgttattat tgtcaggagt gaccttttct    4260
atttgatgca ttaatgtttt aaactacctc ttaagccttt gagggcgtcc caatatgtgc    4320
gtaggggtta atttaaaggg atttcttatt gtacagtttt ctgtattact tatttgggct    4380
tgaagacata gttaagattt gccgaaatgc tctccagtca attccatccc ctctcagaaa    4440
agacgtgctg ttcaaagagt cttaatttat aaccaactat tgcaagaatt aatttacttt    4500
ttccgttata cttagttaca ttaatctttt gactgttcag cattattaac gacttgtctt    4560
aattcaatcg ttcggatgaa attcataagg aaaaatgagc ctccttcccc ctattctggg    4620
ctgagaaaat ttctcttatc cgcctaaaat cagatctgtt aggtcatggg tccttcataa    4680
tctgtttgag catgaatatt gatgaaatga ccaaatgata gtgcatttgt atagactcaa    4740
ttatccttta ttaagaaaaa tcgacctgca ggcatgcaag cttcaggatc cagatctgct    4800
gtgccttcta gttgccagcc atctgttgtt tgcccctccc ccgtgccttc cttgaccctg    4860
gaaggtgcca ctcccactgt cctttcctaa taaaatgagg aaattgcatc gcattgtctg    4920
agtaggtgtc attctattct gggggtggg gtgggcagc acagcaaggg ggaggattgg    4980
gaagacaata gcaggcatgc tggggatgcg gtgggctcta tgggtaccca ggtgctgaag    5040
aattgacccg gttcctcctg ggccagaaag aagcaggcac atccccttct ctgtgacaca    5100
ccctgtccac gcccctggtt cttagttcca gccccactca taggacactc atagctcagg    5160
agggctccgc cttcaatccc acccgctaaa gtacttggag cggtctctcc ctccctcatc    5220
agcccaccaa accaaaccta gcctccaaga gtgggaagaa attaaagcaa gataggctat    5280
taagtgcaga gggagagaaa atgcctccaa catgtgagga agtaatgaga gaaatcatag    5340
aatttcttcc gcttcctcgc tcactgactc gctgcgctcg gtcgttcggc tgcggcgagc    5400
ggtatcagct cactcaaagg cggtaatacg gttatccaca gaatcagggg ataacgcagg    5460
aaagaacatg tgagcaaaag gccagcaaaa ggccaggaac cgtaaaaagg ccgcgttgct    5520
ggcgtttttc cataggctcc gcccccctga cgagcatcac aaaaatcgac gctcaagtca    5580
gaggtggcga aacccgacag gactataaag ataccaggcg tttccccctg gaagctccct    5640
cgtgcgctct cctgttccga ccctgccgct taccggatac ctgtccgcct ttctcccttc    5700
gggaagcgtg gcgctttctc aatgctcacg ctgtaggtat ctcagttcgg tgtaggtcgt    5760
tcgctccaag ctgggctgtg tgcacgaacc ccccgttcag cccgaccgct gcgccttatc    5820
cggtaactat cgtcttgagt ccaacccggt aagacacgac ttatcgccac tggcagcagc    5880
cactggtaac aggattagca gagcgaggta tgtaggcggt gctacagagt tcttgaagtg    5940
gtggcctaac tacggctaca ctagaaggac agtatttggt atctgcgctc tgctgaagcc    6000
```

-continued

```
agttaccttc ggaaaaagag ttggtagctc ttgatccggc aaacaaacca ccgctggtag      6060
cggtggtttt tttgtttgca agcagcagat tacgcgcaga aaaaaggat ctcaagaaga       6120 tcctttgatc ttttctacgg ggtctgacgc tcagtggaac gaaaactcac gttaagggat     6180
tttggtcatg agattatcaa aaaggatctt cacctagatc cttttaaatt aaaaatgaag     6240
ttttaaatca atctaaagta tatatgagta aacttggtct gacagttacc aatgcttaat     6300
cagtgaggca cctatctcag cgatctgtct atttcgttca tccatagttg cctgactccg     6360
gggggggggg gcgctgaggt ctgcctcgtg aagaaggtgt tgctgactca taccaggcct     6420
gaatcgcccc atcatccagc cagaaagtga gggagccacg gttgatgaga gctttgttgt     6480
aggtggacca gttggtgatt ttgaactttt gctttgccac ggaacggtct gcgttgtcgg     6540
gaagatgcgt gatctgatcc ttcaactcag caaaagttcg atttattcaa caaagccgcc     6600
gtcccgtcaa gtcagcgtaa tgctctgcca gtgttacaac caattaacca attctgatta     6660
gaaaaactca tcgagcatca aatgaaactg caatttattc atatcaggat tatcaatacc     6720
atatttttga aaaagccgtt tctgtaatga aggagaaaac tcaccgaggc agttccatag     6780
gatggcaaga tcctggtatc ggtctgcgat tccgactcgt ccaacatcaa tacaacctat     6840
taatttcccc tcgtcaaaaa taaggttatc aagtgagaaa tcaccatgag tgacgactga     6900
atccggtgag aatggcaaaa gcttatgcat ttctttccag acttgttcaa caggccagcc     6960
attacgctcg tcatcaaaat cactcgcatc aaccaaaccg ttattcattc gtgattgcgc     7020
ctgagcgaga cgaaatacgc gatcgctgtt aaaaggacaa ttacaaacag gaatcgaatg     7080
caaccggcgc aggaacactg ccagcgcatc aacaatattt tcacctgaat caggatattc     7140
ttctaatacc tggaatgctg ttttcccggg gatcgcagtg gtgagtaacc atgcatcatc     7200
aggagtacgg ataaaatgct tgatggtcgg aagaggcata aattccgtca gccagtttag     7260
tctgaccatc tcatctgtaa catcattggc aacgctacct ttgccatgtt tcagaaacaa     7320
ctctggcgca tcgggcttcc catacaatcg atagattgtc gcacctgatt gcccgacatt     7380
atcgcgagcc catttatacc catataaatc agcatccatg ttggaattta atcgcggcct     7440
cgagcaagac gtttcccgtt gaatatggct cataacaccc cttgtattac tgtttatgta     7500
agcagacagt tttattgttc atgatgatat ttttttatct tgtgcaatgt aacatcagag     7560
attttgagac acaacgtggc tttccccccc ccccccattat tgaagcattt atcagggtta     7620
ttgtctcatg agcggataca tatttgaatg tatttagaaa aataaacaaa tagggggttcc    7680 gcgcacattt ccccgaaaag tgccacctga cgtctaagaa accattatta tcatgacatt    7740
aacctataaa aataggcgta tcacgaggcc ctttcgtc                              7778
```

<210> SEQ ID NO 31
<211> LENGTH: 7005
<212> TYPE: DNA
<213> ORGANISM: Artificial Sequence
<220> FEATURE:
<223> OTHER INFORMATION: Synthetic Construct pVR1012x/s Marburg GP(dTM)

<400> SEQUENCE: 31

```
tc

```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccccg cccattgacg tcaataatga cgtatgttcc   480
catagtaacg ccaatagggga ctttccattg acgtcaatgg gtggagtatt tacggtaaac   540
tgcccacttg gcagtacatc aagtgtatca tatgccaagt acgccccccta ttgacgtcaa   600 tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg ggcctatac accccgctt ccttatgcta     1140 taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca caacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg gctcgcacg gctgacgcag atggaagact taaggcagcg    1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga gtcgaatgaa   1920
gaacattaat tgctgggtaa aagtgattaa tttctttaaa tttgaccaga ataatatttt    1980
gtcagtgaat atattctcat atcacttgat taaaaacaga aaattaccct aacatgaaga   2040
ccacatgttt ccttatcagt cttatcttaa ttcaagggac aaaaaatctc cccattttag   2100
agatagctag taataatcaa ccccaaaatg tggattcggt atgctccgga actctccaga   2160
agacagaaga cgtccatctg atgggattca cactgagtgg gcaaaaagtt gctgattccc   2220 cttggaggc atccaagcga tgggctttca ggacaggtgt acctcccaag aatgttgagt    2280
acacagaggg ggaggaagcc aaaacatgct acaatataag tgtaacggat ccctctggaa   2340
aatccttgct gttagatcct cctaccaaca tccgtgacta tcctaaatgc aaaactatcc   2400
atcatattca aggtcaaaac cctcatgcac aggggatcgc ccttcattta tggggagcat   2460 ttttttctgta tgatcgcatt gcctccacaa caatgtaccg aggcaaagtc ttcactgaag   2520
ggaacatagc agctatgatt gtcaataaga cagtgcacaa aatgattttc tcgcggcaag   2580
gacaagggta ccgtcatatg aatctgactt ctactaataa atattggaca agtagtaacg   2640
gaacgcaaac gaatgacact ggatgtttcg gcgctcttca agaatacaat tctacaaaga   2700
```

-continued

```
accaaacatg tgctccgtcc aaaatacctc caccactgcc cacagcccgt ccggagatca    2760
aactcacaag caccccaact gatgccacca aactcaatac cacggaccca agcagtgatg    2820
atgaggacct cgcaacatcc ggctcagggt ccggagaacg agaacccac acaacttctg     2880 atgcggtcac caagcaaggg ctttcatcaa caatgccacc cactccctca ccacaaccaa    2940
gcacgccaca gcaaggagga acaacacaca accattccca agatgctgtg actgaactag    3000
acaaaaataa cacaactgca caaccgtcca tgcccctca taacactacc acaatctcta     3060
ctaacaacac ctccaaacac aacttcagca ctctctctgc accattacaa acaccacca     3120 atgacaaacac acagagcaca atcactgaaa atgagcaaac cagtgccccc tcgataacaa   3180
ccctgcctcc aacgggaaat cccaccacag caaagagcac cagcagcaaa aaaggccccg    3240
ccacaacggc accaaacacg acaaatgagc atttcaccag tcctccccc accccagct      3300 cgactgcaca acatcttgta tatttcagaa gaaagcgaag tatcctctgg agggaaggcg    3360
acatgttccc ttttctggat gggttaataa atgctccaat tgattttgac ccagttccaa    3420
atacaaaaac aatctttgat gaatcctcta gttctggtgc ctcggctgag aagatcaac    3480 atgcctcccc caatattagt ttaactttat cttatttcc taatataaat gagaacactg     3540
cctactctgg agaaaatgag aatgattgtg atgcagagtt aagaatttgg agcgttcagg   3600
aggatgacct ggccgcaggg ctcagttgga taccgttttt tggccctgga attgaaggac    3660
tttacactgc tgttttaatt aaaaatcaaa acaatttggt ctgcaggttg aggcgtctag    3720
ccaatcaaac tgccaaatcc ttggaactct tattgagagt cacaactgag gaaagaacat    3780
tctccttaat caatagacat gctattgact ttctactcac aagatggga ggaacatgca     3840 aagtgcttgg acctgattgt tgcatcggga tagaagactt gtccaaaaat atttcagagc   3900
aaattgacca aattaaaaag gacgaacaaa agagggac tggttggggt ctgggtggta      3960
aatggtggac atccgactgg ggttaagatc tgctgtgcct tctagttgcc agccatctgt    4020
tgtttgcccc tcccccgtgc cttccttgac cctggaaggt gccactccca ctgtcctttc   4080
ctaataaaat gaggaaattg catcgcattg tctgagtagg tgtcattcta ttctgggggg    4140
tggggtgggg caggacagca aggggagga ttgggaagac aatagcaggc atgctgggga    4200
tgcggtgggc tctatgggta cccaggtgct gaagaattga cccggttcct cctgggccag   4260
aaagaagcag gcacatcccc ttctctgtga cacaccctgt ccacgcccct ggttcttagt    4320
tccagcccca ctcataggac actcatagct caggagggct ccgccttcaa tcccacccgc    4380
taaagtactt ggagcggtct ctccctccct catcagccca ccaaaccaaa cctagcctcc    4440
aagagtggga agaaattaaa gcaagatagg ctattaagtg cagagggaga gaaaatgcct    4500
ccaacatgtg aggaagtaat gagagaaatc atagaattt aaggccatga tttaaggcca    4560
tcatggccct aatcttccgc ttcctcgctc actgactcgc tgcgctcggt cgttcggctg    4620
cggcgagcgg tatcagctca ctcaaaggcg gtaatacgg tatccacaga atcagggat      4680 aacgcaggaa agaacatgtg agcaaaaggc cagcaaaagg ccaggaaccg taaaaaggcc    4740
gcgttgctgg cgttttttcca taggctccgc ccccctgacg agcatcacaa aaatcgacgc    4800
tcaagtcaga ggtggcgaaa cccgacagga ctataaagat accaggcgtt ccccctgga    4860 agctccctcg tgcgctctcc tgttccgacc ctgccgctta ccggatacct gtccgccttt    4920
ctcccttcgg gaagcgtggc gctttctcat agctcacgct gtaggtatct cagttcggtg    4980
taggtcgttc gctccaagct gggctgtgtg cacgaacccc ccgttcagcc cgaccgctgc    5040
gccttatccg gtaactatcg tcttgagtcc aacccggtaa gacacgactt atcgccactg    5100
```

-continued

```
gcagcagcca ctggtaacag gattagcaga gcgaggtatg taggcggtgc tacagagttc   5160
ttgaagtggt ggcctaacta cggctacact agaagaacag tatttggtat ctgcgctctg   5220
ctgaagccag ttaccttcgg aaaaagagtt ggtagctctt gatccggcaa acaaaccacc   5280
gctggtagcg gtggtttttt tgtttgcaag cagcagatta cgcgcagaaa aaaaggatct   5340
caagaagatc ctttgatctt ttctacgggg tctgacgctc agtggaacga aaactcacgt   5400
taagggattt tggtcatgag attatcaaaa aggatcttca cctagatcct tttaaattaa   5460
aaatgaagtt ttaaatcaat ctaaagtata tatgagtaaa cttggtctga cagttaccaa   5520
tgcttaatca gtgaggcacc tatctcagcg atctgtctat ttcgttcatc catagttgcc   5580
tgactcgggg gggggggcg ctgaggtctg cctcgtgaag aaggtgttgc tgactcatac   5640
caggcctgaa tcgccccatc atccagccag aaagtgaggg agccacggtt gatgagagct   5700
ttgttgtagg tggaccagtt ggtgattttg aacttttgct ttgccacgga acggtctgcg   5760
ttgtcgggaa gatgcgtgat ctgatccttc aactcagcaa aagttcgatt tattcaacaa   5820
agccgccgtc ccgtcaagtc agcgtaatgc tctgccagtg ttacaaccaa ttaaccaatt   5880
ctgattagaa aaactcatcg agcatcaaat gaaactgcaa tttattcata tcaggattat   5940
caataccata tttttgaaaa agccgtttct gtaatgaagg agaaaactca ccgaggcagt   6000
tccataggat ggcaagatcc tggtatcggt ctgcgattcc gactcgtcca acatcaatac   6060
aacctattaa tttcccctcg tcaaaaataa ggttatcaag tgagaaatca ccatgagtga   6120
cgactgaatc cggtgagaat ggcaaaagct tatgcatttc tttccagact tgttcaacag   6180
gccagccatt acgctcgtca tcaaaatcac tcgcatcaac caaaccgtta ttcattcgtg   6240
attgcgcctg agcgagacga aatacgcgat cgctgttaaa aggacaatta caaacaggaa   6300
tcgaatgcaa ccggcgcagg aacactgcca gcgcatcaac aatattttca cctgaatcag   6360
gatattcttc taatacctgg aatgctgttt tcccggggat cgcagtggtg agtaaccatg   6420
catcatcagg agtacggata aaatgcttga tggtcggaag aggcataaat tccgtcagcc   6480
agtttagtct gaccatctca tctgtaacat cattggcaac gctacctttg ccatgtttca   6540
gaaacaactc tggcgcatcg ggcttcccat acaatcgata gattgtcgca cctgattgcc   6600
cgacattatc gcgagcccat ttatacccat ataaatcagc atccatgttg gaatttaatc   6660
gcggcctcga gcaagacgtt tcccgttgaa tatggctcat aacacccctt gtattactgt   6720
ttatgtaagc agacagtttt attgttcatg atgatatatt tttatcttgt gcaatgtaac   6780
atcagagatt ttgagacaca acgtggcttt cccccccccc ccattattga agcatttatc   6840
agggttattg tctcatgagc ggatacatat ttgaatgtat ttagaaaaat aaacaaatag   6900
gggttccgcg cacatttccc cgaaaagtgc cacctgacgt ctaagaaacc attattatca   6960
tgacattaac ctataaaaat aggcgtatca cgaggccctt tcgtc                   7005
```

<210> SEQ ID NO 32
<211> LENGTH: 8256
<212> TYPE: DNA
<213> ORGANISM: Artificial Sequence
<220> FEATURE:
<223> OTHER INFORMATION: Synthetic Construct pAdApt Marburg GP(dTM)

<400> SEQUENCE: 32

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
```

```
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg ttttctcag gtgttttccg cgttccgggt caaagttggc gttttattat     480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta atggcccgc ctggcattat      900 gcccagtaca tgaccttatg ggactttcct acttggcagt acatctacgt attagtcatc    960
gctattacca tggtgatgcg gttttggcag tacatcaatg ggcgtggata gcggtttgac    1020
tcacggggat ttccaagtct ccaccccatt gacgtcaatg ggagtttgtt ttggcaccaa    1080
aatcaacggg actttccaaa atgtcgtaac aactccgccc cattgacgca atgggcggt     1140 aggcgtgtac ggtgggaggt ctatataagc agagctcgtt tagtgaaccg tcagatcgcc    1200
tggagacgcc atccacgctg ttttgacctc catagaagac accgggaccg atccagcctc    1260
cgtcaccgtc gtcgacacgt gtgatcagat atcgcggccg ctctagagtc gaatgaagaa    1320
cattaattgc tgggtaaaag tgattaattt ctttaaattt gaccagaata atattttgtc    1380
agtgaatata ttctcatatc acttgattaa aaacagaaaa ttaccctaac atgaagacca    1440
catgtttcct tatcagtctt atcttaattc aagggacaaa aaatctcccc attttagaga    1500
tagctagtaa taatcaaccc caaaatgtgg attcggtatg ctccggaact ctccagaaga    1560
cagaagacgt ccatctgatg ggattcacac tgagtgggca aaaagttgct gattcccctt    1620
tggaggcatc caagcgatgg gctttcagga caggtgtacc tcccaagaat gttgagtaca    1680
cagaggggga ggaagccaaa acatgctaca atataagtgt aacggatccc tctggaaaat    1740
ccttgctgtt agatcctcct accaacatcc gtgactatcc taaatgcaaa actatccatc    1800
atattcaagg tcaaaaccct catgcacagg ggatcgccct tcatttatgg ggagcatttt    1860
ttctgtatga tcgcattgcc tccacaacaa tgtaccgagg caaagtcttc actgaaggga    1920
acatagcagc tatgattgtc aataagacag tgcacaaaat gattttctcg cggcaaggac    1980
aagggtaccg tcatatgaat ctgacttcta ctaataaata ttggacaagt agtaacggaa    2040
cgcaaacgaa tgacactgga tgtttcggcg ctcttcaaga atacaattct acaagaacc     2100 aaacatgtgc tccgtccaaa atacctccac cactgcccac agcccgtccg gagatcaaac    2160
tcacaagcac cccaactgat gccaccaaac tcaataccac ggacccaagc agtgatgatg    2220
aggacctcgc aacatccggc tcagggtccg agaacgaga accccacaca acttctgatg     2280
cggtcaccaa gcaagggctt tcatcaacaa tgccacccac tccctcacca caaccaagca    2340
cgccacagca aggaggaaac aacacaaacc attcccaaga tgctgtgact gaactagaca    2400
aaaataacac aactgcacaa ccgtccatgc ccctcataa cactaccaca atctctacta      2460
acaacacctc caaacacaac ttcagcactc tctctgcacc attacaaaac accaccaatg    2520
acaacacaca gagcacaatc actgaaaatg agcaaaccag tgcccctcg ataacaaccc     2580
```

```
tgcctccaac gggaaatccc accacagcaa agagcaccag cagcaaaaaa ggccccgcca    2640
caacggcacc aaacacgaca aatgagcatt tcaccagtcc tccccccacc cccagctcga    2700
ctgcacaaca tcttgtatat ttcagaagaa agcgaagtat cctctggagg gaaggcgaca    2760
tgttcccttt tctggatggg ttaataaatg ctccaattga ttttgaccca gttccaaata    2820
caaaaacaat ctttgatgaa tcctctagtt ctggtgcctc ggctgaggaa gatcaacatg    2880
cctcccccaa tattagttta actttatctt attttcctaa tataaatgag aacactgcct    2940
actctggaga aaatgagaat gattgtgatg cagagttaag aatttggagc gttcaggagg    3000
atgacctggc cgcagggctc agttggatac cgttttttgg ccctggaatt gaaggacttt    3060
acactgctgt tttaattaaa aatcaaaaca atttggtctg caggttgagg cgtctagcca    3120
atcaaactgc caaatccttg gaactcttat tgagagtcac aactgaggaa agaacattct    3180
ccttaatcaa tagacatgct attgactttc tactcacaag atggggagga acatgcaaag    3240
tgcttggacc tgattgttgc atcgggatag aagacttgtc caaaaatatt tcagagcaaa    3300
ttgaccaaat taaaaaggac gaacaaaaag aggggactgg ttggggtctg ggtggtaaat    3360
ggtggacatc cgactgggt taagatctgc tgtgccttct agttgccagc catctgttgt    3420
ttgcccctcc cccgtgcctt ccttgacccT ggaaggtgcc actcccactg tcctttccta    3480
ataaaatgag gaaattgcat cgcattgtct gagtaggtgt cattctattc tggggggtgg    3540
ggtggggcag cacagcaagg gggaggattg ggaagacaat agcaggcatg ctggggatgc    3600
ggtgggctct atgggtaccc agggccgcat aacttcgtat aatgtatgct atacgaagtt    3660
ataagatctg tactgaaatg tgtgggcgtg gcttaagggt gggaaagaat atataaggtg    3720
ggggtcttat gtagttttgt atctgttttg cagcagccgc cgccgccatg agcaccaact    3780
cgtttgatgg aagcattgtg agctcatatt tgacaacgcg catgccccca tgggccgggg    3840
tgcgtcagaa tgtgatgggc tccagcattg atggtcgccc cgtcctgccc gcaaactcta    3900
ctaccttgac ctacgagacc gtgtctggaa cgccgttgga gactgcagcc tccgccgccg    3960
cttcagccgc tgcagccacc gcccgcggga ttgtgactga ctttgctttc ctgagcccgc    4020
ttgcaagcag tgcagcttcc cgttcatccg cccgcgatga caagttgacg gctctttgg    4080 cacaattgga ttctttgacc cgggaactta atgtcgtttc tcagcagctg ttggatctgc    4140
gccagcaggt ttctgccctg aaggcttcct cccctcccaa tgcggtttaa aacataaata    4200
aaaaaccaga ctctgtttgg atttggatca agcaagtgtc ttgctgtctt tatttagggg    4260
ttttgcgcgc gcggtaggcc cgggaccagc ggtctcggtc gttgagggtc ctgtgtattt    4320
tttccaggac gtggtaaagg tgactctgga tgttcagata catgggcata agcccgtctc    4380
tggggtggag gtagcaccac tgcagagctt catgctgcgg ggtggtgttg tagatgatcc    4440
agtcgtagca ggagcgctgg gcgtggtgcc taaaaatgtc tttcagtagc aagctgattg    4500
ccaggggcag gcccttggtg taagtgttta caaagcggtt aagctgggat gggtgcatac    4560
gtggggatat gagatgcatc ttggactgta ttttaggtt ggctatgttc ccagccatat    4620
ccctccgggg attcatgttg tgcagaacca ccagcacagt gtatccggtg cacttgggaa    4680
atttgtcatg tagcttagaa ggaaatgcgt ggaagaactt ggagacgccc ttgtgacctc    4740
caagattttc catgcattcg tccataatga tggcaatggg cccacgggcg gcggcctggg    4800
cgaagatatt tctgggatca ctaacgtcat agttgtgttc caggatgaga tcgtcatagg    4860
ccatttttac aaagcgcggg cggagggtgc cagactgcgg tataatggtt ccatccggcc    4920
caggggcgta gttaccctca cagatttgca tttcccacgc tttgagttca gatgggggga    4980
```

-continued

```
tcatgtctac ctgcggggcg atgaagaaaa cggtttccgg ggtaggggag atcagctggg      5040
aagaaagcag gttcctgagc agctgcgact taccgcagcc ggtgggcccg taaatcacac      5100
ctattaccgg ctgcaactgg tagttaagag agctgcagct gccgtcatcc ctgagcaggg      5160
gggccacttc gttaagcatg tccctgactc gcatgttttc cctgaccaaa tccgccagaa      5220
ggcgctcgcc gcccagcgat agcagttctt gcaaggaagc aaagtttttc aacggtttga      5280
gaccgtccgc cgtaggcatg cttttgagcg tttgaccaag cagttccagg cggtcccaca      5340
gctcggtcac ctgctctacg gcatctcgat ccagcatatc tcctcgtttc gcgggttggg      5400
gcggctttcg ctgtacggca gtagtcggtg ctcgtccaga cgggccaggg tcatgtcttt      5460
ccacgggcgc aggtcctcg tcagcgtagt ctgggtcacg gtgaaggggt gcgctccggg       5520
ctgcgcgctg gccagggtgc gcttgaggct ggtcctgctg gtgctgaagc gctgccggtc      5580
ttcgccctgc gcgtcggcca ggtagcattt gaccatggtg tcatagtcca gccctccgc      5640 ggcgtggccc ttggcgcgca gcttgccctt ggaggaggcg ccgcacgagg ggcagtgcag      5700
acttttgagg gcgtagagct tgggcgcgag aaataccgat tccggggagt aggcatccgc      5760
gccgcaggcc ccgcagacgg tctcgcattc cacgagccag gtgagctctg gccgttcggg      5820
gtcaaaaacc aggtttcccc catgctttt gatgcgtttc ttacctctgg tttccatgag      5880
ccggtgtcca cgctcggtga cgaaaaggct gtccgtgtcc ccgtatacag acttgagagg      5940
cctgtcctcg agcggtgttc cgcggtcctc ctcgtataga aactcggacc actctgagac      6000
aaaggctcgc gtccaggcca gcacgaagga ggctaagtgg gaggggtagc ggtcgttgtc      6060
cactaggggg tccactcgct ccagggtgtg aagacacatg tcgccctctt cggcatcaag      6120
gaaggtgatt ggtttgtagg tgtaggccac gtgaccgggt gttcctgaag gggggctata      6180
aaagggggtg ggggcgcgtt cgtcctcact ctcttccgca tcgctgtctg cgagggccag      6240 ctgttgggt gagtcgacgc gaggctggat ggccttcccc attatgattc ttctcgcttc       6300
cggcggcatc gggatgcccg cgttgcaggc catgctgtcc aggcaggtag atgacgacca      6360
tcagggacag cttcaaggcc agcaaaaggc caggaaccgt aaaaaggccg cgttgctggc      6420
gtttttccat aggctccgcc ccctgacgag catcacaaaa atcgacgctc aagtcagag       6480 gtggcgaaac ccgacaggac tataaagata ccaggcgttt ccccctggaa gctccctcgt      6540
gcgctctcct gttccgaccc tgccgcttac cggatacctg tccgcctttc tcccttcggg      6600
aagcgtggcg ctttctcata gctcacgctg taggtatctc agttcggtgt aggtcgttcg      6660
ctccaagctg ggctgtgtgc acgaaccccc cgttcagccc gaccgctgcg ccttatccgg      6720
taactatcgt cttgagtcca acccggtaag acacgactta tcgccactgg cagcagccac      6780
tggtaacagg attagcagag cgaggtatgt aggcggtgct acagagttct tgaagtggtg      6840
gcctaactac ggctacacta gaaggacagt atttggtatc tgcgctctgc tgaagccagt      6900
taccttcgga aaaagagttg gtagctcttg atccggcaaa caaaccaccg ctggtagcgg      6960 tggtttttt gtttgcaagc agcagattac gcgcagaaaa aaaggatctc aagaagatcc      7020
tttgatcttt tctacggggt ctgacgctca gtggaacgaa aactcacgtt aagggatttt      7080
ggtcatgaga ttatcaaaaa ggatcttcac ctagatcctt ttaaattaaa aatgaagttt      7140
taaatcaatc taaagtatat atgagtaaac ttggtctgac agttaccaat gcttaatcag      7200
tgaggcacct atctcagcga tctgtctatt tcgttcatcc atagttgcct gactccccgt      7260
cgtgtagata actacgatac gggagggctt accatctggc cccagtgctg caatgatacc      7320
gcgagaccca cgctcaccgg ctccagattt atcagcaata aaccagccag ccggaagggc      7380
```

-continued cgagcgcaga agtggtcctg caactttatc cgcctccatc cagtctatta attgttgccg 7440
ggaagctaga gtaagtagtt cgccagttaa tagtttgcgc aacgttgttg ccattgctgc 7500
aggcatcgtg gtgtcacgct cgtcgtttgg tatggcttca ttcagctccg gttcccaacg 7560
atcaaggcga gttacatgat cccccatgtt gtgcaaaaaa gcggttagct ccttcggtcc 7620
tccgatcgtt gtcagaagta agttggccgc agtgttatca ctcatggtta tggcagcact 7680
gcataattct cttactgtca tgccatccgt aagatgcttt tctgtgactg gtgagtactc 7740
aaccaagtca ttctgagaat agtgtatgcg gcgaccgagt tgctcttgcc cggcgtcaac 7800
acgggataat accgcgccac atagcagaac tttaaaagtg ctcatcattg gaaaacgttc 7860
ttcggggcga aaactctcaa ggatcttacc gctgttgaga tccagttcga tgtaacccac 7920
tcgtgcaccc aactgatctt cagcatcttt tactttcacc agcgtttctg ggtgagcaaa 7980
aacaggaagg caaaatgccg caaaaaaggg aataagggcg acacggaaat gttgaatact 8040
catactcttc ctttttcaat attattgaag catttatcag ggttattgtc tcatgagcgg 8100
atacatattt gaatgtattt agaaaaataa acaaataggg gttccgcgca catttccccg 8160
aaaagtgcca cctgacgtct aagaaaccat tattatcatg acattaacct ataaaaatag 8220
gcgtatcacg aggccctttc gtcttcaaga attgtt 8256

<210> SEQ ID NO 33
<211> LENGTH: 6447
<212> TYPE: DNA
<213> ORGANISM: Artificial Sequence
<220> FEATURE:
<223> OTHER INFORMATION: Synthetic Construct pVR1012x/s Lassa GP

<400> SEQUENCE: 33
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200

```
tattggtgac gatactttcc attactaatc cataacatgg ctctttgcca caactatctc    1260
tattggctat atgccaatac tctgtccttc agagactgac acggactctg tattttttaca   1320 ggatggggtc ccatttatta tttacaaatt cacatataca acaacgccgt cccccgtgcc    1380
cgcagttttt attaaacata gcgtgggatc tccacgcgaa tctcgggtac gtgttccgga    1440 catggctct tctccggtag cggcggagct tccacatccg agccctggtc ccatgcctcc     1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga atttaggatt    1920
gcgcttttag agattcacta ctagttagga attcctaaat catgggcag attattacat     1980 tctttcaaga agtgccacat gtaatagagg aagtcatgaa cattgtgcta attgcgcttt    2040
ctctattggc aatcttgaag ggcttgtata acatcgctac atgtgggatt attggattgg    2100 ttgcctttt attcttgtgt ggcaagtctt gttccctaac ccttaaaggg ggatatgagc     2160
tgcaaacctt agaattaaat atggagaccc taaacatgac catgccctta tcatgcacca    2220
agaacagcag tcatcattac ataagagtgg gcaatgagac tggattagaa ttgactttaa    2280
ctaacaccag cattataaat cacaaatttt gcaacttatc cgatgctcac aaaaagaatc    2340
tttatgatca tgctctcatg agcatcatct caacattcca tctatccatt ccaaacttca    2400
atcagtatga agccatgagt tgtgatttca atggagggaa aatcagtgtg caatacaacc    2460
tctctcattc ctatgctggg gatgcggccg aacactgtgg gacagttgcc aacggagtgt    2520
tgcaaacatt tatgagaatg gcctggggtg gaagatacat tgcattagac tcaggaaagg    2580
gaaactggga ctgtataatg accagctacc agtacctgat aattcaaaat acaacatggg    2640
aggaccactg ccaattctca agaccgtctc ctatcgggta ccttggcctt ttgtcacaaa    2700
ggacaagaga tatatatata gtaggaggc tcttggggac cttcacctgg acattgtcag    2760
attctgaggg caatgaaaca ccaggtggtt attgtttaac caggtggatg ctaattgaag    2820
cagaactcaa gtgttttggg aatacagctg tggcaaaatg caatgagaag catgatgagg    2880
agttttgtga catgctgaga ttgtttgatt tcaacaagca agcaatccgt aggttgaagg    2940
ctgaggccca gatgagtatt caattaataa ataaagccgt gaatgcctta atcaatgatc    3000
aattaatcat gaagaaccat ttaagagaca tcatgggcat tccctactgc aattacagca    3060
agtattggta ccttaatcat actagtagcg ggagaacatc actaccaaag tgttggctta    3120
tatccaatgg gtcatatcta aatgaaaccc agttctctga tgcacatagaa cagcaagccg    3180 acaatatgat cacagagatg cttcagaaag aatacattga agacaagggg aaaacgccct    3240
tgggactagt ggacattttc atcttttagca caagcttta tctgatcagc atttcttgc      3300 atttaattaa aatccctaca catcgacaca tcgttgggaa accctgtccc aaacccata     3360 gactaaatca catgggagta tgttcctgtg gactgtacaa acaccctggt gttccaacaa    3420
agtggaagag atagggatcc agatctgctg tgccttctag ttgccagcca tctgttgttt    3480
gcccctcccc cgtgccttcc ttgacccctgg aaggtgccac tcccactgtc ctttcctaat   3540
aaaatgagga aattgcatcg cattgtctga gtaggtgtca ttctattctg ggggtgggg     3600
```

```
tggggcagga cagcaagggg gaggattggg aagacaatag caggcatgct ggggatgcgg    3660
tgggctctat gggtacccag gtgctgaaga attgacccgg ttcctcctgg gccagaaaga    3720
agcaggcaca tccccttctc tgtgacacac cctgtccacg ccctggttc ttagttccag     3780 ccccactcat aggacactca tagctcagga gggctccgcc ttcaatccca cccgctaaag    3840
tacttggagc ggtctctccc tccctcatca gcccaccaaa ccaaacctag cctccaagag    3900
tgggaagaaa ttaaagcaag ataggctatt aagtgcagag ggagagaaaa tgcctccaac    3960
atgtgaggaa gtaatgagag aaatcataga attttaaggc catcatggcc ttaatcttcc    4020
gcttcctcgc tcactgactc gctgcgctcg gtcgttcggc tgcggcgagc ggtatcagct    4080
cactcaaagg cggtaatacg gttatccaca gaatcagggg ataacgcagg aaagaacatg    4140
tgagcaaaag gccagcaaaa ggccaggaac cgtaaaaagg ccgcgttgct ggcgtttttc    4200
cataggctcc gcccccctga cgagcatcac aaaaatcgac gctcaagtca gaggtggcga    4260
aacccgacag gactataaag ataccaggcg tttccccctg gaagctccct cgtgcgctct    4320
cctgttccga ccctgccgct taccggatac ctgtccgcct ttctcccttc gggaagcgtg    4380
gcgctttctc atagctcacg ctgtaggtat ctcagttcgg tgtaggtcgt tcgctccaag    4440
ctgggctgtg tgcacgaacc ccccgttcag cccgaccgct gcgccttatc cggtaactat    4500
cgtcttgagt ccaacccggt aagacacgac ttatcgccac tggcagcagc cactggtaac    4560
aggattagca gagcgaggta tgtaggcggt gctacagagt tcttgaagtg gtggcctaac    4620
tacggctaca ctagaagaac agtatttggt atctgcgctc tgctgaagcc agttaccttc    4680
ggaaaaagag ttggtagctc ttgatccggc aaacaaacca ccgctggtag cggtggtttt    4740
tttgtttgca agcagcagat tacgcgcaga aaaaaaggat ctcaagaaga tcctttgatc    4800
ttttctacgg ggtctgacgc tcagtggaac gaaaactcac gttaagggat tttggtcatg    4860
agattatcaa aaaggatctt cacctagatc cttttaaatt aaaaatgaag ttttaaatca    4920
atctaaagta tatatgagta aacttggtct gacagttacc aatgcttaat cagtgaggca    4980
cctatctcag cgatctgtct atttcgttca tccatagttg cctgactcgg ggggggggg    5040 cgctgaggtc tgcctcgtga agaaggtgtt gctgactcat accaggcctg aatcgcccca    5100
tcatccagcc agaaagtgag ggagccacgg ttgatgagag ctttgttgta ggtgaccag    5160 ttggtgattt tgaacttttg ctttgccacg gaacggtctg cgttgtcggg aagatgcgtg    5220
atctgatcct tcaactcagc aaaagttcga tttattcaac aaagccgccg tcccgtcaag    5280
tcagcgtaat gctctgccag tgttacaacc aattaaccaa ttctgattag aaaaactcat    5340
cgagcatcaa atgaaactgc aatttattca tatcaggatt atcaatacca tatttttgaa    5400
aaagccgttt ctgtaatgaa ggagaaaact caccgaggca gttccatagg atggcaagat    5460
cctggtatcg gtctgcgatt ccgactcgtc aacatcaat acaacctatt aatttcccct     5520
cgtcaaaaat aaggttatca agtgagaaat caccatgagt gacgactgaa tccggtgaga    5580
atggcaaaag cttatgcatt tctttccaga cttgttcaac aggccagcca ttacgctcgt    5640
catcaaaatc actcgcatca accaaaccgt tattcattcg tgattgcgcc tgagcgagac    5700
gaaatacgcg atcgctgtta aaaggacaat tacaaacagg aatcgaatgc aaccggcgca    5760
ggaacactgc cagcgcatca acaatatttt cacctgaatc aggatattct tctaatacct    5820
ggaatgctgt ttcccgggg atcgcagtgg tgagtaacca tgcatcatca ggagtacgga    5880
taaaatgctt gatggtcgga agaggcataa attccgtcag ccagtttagt ctgaccatct    5940
catctgtaac atcattggca acgctacctt tgccatgttt cagaaacaac tctggcgcat    6000
```

-continued

```
cgggcttccc atacaatcga tagattgtcg cacctgattg cccgacatta tcgcgagccc      6060
atttataccc atataaatca gcatccatgt tggaatttaa tcgcggcctc gagcaagacg      6120
tttcccgttg aatatggctc ataacacccc ttgtattact gtttatgtaa gcagacagtt      6180
ttattgttca tgatgatata tttttatctt gtgcaatgta acatcagaga ttttgagaca      6240
caacgtggct ttcccccccc ccccattatt gaagcattta tcagggttat tgtctcatga      6300
gcggatacat atttgaatgt atttagaaaa ataaacaaat aggggttccg cgcacatttc      6360
cccgaaaagt gccacctgac gtctaagaaa ccattattat catgacatta acctataaaa      6420
ataggcgtat cacgaggccc tttcgtc                                          6447
```

<210> SEQ ID NO 34
<211> LENGTH: 6258
<212> TYPE: DNA
<213> ORGANISM: Artificial Sequence
<220> FEATURE:
<223> OTHER INFORMATION: Synthetic Construct pVR1012x/s Lassa GP(dTM)

<400> SEQUENCE: 34

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcgggctgg cttaactatg cggcatcaga gcagattgta ctgagagtgc        180
accatatgcg gtgtgaaata ccgcacagat gcgtaaggag aaaataccgc atcagattgg       240
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgacccccg cccattgacg tcaataatga cgtatgttcc       480
catagtaacg ccaatagggα ctttccattg acgtcaatgg gtggagtatt tacggtaaac       540
tgcccacttg gcagtacatc aagtgtatca tatgccaagt acgcccccta ttgacgtcaa       600
tgacggtaaa tggcccgcct ggcattatgc ccagtacatg accttatggg actttcctac       660
ttggcagtac atctacgtat tagtcatcgc tattaccatg gtgatgcggt tttggcagta       720
catcaatggg cgtggatagc ggtttgactc acggggattt ccaagtctcc accccattga       780
cgtcaatggg agtttgtttt ggcaccaaaa tcaacgggac tttccaaaat gtcgtaacaa       840
ctccgcccca ttgacgcaaa tgggcggtag gcgtgtacgg tgggaggtct atataagcag       900
agctcgttta gtgaaccgtc agatcgcctg gagacgccat ccacgctgtt ttgacctcca       960
tagaagacac cggaccgat ccagcctccg cggccgggaa cggtgcattg gaacgcggat       1020
tccccgtgcc aagagtgacg taagtaccgc ctatagactc tataggcaca cccctttggc      1080
tcttatgcat gctatactgt ttttggcttg gggcctatac accccgcttc cttatgctat      1140
taggtgatgg tatagcttag cctataggtg tgggttattg accattattg accactcccc      1200
tattggtgac gtactttcc attactaatc cataacatgg ctctttgcca caactatctc       1260
tattggctat atgccaatac tctgtccttc agagactgac acggactctg tatttttaca      1320
ggatggggtc ccatttatta tttacaaatt cacatataca acaacgccgt ccccgtgccc      1380
cgcagttttt attaaacata gcgtgggatc tccacgcgaa tctcgggtac gtgttccgga      1440
catgggctct tctccggtag cggcggagct tccacatccg agccctggtc ccatgcctcc      1500
agcggctcat ggtcgctcgg cagctccttg ctcctaacag tggaggccag acttaggcac      1560
agcacaatgc ccaccaccac cagtgtgccg cacaaggccg tggcggtagg gtatgtgtct      1620
```

```
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga atttaggatt   1920
gcgcttttag agattcacta ctagttagga attcctaaat catggggcag attattacat   1980
tctttcaaga agtgccacat gtaatagagg aagtcatgaa cattgtgcta attgcgcttt   2040
ctctattggc aatcttgaag ggcttgtata acatcgctac atgtgggatt attggattgg   2100 ttgcctttt attcttgtgt ggcaagtctt gttccctaac ccttaaaggg ggatatgagc   2160
tgcaaacctt agaattaaat atggagaccc taaacatgac catgccctta tcatgcacca   2220
agaacagcag tcatcattac ataagagtgg gcaatgagac tggattagaa ttgactttaa   2280
ctaacaccag cattataaat cacaaatttt gcaacttatc cgatgctcac aaaaagaatc   2340
tttatgatca tgctctcatg agcatcatct caacattcca tctatccatt ccaaacttca   2400
atcagtatga agccatgagt tgtgatttca atggagggaa aatcagtgtg caatacaacc   2460
tctctcattc ctatgctggg gatgcggccg aacactgtgg gacagttgcc aacggagtgt   2520
tgcaaacatt tatgagaatg gcctggggtg aagatacat tgcattagac tcaggaaagg   2580
gaaactggga ctgtataatg accagctacc agtacctgat aattcaaaat acaacatggg   2640
aggaccactg ccaattctca agaccgtctc ctatcgggta ccttggcctt ttgtcacaaa   2700
ggacaagaga tatatatata agtaggaggc tcttggggac cttcacctgg acattgtcag   2760
attctgaggg caatgaaaca ccaggtggtt attgtttaac caggtggatg ctaattgaag   2820
cagaactcaa gtgttttggg aatacagctg tggcaaaatg caatgagaag catgatgagg   2880
agttttgtga catgctgaga ttgtttgatt caacaagca agcaatccgt aggttgaagg   2940
ctgaggccca gatgagtatt caattaataa ataaagccgt gaatgcctta atcaatgatc   3000
aattaatcat gaagaaccat ttaagagaca tcatgggcat tccctactgc aattacagca   3060
agtattggta ccttaatcat actagtagcg ggagaacatc actaccaaag tgttggctta   3120
tatccaatgg gtcatatcta aatgaaaccc agttctctga tgacatagaa cagcaagccg   3180
acaatatgat cacagagatg cttcagaaag aatacattga aagacaaggg aaaacgccct   3240
tgtagggatc cagatctgct gtgccttcta gttgccagcc atctgttgtt tgcccctccc   3300
ccgtgccttc cttgaccctg gaaggtgcca ctcccactgt cctttcctaa taaaatgagg   3360
aaattgcatc gcattgtctg agtaggtgtc attctattct ggggggtggg gtggggcagg   3420
acagcaaggg ggaggattgg gaagacaata gcaggcatgc tggggatgcg gtgggctcta   3480
tgggtaccca ggtgctgaag aattgacccg gttcctcctg ggccagaaag aagcaggcac   3540
atccccttct ctgtgacaca ccctgtccac gcccctggtt cttagttcca gccccactca   3600
taggacactc atagctcagg agggctccgc cttcaatccc acccgctaaa gtacttggag   3660
cggtctctcc ctccctcatc agcccaccaa accaaaccta gcctccaaga gtgggaagaa   3720
attaaagcaa gataggctat taagtgcaga gggagagaaa atgcctccaa catgtgagga   3780
agtaatgaga gaaatcatag aattttaagg ccatcatggc cttaatcttc gcttcctcg   3840 ctcactgact cgctgcgctc ggtcgttcgg ctgcggcgag cggtatcagc tcactcaaag   3900
gcggtaatac ggttatccac agaatcaggg gataacgcag gaaagaacat gtgagcaaaa   3960
ggccagcaaa aggccaggaa ccgtaaaaag gccgcgttgc tggcgttttt ccataggctc   4020
```

-continued

```
cgcccccctg acgagcatca caaaaatcga cgctcaagtc agaggtggcg aaacccgaca    4080
ggactataaa gataccaggc gtttccccct ggaagctccc tcgtgcgctc tcctgttccg    4140
accctgccgc ttaccggata cctgtccgcc tttctccctt cgggaagcgt ggcgctttct    4200
catagctcac gctgtaggta tctcagttcg gtgtaggtcg ttcgctccaa gctgggctgt    4260
gtgcacgaac cccccgttca gcccgaccgc tgcgccttat ccgtaactat cgtcttgag    4320 tccaacccgg taagacacga cttatcgcca ctggcagcag ccactggtaa caggattagc    4380
agagcgaggt atgtaggcgg tgctacagag ttcttgaagt ggtggcctaa ctacggctac    4440
actagaagaa cagtatttgg tatctgcgct ctgctgaagc cagttacctt cggaaaaaga    4500
gttggtagct cttgatccgg caaacaaacc accgctggta gcggtggttt ttttgtttgc    4560
aagcagcaga ttacgcgcag aaaaaaagga tctcaagaag atcctttgat cttttctacg    4620
gggtctgacg ctcagtggaa cgaaaactca cgttaaggga ttttggtcat gagattatca    4680
aaaggatctt cacctagatc cttttaaatt aaaaatgaag ttttaaatca atctaaagt    4740 atatatgagt aaacttggtc tgacagttac caatgcttaa tcagtgaggc acctatctca    4800
gcgatctgtc tatttcgttc atccatagtt gcctgactcg ggggggggg gcgctgaggt    4860 ctgcctcgtg aagaaggtgt tgctgactca taccaggcct gaatcgcccc atcatccagc    4920
cagaaagtga gggagccacg gttgatgaga gctttgttgt aggtggacca gttggtgatt    4980
ttgaactttt gctttgccac ggaacggtct gcgttgtcgg aagatgcgt gatctgatcc    5040 ttcaactcag caaaagttcg atttattcaa caaagccgcc gtcccgtcaa gtcagcgtaa    5100
tgctctgcca gtgttacaac caattaacca attctgatta gaaaaactca tcgagcatca    5160
aatgaaactg caatttattc atatcaggat tatcaatacc atattttga aaaagccgtt    5220 tctgtaatga aggagaaaac tcaccgaggc agttccatag gatggcaaga tcctggtatc    5280
ggtctgcgat tccgactcgt ccaacatcaa tacaacctat taatttcccc tcgtcaaaaa    5340
taaggttatc aagtgagaaa tcaccatgag tgacgactga atccggtgag aatggcaaaa    5400
gcttatgcat ttctttccag acttgttcaa caggccagcc attacgctcg tcatcaaaat    5460
cactcgcatc aaccaaaccg ttattcattc gtgattgcgc ctgagcgaga cgaaatacgc    5520
gatcgctgtt aaaaggacaa ttacaaacag gaatcgaatg caaccggcgc aggaacactg    5580
ccagcgcatc aacaatattt tcacctgaat caggatattc ttctaatacc tggaatgctg    5640
ttttcccggg gatcgcagtg gtgagtaacc atgcatcatc aggagtacgg ataaaatgct    5700
tgatggtcgg aagaggcata aattccgtca gccagtttag tctgaccatc tcatctgtaa    5760
catcattggc aacgctacct ttgccatgtt tcagaaacaa ctctgcgca tcgggcttcc    5820 catacaatcg atagattgtc gcacctgatt gcccgacatt atcgcgagcc catttatacc    5880
catataaatc agcatccatg ttggaattta atcgcggcct cgagcaagac gtttcccgtt    5940
gaatatggct cataacaccc cttgtattac tgtttatgta agcagacagt tttattgttc    6000
atgatgatat ttttttatct tgtgcaatgt aacatcagag attttgagac acaacgtggc    6060 tttcccccccc ccccattat tgaagcattt atcagggtta ttgtctcatg agcggataca    6120
tatttgaatg tatttagaaa aataaacaaa taggggttcc gcgcacattt ccccgaaaag    6180
tgccacctga cgtctaagaa accattatta tcatgacatt aacctataaa aataggcgta    6240
tcacgaggcc ctttcgtc                                                  6258
```

-continued

<210> SEQ ID NO 35
<211> LENGTH: 7711
<212> TYPE: DNA
<213> ORGANISM: Artificial Sequence
<220> FEATURE:
<223> OTHER INFORMATION: Synthetic Construct pAdApt Lassa GP

<400> SEQUENCE: 35

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260
cgtcaccgtc gtcgacacgt gtgatcagat atcgcggccg ctctagaatt taggattgcg   1320
cttttagaga ttcactacta gttaggaatt cctaaatcat ggggcagatt attacattct   1380
ttcaagaagt gccacatgta atagaggaag tcatgaacat tgtgctaatt gcgctttctc   1440
tattggcaat cttgaagggc ttgtataaca tcgctacatg tgggattatt ggattggttg   1500
cctttttatt cttgtgtggc aagtcttgtt ccctaaccct taaaggggga tatgagctgc   1560
aaaccttaga attaaatatg gagaccctaa acatgaccat gcccttatca tgcaccaaga   1620
acagcagtca tcattacata agagtgggca atgagactgg attagaattg actttaacta   1680
acaccagcat tataaatcac aaattttgca acttatccga tgctcacaaa aagaatcttt   1740
atgatcatgc tctcatgagc atcatctcaa cattccatct atccattcca aacttcaatc   1800
agtatgaagc catgagttgt gatttcaatg gagggaaaat cagtgtgcaa tacaacctct   1860
ctcattccta tgctggggat gcggccgaac actgtgggac agttgccaac ggagtgttgc   1920
aaacatttat gagaatggcc tggggtggaa gatacattgc attagactca ggaaagggaa   1980
actgggactg tataatgacc agctaccagt acctgataat tcaaaataca acatgggagg   2040
accactgcca attctcaaga ccgtctccta tcgggtacct tggccttttg tcacaaagga   2100
```

```
caagagatat atatataagt aggaggctct tggggacctt cacctggaca ttgtcagatt      2160
ctgagggcaa tgaaacacca ggtggttatt gtttaaccag gtggatgcta attgaagcag      2220
aactcaagtg ttttgggaat acagctgtgg caaaatgcaa tgagaagcat gatgaggagt      2280
tttgtgacat gctgagattg tttgatttca acaagcaagc aatccgtagg ttgaaggctg      2340
aggcccagat gagtattcaa ttaataaata aagccgtgaa tgccttaatc aatgatcaat      2400
taatcatgaa gaaccattta agagacatca tgggcattcc ctactgcaat tacagcaagt      2460
attggtacct taatcatact agtagcggga gaacatcact accaaagtgt tggcttatat      2520
ccaatgggtc atatctaaat gaaacccagt tctctgatga catagaacag caagccgaca      2580
atatgatcac agagatgctt cagaaagaat acattgaaag acaagggaaa acgcccttgg      2640
gactagtgga cattttcatc tttagcacaa gcttttatct gatcagcatt ttcttgcatt      2700
taattaaaat ccctacacat cgacacatcg ttgggaaacc ctgtcccaaa ccccatagac      2760
taaatcacat gggagtatgt tcctgtggac tgtacaaaca ccctggtgtt ccaacaaagt      2820
ggaagagata gggatccaga tctgctgtgc cttctagttg ccagccatct gttgtttgcc      2880
cctcccccgt gccttccttg accctggaag gtgccactcc cactgtcctt tcctaataaa      2940
atgaggaaat tgcatcgcat tgtctgagta ggtgtcattc tattctgggg ggtggggtgg      3000
ggcagcacag caaggggggag gattgggaag acaatagcag gcatgctggg gatgcggtgg      3060
gctctatggg tacccagggc cgcataactt cgtataatgt atgctatacg aagttataag      3120
atctgtactg aaatgtgtgg gcgtggctta agggtgggaa agaatatata aggtgggggt      3180
cttatgtagt tttgtatctg ttttgcagca gccgccgccg ccatgagcac caactcgttt      3240
gatggaagca ttgtgagctc atatttgaca acgcgcatgc ccccatgggc cggggtgcgt      3300
cagaatgtga tgggctccag cattgatggt cgccccgtcc tgcccgcaaa ctctactacc      3360
ttgacctacg agaccgtgtc tggaacgccg ttggagactg cagcctccgc cgccgcttca      3420
gccgctgcag ccaccgcccg cgggattgtg actgactttg cttttcctgag cccgcttgca      3480 agcagtgcag cttcccgttc atccgcccgc gatgacaagt tgacggctct tttggcacaa      3540
ttggattctt tgacccggga acttaatgtc gtttctcagc agctgttgga tctgcgccag      3600
caggtttctg ccctgaaggc ttcctcccct cccaatgcgg tttaaaacat aaataaaaaa      3660
ccagactctg tttggatttg gatcaagcaa gtgtcttgct gtctttattt aggggttttg      3720
cgcgcgcggt aggcccggga ccagcggtct cggtcgttga gggtcctgtg tattttttcc      3780
aggacgtggt aaaggtgact ctggatgttc agatacatgg gcataagccc gtctctgggg      3840
tggaggtagc accactgcag agcttcatgc tgcggggtgg tgttgtagat gatccagtcg      3900
tagcaggagc gctgggcgtg gtgcctaaaa atgtctttca gtagcaagct gattgccagg      3960
ggcaggccct tggtgtaagt gtttacaaag cggttaagct gggatgggtg catacgtggg      4020
gatatgagat gcatcttgga ctgtattttt aggttggcta tgttcccagc catatccctc      4080
cggggattca tgttgtgcag aaccaccagc acagtgtatc cggtgcactt gggaaatttg      4140
tcatgtagct tagaaggaaa tgcgtggaag aacttggaga cgcccttgtg acctccaaga      4200
ttttccatgc attcgtccat aatgatggca atgggcccac gggcggcggc ctgggcgaag      4260
atatttctgg gatcactaac gtcatagttg tgttccagga tgagatcgtc ataggccatt      4320
tttacaaagc gcgggcggag ggtgccagac tgcggtataa tggttccatc cggcccaggg      4380
gcgtagttac cctcacagat ttgcatttcc cacgctttga gttcagatgg gggatcatg      4440 tctacctgcg gggcgatgaa gaaaacggtt tccggggtag gggagatcag ctgggaagaa      4500
```

```
agcaggttcc tgagcagctg cgacttaccg cagccggtgg gcccgtaaat cacacctatt   4560
accggctgca actggtagtt aagagagctg cagctgccgt catccctgag cagggggggcc  4620
acttcgttaa gcatgtccct gactcgcatg ttttccctga ccaaatccgc cagaaggcgc   4680
tcgccgccca gcgatagcag ttcttgcaag gaagcaaagt ttttcaacgg tttgagaccg   4740
tccgccgtag gcatgctttt gagcgtttga ccaagcagtt ccaggcggtc ccacagctcg   4800
gtcacctgct ctacggcatc tcgatccagc atatctcctc gtttcgcggg ttggggcggc   4860
tttcgctgta cggcagtagt cggtgctcgt ccagacgggc cagggtcatg tctttccacg   4920
ggcgcagggt cctcgtcagc gtagtctggg tcacggtgaa ggggtgcgct ccgggctgcg   4980
cgctggccag ggtgcgcttg aggctggtcc tgctggtgct gaagcgctgc cggtcttcgc   5040
cctgcgcgtc ggccaggtag catttgacca tggtgtcata gtccagcccc tccgcggcgt   5100
ggcccttggc gcgcagcttg cccttggagg aggcgccgca cgaggggcag tgcagacttt   5160
tgagggcgta gagcttgggc gcgagaaata ccgattccgg ggagtaggca tccgcgccgc   5220
aggccccgca gacggtctcg cattccacga gccaggtgag ctctggccgt tcgggtcaa    5280
aaaccaggtt tcccccatgc tttttgatgc gtttcttacc tctggtttcc atgagccggt   5340
gtccacgctc ggtgacgaaa aggctgtccg tgtccccgta tacagacttg agaggcctgt   5400
cctcgagcgg tgttccgcgg tcctcctcgt atagaaactc ggaccactct gagacaaagg   5460
ctcgcgtcca ggccagcacg aaggaggcta agtgggaggg gtagcggtcg ttgtccacta   5520
gggggtccac tcgctccagg gtgtgaagac acatgtcgcc ctcttcggca tcaaggaagg   5580
tgattggttt gtaggtgtag gccacgtgac cgggtgttcc tgaaggggg ctataaaagg    5640
gggtgggggc gcgttcgtcc tcactctctt ccgcatcgct gtctgcgagg ccagctgtt    5700
ggggtgagtc gacgcgaggc tggatggcct tccccattat gattcttctc gcttccggcg   5760
gcatcgggat gccgcgttg caggccatgc tgtccaggca ggtagatgac gaccatcagg    5820
gacagcttca aggccagcaa aaggccagga accgtaaaaa ggccgcgttg ctggcgtttt   5880
tccataggct ccgcccccct gacgagcatc acaaaaatcg acgctcaagt cagaggtggc   5940
gaaacccgac aggactataa agataccagg cgtttccccc tggaagctcc ctcgtgcgct   6000
ctcctgttcc gaccctgccg cttaccggat acctgtccgc ctttctccct tcggaagcg    6060
tggcgctttc tcatagctca cgctgtaggt atctcagttc ggtgtaggtc gttcgctcca   6120
agctgggctg tgtgcacgaa ccccccgttc agcccgaccg ctgcgcctta tccggtaact   6180
atcgtcttga gtccaacccg gtaagacacg acttatcgcc actggcagca gccactggta   6240
acaggattag cagagcgagg tatgtaggcg gtgctacaga gttcttgaag tggtggccta   6300
actacggcta cactagaagg acagtatttg gtatctgcgc tctgctgaag ccagttacct   6360
tcggaaaaag agttggtagc tcttgatccg gcaaacaaac caccgctggt agcggtggtt   6420
tttttgtttg caagcagcag attacgcgca gaaaaaaagg atctcaagaa gatcctttga   6480
tcttttctac ggggtctgac gctcagtgga acgaaaactc acgttaaggg attttggtca   6540
tgagattatc aaaaaggatc ttcacctaga tccttttaaa ttaaaaatga agttttaaat   6600
caatctaaag tatatatgag taaacttggt ctgacagtta ccaatgctta atcagtgagg   6660
cacctatctc agcgatctgt ctatttcgtt catccatagt tgcctgactc ccgtcgtgt    6720
agataactac gatacgggag ggcttaccat ctggccccag tgctgcaatg ataccgcgag   6780
acccacgctc accggctcca gatttatcag caataaacca gccagccgga agggccgagc   6840
gcagaagtgg tcctgcaact ttatccgcct ccatccagtc tattaattgt tgccgggaag   6900
```

-continued

```
ctagagtaag tagttcgcca gttaatagtt tgcgcaacgt tgttgccatt gctgcaggca   6960
tcgtggtgtc acgctcgtcg tttggtatgg cttcattcag ctccggttcc caacgatcaa   7020
ggcgagttac atgatccccc atgttgtgca aaaaagcggt tagctccttc ggtcctccga   7080
tcgttgtcag aagtaagttg gccgcagtgt tatcactcat ggttatggca gcactgcata   7140
attctcttac tgtcatgcca tccgtaagat gcttttctgt gactggtgag tactcaacca   7200
agtcattctg agaatagtgt atgcggcgac cgagttgctc ttgcccggcg tcaacacggg   7260
ataataccgc gccacatagc agaactttaa aagtgctcat cattggaaaa cgttcttcgg   7320
ggcgaaaact ctcaaggatc ttaccgctgt tgagatccag ttcgatgtaa cccactcgtg   7380
cacccaactg atcttcagca tcttttactt tcaccagcgt ttctgggtga gcaaaaacag   7440
gaaggcaaaa tgccgcaaaa aagggaataa gggcgacacg gaaatgttga atactcatac   7500
tcttcctttt tcaatattat tgaagcattt atcagggtta ttgtctcatg agcggataca   7560
tatttgaatg tatttagaaa aataaacaaa taggggttcc gcgcacattt ccccgaaaag   7620
tgccacctga cgtctaagaa accattatta tcatgacatt aacctataaa aataggcgta   7680
tcacgaggcc ctttcgtctt caagaattgt t                                  7711
```

<210> SEQ ID NO 36
<211> LENGTH: 7522
<212> TYPE: DNA
<213> ORGANISM: Artificial Sequence
<220> FEATURE:
<223> OTHER INFORMATION: Synthetic Construct pAdApt Lassa GP(dTM)

<400> SEQUENCE: 36

```
ttaattaacc gcaattctca tgtttgacag cttatcatca tcaataatat accttatttt     60
ggattgaagc caatatgata atgagggggt ggagtttgtg acgtggcgcg gggcgtggga    120
acggggcggg tgacgtagta gtgtggcgga agtgtgatgt tgcaagtgtg gcggaacaca    180
tgtaagcgac ggatgtggca aaagtgacgt ttttggtgtg cgccggtgta cacaggaagt    240
gacaattttc gcgcggtttt aggcggatgt tgtagtaaat ttgggcgtaa ccgagtaaga    300
tttggccatt ttcgcgggaa aactgaataa gaggaagtga aatctgaata attttgtgtt    360
actcatagcg cgtaatattt gtctagggcc gcggggactt tgaccgttta cgtggagact    420
cgcccaggtg tttttctcag gtgttttccg cgttccgggt caaagttggc gttttattat    480
tatagtcagt acgtaccagt gcactggcct agagcggccc cattgcatac gttgtatcca    540
tatcataata tgtacattta tattggctca tgtccaacat taccgccatg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagaagac accgggaccg atccagcctc   1260

```
cgtcaccgtc gtcgacacgt gtgatcagat atcgcggccg ctctagaatt taggattgcg   1320
cttttagaga ttcactacta gttaggaatt cctaaatcat ggggcagatt attacattct   1380
ttcaagaagt gccacatgta atagaggaag tcatgaacat tgtgctaatt gcgctttctc   1440
tattggcaat cttgaagggc ttgtataaca tcgctacatg tgggattatt ggattggttg   1500
cctttttatt cttgtgtggc aagtcttgtt ccctaaccct taaagggggga tatgagctgc   1560 aaaccttaga attaaatatg gagaccctaa acatgaccat gcccttatca tgcaccaaga   1620
acagcagtca tcattacata agagtgggca atgagactgg attagaattg actttaacta   1680
acaccagcat tataaatcac aaattttgca acttatccga tgctcacaaa aagaatcttt   1740
atgatcatgc tctcatgagc atcatctcaa cattccatct atccattcca aacttcaatc   1800
agtatgaagc catgagttgt gatttcaatg gagggaaaat cagtgtgcaa tacaacctct   1860
ctcattccta tgctggggat gcggccgaac actgtgggac agttgccaac ggagtgttgc   1920
aaacatttat gagaatggcc tggggtggaa gatacattgc attagactca ggaaagggaa   1980
actgggactg tataatgacc agctaccagt acctgataat tcaaaataca acatgggagg   2040
accactgcca attctcaaga ccgtctccta tcgggtacct tggccttttg tcacaaagga   2100
caagagatat atatataagt aggaggctct tggggacctt cacctggaca ttgtcagatt   2160
ctgagggcaa tgaaacacca ggtggttatt gtttaaccag gtggatgcta attgaagcag   2220
aactcaagtg ttttgggaat acagctgtgg caaaatgcaa tgagaagcat gatgaggagt   2280
tttgtgacat gctgagattg tttgatttca caagcaagc aatccgtagg ttgaaggctg   2340
aggcccagat gagtattcaa ttaataaata aagccgtgaa tgccttaatc aatgatcaat   2400
taatcatgaa gaaccattta agagacatca tgggcattcc ctactgcaat tacagcaagt   2460
attggtaccc taatcatact agtagcggga gaacatcact accaaagtgt tggcttatat   2520
ccaatgggtc atatctaaat gaaacccagt tctctgatga catagaacag caagccgaca   2580
atatgatcac agagatgctt cagaaagaat acattgaaag acaagggaaa acgcccttgt   2640
agggatccag atctgctgtg ccttctagtt gccagccatc tgttgtttgc ccctccccg   2700 tgccttcctt gaccctggaa ggtgccactc ccactgtcct ttcctaataa aatgaggaaa   2760
ttgcatcgca ttgtctgagt aggtgtcatt ctattctggg gggtgggtg gggcagcaca   2820 gcaaggggga ggattgggaa gacaatagca ggcatgctgg ggatgcggtg ggctctatgg   2880
gtacccaggg ccgcataact tcgtataatg tatgctatac gaagttataa gatctgtact   2940
gaaatgtgtg ggcgtggctt aagggtggga agaatatat aaggtggggg tcttatgtag   3000
ttttgtatct gttttgcagc agccgccgcc gccatgagca ccaactcgtt tgatggaagc   3060
attgtgagct catatttgac aacgcgcatg cccccatggg ccggggtgcg tcagaatgtg   3120
atgggctcca gcattgatgg tcgccccgtc ctgcccgcaa actctactac cttgacctac   3180
gagaccgtgt ctggaacgcc gttggagact gcagcctccg ccgccgcttc agccgctgca   3240
gccaccgccc gcgggattgt gactgacttt gctttcctga gcccgcttgc aagcagtgca   3300
gcttcccgtt catccgcccg cgatgacaag ttgacggctc ttttggcaca attggattct   3360
ttgacccggg aacttaatgt cgtttctcag cagctgttgg atctgcgcca gcaggtttct   3420
gccctgaagg cttcctcccc tcccaatgcg gtttaaaaca taaataaaaa accagactct   3480
gtttggattt ggatcaagca agtgtcttgc tgtcttattt tagggttttt gcgcgcgcgg   3540
taggcccggg accagcggtc tcggtcgttg agggtcctgt gtatttttc caggacgtgg   3600 taaaggtgac tctggatgtt cagatacatg ggcataagcc cgtctctggg gtggaggtag   3660
```

```
caccactgca gagcttcatg ctgcggggtg gtgttgtaga tgatccagtc gtagcaggag    3720
cgctgggcgt ggtgcctaaa aatgtctttc agtagcaagc tgattgccag gggcaggccc    3780
ttggtgtaag tgtttacaaa gcggttaagc tgggatgggt gcatacgtgg ggatatgaga    3840
tgcatcttgg actgtatttt taggttggct atgttcccag ccatatccct ccggggattc    3900
atgttgtgca gaaccaccag cacagtgtat ccggtgcact tgggaaattt gtcatgtagc    3960
ttagaaggaa atgcgtggaa gaacttggag acgcccttgt gacctccaag attttccatg    4020
cattcgtcca taatgatggc aatgggccca cgggcggcgg cctgggcgaa gatatttctg    4080
ggatcactaa cgtcatagtt gtgttccagg atgagatcgt cataggccat ttttacaaag    4140
cgcgggcgga gggtgccaga ctgcggtata atggttccat ccggcccagg ggcgtagtta    4200
ccctcacaga tttgcatttc ccacgctttg agttcagatg gggggatcat gtctacctgc    4260
ggggcgatga agaaaacggt tccggggta ggggagatca gctgggaaga aagcaggttc    4320
ctgagcagct gcgacttacc gcagccgtg ggcccgtaaa tcacacctat taccggctgc    4380
aactggtagt taagagagct gcagctgccg tcatccctga gcagggggc cacttcgtta    4440 agcatgtccc tgactcgcat gttttccctg accaaatccg ccagaaggcg ctcgccgccc    4500
agcgatagca gttcttgcaa ggaagcaaag ttttcaacg gtttgagacc gtccgccgta    4560
ggcatgcttt tgagcgtttg accaagcagt tccaggcggt cccacagctc ggtcacctgc    4620
tctacggcat ctcgatccag catatctcct cgtttcgcgg gttggggcgg ctttcgctgt    4680
acggcagtag tcggtgctcg tccagacggg ccagggtcat gtctttccac gggcgcaggg    4740
tcctcgtcag cgtagtctgg gtcacggtga aggggtgcgc tccgggctgc gcgctggcca    4800
gggtgcgctt gaggctggtc ctgctggtgc tgaagcgctg ccgtcttcg ccctgcgcgt    4860 cggccaggta gcatttgacc atggtgtcat agtccagccc ctccgcggcg tggcccttgg    4920
cgcgcagctt gcccttggag gaggcgccgc acgaggggca gtgcagactt ttgagggcgt    4980
agagcttggg cgcgagaaat accgattccg gggagtaggc atccgcgccg caggccccgc    5040
agacggtctc gcattccacg agccaggtga gctctggccg ttcggggtca aaaaccaggt    5100 ttccccatg ctttttgatg cgtttcttac ctctggtttc catgagccgg tgtccacgct    5160
cggtgacgaa aaggctgtcc gtgtccccgt atacagactt gagaggcctg tcctcgagcg    5220
gtgttccgcg gtcctcctcg tatagaaact cggaccactc tgagacaaag gctcgcgtcc    5280
aggccagcac gaaggaggct aagtgggagg ggtagcggtc gttgtccact aggggtccca    5340
ctcgctccag ggtgtgaaga cacatgtcgc cctcttcggc atcaaggaag gtgattggtt    5400
tgtaggtgta ggccacgtga ccgggtgttc ctgaaggggg gctataaaag ggggtggggg    5460
cgcgttcgtc ctcactctct tccgcatcgc tgtctgcgag ggccagctgt tggggtgagt    5520
cgacgcgagg ctggatggcc ttccccatta tgattcttct cgcttccggc ggcatcggga    5580
tgcccgcgtt gcaggccatg ctgtccaggc aggtagatga cgaccatcag ggacagcttc    5640
aaggccagca aaaggccagg aaccgtaaaa aggccgcgtt gctggcgttt ttccataggc    5700 tccgccccc tgacgagcat cacaaaaatc gacgctcaag tcagaggtgg cgaaacccga    5760
caggactata aagataccag gcgtttcccc ctggaagctc cctcgtgcgc tctcctgttc    5820
cgaccctgcc gcttaccgga tacctgtccg ccttctccc ttcgggaagc gtggcgcttt    5880
ctcatagctc acgctgtagg tatctcagtt cggtgtaggt cgttcgctcc aagctgggct    5940
gtgtgcacga accccccgtt cagcccgacc gctgcgcctt atccggtaac tatcgtcttg    6000
agtccaaccc ggtaagacac gacttatcgc cactggcagc agccactggt aacaggatta    6060
```

```
gcagagcgag gtatgtaggc ggtgctacag agttcttgaa gtggtggcct aactacggct    6120
acactagaag gacagtattt ggtatctgcg ctctgctgaa gccagttacc ttcggaaaaa    6180
gagttggtag ctcttgatcc ggcaaacaaa ccaccgctgg tagcggtggt ttttttgttt    6240
gcaagcagca gattacgcgc agaaaaaaag gatctcaaga agatcctttg atcttttcta    6300
cggggtctga cgctcagtgg aacgaaaact cacgttaagg gattttggtc atgagattat    6360 caaaaggat cttcacctag atccttttaa attaaaaatg aagttttaaa tcaatctaaa    6420
gtatatatga gtaaacttgg tctgacagtt accaatgctt aatcagtgag gcacctatct    6480
cagcgatctg tctatttcgt tcatccatag ttgcctgact ccccgtcgtg tagataacta    6540
cgatacggga gggcttacca tctggcccca gtgctgcaat gataccgcga gacccacgct    6600
caccggctcc agatttatca gcaataaacc agccagccgg aagggccgag cgcagaagtg    6660
gtcctgcaac tttatccgcc tccatccagt ctattaattg ttgccgggaa gctagagtaa    6720
gtagttcgcc agttaatagt ttgcgcaacg ttgttgccat tgctgcaggc atcgtggtgt    6780
cacgctcgtc gtttggtatg gcttcattca gctccggttc caacgatcaa ggcgagtta    6840 catgatcccc catgttgtgc aaaaaagcgg ttagctcctt cggtcctccg atcgttgtca    6900
gaagtaagtt ggccgcagtg ttatcactca tggttatggc agcactgcat aattctctta    6960
ctgtcatgcc atccgtaaga tgcttttctg tgactggtga gtactcaacc aagtcattct    7020
gagaatagtg tatgcggcga ccgagttgct cttgcccggc gtcaacacgg gataataccg    7080
cgccacatag cagaacttta aaagtgctca tcattggaaa acgttcttcg gggcgaaaac    7140
tctcaaggat cttaccgctg ttgagatcca gttcgatgta acccactcgt gcacccaact    7200
gatcttcagc atcttttact ttcaccagcg tttctgggtg agcaaaaaca ggaaggcaaa    7260
atgccgcaaa aaagggaata agggcgacac ggaaatgttg aatactcata ctcttccttt    7320
ttcaatatta ttgaagcatt tatcagggtt attgtctcat gagcggatac atatttgaat    7380
gtatttagaa aaataaacaa ataggggttc cgcgcacatt tccccgaaaa gtgccacctg    7440
acgtctaaga aaccattatt atcatgacat taacctataa aaataggcgt atcacgaggc    7500
cctttcgtct tcaagaattg tt    7522
```

<210> SEQ ID NO 37
<211> LENGTH: 6324
<212> TYPE: DNA
<213> ORGANISM: Artificial Sequence
<220> FEATURE:
<223> OTHER INFORMATION: Synthetic Construct CMV/R Ebola GP(Z) delta TM/h

<400> SEQUENCE: 37

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccc ccattgacg tcaataatga cgtatgttcc    480
catagtaacg ccaatagga cttccattg acgtcaatgg gtggagtatt tacggtaaac    540
```

-continued

| | |
|---|---|
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccttacct gaggccgcca tccacgccgg ttgagtcgcg ttctgccgcc tcccgcctgt | 1080 |
| ggtgcctcct gaactacgtc cgccgtctag gtaagtttag agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacga tatcgccgcc atgggcgtga ccggcatcct | 1380 |
| gcagctgccc agggacaggt tcaagaggac cagcttcttc ctgtgggtga tcatcctgtt | 1440 |
| ccagaggacc ttcagcatcc ccctgggcgt gatccacaac agcaccctgc aggtgagcga | 1500 |
| cgtggacaag ctggtgtgca gggacaagct gagcagcacc aaccagctga ggagcgtggg | 1560 |
| cctgaacctg gagggcaacg cgcgtggcca cgacgtgccc agcgccacca agaggtgggg | 1620 |
| cttcaggagc ggcgtgcctc ccaaggtggt gaactacgag gccggcgagt gggccgagaa | 1680 |
| ctgctacaac ctggagatca agaagcccga cggcagcgag tgcctgcccg ccgcccctga | 1740 |
| cggcatcagg ggcttcccca ggtgcaggta cgtgcacaag gtgagcggca ccggcccctg | 1800 |
| cgccggcgac ttcgccttcc acaaggaggg cgccttcttc ctgtacgaca ggctggccag | 1860 |
| caccgtgatc tacaggggca ccaccttcgc cgagggcgtg gtggccttcc tgatcctgcc | 1920 |
| ccaggccaag aaggacttct tcagcagcca ccctctgagg gagcccgtga acgccaccga | 1980 |
| ggaccccagc agcggctact acagcaccac catcaggtac caggccaccg cttcggcac | 2040 |
| caacgagacc gagtacctgt cgaggtgga caacctgacc tacgtgcagc tggagtctag | 2100 |
| attcacccct cagttcctgc tgcagctgaa cgagaccatc tacaccagcg gcaagaggag | 2160 |
| caacaccacc ggcaagctga tctggaaggt gaaccccgag atcgacacca ccatcggcga | 2220 |
| gtgggccttc tgggagacca agaagaacct gaccaggaag atcaggagcg aggagctgag | 2280 |
| cttcaccgtc gtgagcaacg gggccaagaa catcagcggc cagagccccg ccaggaccag | 2340 |
| cagcgacccc ggcaccaaca ccaccaccga ggaccacaag atcatggcca gcgagaacag | 2400 |
| cagcgccatg gtgcaggtgc acagccaggg cagggaggcc gccgtgagcc acctgaccac | 2460 |
| cctggccacc atcagcacca gccctcagtc tttaaccacc aagcccggcc ccgacaacag | 2520 |
| cacccacaac accctgtgt acaagctgga catcagcgag ccacccagg tggagcagca | 2580 |
| ccacaggagg accgacaacg acagcaccgc cagcgacacc ccttccgcca ccaccgccgc | 2640 |
| cggccctccg aaggccgaga acaccaacac cagcaagagc accgactttc tggatcccgc | 2700 |
| caccaccacc agccctcaga accacagcga ccgccggc aacaacaaca cccaccacca | 2760 |
| ggacaccggc gaggagagcg ccagcagcgg caagctgggc ctgatcacca acaccatcgc | 2820 |
| cggcgtggcc ggcctgatca ccggcggcag gaggaccagg agggaggcca tcgtgaacgc | 2880 |
| ccagcccaag tgcaaccccca acctgcacta ctggaccacc caggacgagg gcgccgccat | 2940 |

```
cggcctggcc tggattccct acttcggccc cgccgccgag ggcatctaca tcgagggcct   3000
gatgcacaac caggacggcc tgatctgcgg cctgaggcag ctggccaacg agaccaccca   3060
ggccctgcag ctgttcctga gggccaccac cgagctgagg accttcagca tcctgaacag   3120
gaaggccatc gacttcctgc tgcagaggtg gggcggcacc tgccacatcc tgggccccga   3180
ctgctgcatc gagccccacg actggaccaa gaacatcacc gacaagatcg accagatcat   3240
ccacgacttc gtggacaaga ccctgcccga ccagggcgac aacgacaact ggtggaccgg   3300
ctgaacacgt ggaattcaga tctgctgtgc cttctagttg ccagccatct gttgtttgcc   3360
cctcccccgt gccttccttg accctggaag gtgccactcc cactgtcctt tcctaataaa   3420
atgaggaaat tgcatcgcat tgtctgagta ggtgtcattc tattctgggg ggtggggtgg   3480
ggcaggacag caaggggagg gattgggaag acaatagcag gcatgctggg gatgcggtgg   3540
gctctatggg tacccaggtg ctgaagaatt gacccggttc ctcctgggcc agaaagaagc   3600
aggcacatcc ccttctctgt gacacaccct gtccacgccc ctggttctta gttccagccc   3660
cactcatagg acactcatag ctcaggaggg ctccgccttc aatcccaccc gctaaagtac   3720
ttggagcggt ctctccctcc ctcatcagcc caccaaacca aacctagcct caagagtgg    3780
gaagaaatta aagcaagata ggctattaag tgcagaggga gagaaaatgc ctccaacatg   3840
tgaggaagta atgagagaaa tcatagaatt ttaaggccat catggcctta atcttccgct   3900
tcctcgctca ctgactcgct cgctcggtc gttcggctgc ggcgagcggt atcagctcac    3960
tcaaaggcgg taatacggtt atccacagaa tcagggata cgcaggaaa gaacatgtga    4020
gcaaaaggcc agcaaaaggc caggaaccgt aaaaaggccg cgttgctggc gtttttccat   4080
aggctccgcc cccctgacga gcatcacaaa aatcgacgct caagtcagag gtggcgaaac   4140
ccgacaggac tataaagata ccaggcgttt ccccctggaa gctccctcgt gcgctctcct   4200
gttccgaccc tgccgcttac cggatacctg tccgccttc tcccttcggg aagcgtggcg    4260
ctttctcata gctcacgctg taggtatctc agttcggtgt aggtcgttcg ctccaagctg   4320
ggctgtgtgc acgaacccc cgttcagccc gaccgctgcg ccttatccgg taactatcgt    4380
cttgagtcca acccggtaag acacgactta tcgccactgg cagcagccac tggtaacagg   4440
attagcagag cgaggtatgt aggcggtgct acagagttct tgaagtggtg gcctaactac   4500
ggctacacta gaagaacagt atttggtatc tgcgctctgc tgaagccagt taccttcgga   4560
aaaagagttg gtagctcttg atccggcaaa caaaccaccg ctggtagcgg tggttttttt   4620
gtttgcaagc agcagattac gcgcagaaaa aaaggatctc aagaagatcc tttgatcttt   4680
tctacgggt ctgacgctca gtggaacgaa aactcacgtt aagggatttt ggtcatgaga    4740
ttatcaaaaa ggatcttcac ctagatcctt ttaaattaaa aatgaagttt taaatcaatc   4800
taaagtatat atgagtaaac ttggtctgac agttaccaat gcttaatcag tgaggcacct   4860
atctcagcga tctgtctatt tcgttcatcc atagttgcct gactcggggg ggggggcgc    4920
tgaggtctgc ctcgtgaaga aggtgttgct gactcatacc aggcctgaat cgccccatca   4980
tccagccaga aagtgaggga gccacggttg atgagagctt gttgtaggt ggaccagttg    5040
gtgattttga acttttgctt tgccacggaa cggtctgcgt tgtcgggaag atgcgtgatc   5100
tgatccttca actcagcaaa agttcgattt attcaacaaa gccgccgtcc cgtcaagtca   5160
gcgtaatgct ctgccagtgt tacaaccaat taaccaattc tgattagaaa aactcatcga   5220
gcatcaaatg aaactgcaat ttattcatat caggattatc aataccatat ttttgaaaaa   5280
gccgtttctg taatgaagga gaaaactcac cgaggcagtt ccataggatg caagatcct    5340
```

```
ggtatcggtc tgcgattccg actcgtccaa catcaataca acctattaat ttccctcgt    5400 caaaataag gttatcaagt gagaaatcac catgagtgac gactgaatcc ggtgagaatg    5460
gcaaaagctt atgcatttct ttccagactt gttcaacagg ccagccatta cgctcgtcat    5520
caaaatcact cgcatcaacc aaaccgttat tcattcgtga ttgcgcctga gcgagacgaa    5580
atacgcgatc gctgttaaaa ggacaattac aaacaggaat cgaatgcaac cggcgcagga    5640
acactgccag cgcatcaaca atattttcac ctgaatcagg atattcttct aatacctgga    5700
atgctgtttt cccggggatc gcagtggtga gtaaccatgc atcatcagga gtacggataa    5760
aatgcttgat ggtcggaaga ggcataaatt ccgtcagcca gtttagtctg accatctcat    5820
ctgtaacatc attggcaacg ctacctttgc catgtttcag aaacaactct ggcgcatcgg    5880
gcttcccata caatcgatag attgtcgcac ctgattgccc gacattatcg cgagcccatt    5940
tatacccata taaatcagca tccatgttgg aatttaatcg cggcctcgag caagacgttt    6000
cccgttgaat atggctcata caccccttg tattactgtt tatgtaagca gacagtttta    6060
ttgttcatga tgatatattt ttatcttgtg caatgtaaca tcagagattt tgagacacaa    6120
cgtggctttc ccccccccc cattattgaa gcatttatca gggttattgt ctcatgagcg    6180
gatacatatt tgaatgtatt tagaaaaata acaaataggg gttccgcgc acatttcccc    6240 gaaaagtgcc acctgacgtc taagaaacca ttattatcat gacattaacc tataaaaata    6300
ggcgtatcac gaggcccttt cgtc                                          6324
```

<210> SEQ ID NO 38
<211> LENGTH: 6868
<212> TYPE: DNA
<213> ORGANISM: Artificial Sequence
<220> FEATURE:
<223> OTHER INFORMATION: Synthetic Construct pVR1012x/s Ebola GP(Z)
      delta TM/h (P87666)

<400> SEQUENCE: 38

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaatagggga cttccattg acgtcaatgg gtggagtatt tacggtaaac     540
tgcccacttg gcagtacatc aagtgtatca tatgccaagt acgccccta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
```

```
tccccgtgcc aagagtgacg taagtaccgc ctatagactc tataggcaca cccctttggc   1080
tcttatgcat gctatactgt ttttggcttg gggcctatac accccgcttc ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgacg atatcgccgc catggagggc ctgagcctgc tgcagctgcc   1920
cagggacaag ttcaggaaga gcagcttctt cgtgtgggtg atcatcctgt tccagaaggc   1980
cttcagcatg cccctgggcg tggtgaccaa cagcaccctg gaggtgaccg agatcgacca   2040
gctggtgtgc aaggaccacc tggccagcac cgaccagctg aagagcgtgg gcctgaacct   2100
ggagggcagc ggcgtgagca ccgacatccc cagcgccacc aagaggtggg gcttcaggag   2160
cggcgtgcct ccccaggtgg tgagctacga ggccggcgag tgggccgaga actgctacaa   2220
cctggagatc aagaagcccg acggcagcga gtgcctgcct cctcctcctg acggcgtgag   2280
gggcttcccc aggtgcaggt acgtgcacaa ggcccagggc accggcccct gcccggcga   2340
ctacgccttc cacaaggacg gcgccttctt cctgtacgac aggctggcca gcaccgtgat   2400
ctacagggc gtgaacttcg ccgagggcgt gatcgccttc ctgatcctgg ccaagcccaa   2460
ggagaccttc ctgcagagcc ctcccatcag ggaggccgcc aactacaccg agaacaccag   2520
cagctactac gccaccagct atctagagta cgagatcgag aacttcggcg cccagcacag   2580
caccaccctg ttcaagatca caacaacac cttcgtgctg ctggacaggc cccacacccc   2640
tcagttcctg ttccagctga acgacaccat ccagctgcac cagcagctga gcaacaccac   2700
cggcaagctg atctggaccc tggacgccaa catcaacgcc gacatcggcg agtgggcctt   2760
ctgggagaac aagaagaacc tgagcgagca gctgagggc gaggagctga gcttcgagac   2820
cctgagcctg aacgagaccg aggacgacga cgccaccagc agcaggacca ccaagggcag   2880
gatcagcgac agggccacca ggaagtacag cgacctggtg cccaaggaca gccccggcat   2940
ggtgagcctg cacgtgcccg agggcgagac caccctgccc agcagaaaca gcaccgaggg   3000
caggagggtg gacgtgaaca cccaggagac catcaccgag accaccgcca ccatcatcgg   3060
caccaacggc aacaacatgc agatcagcac catcggcacc ggcctgagca gcagccagat   3120
cctgagcagc agccccacca tggcccctag ccccgagacc cagaccagca ccacctacac   3180
ccctaagctg cccgtgatga ccaccgagga gccaccacc cctccaagga cagcccgg   3240
atccaccacc gaggccccta cccctgacca cctgagaac atcaccaccg ccgtgaagac   3300
cgtgtgggcc caggagagca ccagcaacgg cctgatcacc agcaccgtga ccggcatcct   3360
gggcagcctg ggcctgagga agaggagcag gaggcaggtg aacaccaggg ccaccggcaa   3420
```

```
gtgcaacccc aacctgcact actggaccgc ccaggagcag cacaacgccg ccggcatcgc    3480
ctggattccc tacttcggcc ccggcgccga gggcatctac accgagggcc tgatgcacaa    3540
ccagaacgcc ctggtgtgcg gcctgaggca gctggccaac gagaccaccc aggccctgca    3600
gctgttcctg agggccacca ccgagctgag gacctacacc atcctgaaca ggaaggccat    3660
cgacttcctg ctgaggaggt ggggcggcac ctgcaggatt ctgggccccg actgctgcat    3720
cgagccccac gactggacca agaacatcac cgacaagatc aaccagatca tccacgactt    3780
catcgacaac cctctgccca accaggacaa cgacgacaac tggtggaccg gctgaacacg    3840
tggaattcag atctgctgtg ccttctagtt gccagccatc tgttgtttgc ccctcccccg    3900
tgccttcctt gaccctggaa ggtgccactc ccactgtcct ttcctaataa aatgaggaaa    3960
ttgcatcgca ttgtctgagt aggtgtcatt ctattctggg gggtggggtg gggcaggaca    4020 gcaagggga ggattgggaa gacaatagca ggcatgctgg ggatgcggtg ggctctatgg     4080
gtacccaggt gctgaagaat tgacccggtt cctcctgggc cagaaagaag caggcacatc    4140
cccttctctg tgacacaccc tgtccacgcc cctggttctt agttccagcc ccactcatag    4200
gacactcata gctcaggagg gctccgcctt caatcccacc cgctaaagta cttggagcgg    4260
tctctccctc cctcatcagc ccaccaaacc aaacctagcc tccaagagtg ggaagaaatt    4320
aaagcaagat aggctattaa gtgcagaggg agagaaaatg cctccaacat gtgaggaagt    4380
aatgagagaa atcatagaat tttaaggcca tgatttaagg ccatcatggc cttaatcttc    4440
cgcttcctcg ctcactgact cgctgcgctc ggtcgttcgg ctgcggcgag cggtatcagc    4500
tcactcaaag gcggtaatac ggttatccac agaatcaggg gataacgcag gaaagaacat    4560
gtgagcaaaa ggccagcaaa aggccaggaa ccgtaaaaag gccgcgttgc tggcgttttt    4620
ccataggctc cgcccccctg acgagcatca caaaaatcga cgctcaagtc agaggtggcg    4680
aaacccgaca ggactataaa gataccaggc gtttccccct ggaagctccc tcgtgcgctc    4740
tcctgttccg accctgccgc ttaccggata cctgtccgcc tttctccctt cgggaagcgt    4800
ggcgctttct catagctcac gctgtaggta tctcagttcg gtgtaggtcg ttcgctccaa    4860
gctgggctgt gtgcacgaac cccccgttca gcccgaccgc tgcgccttat ccggtaacta    4920
tcgtcttgag tccaacccgg taagacacga cttatcgcca ctggcagcag ccactggtaa    4980
caggattagc agagcgaggt atgtaggcgg tgctacagag ttcttgaagt ggtggcctaa    5040
ctacggctac actagaagaa cagtatttgg tatctgcgct ctgctgaagc cagttacctt    5100
cggaaaaaga gttggtagct cttgatccgg caaacaaacc accgctggta gcggtggttt    5160
ttttgtttgc aagcagcaga ttacgcgcag aaaaaaagga tctcaagaag atcctttgat    5220
cttttctacg gggtctgacg ctcagtggaa cgaaaactca cgttaaggga ttttggtcat    5280
gagattatca aaaggatct tcacctagat ccttttaaat taaaaatgaa gttttaaatc     5340
aatctaaagt atatatgagt aaacttggtc tgacagttac caatgcttaa tcagtgaggc    5400
acctatctca gcgatctgtc tatttcgttc atccatagtt gcctgactcg ggggggggg     5460 gcgctgaggt ctgcctcgtg aagaaggtgt tgctgactca taccaggcct gaatcgcccc    5520
atcatccagc cagaaagtga gggagccacg gttgatgaga gctttgttgt aggtggacca    5580
gttggtgatt tgaactttt gctttgccac ggaacggtct gcgttgtcgg gaagatgcgt     5640
gatctgatcc ttcaactcag caaaagttcg atttattcaa caaagccgcc gtcccgtcaa    5700
gtcagcgtaa tgctctgcca gtgttacaac caattaacca attctgatta gaaaaactca    5760
tcgagcatca aatgaaactg caatttattc atatcaggat tatcaatacc atattttga     5820
```

```
aaaagccgtt tctgtaatga aggagaaaac tcaccgaggc agttccatag gatggcaaga      5880
tcctggtatc ggtctgcgat tccgactcgt ccaacatcaa tacaacctat taatttccc       5940 tcgtcaaaaa taaggttatc aagtgagaaa tcaccatgag tgacgactga atccggtgag      6000
aatggcaaaa gcttatgcat ttctttccag acttgttcaa caggccagcc attacgctcg      6060
tcatcaaaat cactcgcatc aaccaaaccg ttattcattc gtgattgcgc ctgagcgaga      6120
cgaaatacgc gatcgctgtt aaaaggacaa ttacaaacag gaatcgaatg caaccggcgc      6180
aggaacactg ccagcgcatc aacaatattt tcacctgaat caggatattc ttctaatacc      6240
tggaatgctg ttttcccggg gatcgcagtg gtgagtaacc atgcatcatc aggagtacgg      6300
ataaaatgct tgatggtcgg aagaggcata aattccgtca gccagtttag tctgaccatc      6360
tcatctgtaa catcattggc aacgctacct ttgccatgtt tcagaaacaa ctctggcgca      6420
tcgggcttcc catacaatcg atagattgtc gcacctgatt gcccgacatt atcgcgagcc      6480
catttatacc catataaatc agcatccatg ttggaattta atcgcggcct cgagcaagac      6540
gtttcccgtt gaatatggct cataacaccc cttgtattac tgtttatgta agcagacagt      6600
tttattgttc atgatgatat atttttatct tgtgcaatgt aacatcagag attttgagac      6660
acaacgtggc tttccccccc cccccattat tgaagcattt atcagggtta ttgtctcatg      6720
agcggataca tatttgaatg tatttagaaa aataaacaaa tagggggttcc gcgcacattt      6780 ccccgaaaag tgccacctga cgtctaagaa accattatta tcatgacatt aacctataaa      6840
aataggcgta tcacgaggcc ctttcgtc                                         6868
```

<210> SEQ ID NO 39  
<211> LENGTH: 6322  
<212> TYPE: DNA  
<213> ORGANISM: Artificial Sequence  
<220> FEATURE:  
<223> OTHER INFORMATION: Synthetic Construct CMV/R-GP(S/G)(deltaTM)/h

<400> SEQUENCE: 39

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcagattgg       240
ctattggcca ttgcatacgt tgtatccata tcataatatg tacatttata ttggctcatg       300
tccaacatta ccgccatgtt gacattgatt attgactagt tattaatagt aatcaattac       360
ggggtcatta gttcatagcc catatatgga gttccgcgtt acataactta cggtaaatgg       420
cccgcctggc tgaccgccca acgacccccg cccattgacg tcaataatga cgtatgttcc       480
catagtaacg ccaatagggga ctttccattg acgtcaatgg gtggagtatt tacggtaaac      540
tgcccacttg gcagtacatc aagtgtatca tatgccaagt acgccccctta ttgacgtcaa      600 tgacggtaaa tggcccgcct ggcattatgc ccagtacatg accttatggg actttcctac       660
ttggcagtac atctacgtat tagtcatcgc tattaccatg gtgatgcggt tttggcagta       720
catcaatggg cgtggatagc ggtttgactc acggggattt ccaagtctcc accccattga       780
cgtcaatggg agtttgtttt ggcaccaaaa tcaacgggac tttccaaaat gtcgtaacaa       840
ctccgcccca ttgacgcaaa tgggcggtag gcgtgtacgg tgggaggtct atataagcag       900
agctcgttta gtgaaccgtc agatcgcctg gagacgccat ccacgctgtt ttgacctcca       960
tagaagacac cgggaccgat ccagcctcca tcggctcgca tctctccttc acgcgcccgc      1020
```

```
cgccttacct gaggccgcca tccacgccgg ttgagtcgcg ttctgccgcc tcccgcctgt    1080
ggtgcctcct gaactacgtc cgccgtctag gtaagtttag agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacga tatcgccgcc atggagggcc tgagcctgct    1380
gcagctgccc agggacaagt tcaggaagag cagcttcttc gtgtgggtga tcatcctgtt    1440
ccagaaggcc ttcagcatgc ccctgggcgt ggtgaccaac agcaccctgg aggtgaccga    1500
gatcgaccag ctggtgtgca aggaccacct ggccagcacc gaccagctga gagcgtggg    1560 cctgaacctg gagggcagcg gcgtgagcac cgacatcccc agcgccacca agaggtgggg    1620
cttcaggagc ggcgtgcctc ccaaggtggt gagctacgag gccggcgagt gggccgagaa    1680
ctgctacaac ctgagagatca agaagcccga cggcagcgag tgcctgcctc ctcctcctga    1740
cggcgtgagg ggcttcccca ggtgcaggta cgtgcacaag gcccagggca ccggcccctg    1800
ccccggcgac tacgccttcc acaaggacgc cgccttcttc ctgtacgaca ggctggccag    1860
caccgtgatc tacaggggcg tgaacttcgc cgagggcgtg atcgccttcc tgatcctggc    1920
caagcccaag gagaccttcc tgcagagccc tcccatcagg gaggccgtga actacaccga    1980
gaacaccagc agctactacg ccaccagcta tctagagtac gagatcgaga acttcggcgc    2040
ccagcacagc accaccctgt tcaagatcga caacaacacc ttcgtgaggc tggacaggcc    2100
ccacacccct cagttcctgt tccagctgaa cgacaccatc cacctgcacc agcagctgag    2160
caacaccacc ggcaggctga tctggaccct ggacgccaac atcaacgccg acatcggcga    2220
gtgggccttc tgggagaaca agaagaacct gagcgagcag ctgagggcg aggagctgag    2280 cttcgaggcc ctgagcctga acgagaccga ggacgacgac gccgccagca gcaggatcac    2340
caagggcagg atcagcgaca gggccaccag gaagtacagc gacctggtgc ccaagaacag    2400 cccccggcatg gtgcccctgc acatccccga gggcagacc accctgccca gccagaacag    2460
caccgagggc aggagggtgg gcgtgaacac ccaggagacc atcaccgaga ccgccgccac    2520
catcatcggc accaacggca accacatgca gatcagcacc atcggcatca ggcccagcag    2580
cagccagatc cccagcagca gccccaccac cgcccctagc cccgaggccc agaccccac    2640 cacccacacc agcggaccca gcgtgatggc caccgaggag cccaccaccc ctccccggcag    2700 cagccccgga cccaccaccg aggcccctac cctgaccacc cctgagaaca tcaccaccgc    2760
cgtgaagacc gtgctgcccc aggagagcac cagcaacggc ctgatcacca gcaccgtgac    2820
cggcatcctg ggcagcctgg gcctgaggaa gaggagcagg aggcagacca acaccaaggc    2880
caccggcaag tgcaacccca acctgcacta ctggaccgcc caggagcagc acaacgccgc    2940
cggcatcgcc tggattccct acttcggccc cggcgccgag ggcatctaca ccgagggcct    3000
gatgcacaac cagaacgccc tggtgtgcgg cctgaggcag ctggccaacg agaccaccca    3060
ggccctgcag ctgttcctga gggccaccac cgagctgagg acctacacca tcctgaacag    3120
gaaggccatc gacttcctgc tgaggaggtg gggcggcacc tgcaggattc tgggccccga    3180
ctgctgcatc gagccccacg actggaccaa gaacatcacc gacaagatca ccagatcat    3240 ccacgacttc atcgacaacc ctctgcccaa ccaggacaac gacgacaact ggtggaccgg    3300
ctgaacacgt ggaattgatc tgctgtgcct tctagttgcc agccatctgt tgtttgcccc    3360
tcccccgtgc cttccttgac cctggaaggt gccactccca ctgtccttc ctaataaaat    3420
```

```
gaggaaattg catcgcattg tctgagtagg tgtcattcta ttctgggggg tggggtgggg    3480
caggacagca aggggagga ttgggaagac aatagcaggc atgctgggga tgcggtgggc    3540
tctatgggta cccaggtgct gaagaattga cccggttcct cctgggccag aaagaagcag    3600
gcacatcccc ttctctgtga cacaccctgt ccacgcccct ggttcttagt tccagcccca    3660
ctcataggac actcatagct caggagggct ccgccttcaa tcccaccgc taaagtactt     3720 ggagcggtct ctccctccct catcagccca ccaaaccaaa cctagcctcc aagagtggga    3780
agaaattaaa gcaagatagg ctattaagtg cagagggaga gaaatgcct ccaacatgtg     3840 aggaagtaat gagagaaatc atagaatttt aaggccatca tggccttaat cttccgcttc    3900
ctcgctcact gactcgctgc gctcggtcgt tcggctgcgg cgagcggtat cagctcactc    3960
aaaggcggta atacggttat ccacagaatc agggggataac gcaggaaaga acatgtgagc   4020
aaaaggccag caaaaggcca ggaaccgtaa aaaggccgcg ttgctggcgt ttttccatag    4080
gctccgcccc cctgacgagc atcacaaaaa tcgacgctca gtcagaggt ggcgaaaccc     4140 gacaggacta taaagatacc aggcgtttcc ccctggaagc tccctcgtgc gctctcctgt    4200
tccgaccctg ccgcttaccg gatacctgtc cgcctttctc ccttcgggaa gcgtggcgct    4260
ttctcatagc tcacgctgta ggtatctcag ttcggtgtag gtcgttcgct ccaagctggg    4320
ctgtgtgcac gaaccccccg ttcagcccga ccgctgcgcc ttatccggta actatcgtct    4380
tgagtccaac ccggtaagac acgacttatc gccactggca gcagccactg gtaacaggat    4440
tagcagagcg aggtatgtag gcggtgctac agagttcttg aagtggtggc ctaactacgg    4500
ctacactaga agaacagtat ttggtatctg cgctctgctg aagccagtta ccttcggaaa    4560
aagagttggt agctcttgat ccggcaaaca aaccaccgct ggtagcggtg gtttttttgt    4620
ttgcaagcag cagattacgc gcagaaaaaa aggatctcaa gaagatcctt tgatcttttc    4680 tacgggtct gacgctcagt ggaacgaaaa ctcacgttaa gggattttgg tcatgagatt      4740
atcaaaaagg atcttcacct agatcctttt aaattaaaaa tgaagtttta atcaatcta     4800 aagtatatat gagtaaactt ggtctgacag ttaccaatgc ttaatcagtg aggcaccta     4860 ctcagcgatc tgtctatttc gttcatccat agttgcctga ctcggggggg ggggcgctg     4920 aggtctgcct cgtgaagaag gtgttgctga ctcataccag gcctgaatcg ccccatcatc    4980
cagccagaaa gtgagggagc cacggttgat gagagctttg ttgtaggtgg accagttggt    5040
gattttgaac ttttgctttg ccacggaacg gtctgcgttg tcgggaagat gcgtgatctg    5100
atccttcaac tcagcaaaag ttcgatttat tcaacaaagc cgccgtcccg tcaagtcagc    5160
gtaatgctct gccagtgtta caaccaatta accaattctg attagaaaaa ctcatcgagc    5220
atcaaatgaa actgcaattt attcatatca ggattatcaa taccatattt ttgaaaaagc    5280
cgtttctgta atgaaggaga aaactcaccg aggcagttcc ataggatggc aagatcctgg    5340
tatcggtctg cgattccgac tcgtccaaca tcaatacaac ctattaattt ccctcgtca    5400 aaaataaggt tatcaagtga gaaatcacca tgagtgacga ctgaatccgg tgagaatggc    5460
aaaagcttat gcatttcttt ccagacttgt tcaacaggcc agccattacg ctcgtcatca    5520
aaatcactcg catcaaccaa accgttattc attcgtgatt gcgcctgagc gagacgaaat    5580
acgcgatcgc tgttaaaagg acaattacaa acaggaatcg aatgcaaccg gcgcaggaac    5640
actgccagcg catcaacaat attttcacct gaatcaggat attcttctaa tacctggaat    5700
gctgttttcc cggggatcgc agtggtgagt aaccatgcat catcaggagt acggataaaa    5760
tgcttgatgg tcggaagagg cataaattcc gtcagccagt ttagtctgac catctcatct    5820
```

-continued

```
gtaacatcat tggcaacgct acctttgcca tgtttcagaa acaactctgg cgcatcgggc     5880
ttcccataca atcgatagat tgtcgcacct gattgcccga cattatcgcg agcccattta     5940
tacccatata aatcagcatc catgttggaa tttaatcgcg gcctcgagca agacgtttcc     6000
cgttgaatat ggctcataac accccttgta ttactgttta tgtaagcaga cagttttatt     6060
gttcatgatg atatatttt atcttgtgca atgtaacatc agagattttg agacacaacg     6120
tggctttccc ccccccccca ttattgaagc atttatcagg gttattgtct catgagcgga     6180
tacatatttg aatgtattta gaaaaataaa caaataggg ttccgcgcac atttccccga     6240
aaagtgccac ctgacgtcta agaaaccatt attatcatga cattaaccta aaaaatagg     6300 cgtatcacga ggccctttcg tc                                              6322
```

<210> SEQ ID NO 40
<211> LENGTH: 6324
<212> TYPE: DNA
<213> ORGANISM: Artificial Sequence
<220> FEATURE:
<223> OTHER INFORMATION: Synthetic Construct CMV/R-GP(S, Q66798)(dTM)/h

<400> SEQUENCE: 40

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540 tgccccacttg gcagtacatc aagtgtatca tatgccaagt acgccccctta ttgacgtcaa     600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctcca tcggctcgca tctctccttc acgcgcccgc    1020
cgccttacct gaggccgcca tccacgccgg ttgagtcgcg ttctgccgcc tcccgcctgt    1080
ggtgcctcct gaactacgtc cgccgtctag gtaagtttag agctcaggtc gagaccgggc    1140
ctttgtccgg cgctcccttg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacga tatcgccgcc atggagggcc tgagcctgct    1380
gcagctgccc agggacaagt tcaggaagag cagcttcttc gtgtgggtga tcatcctgtt    1440
ccagaaggcc ttcagcatgc cctgggcgt ggtgaccaac agcacctgg aggtgaccga    1500 gatcgaccag ctggtgtgca aggaccacct ggccagcacc gaccagctga agagcgtggg    1560
```

-continued

```
cctgaacctg gagggcagcg gcgtgagcac cgacatcccc agcgccacca agaggtgggg    1620
cttcaggagc ggcgtgcctc cccaggtggt gagctacgag gccggcgagt gggccgagaa    1680
ctgctacaac ctggagatca agaagcccga cggcagcgag tgcctgcctc ctcctcctga    1740
cggcgtgagg ggcttcccca ggtgcaggta cgtgcacaag gcccagggca ccggcccctg    1800
ccccggcgac tacgccttcc acaaggacgg cgccttcttc ctgtacgaca ggctggccag    1860
caccgtgatc tacaggggcg tgaacttcgc cgagggcgtg atcgccttcc tgatcctggc    1920
caagcccaag gagaccttcc tgcagagccc tcccatcagg gaggccgcca actacaccga    1980
gaacaccagc agctactacg ccaccagcta tctagagtac gagatcgaga acttcggcgc    2040
ccagcacagc accaccctgt tcaagatcaa caacaacacc ttcgtgctgc tggacaggcc    2100
ccacacccct cagttcctgt tccagctgaa cgacaccatc cagctgcacc agcagctgag    2160
caacaccacc ggcaagctga tctggaccct ggacgccaac atcaacgccg acatcggcga    2220
gtgggccttc tgggagaaca agaagaacct gagcgagcag ctgaggggcg aggagctgag    2280
cttcgagacc ctgagcctga cgagaccga ggacgacgac gccaccagca gcaggaccac    2340
caagggcagg atcagcgaca gggccaccag gaagtacagc gacctggtgc caaggacag    2400 ccccggcatg gtgagcctgc acgtgcccga gggcgagacc accctgccca gccagaacag    2460
caccgagggc aggagggtgg acgtgaacac caggagacc atcaccgaga ccaccgccac    2520
catcatcggc accaacggca acaacatgca gatcagcacc atcggcaccg gcctgagcag    2580
cagccagatc ctgagcagca gccccaccat ggcccctagc cccgagaccc agaccagcac    2640
cacctacacc cctaagctgc ccgtgatgac caccgaggag cccaccaccc ctcccaggaa    2700
cagccccgga tccaccaccg aggccctac cctgaccacc cctgagaaca tcaccaccgc    2760
cgtgaagacc gtgtgggccc aggagagcac cagcaacggc ctgatcacca gcaccgtgac    2820
cggcatcctg ggcagcctgg gcctgaggaa gaggagcagg aggcaggtga acaccagggc    2880
caccggcaag tgcaaccca acctgcacta ctggaccgcc caggagcagc acacgccgc    2940 cggcatcgcc tggattccct acttcggccc cggcgccgag ggcatctaca ccgagggcct    3000
gatgcacaac cagaacgccc tggtgtgcgg cctgaggcag ctggccaacg agaccaccca    3060
ggccctgcag ctgttcctga gggccaccac cgagctgagg acctaccaca tcctgaacag    3120
gaaggccatc gacttcctgc tgaggaggtg gggcggcacc tgcaggattc tgggccccga    3180
ctgctgcatc gagccccacg actgaccaa gaacatcacc gacaagatca accagatcat    3240
ccacgacttc atcgacaacc ctctgcccaa ccaggacaac gacgacaact ggtggaccgg    3300
ctgaacacgt ggaattcaga tctgctgtgc cttctagttg ccagccatct gttgtttgcc    3360
cctcccccgt gccttccttg accctggaag gtgccactcc cactgtcctt tcctaataaa    3420
atgaggaaat tgcatcgcat tgtctgagta ggtgtcattc tattctgggg ggtggggtgg    3480
ggcaggacag caaggggag gattgggaag acaatagcag gcatgctggg gatgcggtgg    3540
gctctatggg tacccaggtg ctgaagaatt gacccggttc ctcctgggcc agaaagaagc    3600
aggcacatcc ccttctctgt gacacaccct gtccacgccc ctggttctta gttccagccc    3660
cactcatagg acactcatag ctcaggaggg ctccgccttc aatcccaccc gctaaagtac    3720
ttggagcggt ctctccctcc ctcatcagcc caccaaacca aacctagcct caagagtgg    3780 gaagaaatta agcaagata ggctattaag tgcagaggga gagaaatgc ctccaacatg    3840 tgaggaagta atgagagaaa tcatagaatt ttaaggccat catggcctta atcttccgct    3900
tcctcgctca ctgactcgct gcgctcggtc gttcggctgc ggcgagcggt atcagctcac    3960
```

-continued

```
tcaaaggcgg taatacggtt atccacagaa tcaggggata acgcaggaaa gaacatgtga    4020
gcaaaaggcc agcaaaaggc caggaaccgt aaaaaggccg cgttgctggc gttttttccat    4080 aggctccgcc ccctgacga gcatcacaaa atcgacgct caagtcagag gtggcgaaac     4140
ccgacaggac tataaagata ccaggcgttt ccccctggaa gctccctcgt gcgctctcct    4200
gttccgaccc tgccgcttac cggatacctg tccgccttc tcccttcggg aagcgtggcg    4260
ctttctcata gctcacgctg taggtatctc agttcggtgt aggtcgttcg ctccaagctg    4320
ggctgtgtgc acgaaccccc cgttcagccc gaccgctgcg ccttatccgg taactatcgt    4380
cttgagtcca acccggtaag acacgactta tcgccactgg cagcagccac tggtaacagg    4440
attagcagag cgaggtatgt aggcggtgct acagagttct tgaagtggtg cctaactac    4500 ggctacacta gaagaacagt atttggtatc tgcgctctgc tgaagccagt taccttcgga    4560
aaaagagttg gtagctcttg atccggcaaa caaaccaccg ctggtagcgg tggttttttt    4620
gtttgcaagc agcagattac gcgcagaaaa aaggatctc aagaagatcc tttgatcttt    4680 tctacgggt ctgacgctca gtggaacgaa aactcacgtt aagggatttt ggtcatgaga    4740
ttatcaaaaa ggatcttcac ctagatcctt taaattaaa aatgaagttt taaatcaatc    4800
taaagtatat atgagtaaac ttggtctgac agttaccaat gcttaatcag tgaggcacct    4860
atctcagcga tctgtctatt tcgttcatcc atagttgcct gactcggggg ggggggcgc    4920 tgaggtctgc ctcgtgaaga aggtgttgct gactcatacc aggcctgaat cgccccatca    4980
tccagccaga aagtgaggga gccacggttg atgagagctt tgttgtaggt ggaccagttg    5040
gtgattttga acttttgctt tgccacggaa cggtctgcgt tgtcgggaag atgcgtgatc    5100
tgatccttca actcagcaaa agttcgattt attcaacaaa gccgccgtcc cgtcaagtca    5160
gcgtaatgct ctgccagtgt acaaccaat taaccaattc tgattagaaa aactcatcga    5220
gcatcaaatg aaactgcaat ttattcatat caggattatc aataccatat ttttgaaaaa    5280
gccgtttctg taatgaagga gaaaactcac cgaggcagtt ccataggatg caagatcct    5340 ggtatcggtc tgcgattccg actcgtccaa catcaataca acctattaat ttcccctcgt    5400 caaaataag gttatcaagt gagaaatcac catgagtgac gactgaatcc ggtgagaatg    5460
gcaaaagctt atgcatttct ttccagactt gttcaacagg ccagccatta cgctcgtcat    5520
caaaatcact cgcatcaacc aaaccgttat tcattcgtga ttgcgcctga gcgagacgaa    5580
atacgcgatc gctgttaaaa ggacaattac aaacaggaat cgaatgcaac cggcgcagga    5640
acactgccag cgcatcaaca atattttcac ctgaatcagg atattcttct aatacctgga    5700
atgctgtttt cccggggatc gcagtggtga gtaaccatgc atcatcagga gtacggataa    5760
aatgcttgat ggtcggaaga ggcataaatt ccgtcagcca gtttagtctg accatctcat    5820
ctgtaacatc attggcaacg ctacctttgc catgtttcag aaacaactct ggcgcatcgg    5880
gcttcccata caatcgatag attgtcgcac ctgattgccc gacattatcg cgagcccatt    5940
tatacccata taaatcagca tccatgttgg aatttaatcg cggcctcgag caagacgttt    6000
cccgttgaat atggctcata caccccttg tattactgtt tatgtaagca gacagtttta    6060
ttgttcatga tgatatattt ttatcttgtg caatgtaaca tcagagattt tgagacacaa    6120
cgtggctttc ccccccccc cattattgaa gcatttatca gggttattgt ctcatgagcg    6180
gatacatatt tgaatgtatt tagaaaaata acaaataggg gttccgcgc acatttcccc    6240 gaaaagtgcc acctgacgtc taagaaacca ttattatcat gacattaacc tataaaaata    6300
ggcgtatcac gaggcccttt cgtc                                         6324
```

-continued

<210> SEQ ID NO 41
<211> LENGTH: 6236
<212> TYPE: DNA
<213> ORGANISM: Artificial Sequence
<220> FEATURE:
<223> OTHER INFORMATION: Synthetic Construct pVR1012x/s Lassa (codon optimized)

<400> SEQUENCE: 41

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga gatatcgccg   1920
ccatgggcca gatcgtgacc ttcttccagg aggtgcccca tgtgatcgag gaggtgatga   1980
acatcgtgct gatcgccctg agcgtgctgg ccgtgctgaa gggcctgtac aacttcgcca   2040
cctgcggcct ggtgggcctg gtgaccttcc tgctgctgtg cggcaggagc tgcaccacca   2100
```

```
gcctgtacaa gggcgtgtac gagctgcaga ccctggagct gaacatggag accctgaaca  2160
tgaccatgcc cctgagctgc accaagaaca acagccacca ctacatcatg gtgggcaacg  2220
agaccggcct ggagctaacc ctgaccaaca ccagcatcat caaccacaag ttctgcaacc  2280
tgagcgacgc ccacaagaag aacctgtacg accacgccct gatgagcatc atcagcacct  2340
tccacctgag catccccaac ttcaaccagt acgaggccat gagctgcgac ttcaacggcg  2400
gcaagatcag cgtgcagtac aacctgagcc acagctacgc cggcgacgcc gccaaccact  2460
gcggcaccgt ggccaacggc gtgctgcaga ccttcatgag gatggcctgg ggcggcagct  2520
acatcgccct ggacagcggc aggggcaact gggactgcat catgaccagc taccagtacc  2580
tgatcatcca gaacaccacc tgggaggacc actgccagtt cagcaggccc agccccatcg  2640
gctacctggg cctgctgagc cagaggacca gggacatcta catcagcagg aggctgctgg  2700
gcaccttcac ctggaccctg agcgacagcg agggcaagga cacacccggc ggctactgcc  2760
tgaccaggtg gatgctgatc gaggccgagc tgaagtgctt cggcaacacc gccgtggcca  2820
agtgcaacga gaagcacgac gaggagttct gcgacatgct gaggctgttc gacttcaaca  2880
agcaggccat ccgagggctg aaggccgagc cccagatgag catccagctg atcaacaagg  2940
ccgtgaacgc cctgatcaac gaccagctga tcatgaagaa ccacctgagg gacatcatgg  3000
gcatccccta ctgcaactac agcaagtact ggtacctgaa ccacaccacc accggcagga  3060
ccagcctgcc caagtgctgg ctggtgagca acggcagcta cctgaacgag acccacttca  3120
gcgacgacat cgagcagcag gccgacaaca tgatcaccga gatgctgcag aaggagtaca  3180
tggagaggca gggcaagacc tgaacacgtg ggatccagat ctgctgtgcc ttctagttgc  3240
cagccatctg ttgtttgccc ctcccccgtg ccttccttga ccctggaagg tgccactccc  3300
actgtccttt cctaataaaa tgaggaaatt gcatcgcatt gtctgagtag gtgtcattct  3360
attctggggg gtggggtggg gcaggacagc aaggggagg attgggaaga caatagcagg  3420
catgctgggg atgcggtggg ctctatgggt acccaggtgc tgaagaattg acccggttcc  3480
tcctgggcca gaaagaagca ggcacatccc cttctctgtg acacccctg tccacgcccc  3540 tggttcttag ttccagcccc actcatagga cactcatagc tcaggagggc tccgccttca  3600
atcccacccg ctaaagtact tggagcggtc tctccctccc tcatcagccc accaaaccaa  3660
acctagcctc caagagtggg aagaaattaa agcaagatag gctattaagt gcagagggag  3720
agaaaatgcc tccaacatgt gaggaagtaa tgagagaaat catagaattt taaggccatg  3780
atttaaggcc atcatggcct taatcttccg cttcctcgct cactgactcg ctgcgctcgg  3840
tcgttcggct gcggcgagcg gtatcagctc actcaaaggc ggtaatacgg ttatccacag  3900
aatcagggga taacgcagga agaacatgt gagcaaaagg ccagcaaaag gccaggaacc  3960
gtaaaaaggc cgcgttgctg gcgttttcc ataggctccg cccccctgac gagcatcaca  4020
aaaatcgacg ctcaagtcag aggtggcgaa acccgacagg actataaaga taccaggcgt  4080
ttccccctgg aagctccctc gtgcgctctc ctgttccgac cctgccgctt accggatacc  4140
tgtccgcctt tctcccttcg ggaagcgtgg cgctttctca tagctcacgc tgtaggtatc  4200
tcagttcggt gtaggtcgtt cgctccaagc tgggctgtgt gcacgaaccc cccgttcagc  4260
ccgaccgctg cgccttatcc ggtaactatc gtcttgagtc aacccggta agacacgact  4320 tatcgccact ggcagcagcc actggtaaca ggattagcag agcgaggtat gtaggcggtg  4380
ctacagagtt cttgaagtgg tggcctaact acggctacac tagaagaaca gtatttggta  4440
tctgcgctct gctgaagcca gttaccttcg gaaaaagagt tggtagctct tgatccggca  4500
```

```
aacaaaccac cgctggtagc ggtggttttt ttgtttgcaa gcagcagatt acgcgcagaa   4560 aaaaggatc tcaagaagat cctttgatct tttctacggg gtctgacgct cagtggaacg    4620
aaaactcacg ttaagggatt ttggtcatga gattatcaaa aaggatcttc acctagatcc   4680
ttttaaatta aaaatgaagt tttaaatcaa tctaaagtat atatgagtaa acttggtctg   4740
acagttacca atgcttaatc agtgaggcac ctatctcagc gatctgtcta tttcgttcat   4800
ccatagttgc ctgactcggg gggggggggc gctgaggtct gcctcgtgaa gaaggtgttg   4860
ctgactcata ccaggcctga atcgccccat catccagcca gaaagtgagg gagccacggt   4920
tgatgagagc tttgttgtag gtggaccagt tggtgatttt gaacttttgc tttgccacgg   4980
aacggtctgc gttgtcggga agatgcgtga tctgatcctt caactcagca aaagttcgat   5040
ttattcaaca aagccgccgt cccgtcaagt cagcgtaatg ctctgccagt gttacaacca   5100
attaaccaat tctgattaga aaaactcatc gagcatcaaa tgaaactgca atttattcat   5160
atcaggatta tcaataccat ttttttgaaa agccgtttc tgtaatgaag gagaaaactc      5220
accgaggcag ttccatagga tggcaagatc ctggtatcgg tctgcgattc cgactcgtcc   5280
aacatcaata caacctatta atttcccctc gtcaaaaata aggttatcaa gtgagaaatc   5340
accatgagtg acgactgaat ccggtgagaa tggcaaaagc ttatgcattt ctttccagac   5400
ttgttcaaca ggccagccat tacgctcgtc atcaaaatca ctcgcatcaa ccaaaccgtt   5460
attcattcgt gattgcgcct gagcgagacg aaatacgcga tcgctgttaa aaggacaatt   5520
acaaacagga tcgaatgcaa ccggcgcag gaacactgcc agcgcatcaa caatattttc     5580
acctgaatca ggatattctt ctaataccty gaatgctgtt ttcccgggga tcgcagtggt   5640
gagtaaccat gcatcatcag gagtacggat aaaatgcttg atggtcggaa gaggcataaa   5700
ttccgtcagc cagtttagtc tgaccatctc atctgtaaca tcattggcaa cgctacctttt   5760 gccatgtttc agaaacaact ctggcgcatc gggcttccca taaatcgat agattgtcgc     5820 acctgattgc ccgacattat cgcgagccca tttatacccta tataaatcag catccatgtt   5880
ggaatttaat cgcggcctcg agcaagacgt ttcccgttga atatggctca taacacccct   5940
tgtattactg tttatgtaag cagacagttt tattgttcat gatgatatat ttttatcttg   6000
tgcaatgtaa catcagagat tttgagacac aacgtggctt tccccccccc cccattattg   6060
aagcatttat cagggttatt gtctcatgag cggatacata tttgaatgta tttagaaaaa   6120
taaacaaata ggggttccgc gcacatttcc ccgaaaagtg ccacctgacg tctaagaaac   6180
cattattatc atgacattaa cctataaaaa taggcgtatc acgaggccct ttcgtc       6236
```

<210> SEQ ID NO 42
<211> LENGTH: 6902
<212> TYPE: DNA
<213> ORGANISM: Artificial Sequence
<220> FEATURE:
<223> OTHER INFORMATION: Synthetic Construct pVR1012x/s Marburg (codon optimized)

<400> SEQUENCE: 42

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
```

-continued

```
tccaacatta ccgccatgtt gacattgatt attgactagt tattaatagt aatcaattac    360
ggggtcatta gttcatagcc catatatgga gttccgcgtt ataacttac cggtaaatgg     420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960
tagaagacac cgggaccgat ccagcctccg cggccgggaa cggtgcattg aacgcggat   1020
tccccgtgcc aagagtgacg taagtaccgc ctatagactc tataggcaca ccctttggc   1080
tcttatgcat gctatactgt ttttggcttg gggcctatac accccgctt ccttatgcta    1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcgtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga gatatcgccg    1920
ccatgaagac cacctgcctg ttcatcagcc tgatcctgat ccagggcatc aagaccctgc    1980
ccatcctgga gatcgccagc aacaaccagc cccagaacgt ggacagcgtg tgcagcggca    2040
ccctgcagaa gaccgaggac gtgcacctga tgggcttcac cctgagcggc cagaaggtgg    2100
ccgacagccc tctggaggcc agcaagaggt gggccttcag gaccggcgtg ccccccaaga    2160
acgtggagta caccgagggc gaggaggcca agacctgcta caacatcagc gtgaccgacc    2220
ccagcggcaa gagcctgctg ctggaccctc caccaacat cagggactac cctaagtgca    2280
agaccatcca ccacatccag ggccagaacc ctcacgccca gggcatcgcc ctgcacctgt    2340
ggggcgcctt cttcctgtac gacaggatcc cagcaccac catgtacagg gcagggtgt    2400
tcaccgaggg caacatcgcc gccatgatcg ttaacaagac cgtgcacaag atgatcttca    2460
gcaggcaggg ccaggctac aggcacatga acctgaccag caccaacaag tactggacca    2520
gcaacaacgg cacccagacc aacgacaccg gctgcttcgg cgccctgcag gagtacaaca    2580
gcaccaagaa ccagacctgc gccccagca agatccccag ccccctgccc accgccaggc    2640
ccgagatcaa gcccaccagc accccaccg acgccaccac cctgaacacc accgacccca    2700
```

```
acaacgacga cgaggacctg atcaccagcg gcagcggcag cggcgagcag gagccctaca   2760
ccaccagcga cgccgtgacc aagcagggcc tgagcagcac catgcctcct accccctagcc  2820
ctcagcccag caccccctcag caggagggca acaacaccga ccacagccag ggcaccgtga   2880
ccgagcccaa caagaccaac accaccgccc agcccagcat gcctcctcac aacaccaccg   2940
ccatcagcac caacaacacc agcaagaaca acttcagcac cctgagcgtg agcctgcaga   3000
acaccaccaa ctacgacacc cagagcaccg ccaccgagaa cgagcagacc agcgccccta   3060
gcaagaccac cctgcctccc accggcaacc tgaccaccgc caagagcacc aacaacacca   3120
agggccccac caccaccgcc cctaacatga ccaacgccca cctgaccagc ccagccccca   3180
cccccaaccc caccacccag cacctggtgt acttcaggaa gaagaggagc atcctgtgga   3240
gggagggcga tatgttcccc ttcctggacg gcctgatcaa cgcccctatc gacttcgacc   3300
ccgtgcccaa caccaagacc atcttcgacg agagcagcag cagcggcgcc agcgccgagg   3360
aggaccagca cgccagcccc aacatcagcc tgaccctgag ctacttcccc aacatcaacg   3420
agaacaccgc ctacagcggc gagaacgaga cgactgcga cgccgagctg aggatctgga   3480
gcgtgcagga ggacgacctg gccgccgcc  tgagctggat tcccttcttc ggccccggca   3540
tcgagggcct gtacaccgcc ggcctgatca agaaccagaa caacctggtg tgcaggctga   3600
ggaggctggc caaccagacc gccaagagcc tggagctgct gctgagggtg accaccgagg   3660
agaggaccct cagcctgatc aacaggcacg ccatcgactt cctgctgacc aggtggggcg   3720
gcacctgcaa ggtgctgggc cccgactgct gcatcggcat cgaggacctg agcaggaaca   3780
tcagcgagca gatcgaccag atcaagaagg acgagcagaa ggagggcacc ggctggggcc   3840
tgggcggcaa gtggtggacc agcgactgaa cacgtgggat ccagatctgc tgtgccttct   3900
agttgccagc catctgttgt ttgcccctcc cccgtgcctt ccttgaccct ggaaggtgcc   3960
actcccactg tcctttccta ataaaatgag gaaattgcat cgcattgtct gagtaggtgt   4020
cattctattc tggggggtgg ggtggggcag gacagcaagg gggaggattg ggaagacaat   4080
agcaggcatg ctgggatgc ggtgggctct atgggtaccc aggtgctgaa gaattgaccc    4140
ggttcctcct gggccagaaa gaagcaggca catcccttc tctgtgacac accctgtcca    4200
cgccctggt tcttagttcc agccccactc ataggacact catagctcag gagggctccg    4260
ccttcaatcc caccgctaa agtacttgga gcggtctctc cctccctcat cagcccacca    4320
aaccaaacct agcctccaag agtgggaaga aattaaagca agataggcta ttaagtgcag   4380
agggagagaa aatgcctcca acatgtgagg aagtaatgag agaaatcata gaattttaag   4440
gccatgattt aaggccatca tggccttaat cttccgcttc ctcgctcact gactcgctgc   4500
gctcggtcgt tcggctgcgg cgagcggtat cagctcactc aaaggcggta atacggttat   4560
ccacagaatc aggggataac gcaggaaaga acatgtgagc aaaaggccag caaaaggcca   4620
ggaaccgtaa aaaggccgcg ttgctggcgt ttttccatag gctccgcccc cctgacgagc   4680
atcacaaaaa tcgacgctca agtcagaggt ggcgaaaccc gacaggacta taaagatacc   4740
aggcgtttcc ccctggaagc tccctcgtgc gctctcctgt tccgaccctg ccgcttaccg   4800
gatacctgtc cgcctttctc ccttcgggaa gcgtggcgct ttctcatagc tcacgctgta   4860
ggtatctcag ttcggtgtag gtcgttcgct ccaagctggg ctgtgtgcac gaaccccccg   4920
ttcagcccga ccgctgcgcc ttatccggta actatcgtct tgagtccaac ccggtaagac   4980
acgacttatc gccactggca gcagccactg gtaacaggat tagcagagcg aggtatgtag   5040
gcggtgctac agagttcttg aagtggtggc ctaactacgg ctacactaga agaacagtat   5100
```

```
ttggtatctg cgctctgctg aagccagtta ccttcggaaa aagagttggt agctcttgat    5160
ccggcaaaca aaccaccgct ggtagcggtg gttttttgt ttgcaagcag cagattacgc      5220
gcagaaaaaa aggatctcaa gaagatcctt tgatctttc tacggggtct gacgctcagt      5280
ggaacgaaaa ctcacgttaa gggattttgg tcatgagatt atcaaaaagg atcttcacct    5340 agatccttt aaattaaaaa tgaagtttta aatcaatcta agtatatat gagtaaactt       5400 ggtctgacag ttaccaatgc ttaatcagtg aggcacctat ctcagcgatc tgtctatttc    5460
gttcatccat agttgcctga ctcgggggg ggggcgctg aggtctgcct cgtgaagaag       5520
gtgttgctga ctcataccag gcctgaatcg ccccatcatc cagccagaaa gtagggagc     5580 cacggttgat gagagctttg ttgtaggtgg accagttggt gattttgaac ttttgctttg    5640
ccacggaacg gtctgcgttg tcgggaagat gcgtgatctg atccttcaac tcagcaaaag   5700
ttcgatttat tcaacaaagc cgccgtcccg tcaagtcagc gtaatgctct gccagtgtta    5760
caaccaatta accaattctg attagaaaaa ctcatcgagc atcaaatgaa actgcaattt   5820
attcatatca ggattatcaa taccatattt ttgaaaaagc cgtttctgta atgaaggaga   5880
aaactcaccg aggcagttcc ataggatggc aagatcctgg tatcggtctg cgattccgac    5940
tcgtccaaca tcaatacaac ctattaattt cccctcgtca aaataaggt tatcaagtga     6000 gaaatcacca tgagtgacga ctgaatccgg tgagaatggc aaaagcttat gcatttcttt   6060
ccagacttgt tcaacaggcc agccattacg ctcgtcatca aaatcactcg catcaaccaa   6120
accgttattc attcgtgatt gcgcctgagc gagacgaaat acgcgatcgc tgttaaaagg    6180
acaattacaa acaggaatcg aatgcaaccg gcgcaggaac actgccagcg catcaacaat   6240
attttcacct gaatcaggat attcttctaa tacctggaat gctgttttcc cggggatcgc   6300
agtggtgagt aaccatgcat catcaggagt acggataaaa tgcttgatgg tcggaagagg   6360
cataaattcc gtcagccagt ttagtctgac catctcatct gtaacatcat ggcaacgct    6420 accttttgcca tgtttcagaa acaactctgg cgcatcgggc ttcccataca atcgatagat   6480
tgtcgcacct gattgcccga cattatcgcg agcccattta tacccatata atcagcatc    6540 catgttggaa tttaatcgcg gcctcgagca agacgtttcc cgttgaatat ggctcataac   6600
accccttgta ttactgttta tgtaagcaga cagtttttatt gttcatgatg atatattttt   6660
atcttgtgca atgtaacatc agagattttg agacacaacg tggctttccc cccccccca    6720 ttattgaagc atttatcagg gttattgtct catgagcgga tacatatttg aatgtatta    6780 gaaaataaa caaatagggg ttccgcgcac atttccccga aaagtgccac ctgacgtcta   6840
agaaaccatt attatcatga cattaaccta taaaatagg cgtatcacga ggccctttcg    6900
tc                                                                    6902
```

<210> SEQ ID NO 43
<211> LENGTH: 6625
<212> TYPE: DNA
<213> ORGANISM: Artificial Sequence
<220> FEATURE:
<223> OTHER INFORMATION: Synthetic Construct CMV/R Ebola NP

<400> SEQUENCE: 43

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
```

-continued

| | |
|---|---|
| ctattggcca ttgcatacgt tgtatccata tcataatatg tacatttata ttggctcatg | 300 |
| tccaacatta ccgccatgtt gacattgatt attgactagt tattaatagt aatcaattac | 360 |
| ggggtcatta gttcatagcc catatatgga gttccgcgtt acataactta cggtaaatgg | 420 |
| cccgcctggc tgaccgccca acgacccccg cccattgacg tcaataatga cgtatgttcc | 480 |
| catagtaacg ccaataggga ctttccattg acgtcaatgg gtggagtatt tacggtaaac | 540 |
| tgcccacttg gcagtacatc aagtgtatca tatgccaagt acgcccccta ttgacgtcaa | 600 |
| tgacggtaaa tggcccgcct ggcattatgc ccagtacatg accttatggg actttcctac | 660 |
| ttggcagtac atctacgtat tagtcatcgc tattaccatg gtgatgcggt tttggcagta | 720 |
| catcaatggg cgtggatagc ggtttgactc acggggattt ccaagtctcc accccattga | 780 |
| cgtcaatggg agtttgtttt ggcaccaaaa tcaacgggac tttccaaaat gtcgtaacaa | 840 |
| ctccgcccca ttgacgcaaa tgggcggtag gcgtgtacgg tgggaggtct atataagcag | 900 |
| agctcgttta gtgaaccgtc agatcgcctg gagacgccat ccacgctgtt ttgacctcca | 960 |
| tagaagacac cgggaccgat ccagcctcca tcggctcgca tctctccttc acgcgcccgc | 1020 |
| cgccttacct gaggccgcca tccacgccgg ttgagtcgcg ttctgccgcc tcccgcctgt | 1080 |
| ggtgcctcct gaactacgtc cgccgtctag gtaagtttag agctcaggtc gagaccgggc | 1140 |
| ctttgtccgg cgctcccttg gagcctacct agactcagcc ggctctccac gctttgcctg | 1200 |
| accctgcttg ctcaactcta gttaacggtg gagggcagtg tagtctgagc agtactcgtt | 1260 |
| gctgccgcgc gcgccaccag acataatagc tgacagacta acagactgtt cctttccatg | 1320 |
| ggtcttttct gcagtcaccg tcgtcgacac gtgtgatcag atatcgcggc cgctctagac | 1380 |
| caggccctgg atccagatcg atccgagtat ggattctcgt cctcagaaaa tctggatggc | 1440 |
| gccgagtctc actgaatctg acatggatta ccacaagatc ttgacagcag gtctgtccgt | 1500 |
| tcaacagggg attgttcggc aaagagtcat cccagtgtat caagtaaaca atcttgaaga | 1560 |
| aatttgccaa cttatcatac aggcctttga agcaggtgtt gattttcaag agagtgcgga | 1620 |
| cagtttcctt ctcatgcttt gtcttcatca tgcgtaccag ggagattaca aacttttctt | 1680 |
| ggaaagtggc gcagtcaagt atttggaagg gcacgggttc cgttttgaag tcaagaagcg | 1740 |
| tgatggagtg aagcgccttg aggaattgct gccagcagta tctagtggaa aaaacattaa | 1800 |
| gagaacactt gctgccatgc cggaagagga gacaactgaa gctaatgccg gtcagtttct | 1860 |
| ctcctttgca gtctattcc ttccgaaatt ggtagtagga gaaaaggctt gccttgagaa | 1920 |
| ggttcaaagg caaattcaag tacatgcaga gcaaggactg atacaatatc caacagcttg | 1980 |
| gcaatcagta ggacacatga tggtgatttt ccgtttgatg cgaacaaatt ttctgatcaa | 2040 |
| atttctccta atacaccaag ggatgcacat ggttgccggg catgatgcca acgatgctgt | 2100 |
| gatttcaaat tcagtggctc aagctcgttt ttcaggctta ttgattgtca aaacagtact | 2160 |
| tgatcatatc ctacaaaaga cagaacgagg agttcgtctc catcctcttg caaggaccgc | 2220 |
| caaggtaaaa aatgaggtga actccttttaa ggctgcactc agctccctgg ccaagcatgg | 2280 |
| agagtatgct cctttcgccc gacttttgaa ccttt ctgga gtaaataatc ttgagcatgg | 2340 |
| tcttttccct caactatcgg caattgcact cggagtcgcc acagcacacg ggagtaccct | 2400 |
| cgcaggagta aatgttggag aacagtcatc acaactcaga gaggctgcca ctgaggctga | 2460 |
| gaagcaactc caacaatatg cagagtctcg cgaacttgac catcttggac ttgatgatca | 2520 |
| ggaaaagaaa attcttatga acttccatca gaaaaagaac gaaatcagct tccagcaaac | 2580 |
| aaacgctatg gtaactctaa gaaaagagcg cctggccaag ctgacagaag ctatcactgc | 2640 |

```
tgcgtcactg cccaaaacaa gtggacatta cgatgatgat gacgacattc cctttccagg    2700
acccatcaat gatgacgaca atcctggcca tcaagatgat gatccgactg actcacagga    2760
tacgaccatt cccgatgtgg tggttgatcc cgatgatgga agctacggcg aataccagag    2820
ttactcggaa aacggcatga atgcaccaga tgacttggtc ctattcgatc tagacgagga    2880
cgacgaggac actaagccag tgcctaatag atcgaccaag ggtggacaac agaagaacag    2940
tcaaaagggc cagcatatag agggcagaca gacacaatcc aggccaattc aaaatgtccc    3000
aggccctcac agaacaatcc accacgccag tgcgccactc acggacaatg acagaagaaa    3060
tgaaccctcc ggctcaacca gccctcgcat gctgacacca attaacgaag aggcagaccc    3120
actggacgat gccgacgacg agacgtctag ccttccgccc ttggagtcag atgatgaaga    3180
gcaggacagg gacggaactt ccaaccgcac acccactgtc gccccaccgg ctcccgtata    3240
cagagatcac tctgaaaaga aagaactccc gcaagacgag caacaagatc aggaccacac    3300
tcaagaggcc aggaaccagg acagtgacaa cacccagtca gaacactctt ttgaggagat    3360
gtatcgccac attctaagat cacaggggcc atttgatgct gttttgtatt atcatatgat    3420
gaaggatgag cctgtagttt tcagtaccag tgatggcaaa gagtacacgt atccagactc    3480
ccttgaagag gaatatccac catggctcac tgaaaaagag gctatgaatg aagagaatag    3540
atttgttaca ttggatggtc aacaatttta ttggccggtg atgaatcaca agaataaatt    3600
catggcaatc ctgcaacatc atcagctgtg ccttctagtt gccagccatc tgttgtttgc    3660
ccctccccg tgccttcctt gaccctggaa ggtgccactc ccactgtcct ttcctaataa    3720
aatgaggaaa ttgcatcgca ttgtctgagt aggtgtcatt ctattctggg gggtggggtg    3780
gggcaggaca gcaaggggga ggattgggaa gacaatagca ggcatgctgg ggatgcggtg    3840
ggctctatgg gtacccaggt gctgaagaat tgacccggtt cctcctgggc cagaaagaag    3900
caggcacatc cccttctctg tgacacaccc tgtccacgcc cctggttctt agttccagcc    3960
ccactcatag gacactcata gctcaggagg gctccgcctt caatcccacc cgctaaagta    4020
cttggagcgg tctctccctc cctcatcagc ccaccaaacc aaacctagcc tccaagagtg    4080
ggaagaaatt aaagcaagat aggctattaa gtgcagaggg agagaaaatg cctccaacat    4140
gtgaggaagt aatgagagaa atcatagaat tttaaggcca tcatggcctt aatcttccgc    4200
ttcctcgctc actgactcgc tgcgctcggt cgttcggctg cggcgagcgg tatcagctca    4260
ctcaaaggcg gtaatacggt tatccacaga atcaggggat aacgcaggaa agaacatgtg    4320
agcaaaaggc cagcaaaagg ccaggaaccg taaaaaggcc gcgttgctgg cgttttttcca    4380
taggctccgc ccccctgacg agcatcacaa aaatcgacgc tcaagtcaga ggtggcgaaa    4440
cccgacagga ctataaagat accaggcgtt tcccccctgga agctccctcg tgcgctctcc    4500
tgttccgacc ctgccgctta ccggatacct gtccgccttt ctcccttcgg aagcgtggc    4560
gctttctcat agctcacgct gtaggtatct cagttcggtg taggtcgttc gctccaagct    4620
gggctgtgtg cacgaacccc ccgttcagcc cgaccgctgc gccttatccg gtaactatcg    4680
tcttgagtcc aacccggtaa gacacgactt atcgccactg gcagcagcca ctggtaacag    4740
gattagcaga gcgaggtatg taggcggtgc tacagagttc ttgaagtggt ggcctaacta    4800
cggctacact agaagaacag tatttggtat ctgcgctctg ctgaagccag ttaccttcgg    4860
aaaaagagtt ggtagctctt gatccggcaa acaaaccacc gctggtagcg gtggtttttt    4920
tgtttgcaag cagcagatta cgcgcagaaa aaaaggatct caagaagatc ctttgatctt    4980
ttctacgggg tctgacgctc agtggaacga aaactcacgt taagggattt tggtcatgag    5040
```

-continued

```
attatcaaaa aggatcttca cctagatcct tttaaattaa aaatgaagtt ttaaatcaat      5100
ctaaagtata tatgagtaaa cttggtctga cagttaccaa tgcttaatca gtgaggcacc      5160
tatctcagcg atctgtctat ttcgttcatc catagttgcc tgactcgggg ggggggggcg      5220
ctgaggtctg cctcgtgaag aaggtgttgc tgactcatac caggcctgaa tcgccccatc      5280
atccagccag aaagtgaggg agccacggtt gatgagagct tgttgtagg tggaccagtt       5340 ggtgattttg aacttttgct tgccacggaa acggtctgcg ttgtcgggaa gatgcgtgat      5400
ctgatccttc aactcagcaa aagttcgatt tattcaacaa agccgccgtc ccgtcaagtc      5460
agcgtaatgc tctgccagtg ttacaaccaa ttaaccaatt ctgattagaa aaactcatcg      5520
agcatcaaat gaaactgcaa tttattcata tcaggattat caataccata tttttgaaaa      5580
agccgtttct gtaatgaagg agaaaactca ccgaggcagt tccataggat ggcaagatcc      5640
tggtatcggt ctgcgattcc gactcgtcca acatcaatac aacctattaa tttcccctcg      5700
tcaaaaataa ggttatcaag tgagaaatca ccatgagtga cgactgaatc cggtgagaat      5760
ggcaaaagct tatgcatttc tttccagact tgttcaacag gccagccatt acgctcgtca      5820
tcaaaatcac tcgcatcaac caaaccgtta ttcattcgtg attgcgcctg agcgagacga      5880
aatacgcgat cgctgttaaa aggacaatta caaacaggaa tcgaatgcaa ccggcgcagg      5940
aacactgcca gcgcatcaac aatattttca cctgaatcag gatattcttc taatacctgg      6000
aatgctgttt tcccggggat cgcagtggtg agtaaccatg catcatcagg agtacggata      6060
aaatgcttga tggtcggaag aggcataaat tccgtcagcc agtttagtct gaccatctca      6120
tctgtaacat cattggcaac gctaccttg ccatgtttca gaaacaactc tggcgcatcg       6180
ggcttcccat acaatcgata gattgtcgca cctgattgcc cgacattatc gcagcccat       6240 ttatacccat ataaatcagc atccatgttg gaatttaatc gcggcctcga gcaagacgtt      6300
tcccgttgaa tatggctcat aacaccccctt gtattactgt ttatgtaagc agacagtttt     6360
attgttcatg atgatatatt tttatcttgt gcaatgtaac atcagagatt ttgagacaca      6420
acgtggcttt ccccccccccc ccattattga agcatttatc agggttattg tctcatgagc     6480
ggatacatat ttgaatgtat ttagaaaaat aaacaaatag gggttccgcg cacatttccc      6540
cgaaaagtgc cacctgacgt ctaagaaacc attattatca tgacattaac ctataaaaat      6600
aggcgtatca cgaggccctt tcgtc                                            6625
```

```
<210> SEQ ID NO 44
<211> LENGTH: 22
<212> TYPE: DNA
<213> ORGANISM: Artificial Sequence
<220> FEATURE:
<223> OTHER INFORMATION: Ebola Sudan GP primer

<400> SEQUENCE: 44
atcttcagga tctcgccatg ga                                               22

<210> SEQ ID NO 45
<211> LENGTH: 24
<212> TYPE: DNA
<213> ORGANISM: Artificial Sequence
<220> FEATURE:
<223> OTHER INFORMATION: Ebola Sudan GP primer

<400> SEQUENCE: 45
gatattcaac aaagcagctt gcag                                             24
```

```
<210> SEQ ID NO 46
<211> LENGTH: 21
<212> TYPE: DNA
<213> ORGANISM: Artificial Sequence
<220> FEATURE:
<223> OTHER INFORMATION: Ebola Ivory Coast GP primer

<400> SEQUENCE: 46
ctaatcacag tcaccatggg a                                             21

<210> SEQ ID NO 47
<211> LENGTH: 24
<212> TYPE: DNA
<213> ORGANISM: Artificial Sequence
<220> FEATURE:
<223> OTHER INFORMATION: Ebola Ivory Coast GP primer

<400> SEQUENCE: 47
aaagtatgat gctatattag ttca                                          24

<210> SEQ ID NO 48
<211> LENGTH: 10
<212> TYPE: PRT
<213> ORGANISM: Ebola Virus

<400> SEQUENCE: 48

Gln Arg Thr Phe Ser Ile Pro Leu Gly Val
 1               5                  10

<210> SEQ ID NO 49
<211> LENGTH: 10
<212> TYPE: PRT
<213> ORGANISM: Ebola Virus

<400> SEQUENCE: 49

Arg Arg Thr Arg Arg Glu Ala Ile Val Asn
 1               5                  10

<210> SEQ ID NO 50
<211> LENGTH: 16
<212> TYPE: PRT
<213> ORGANISM: Ebola Virus

<400> SEQUENCE: 50

Gly Ala Ala Ile Gly Leu Ala Trp Ile Pro Tyr Phe Gly Pro Ala Ala
 1               5                  10                  15

<210> SEQ ID NO 51
<211> LENGTH: 5
<212> TYPE: PRT
<213> ORGANISM: Ebola Virus

<400> SEQUENCE: 51

Arg Arg Thr Arg Arg
 1               5

<210> SEQ ID NO 52
<211> LENGTH: 1087
<212> TYPE: DNA
<213> ORGANISM: Artificial Sequence
<220> FEATURE:
<223> OTHER INFORMATION: The CMV Enhancer/Promoter, R Region (HTVL-1),
      CMV IE Splicing Acceptor sequence
```

-continued

```
<400> SEQUENCE: 52
ccattgcata cgttgtatcc atatcataat atgtacattt atattggctc atgtccaaca      60
ttaccgccat gttgacattg attattgact agttattaat agtaatcaat tacgggtca      120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca agtacgcccc ctattgacgt caatgacggt     360
aaatggcccg cctggcatta tgcccagtac atgacccttat gggactttcc tacttggcag   420
tacatctacg tattagtcat cgctattacc atggtgatgc ggttttggca gtacatcaat     480
gggcgtggat agcggtttga ctcacgggga tttccaagtc tccacccat tgacgtcaat      540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc gtcagatcgc ctggagacgc catccacgct gttttgacct ccatagaaga    720
caccgggacc gatccagcct ccatcggctc gcatctctcc ttcacgcgcc cgccgcctta     780
cctgaggccg ccatccacgc cggttgagtc gcgttctgcc gcctcccgcc tgtggtgcct    840
cctgaactac gtccgccgtc taggtaagtt tagagctcag gtcgagaccg ggcctttgtc    900
cggcgctccc ttggagccta cctagactca gccggctctc cacgctttgc ctgaccctgc    960
ttgctcaact ctagttaacg gtggagggca gtgtagtctg agcagtactc gttgctgccg   1020
cgcgcgccac cagacataat agctgacaga ctaacagact gttcctttcc atgggtcttt  1080
tctgcag                                                              1087
```